US007351719B2

(12) United States Patent
Stenkamp et al.

(10) Patent No.: US 7,351,719 B2
(45) Date of Patent: Apr. 1, 2008

(54) AMIDE COMPOUNDS HAVING MCH-ANTAGONISTIC ACTIVITY AND MEDICAMENTS COMPRISING THESE COMPOUNDS

(75) Inventors: Dirk Stenkamp, Biberach (DE); Stephan Georg Mueller, Warthausen (DE); Gerald Juergen Roth, Biberach (DE); Philipp Lustenberger, Warthausen (DE); Klaus Rudolf, Warthausen (DE); Thorsten Lehmann-Lintz, Ochsenhausen (DE); Kirsten Arndt, Biberach (DE); Ralf Lotz, Schemmerhofen (DE); Martin Lenter, Ulm (DE); Heike-Andrea Wieland, Bad Soden (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 400 days.

(21) Appl. No.: 10/699,089

(22) Filed: Oct. 31, 2003

(65) Prior Publication Data

US 2004/0152742 A1    Aug. 5, 2004

Related U.S. Application Data

(60) Provisional application No. 60/456,482, filed on Mar. 21, 2003.

(30) Foreign Application Priority Data

Oct. 31, 2002    (DE) ................. 102 50 743

(51) Int. Cl.
C07C 233/29 (2006.01)
C07C 235/24 (2006.01)
C07C 255/60 (2006.01)
C07D 209/18 (2006.01)
C07D 211/14 (2006.01)
C07D 213/56 (2006.01)
C07D 295/092 (2006.01)
C07D 401/12 (2006.01)
C07D 413/12 (2006.01)
A61K 31/167 (2006.01)
A61K 31/40 (2006.01)
A61K 31/4453 (2006.01)
A61K 31/445 (2006.01)
A61K 31/404 (2006.01)
A61P 3/04 (2006.01)
A61P 13/02 (2006.01)

(52) U.S. Cl. ............. 514/318; 514/330; 514/331; 514/415; 514/428; 514/539; 514/622; 546/194; 546/227; 546/233; 548/510; 548/568; 558/414; 560/43; 564/182; 544/131; 544/400

(58) Field of Classification Search ........... 546/194, 546/227, 233; 548/510, 568; 560/43; 564/182; 514/318, 330, 331, 415, 428, 539, 622

See application file for complete search history.

(56) References Cited

U.S. PATENT DOCUMENTS

| 3,551,478 | A | * | 12/1970 | Schmitt et al. ............... 560/36 |
| 3,994,900 | A | | 11/1976 | Krapcho et al. |
| 4,146,637 | A | * | 3/1979 | Metz et al. ................. 514/616 |
| 4,294,851 | A | * | 10/1981 | Metz et al. ................. 514/546 |
| 4,948,812 | A | * | 8/1990 | Koppe et al. ................ 514/622 |
| 6,258,953 | B1 | | 7/2001 | Howard et al. |
| 6,366,268 | B1 | | 4/2002 | Forrest et al. |
| 2002/0052383 | A1 | | 5/2002 | Bakthavatchalam et al. |
| 2003/0022891 | A1 | | 1/2003 | Palani et al. |
| 2003/0144261 | A1 | | 7/2003 | Palani et al. |
| 2003/0192132 | A1 | | 10/2003 | Chassot et al. |
| 2004/0082780 | A1 | | 4/2004 | Doherty et al. |
| 2004/0142953 | A1 | | 7/2004 | Delorme et al. |
| 2004/0220191 | A1 | | 11/2004 | Schwink et al. |
| 2005/0009815 | A1 | | 1/2005 | DeVita et al. |
| 2005/0026915 | A1 | | 2/2005 | DeVita et al. |

FOREIGN PATENT DOCUMENTS

DE    1 088 955    9/1960

(Continued)

OTHER PUBLICATIONS

Ariesan et al., Chemical Abstracts, 84:116338, 1976.*

(Continued)

*Primary Examiner*—Fiona T Powers
(74) *Attorney, Agent, or Firm*—Michael P. Morris; Timothy X. Witkowski; Mary-Ellen M. Devlin

(57) ABSTRACT

The present invention relates to amide compounds of general formula I

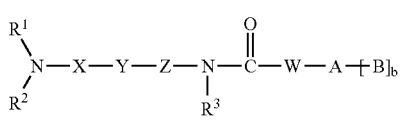

wherein the groups and residues A, B, b, W, X, Y, Z, $R^1$, $R^2$ and $R^3$ have the meanings given in claim 1. Moreover the invention relates to pharmaceutical compositions containing at least one amide according to the invention. In view of the MCH receptor-antagonistic activity the pharmaceutical compositions according to the invention are suitable for the treatment of metabolic disorders and/or eating disorders, particularly obesity, bulimia, anorexia, hyperphagia and diabetes.

17 Claims, No Drawings

FOREIGN PATENT DOCUMENTS

| | | |
|---|---|---|
| DE | 3016827 | 11/1980 |
| EP | 0 237 678 A1 | 9/1987 |
| EP | 0 810 220 A1 | 12/1997 |
| EP | 1 283 199 A1 | 2/2003 |
| EP | 1 593 667 A1 | 9/2005 |
| JP | 04054118 | 2/1992 |
| JP | 2000/086603 | 3/2000 |
| WO | WO 98/38156 | 9/1998 |
| WO | WO 99/02497 A2 | 1/1999 |
| WO | WO 99/29674 | 6/1999 |
| WO | WO 00/06153 A1 | 2/2000 |
| WO | WO 2000/05223 | 2/2000 |
| WO | WO 00/49005 | 8/2000 |
| WO | WO 01/02344 | 1/2001 |
| WO | WO 01/21577 A2 | 3/2001 |
| WO | WO 01/55066 A2 | 8/2001 |
| WO | WO 02/04433 A2 | 1/2002 |
| WO | WO 02/06245 A1 | 1/2002 |
| WO | WO 02/28182 A1 | 4/2002 |
| WO | WO 02/051809 A1 | 7/2002 |
| WO | WO 02/057233 A1 | 7/2002 |
| WO | WO 02/079144 A1 | 10/2002 |
| WO | WO 02/092068 | 11/2002 |
| WO | WO 03/013247 A1 | 2/2003 |
| WO | WO 03/014111 A1 | 2/2003 |
| WO | WO 03/018579 A1 | 3/2003 |
| WO | WO 03/024448 A1 | 3/2003 |
| WO | WO 03/032980 A1 | 4/2003 |
| WO | WO 03/033476 A1 | 4/2003 |
| WO | WO 03/035055 A1 | 5/2003 |
| WO | WO 03/045313 A2 | 6/2003 |
| WO | WO 03/045920 A1 | 6/2003 |
| WO | WO 03/049702 | 6/2003 |
| WO | WO 03/050087 A2 | 6/2003 |
| WO | WO 2004/018467 A2 | 3/2004 |
| WO | WO 2004/024702 | 3/2004 |
| WO | WO 2004/037751 A2 | 5/2004 |
| WO | WO 2004/039780 A1 | 5/2004 |
| WO | WO 2004/041820 A1 | 5/2004 |
| WO | WO 2004/069823 A1 | 8/2004 |
| WO | WO 2004/072018 | 8/2004 |
| WO | WO 2004/072025 A2 | 8/2004 |
| WO | WO 2005/063239 A1 | 7/2005 |
| WO | WO 2005/085221 A1 | 9/2005 |

OTHER PUBLICATIONS

Baker et al., Chemical Abstracts, 69:64778, 1968.*
Fahmy et al., Chemical Abstracts, 137:109242, 2002.*
Khlaponina et al., Chemical Abstracts, 108:68297, 1988.*
Zheng et al., Chemical Abstracts, 113:77848, 1990.*
Guidicelli et al., Chemical Abstracts, 50:2050d-e, 1956.*
Yanyun Chen, et al. "Targeted Disruption of the Melanin-Concentrating Hormone Receptor-1 Results in Hyperphagia and Resistance to Diet-Induced Obesity", Endocrinology 143(7):2469-2477 2002.
Daqing Qu, et al. "A role for melanin-concentrating hormone in the central regulation of feeding behaviour" Nature vol. 380, pp. 243-247 1996.
Masako Shimada, et al. "Mice lacking melanin-concentrating hormone are hypophagic and lean" Nature vol. 396, pp. 670-674 1998.
Beth Borowsky, et al. "Antidepressant, anxiolytic and anorectic effects of a melanin-concentrating hormone-1 receptor antagonist" Nature Medicine vol. 8, No. 8, pp. 825-830, 2002.
Donald J. Marsh, et al. "Melanin-concentrating hormone 1 receptor-deficient mice are lean, hyperactive, and hyperphagic and have altered metabolism" PNAS, vol. 99, No. 5, pp. 3240-3245, 2002.
Shiro Takekawa, et al. "T-226296: a novel, orally active and selective melanin-concentrating hormone receptor antagonist" E. Journal of Pharm. vol. 438, pp. 129-213, 2002.
J. Krapcho, et al; "Immunosuppressive Activity of 2'-(3-Dimethylaminopropylthio)cinnamanilide (Cinanserin) and Related Compounds" J. Med. Chemistry. 1969, 12(1), 164-166.
Tamiz, Amir P., et al; Structure-Activity Relationship of N-(Phenylalkyl)cinnamides as Novel NR2B Subtype-Selective NMDA Receptor Antagonists—J. Med. Chem. 1999, 42, 3412-3420.
Tetsuo, Sato, et al; Japanese Abstract 2002193800; VEGF Receptor antagonists for Treatment of neoangiogenesis-related diseases.
English Abstract of WO 2001/082925.
English Abstract of EP 73016.
English Abstract—FR 1176918.

* cited by examiner

AMIDE COMPOUNDS HAVING MCH-ANTAGONISTIC ACTIVITY AND MEDICAMENTS COMPRISING THESE COMPOUNDS

The present invention relates to new amide compounds, the physiologically acceptable salts thereof as well as their use as MCH antagonists and their use in preparing a pharmaceutical preparation which is suitable for the prevention and/or treatment of symptoms and/or diseases caused by MCH or causally connected with MCH in some other way. The invention also relates to the use of a compound according to the invention for influencing eating behaviour and for reducing body weight and/or for preventing any increase in body weight in a mammal. It further relates to compositions and medicaments containing a compound according to the invention and processes for preparing them.

BACKGROUND TO THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialised countries, have promoted obesity in recent decades. In affected people, obesity leads directly to restricted mobility and a reduction in the quality of life. There is the additional factor that obesity often leads to other diseases such as, for example, diabetes, dyslipidaemia, high blood pressure, arteriosclerosis and coronary heart disease. Moreover, high body weight alone puts an increased strain on the support and mobility apparatus, which can lead to chronic pain and diseases such as arthritis or osteoarthritis. Thus, obesity is a serious health problem for society.

The term obesity means an excess of adipose tissue. In this connection, obesity is fundamentally to be seen as the increased level of fatness which leads to a health risk. In the last analysis it is not precisely possible to draw a distinction between normal individuals and those suffering from obesity, but the health risk accompanying obesity is presumed to rise continuously as the level of fatness increases. For simplicity's sake, in the present invention, individuals with a Body Mass Index (BMI), which is defined as the body weight measured in kilograms divided by the height (in metres) squared, above a value of 25 and more particularly above 30 are preferably regarded as suffering from obesity.

Apart from physical activity and a change in nutrition, there is currently no convincing treatment option for effectively reducing body weight. However, as obesity is a major risk factor in the development of serious and even life-threatening diseases, it is all the more important to have access to pharmaceutical active substances for the prevention and/or treatment of obesity. One approach which has been proposed very recently is the therapeutic use of MCH antagonists (cf. inter alia WO 01/21577, WO 01/82925).

Melanin-concentrating hormone (MCH) is a cyclic neuropeptide consisting of 19 amino acids. It is synthesised predominantly in the hypothalamus in mammals and from there travels to other parts of the brain by the projections of hypothalamic neurones. Its biological activity is mediated in humans through two different G-protein-coupled receptors (GPCRs) from the family of rhodopsin-related GPCRs, namely the MCH receptors 1 and 2 (MCH-1 R, MCH-2R).

Investigations into the function of MCH in animal models have provided good indications for a role of the peptide in regulating the energy balance, i.e. changing metabolic activity and food intake [1,2]. For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. However, experiments with MCH knock-out mice are particularly important in showing the function of MCH. Loss of the neuropeptide results in lean animals with a reduced fat mass, which take in significantly less food than control animals.

The anorectic effects of MCH are mediated in rodents through the $G_{v_s}$-coupled MCH-1R [3-6]. Unlike primates, ferrets and dogs, no second receptor has hitherto been found in rodents. After losing the MCH-1R, knock-out mice have a lower fat mass, an increased energy conversion and, when fed on a high fat diet, do not put on weight, compared with control animals. Another indication of the importance of the MCH-MCH-1 R system in regulating the energy balance results from experiments with a receptor antagonist (SNAP-7941) [3]. In long term trials the animals treated with the antagonist lose significant amounts of weight.

In addition to its anorectic effect, the MCH-1R antagonist SNAP-7941 also achieves additional anxiolytic and antidepressant effects in behavioural experiments on rats [3]. Thus, there are clear indications that the MCH-MCH-1R system is involved not only in regulating the energy balance but also in affectivity.

Literature:
1. Qu, D., et al., A role for melanin-concentrating hormone in the central regulation of feeding behaviour. Nature, 1996. 380(6571): p. 243-7.
2. Shimada, M., et al., Mice lacking melanin-concentrating hormone are hypophagic and lean. Nature, 1998. 396 (6712): p. 670-4.
3. Borowsky, B., et al., Antidepressant, anxiolytic and anorectic effects of a melanin-concentrating hormone-I receptor antagonist Nat Med, 2002. 8(8): p. 825-30.
4. Chen, Y., et al., Targeted disruption of the melanin-concentrating hormone receptor-1 results in hyperphagia and resistance to diet-induced obesity. Endocrinology, 2002.143(7): p. 2469-77.
5. Marsh, D. J., et al., Melanin-concentrating hormone 1 receptor-deficient mice are lean, hyperactive, and hyperphagic and have altered metabolism. Proc Natl Acad Sci USA, 2002. 99(5): p. 3240-5.
6. Takekawa, S., et al., T-226296: A novel, orally active and selective melanin-concentrating hormone receptor antagonist. Eur J Pharmacol, 2002. 438(3): p.129-35.

In the patent literature certain amine compounds are proposed as MCH antagonists. Thus, WO 01/21577 (Takeda) describes compounds of formula

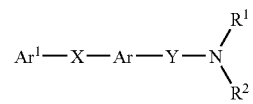

wherein $Ar^1$ denotes a cyclic group, X denotes a spacer, Y denotes a bond or a spacer, Ar denotes an aromatic ring which may be fused with a non-aromatic ring, $R^1$ and $R^2$ independently of one another denote H or a hydrocarbon group, while R¹ and R² together with the adjacent N atom may form an N-containing hetero ring and R² with Ar may also form a spirocyclic ring, R together with the adjacent N atom and Y may form an N-containing hetero ring, as MCH antagonists for the treatment of obesity.

Moreover WO 01/82925 (Takeda) also describes compounds of formula

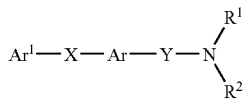

wherein Ar¹ denotes a cyclic group, X and Y represent spacer groups, Ar denotes an optionally substituted fused polycyclic aromatic ring, R¹ and R² independently of one another represent H or a hydrocarbon group, while R¹ and R² together with the adjacent N atom may form an N-containing heterocyclic ring and R² together with the adjacent N atom and Y may form an N-containing hetero ring, as MCH antagonists for the treatment of obesity, inter alia.

In EP 073 016 Al (Boehringer Ingelheim) 1-aryloxy-3-alkylamino-2-propanols of general formula

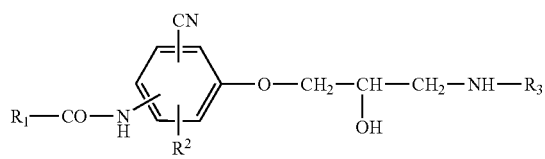

wherein R₁ may represent aryloxyalkylene, inter alia, are proposed for use as cardiac or coronary therapeutic agents or for lowering blood pressure. However, there is no mention of these compounds having an MCH-antagonistic activity.

U.S. Pat. No. 3,994,900 mentions inter alia n-(4-alkoxy-phenyl)-3-phenyl-acrylamides, n-(4-alkylthio-phenyl)-3-phenyl-acrylamides, n-(4-alkylsulphinyl-phenyl)-3-phenyl-acrylamidse and n-(4-alkylsulphonyl-phenyl)-3-phenyl-acrylamides as starting materials for synthesising dihydroquinolinone derivatives.

DE 1088955 lists inter alia the compounds N-[4-(2-diethylamino-ethoxy)-phenyl]-3-phenyl-acrylamide and N-[4-(2-diethylamino-ethoxy)-phenyl]-3-phenyl-propionamide.

WO 00/06153, which proposes compounds with a CCR5 receptor activity, mentions inter alia the compound 3-(3,4-dichloro-phenyl)-N-[3-(2-diisopropylamino-ethoxy)-4-methoxy-phenyl]-acrylamide. FR 1176918 mentions the compounds (N-[4-(2-morpholin-4-ylethoxy)-phenyl]-3-phenyl-propionamide) and N-[4-(2-diethylamino-ethoxy)-phenyl]-3-phenyl-propionamide.

In the article by A. P. Tamiz et al., J. Med. Chem. 42 (17), 1999, 3412-3420, the compound (3-(4-chloro-phenyl )-N-{2-[4-(2-diethylamino-ethoxy)-phenyl]-ethyl}-acrylamide) is mentioned.

In DE 3016827, which relates to compounds having an effect on the cardiovascular system, the compounds N-{2-[3-(4-{2-[2-(4-chloro-phenoxy)-acetylamino]-ethyl}-phenoxy)-2-hydroxy-propylamino]-ethyl}-isobutyramide, cyclopentanecarboxylic acid {2-[3-(4-{2-[2-(4-chloro-phenoxy)-acetylamino]-ethyl}-phenoxy)-2-hydroxy-propylamino]-ethyl}-amide and 2-(4-chloro-phenoxy)-N-(2-{4-[2-hydroxy-3-(2-phenylacetylamino-ethylamino)-propoxy]-phenyl}-ethyl )-acetamide inter alia are mentioned on page 55.

AIM OF THE INVENTION

The aim of the present invention is to discover new amide compounds, particularly those which have an activity as MCH antagonists.

A further aim of the invention is to provide new amide compounds which make it possible to influence the eating behaviour of mammals and in particular achieve a reduction in body weight and/or prevent an increase in body weight in mammals.

The present invention further sets out to provide new pharmaceutical compositions which are suitable for the prevention and/or treatment of symptoms and/or diseases caused by MCH or otherwise causally connected to MCH. In particular, the aim of this invention is to provide pharmaceutical compositions for the treatment of metabolic disorders such as obesity and/or diabetes as well as diseases and/or disorders which are associated with obesity and diabetes. Other objectives of the present invention are concerned with demonstrating advantageous uses of the compounds according to the invention. The invention also sets out to provide a process for preparing the amide compounds according to the invention. Other aims of the present invention will be immediately apparent to the skilled man from the foregoing remarks and those that follow.

SUBJECT MATTER OF THE INVENTION

A first object of the present invention comprises amide compounds of general formula I Amide compounds of general formula I

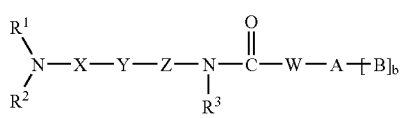

wherein

R¹, R² independently of one another denote H, a $C_{1-8}$-alkyl or $C_{3-7}$-cycloalkyl group optionally substituted by the group R¹¹, while a —CH₂— group in position 3 or 4 of a 5-, 6- or 7-membered cycloalkyl group may be replaced by —O—, —S—, —NH—, —N($C_{1-4}$-alkyl)— or —N(CO—O—$C_{1-4}$-alkyl)—, or a phenyl or pyridinyl group optionally mono- or polysubstituted by the group R¹² and/or monosubstituted by nitro, or R¹ and R² form a $C_{2-8}$-alkylene bridge wherein
one or two —CH₂— groups may be replaced independently of one another by —CH═N— or —CH═CH— and/or
one or two —CH₂— groups may be replaced independently of one another by —O—, —S—, —SO—, —(SO₂)—, —C═N—O—R¹⁸—, —CO—, —C(═CH₂)— or —NR¹³— in such a way that heteroatoms are not directly connected to one another,
while in the above-defined alkylene bridge one or more H atoms may be replaced by R¹⁴, and
while the above-defined alkylene bridge may be substituted by one or two identical or different carbo- or heterocyclic groups Cy in such a way that the bond between the alkylene bridge and the group Cy is formed
  via a single or double bond,
  via a common C atom forming a spirocyclic ring system,
  via two common, adjacent C and/or N atoms forming a fused bicyclic ring system or
  via three or more C and/or N atoms forming a bridged ring system, $R^3$ denotes H, $C_{1-6}$-alkyl, $C_{3-7}$-cycloalkyl or $C_{3-7}$-cycloalkyl-$C_{1-4}$-alkyl, X denotes a $C_{1-8}$-alkylene bridge wherein
  a —$CH_2$— group may be replaced by —CH=CH— or —C≡C— and/or
  one or two —$CH_2$— groups may be replaced independently of one another by —O—, —S—, —(SO)—, —($SO_2$)—, —CO— or —$NR^4$— in such a way that in each case two O, S or N atoms or an O and an S atom are not directly connected to one another,
  while the bridge X may be attached to $R^1$ including the N atom attached to $R^1$ and X forming a heterocyclic group, while the bridge X may additionally also be attached to $R^2$, including the N-atom attached to $R^2$ and X, forming a heterocyclic group, and
  two C atoms or one C and one N atom of the alkylene bridge may be joined together by an additional $C_{1-4}$-alkylene bridge, and
  a C atom may be substituted by $R^{10}$ and/or one or two C atoms in each case may be substituted with one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system, and W is selected from among —$CR^{6a}R^{6b}$—O—, —$CR^{7a}$=$CR^{7c}$—, —$CR^{6a}R^{6b}$—$NR^8$—, —$CR^{7a}R^{7b}$—$CR^{7c}R^{7d}$— and —$NR^8$—$CR^{6a}R^{6b}$—, Z denotes a single bond, $C_{1-4}$-alkylene, wherein two adjacent C atoms may be joined together with an additional $C_{1-4}$-alkylene bridge,
  while a C atom of the alkylene bridge may be substituted with $R^{10}$ and/or one or two C atoms independently of one another may be substituted with one or two identical or different $C_{1-6}$-alkyl groups, while two alkyl groups may be joined together, forming a carbocyclic ring, and Y denotes one of the meanings given for Cy,
  while $R^1$ may be attached to Y including the group X and the N atom attached to $R^1$ and X, forming a heterocyclic group fused to Y, and/or
  X may be attached to Y forming a carbo- or heterocyclic group fused to Y, and A denotes one of the meanings given for Cy,
B denotes one of the meanings given for Cy,
b denotes the value 0 or 1,
Cy denotes a carbo- or heterocyclic group selected from one of the following meanings
  a saturated 3- to 7-membered carbocyclic group,
  an unsaturated 4- to 7-membered carbocyclic group,
  a phenyl group,
  a saturated 4- to 7-membered or unsaturated 5- to 7-membered heterocyclic group with an N, O or S atom as heteroatom,
  a saturated or unsaturated 5- to 7-membered heterocyclic group with two or more N atoms or with one or two N atoms and an O or S atom as heteroatoms,
  an aromatic heterocyclic 5- or 6-membered group with one or more identical or different heteroatoms selected from N, O and/or S,
  while the above-mentioned 4-, 5-, 6- or 7-membered groups may be attached via two common, adjacent C atoms fused to a phenyl or pyridine ring, and
  in the above-mentioned 5-, 6- or 7-membered groups one or two non-adjacent —$CH_2$— groups may be replaced independently of one another by a —CO—, —C(=$CH_2$)—, —(SO)— or —($SO_2$)— group, and
  the above-mentioned saturated 6- or 7-membered groups may also be present as bridged ring systems with an imino, N-($C_{1-4}$-alkyl)-imino, methylene, $C_{1-4}$-alkyl-methylene or di-($C_{1-4}$-alkyl)-methylene bridge, and
  the above-mentioned cyclic groups may be mono- or polysubstituted at one or more C atoms with $R^{20}$, in the case of a phenyl group they may also additionally be monosubstituted with nitro, and/or one or more NH groups may be substituted with $R^{21}$, $R^4$ has one of the meanings given for $R^{17}$, $C_{2-6}$-alkenyl or $C_{3-6}$-alkynyl,
$R^{6a}$, $R^{6b}$ denotes H, $C_{1-4}$-alkyl or $CF_3$,
$R^{7a}$, $R^{7b}$,
$R^{7c}$, $R^{7d}$ denotes H, F, $C_{1-4}$-alkyl or $CF_3$,
$R^8$ denotes H, $C_{1-4}$-alkyl, $C_{3-7}$-cycloalkyl or $C_{3-7}$-cycloalkyl-$C_{1-3}$-alkyl,
$R^{10}$ denotes hydroxy, ω-hydroxy-$C_{1-3}$-alkyl, $C_{1-4}$-alkoxy, ω-($C_{1-4}$-alkoxy)-$C_{1-3}$-alkyl, carboxy, $C_{1-4}$-alkoxycarbonyl, amino, $C_{1-4}$-alkyl-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, amino-$C_{1-3}$-alkoxy, $C_{1-4}$-alkyl-amino-$C_{1-3}$-alkoxy, di-($C_{1-4}$-alkyl)-amino-$C_{1-3}$-alkoxy or cyclo-$C_{3-6}$-alkyleneimino-$C_{1-3}$-alkoxy, aminocarbonyl, $C_{1-4}$-alkyl-aminocarbonyl, di-($C_{1-4}$-alkyl)-aminocarbonyl or cyclo-$C_{3-6}$-alkyleneimino-carbonyl, $R^{11}$ denotes $C_{2-6}$-alkenyl, $C_{2-6}$-alkynyl, $R^{15}$—O, $R^{15}$—O—CO, $R^{15}$—CO—O, $R^{16}R^{17}N$, $R^{18}R^{19}N$—CO or Cy,
$R^{12}$ has one of the meanings given for $R^{20}$,
$R^{13}$ has one of the meanings given for $R^{17}$, with the exception of carboxy,
$R^{14}$ denotes halogen, $C_{1-6}$-alkyl, $C_{2-6}$-alkenyl, $C_{2-6}$-alkynyl, $R^{15}$—O, $R^{15}$—O—CO, $R^{15}$—CO, $R^{15}$—CO—O, $R^{16}R^{17}N$, $R^{18}R^{19}N$—CO, $R^{15}$—O—$C_{1-3}$-alkyl, $R^{15}$—O—CO, $C_{1-3}$-alkyl, $R^{15}$—O—CO—NH, $R^{15}$—$SO_2$—NH, $R^{15}$—O—CO—NH—$C_{1-3}$-alkyl—, $R^{15}$—$SO_2$—NH—$C_{1-3}$-alkyl—, $R^{15}$—CO—$C_{1-3}$-alkyl, $R^{15}$—CO—O—$C_{1-3}$-alkyl, $R^{16}R^{17}N$—$C_{1-3}$-alkyl, $R^{18}R^{19}N$—CO—$C_{1-3}$-alkyl or Cy—$C_{1-3}$-alkyl,
$R^{15}$ denotes H, $C_{1-4}$-alkyl, $C_{3-7}$-cycloalkyl, $C_{3-7}$-cycloalkyl-$C_{1-3}$-alkyl, phenyl, phenyl-$C_{1-3}$-alkyl, pyridinyl or pyridinyl-$C_{1-3}$-alkyl,
$R^{16}$ denotes H, $C_{1-6}$-alkyl, $C_{3-7}$-cycloalkyl, $C_{3-7}$-cycloalkyl-$C_{1-3}$-alkyl, $C_{4-7}$-cycloalkenyl, $C_{4-7}$-cycloalkenyl-$C_{1-3}$-alkyl, ω-hydroxy-$C_{2-3}$-alkyl, ω-($C_{1-4}$-alkoxy)-$C_{C2-3}$-alkyl, amino-$C_{2-6}$-alkyl, $C_{1-4}$-alkyl-amino-$C_{2-6}$-alkyl, di-($C_{1-4}$-alkyl)-amino-$C_{2-6}$-alkyl or cyclo-$C_{3-6}$-alkyleneimino-$C_{2-6}$-alkyl,
$R^{17}$ has one of the meanings given for $R^{16}$ or denotes phenyl, phenyl-$C_{1-3}$-alkyl, pyridinyl, dioxolan-2-yl, —CHO, $C_{1-4}$-alkylcarbonyl, carboxy, hydroxycarbonyl-$C_{1-3}$-alkyl, $C_{1-4}$-alkoxycarbonyl, $C_{1-4}$-alkoxycarbonyl-$C_{1-3}$-alkyl, $C_{1-4}$-alkylcarbonylamino-$C_{2-3}$-alkyl, N-($C_{1-4}$-alkylcarbonyl)-N-($C_{1-4}$-alkyl)-amino-$C_{2-3}$-alkyl, $C_{1-4}$-alkylsulphonyl, $C_{1-4}$-alkylsulphonylamino-$C_{2-3}$-alkyl or N-($C_{1-4}$-alkylsulphonyl)-N($C_{1-4}$-alkyl)-amino-$C_{2-3}$-alkyl $R^{18}$, $R^{19}$ independently of one another denote H or $C_{1-6}$-alkyl, $R^{20}$ denotes halogen, hydroxy, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy-$C_{1-4}$-alkyl, $R^{22}$-$C_{1-3}$-alkyl or one of the meanings given for $R^{22}$, $R^{21}$ denotes $C_{1-4}$-alkyl, ω-hydroxy-$C_{2-3}$-alkyl, ω-$C_{1-4}$-alkoxy-$C_{2-6}$-alkyl, ω-$C_{1-4}$-alkyl-amino-$C_{2-6}$-alkyl, ω-di-($C_{1-4}$-alkyl)-amino-$C_{2-6}$-alkyl, ω-cyclo-$C_{3-6}$-alkyleneimino-$C_{3-6}$-alkyleneimino-$C_{2-6}$-alkyl, phenyl-$C_{1-3}$-alkyl, $C_{1-4}$-alkyl-carbonyl, $C_{1-4}$-alkyoxy-carbonyl or $C_{1-4}$-alkylsulphonyl, $R^{22}$ denotes phenyl-$C_{1-3}$-alkoxy, OHC, HO—N═HC, $C_{1-4}$-alkoxy-N═HC, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, cyclo-$C_{3-6}$-alkyl-amino-carbonyl, cyclo-$C_{3-6}$-alkyleneimino-carbonyl, cyclo-$C_{3-6}$-alkyleneimino-$C_{2-4}$-alkyl-aminocarbonyl, phenyl-amino-carbonyl, $C_{1-4}$-alkyl-sulphonyl, $C_{1-4}$-alkyl-sulphinyl, $C_{1-4}$-alkyl-sulphonylamino, amino, $C_{1-4}$-alkylamino, di-($C_{1-4}$-alkyl)-amino, $C_{1-4}$-alkyl-carbonyl-amino, cyclo-$C_{3-6}$-alkyleneimino, phenyl-$C_{1-3}$-alkylamino or N-($C_{1-4}$-alkyl)-phenyl-$C_{1-3}$-alkylamino, acetylamino, propionylamino, phenylcarbonylamino, phenylcarbonylmethylamino, hydroxy-alkylaminocarbonyl, (4-morpholinyl )carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino or alkylaminocarbonylamino, while in the above-mentioned groups and residues, especially in A, B, W, X, Y, Z, $R^1$ to $R^4$, $R^{6a}$, $R^{6b}$, $R^{7a}$, $R^{7b}$, $R^{7c}$, $R^{7d}$, $R^8$, $R^{10}$ to $R^{22}$, in particular, in each case one or more C atoms may additionally be mono- or polysubstituted by F and/or in each case one or two C atoms may additionally be monosubstituted by Cl or Br independently of one another and/or in each case one or more phenyl rings may additionally, independently of one another, have one, two or three substituents selected from among F, Cl, Br, I, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, cyano, difluoromethoxy, trifluoromethoxy, amino-$C_{1-3}$-alkyl, $C_{1-3}$-alkylamino-$C_{1-3}$-alkyl- and di-($C_{1-3}$-alkyl)-amino-$C_{1-3}$-alkyl and/or may be monosubstituted by nitro, and the H atom of any carboxy group present or an H atom bonded to an N atom may each be replaced by a group which can be cleaved in vivo, the tautomers, the diastereomers, the enantiomers, the mixtures thereof and the salts thereof, with the following provisos (M1), (M2) and (M3)

(M1) in the event that Y denotes phenylene substituted with —CN, X denotes —$CH_2$—CH(OH)—$CH_2$—O—, Z denotes a single bond, $R^1$ denotes a straight-chain or branched alkyl group with 1 to 10 C atoms and $R^2$ and $R^3$ represent H, then W does not represent —$CR^{6a}R^{6b}$—O—, (M2) in the event that W denotes —CH═CH— and Y denotes a phenylene group and Z is a single bond, then the bridges X and Z at the phenylene ring of the group Y are in the para position to one another and at least one of the following conditions is met:

(a) the group Y meaning phenylene is at least monosubstituted, (b) b has the value 0 and the group A is at least disubstituted, (c) b has the value 1;

(M3) the following individual compounds are not included:

N-[4-(2-diethylamino-ethoxy)-phenyl]-3-phenyl-propionamide,

N-[4-(2-morpholin-4-ylethoxy)-phenyl]-3-phenyl-propionamide, 3-(4-chloro-phenyl )-N-{2-[4-(2-diethylamino-ethoxy)-phenyl]-ethyl}-acrylamide, N-{2-[3-(4-{2-[2-(4-chloro-phenoxy)-acetylamino]-ethyl}-phenoxy)-2-hydroxy-propylamino]-ethyl}-isobutyramide, cyclopentanecarboxylic acid {2-[3-(4-{2-[2-(4-chloro-phenoxy)-acetylamino]-ethyl}-phenoxy)-2-hydroxy-propylamino]-ethyl}-amide, 2-(4-chloro-phenoxy)-N-(2-{4-[2-hydroxy-3-(2-phenylacetylamino-ethylamino)-propoxy]-phenyl}-ethyl)-acetamide.

The invention also relates to the compounds in the form of the individual optical isomers, mixtures of the individual enantiomers or racemates, in the form of the tautomers and in the form of the free bases or the corresponding acid addition salts with pharmacologically safe acids. The subject of the invention also includes the compounds according to the invention, including the salts thereof, wherein one or more hydrogen atoms are replaced by deuterium.

This invention also includes the physiologically acceptable salts of the amide compounds according to the invention as described above and hereinafter.

This invention also relates to compositions containing at least one amide compound according to the invention and/or a salt according to the invention optionally together with one or more physiologically acceptable excipients.

Also covered by this invention are pharmaceutical compositions containing at least one amide compound according to the invention and/or a salt according to the invention optionally together with one or more inert carriers and/or diluents.

This invention also relates to the use of at least one amide compound according to the invention and/or a salt according to the invention, including the compounds excluded by provisos (M1), (M2) and (M3), for influencing the eating behaviour of a mammal.

The invention further relates to the use of at least one amide compound according to the invention and/or a salt according to the invention, including the compounds excluded by provisos (M1), (M2) and (M3), for reducing the body weight and/or for preventing an increase in the body weight of a mammal.

The invention also relates to the use of at least one amide compound according to the invention and/or a salt according to the invention, including the compounds excluded by provisos (M1), (M2) and (M3), for preparing a pharmaceutical composition with an MCH receptor-antagonistic activity, particularly with an MCH-1 receptor-antagonistic activity.

This invention also relates to the use of at least one amide compound according to the invention and/or a salt according to the invention, including the compounds excluded by provisos (M1), (M2) and (M3), for preparing a pharmaceutical composition which is suitable for the prevention and/or treatment of symptoms and/or diseases which are caused by MCH or are otherwise causally connected with MCH.

A further object of this invention is the use of at least one amide compound according to the invention and/or a salt according to the invention, including the compounds excluded by provisos (M1), (M2) and (M3), for preparing a pharmaceutical composition which is suitable for the prevention and/or treatment of metabolic disorders and/or eating disorders, particularly obesity, bulimia, bulimia nervosa, cachexia, anorexia, anorexia nervosa and hyperphagia The invention also relates to the use of at least one amide compound according to the invention and/or a salt according to the invention, including the compounds excluded by provisos (M1), (M2) and (M3), for preparing a pharmaceutical composition which is suitable for the prevention and/or treatment of diseases and/or disorders associated with obesity, particularly diabetes, especially type II diabetes, complications of diabetes including diabetic retinopathy, diabetic neuropathy, diabetic nephropathy, insulin resistance, pathological glucose tolerance, encephalorrhagia, cardiac insufficiency, cardiovascular diseases, particularly arteriosclerosis and high blood pressure, arthritis and gonitis.

In addition the present invention relates to the use of at least one amide compound according to the invention and/or a salt according to the invention, including the compounds excluded by provisos (M1), (M2) and (M3), for preparing a pharmaceutical composition which is suitable for the prevention and/or treatment of hyperlipidaemia, cellulitis, fat accumulation, malignant mastocytosis, systemic mastocytosis, emotional disorders, affective disorders, depression, anxiety, sleep disorders, reproductive disorders, sexual disorders, memory disorders, epilepsy, forms of dementia and hormonal disorders.

The invention also relates to the use of at least one amide compound according to the invention and/or a salt according to the invention, including the compounds excluded by provisos (M1), (M2) and (M3), for preparing a pharmaceutical composition which is suitable for the prevention and/or treatment of urinary problems, such as for example urinary incontinence, overactive bladder, urgency, nycturia and enuresis.

The invention further relates to processes for preparing for preparing a pharmaceutical composition according to the invention, characterised in that at least one amide compound according to the invention and/or a salt according to the invention is incorporated in one or more inert carriers and/or diluents by a non-chemical method.

The invention also relates to a pharmaceutical composition containing a first active substance which is selected from the amide compounds according to the invention and/or the corresponding salts, including the compounds excluded by provisos (M1), (M2) and (M3), as well as a second active substance which is selected from the group consisting of active substances for the treatment of diabetes, active substances for the treatment of diabetic complications, active substances for the treatment of obesity, preferably other than MCH antagonists, active substances for the treatment of high blood pressure, active substances for the treatment of hyperlipidaemia, including arteriosclerosis, active substances for the treatment of arthritis, active substances for the treatment of anxiety states and active substances for the treatment of depression, optionally together with one or more inert carriers and/or diluents.

DETAILED DESCRIPTION OF THE INVENTION

Unless otherwise specified the groups, residues and substituents, particularly A, B, W, X, Y, Z, $R^1$ to $R^4$, $R^{6a}$, $R^{6b}$, $R^{7a}$, $R^{7b}$, $R^{7c}$, $R^{7d}$, $R^8$, $R^{10}$ to $R^{22}$, and index b, have the meanings given hereinbefore.

According to one embodiment the groups $R^1$, $R^2$, X, Z, b, $R^{10}$, $R^{14}$, $R^{15}$, $R^{17}$, $R^{20}$, $R^{21}$, $R^{22}$ have the following meanings:

$R^1$, $R^2$ independently of one another denote H, a $C_{1-8}$-alkyl or $C_{3-7}$-cycloalkyl group optionally substituted by the group $R^{11}$, or a phenyl group optionally mono- or polysubstituted by the group $R^{12}$ and/or monosubstituted by nitro, or $R^1$ and $R^2$ form a $C_{2-8}$-alkylene bridge wherein
  one or two —$CH_2$— groups independently of one another may be replaced by —CH=N— or —CH=CH— and/or
  one or two —$CH_2$— groups independently of one another may be replaced by —O—, —S—, —CO—, —C(=$CH_2$)-or —$NR^{13}$— so that heteroatoms are not directly connected to one another,
  while in the alkylene bridge defined above one or more H atoms may be replaced by $R^{14}$, and
  while the alkylene bridge defined hereinbefore may be substituted with one or two identical or different carbo- or heterocyclic groups Cy so that the bond between the alkylene bridge and the group Cy is made
    via a single or double bond,
    via a common C atom forming a spirocyclic ring system,
    via two common adjacent C and/or N atoms forming a fused bicyclic ring system or
    via three or more C and/or N atoms forming a bridged ring system, X denotes a $C_{1-8}$-alkylene bridge wherein
  a —$CH_2$— group may be replaced by —CH=CH— or —C≡C— and/or
  one or two —$CH_2$— groups may be replaced independently of one another by —O—, —S—, —(SO)—, —($SO_2$)—, —CO— or —$NR^4$— in such a way that in each case two O, S or N atoms or an O and an S atom are not directly joined together,
  while the bridge X may be connected to $R^1$ including the N atom attached to $R^1$ and X forming a heterocyclic group, and
  two C atoms or a C and an N atom of the alkylene bridge may be joined together by an additional $C_{1-4}$-alkylene bridge, and
  a C atom may be substituted by $R^{10}$ and/or one or two C atoms in each case may be substituted by one or two identical or different $C_{1-6}$-alkyl groups, and Z denotes a single bond, $C_{1-4}$-alkylene, wherein two adjacent C atoms may be joined together by an additional $C_{1-4}$-alkylene bridge,
  while a C atom of the alkylene bridge may be substituted by $R^{10}$ and/or one or two C atoms independently of one another may be substituted by one or two identical or different $C_{1-6}$-alkyl groups, and b has the value 0, $R^{10}$ denotes hydroxy, ω-hydroxy-$C_{1-3}$-alkyl, $C_{1-4}$-alkoxy, ω-($C_{1-4}$-alkoxy)-$C_{1-3}$-alkyl, amino, $C_{1-4}$-alkyl-amino, di-($C_{1-4}$-alkyl)-amino, cyclo-$C_{3-6}$-alkyleneimino, amino-$C_{1-3}$- alkyl, $C_{1-4}$-alkyl-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, amino-$C_{1-3}$-alkoxy, $C_{1-4}$-alkyl-amino-$C_{1-3}$-alkoxy, di-($C_{1-4}$-alkyl)-amino-$C_{1-3}$-alkoxy or cyclo-$C_{3-6}$-alkyleneimino-$C_{1-3}$-alkoxy, $R^{14}$ denotes halogen, $C_{1-6}$-alkyl, $R^{15}$—O, $R^{15}$O—CO, $R^{15}$—CO, $R^{15}$—CO—O, $R^{16}R^{17}N$, $R^{18}R^{19}N$—CO, $R^{15}$—O—$C_{1-3}$-alkyl-, $R^{15}$—O—CO—$C_{1-3}$-alkyl, $R^{15}$—

CO—$C_{1-3}$-alkyl, $R^{15}$—CO—O—$C_{1-3}$-alkyl, $R^{16}R^{17}$N—$C_{1-3}$-alkyl, $R^{18}R^{19}$N—CO—$C_{1-3}$-alkyl or Cy-$C_{1-3}$-alkyl, $R^{15}$ denotes H, $C_{1-4}$-alkyl, $C_{3-7}$-cycloalkyl, $C_{3-7}$-cycloalkyl-$C_{1-3}$-alkyl, phenyl or phenyl-$C_{1-3}$-alkyl, $R^{17}$ has one of the meanings given for $R^{16}$ or denotes phenyl, phenyl-$C_{1-3}$-alkyl, $C_{1-4}$-alkylcarbonyl, hydroxycarbonyl-$C_{1-3}$-alkyl, $C_{1-4}$-alkylcarbonylamino-$C_{2-3}$-alkyl, N-($C_{1-4}$-alkylcarbonyl)-N-($C_{1-4}$-alkyl)-amino-$C_{2-3}$-alkyl, $C_{1-4}$-alkylsulphonyl, $C_{1-4}$-alkylsulphonylamino-$C_{2-3}$-alkyl or N-($C_{1-4}$-alkylsulphonyl)-N-($C_{1-4}$-alkyl)-amino-$C_{2-3}$-alkyl, $R^{20}$ denotes halogen, hydroxy, cyano, $C_{1-6}$-alkyl, $C_{3-7}$-cycloalkyl, $C_{3-7}$-cycloalkyl-$C_{1-3}$-alkyl, hydroxy-$C_{1-4}$-alkyl, $R^{22}$-$C_{1-3}$-alkyl or one of the meanings given for $R^{22}$, $R^{21}$ denotes $C_{1-4}$-alkyl, (ω-hydroxy-$C_{2-3}$-alkyl, (ω-$C_{1-4}$-alkoxy-$C_{2-6}$-alkyl, ω-$C_{1-4}$-alkyl-amino-$C_{2-6}$-alkyl, ω-di-($C_{1-4}$-alkyl)-amino-$C_{2-6}$-alkyl, ω-cyclo-$C_{3-6}$-alkyleneimino-$C_{2-6}$-alkyl, phenyl, phenyl-$C_{1-3}$-alkyl, $C_{1-4}$-alkylcarbonyl, carboxy, $C_{1-4}$-alkoxy-carbonyl or $C_{1-4}$-alkylsulphonyl, $R^{22}$ denotes phenyl, phenyl-$C_{1-3}$-alkoxy, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, cyclo-$C_{3-6}$-alkyleneimino-carbonyl, $C_{1-4}$-alkyl-sulphonyl, $C_{1-4}$-alkylsulphinyl, $C_{1-4}$-alkyl-sulphonylamino, amino, $C_{1-4}$-alkylamino, di-($C_{1-4}$-alkyl)-amino, cyclo-$C_{3-6}$-alkyleneimino, phenyl-$C_{1-3}$-alkylamino or N-($C_{1-4}$-alkyl)-phenyl-$C_{1-3}$-alkylamino, acetylamino, propionylamino, phenylcarbonylamino, phenylcarbonylmethylamino, hydroxy-alkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino or alkylaminocarbonylamino, while the groups and residues $R^3$, $R^4$, $R^{6a}$, $R^{6b}$, $R^{7a}$, $R^{7b}$, $R^{7c}$, $R^{7d}$, $R^8$, $R^{11}$, $R^{12}$, $R^{16}$, $R^{18}$, $R^{19}$, W, Y, A, Cy have the meanings given hereinbefore.

Preferably the group $R^3$ denotes H or $C_{1-4}$-alkyl, particularly preferably H or methyl, particularly H.

If $R^1$ and $R^2$ are not joined together via an alkylene bridge, $R^1$ and $R^2$ independently of one another preferably represent a $C_{1-8}$-alkyl or $C_{3-7}$-cycloalkyl group optionally substituted by the group $R^{11}$, while a —$CH_2$— group in position 3 or 4 of a 5-, 6- or 7-membered cycloalkyl group may be replaced by —O—, —S— or —NH—, —N($C_{1-4}$-alkyl)— or —N(CO—O—$C_{1-4}$-alkyl)—, or a phenyl or pyridinyl group optionally mono- or polysubstituted by the group $R^{12}$ and/or monosubstituted by nitro, and one of the groups $R^1$ and $R^2$ may also represent H.

Preferably the groups $R^1$, $R^2$ independently of one another represent H, $C_{1-6}$-alkyl, $C_{3-7}$-cycloalkyl, $C_{3-7}$-cycloalkyl-$C_{1-3}$-alkyl, ω-hydroxy-$C_{2-3}$-alkyl, ω-($C_{1-4}$-alkoxy)-$C_{2-3}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkyl-amino-$C_{2-4}$-alkyl, di-($C_{1-4}$-alkyl)-amino-$C_{2-4}$-alkyl, cyclo-$C_{3-6}$-alkyleneimino-$C_{2-4}$-alkyl, pyrrolidin-3-yl, N-($C_{1-4}$-alkyl)-pyrrolidinyl, pyrrolidinyl-$C_{1-3}$-alkyl, N-($C_{1-4}$-alkyl)-pyrrolidinyl-$C_{1-3}$-alkyl, piperidinyl, N-($C_{1-4}$-alkyl)-piperidinyl, piperidinyl-$C_{1-3}$-alkyl, N-($C_{1-4}$-alkyl)-piperidinyl-$C_{1-3}$-alkyl, phenyl, phenyl-$C_{1-3}$-alkyl, pyridyl or pyridyl-$C_{1-3}$-alkyl, while in the above-mentioned groups and residues one or more C atoms may be mono- or polysubstituted by F and/or one or two C atoms may independently of one another be monosubstituted by Cl or Br, and the phenyl or pyridyl group may be mono- or polysubstituted by the group $R^{12}$ as hereinbefore defined and/or may be monosubstituted by nitro. Preferred substituents of the above-mentioned phenyl or pyridyl groups are selected from the group F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl- and di-($C_{1-3}$-alkyl)-amino-$C_{1-3}$-alkyl, while a phenyl group may also be monosubstituted by nitro.

Particularly preferred definitions of the groups $R^1$ and/or $R^2$ are selected from among $C_{1-6}$-alkyl, $C_{3-7}$-cycloalkyl, $C_{3-7}$-cycloalkyl-$C_{1-3}$-alkyl, ω-hydroxy-$C_{2-3}$-alkyl, ω-($C_{1-4}$-alkoxy)-$C_{2-3}$-alkyl, $C_{1-4}$-alkoxy-carbonyl-$C_{1-4}$-alkyl, carboxyl-$C_{1-4}$-alkyl, while one of the groups $R^1$ and $R^2$ may also represent H.

Particularly preferably, at least one of the groups $R^1$, $R^2$, and most preferably both groups, has a meaning other than H.

If $R^1$ and $R^2$ form an alkylene bridge, it is preferably a $C_{3-7}$-alkylene bridge wherein
  a —$CH_2$— group not adjacent to the N atom of the $R^1R^2$N group may be replaced by —CH=N— or —CH=CH— and/or
  a —$CH_2$— group which is preferably not adjacent to the N atom of the $R^1R^2$N group, may be replaced by —O—, —S—, —C(=N—O—$R^{18}$)—, —CO—, —C(=$CH_2$)— or —$NR^{13}$—most preferably by —O—, —S— or —$NR^{13}$—, in such a way that heteroatoms are not directly connected to one another, while in the alkylene bridge defined above one or more H atoms may be replaced by $R^{14}$, and the alkylene bridge defined hereinbefore may be substituted by a carbo- or heterocyclic group Cy in such a way that the bond between the alkylene bridge and the group Cy is made
  via a single or double bond,
  via a common C atom forming a spirocyclic ring system,
  via two common adjacent C and/or N atoms forming a fused bicyclic ring system or
  via three or more C and/or N atoms forming a bridged ring system.

Also preferably, $R^1$ and R form an alkylene bridge in such a way that $R^1R^2$N— denotes a group selected from azetidine, pyrrolidine, piperidine, azepan, 2,5-dihydro-1H-pyrrole, 1,2,3,6-tetrahydro-pyridine, 2,3,4,7-tetrahydro-1H-azepine, 2,3,6,7-tetrahydro-1H-azepine, piperazine, wherein the free imine function is substituted by $R^{13}$, piperidin-4-one, piperidin-4-one-oxime, piperidin-4-one-O—$C_{1-4}$-alkyl-oxime, morpholine and thiomorpholine, while according to the general definition of $R^1$ and $R^2$ one or more H atoms may be replaced by $R^{14}$, and/or the above-mentioned groups may be substituted by one or two identical or different carbo- or heterocyclic groups Cy in a manner specified according to the general definition of $R^1$ and $R^2$. Particularly preferred groups Cy are $C_{3-4}$-cycloalkyl, aza-$C_{4-7}$-cycloalkyl, particularly cyclo-$C_{3-6}$-alkyleneimino, as well as 1-$C_{1-4}$-alkyl-aza-$C_{4-7}$-cycloalkyl.

The $C_{2-8}$-alkylene bridge formed by $R^1$ and $R^2$ wherein —$CH_2$— groups may be replaced as specified may be substituted by one or two identical or different carbo- or heterocyclic groups Cy as described.

If the alkylene bridge is linked to a group Cy via a single bond, Cy is preferably selected from among $C_{3-7}$-cycloalkyl, cyclo-$C_{3-6}$-alkyleneimino, 1H-imidazol, thienyl and phenyl.

If the alkylene bridge is linked to a group Cy via a common C atom forming a spirocyclic ring system, Cy is preferably selected from among $C_{3-7}$-cycloalkyl, aza-$C_{4-8}$-cycloalky, oxa-$C_{4-8}$-cycloalkyl, 2,3-dihydro-1H-quinazolin4-one.

If the alkylene bridge is linked to a group Cy via two common adjacent C and/or N atoms forming a fused bicyclic ring system, Cy is preferably selected from among $C_{4-7}$-cycloalkyl, phenyl, thienyl.

If the alkylene bridge is linked to a group Cy via three or more C and/or N atoms forming a bridged ring system, Cy preferably denotes $C_{4-8}$-cycloalkyl or aza-$C_{4-8}$-cycloalkyl.

Preferably, the group

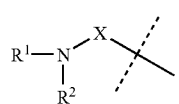

is defined according to one of the following partial formulae

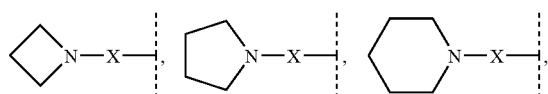

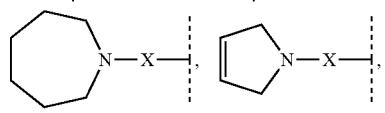

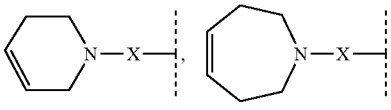

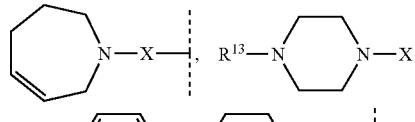

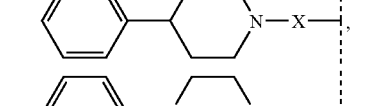

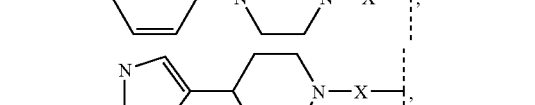

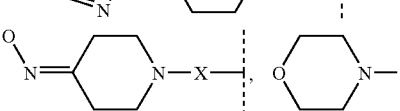

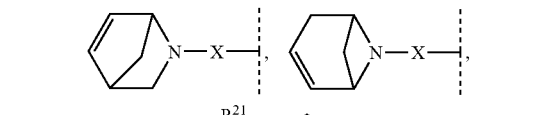

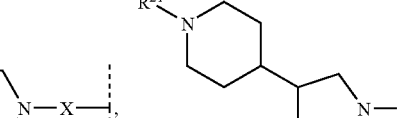

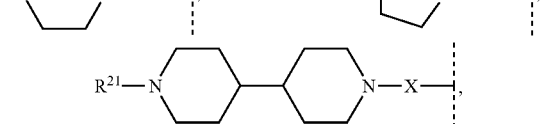

-continued

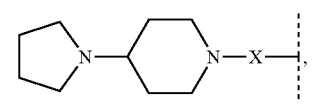

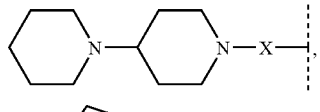

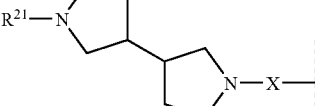

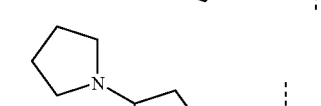

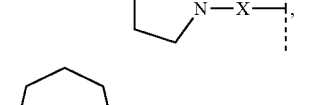

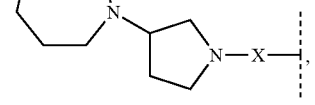

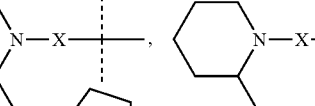

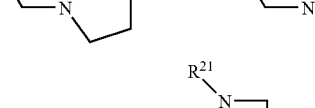

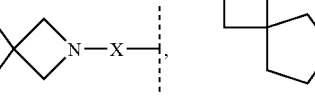

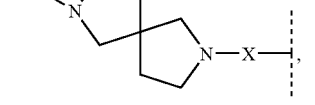

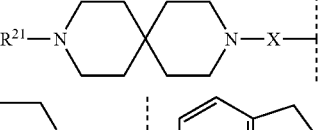

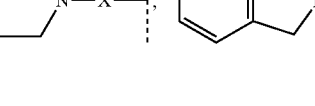

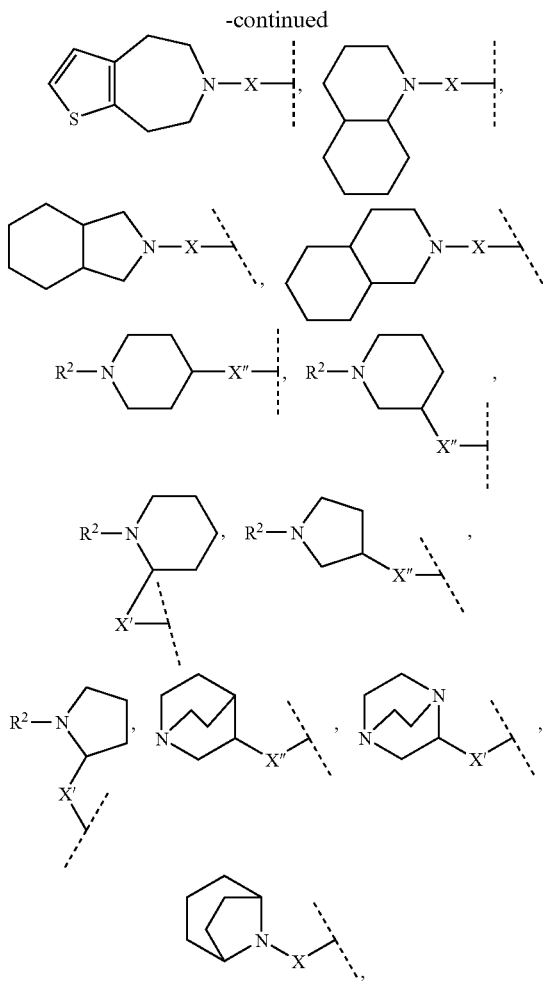

wherein one or more H atoms of the heterocycle formed by the group $R^1R^2N—$ may be replaced by $R^{14}$ and the ring attached to the heterocycle formed by the group $R^1R^2N—$ may be mono- or polysubstituted by $R^{20}$ at one or more C atoms, and in the case of a phenyl ring it may also additionally be monosubstituted by nitro and X', X" independently of one another denote a single bond or $C_{1-3}$-alkylene and if the group Y is linked to X' or X" via a C atom, may also denote $—C_{1-3}$-alkylene-—O—, $C_{1-3}$-alkylene-NH— or $—C_{1-3}$-alkylene-N($C_{1-3}$-alkyl)—, and X" may additionally also denote $—O—C_{1-3}$-alkylene-, $—NH—C_{1-3}$-alkylene- or $—N(C_{1-3}$-alkyl)-$C_{1-3}$-alkylene- and if the group Y is linked to X" via a C atom, may also denote —NH—, —N($C_{1-3}$-alkyl)— or —O—, while in the definitions given hereinbefore for X', X" in each case a C atom may be substituted by $R^{10}$, preferably by a hydroxy, ω-hydroxy-$C_{1-3}$-alkyl, ω-($C_{1-4}$-alkoxy)-$C_{1-3}$-alkyl and/or $C_{1-4}$-alkoxy group, and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together forming a carbocyclic ring system, and in X', X" independently of one another in each case one or more C atoms may be mono- or polysubstituted by F and/or in each case one or two C atoms independently of one another may be monosubstituted by Cl or Br and wherein $R^2$, $R^{10}$, $R^{13}$, $R^{14}$, $R^{18}$, $R^{20}$, $R^{21}$ and X have the meanings given hereinbefore and hereinafter.

In the preferred and particularly preferred definitions of $R^1R^2N$ listed above the following definitions of the substituent $R^{14}$ are preferred: $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, ω-hydroxy-$C_{1-3}$-alkyl, $C_{1-4}$-alkoxy, ω-($C_{1-4}$-alkoxy)-$C_{1-3}$-alkyl, $C_{1-4}$-alkyl-carbonyl, carboxy, $C_{1-4}$-alkoxy-carbonyl, hydroxy-carbonyl-$C_{1-3}$-alkyl, $C_{1-4}$-alkoxycarbonyl-$C_{1-3}$-alkyl, $C_{1-4}$-alkoxy-carbonylamino, $C_{1-4}$-alkoxy-carbonylamino-$C_{1-3}$-alkyl, amino, $C_{1-4}$-alkyl-amino, $C_{3-7}$-cycloalkyl-amino, N-($C_{3-7}$-cycloalkyl)-N-($C_{1-4}$-alkyl)-amino, di-($C_{1-4}$-alkyl)-amino, amino-$C_{1-3}$-alkyl, $C_{1-4}$-alkyl-amino-$C_{1-3}$-alkyl, $C_{3-7}$-cycloalkyl-amino-$C_{1-3}$-alkyl, N-($C_{3-7}$-cycloalkyl)-N-($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, $C_{1-4}$-alkyl-amino-carbonyl, $C_{3-7}$-cycloalkyl-amino-carbonyl, N-($C_{3-7}$-cycloalkyl)-N-($C_{1-4}$-alkyl)-amino-carbonyl, di-($C_{1-4}$-alkyl)-amino-carbonyl, pyridinyl-oxy, pyridinyl-amino, pyridinyl-$C_{1-3}$-alkyl-amino.

Most particularly preferred definitions of the substituent $R^{14}$ are $C_{1-4}$-alkyl, hydroxy, ω-hydroxy-$C_{1-3}$-alkyl, $C_{1-4}$-alkoxy, ω-($C_{1-4}$-alkoxy)-$C_{1-3}$-alkyl, amino-$C_{1-3}$-alkyl, $C_{1-4}$-alkyl-amino-$C_{1-3}$-alkyl, $C_{3-7}$-cycloalkyl-amino-$C_{1-3}$-alkyl, N-($C_{3-7}$-cycloalkyl)-N-($C_{1-4}$-alkyl)-amino-$C_{1-3}$-alkyl, di-($C_{1-4}$-alkyl)-amino-$C_{1-3}$-alkyl- and cyclo-$C_{3-6}$-alkyleneimino-$C_{1-3}$-alkyl.

Preferably X denotes a $C_{1-6}$-alkylene bridge wherein a —$CH_2$— group not adjacent to the N atom of the $R^1R^2N$ group may be replaced by —CH=CH— or —C≡C— and/or a —$CH_2$— group not adjacent to the N atom of the $R^1R^2N$ group may be replaced by —O—, —S—, —CO— or —$NR^4$—, particularly preferably by —O—, —S— or —$NR^4$—, in such a way that in each case two O, S or N atoms or an O and an S atom are not directly joined together, while $R^4$ and Y may be joined together forming a heterocyclic ring system, while the bridge X may be connected to $R^1$ including the N atom attached to $R^1$ and X, forming a heterocyclic group, while the bridge X may additionally also be connected to $R^2$ including the N atom attached to $R^2$ and X, forming a heterocyclic group, and two C atoms or a C and an N atom of the alkylene bridge may be joined together by an additional $C_{1-4}$-alkylene bridge, and a C atom may be substituted by $R^{10}$ and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system, particularly a cyclopropyl, cyclobutyl or cyclopentyl group.

Preferably in the group X a —$CH_2$— group immediately adjacent to the group $R^1R^2N—$ is not replaced by —O—, —S—, —(SO)—, —(SO_2)—, —CO— or —$NR^4$—.

If in the group X a —CH$_2$— group of the alkylene bridge is replaced according to the invention, this —CH$_2$— group is preferably not directly connected to a heteroatom, a double or triple bond.

Preferably the alkylene bridge X, X' or X" has no or not more than one imino group. The position of the imino group within the alkylene bridge X, X' or X" is preferably such that no aminal function is formed together with the amino group NR$^1$R$^2$ or another adjacent amino group or two N atoms are not adjacent to one another.

Preferably X denotes an unbranched C$_{1-4}$-alkylene bridge and if the group Y is linked to X via a C atom, it may also denote —CH$_2$—CH═CH—, —CH$_2$—C≡C—, C$_{2-4}$-alkylenoxy or C$_{2-4}$-alkylene-NR$^4$, while R$^4$ and Y may be joined together forming a heterocyclic ring system, while the bridge X may be connected to R$^1$ including the N atom attached to R$^1$ and X, forming a heterocyclic group, and in X a C atom may be substituted by R$^{10}$ and/or one or two C atoms in each case may be substituted by one or two identical or different substituents selected from C$_{1-6}$-alkyl, C$_{2-6}$-alkenyl, C$_{2-6}$-alkynyl, C$_{3-7}$-cycloalkyl, C$_{3-7}$-cycloalkyl-C$_{1-3}$-alkyl, C$_{4-7}$-cycloalkenyl and C$_{4-7}$-cycloalkenyl-C$_{1-3}$-alkyl-, while two alkyl and/or alkenyl substituents may be joined together, forming a carbocyclic ring system and in the above-mentioned groups and residues one or more C atoms may be mono- or polysubstituted by F and/or one or two C atoms independently of one another may be monosubstituted by Cl or Br and wherein R$^1$, R$^4$ and R$^{10}$ are defined as hereinbefore and hereinafter.

Particularly preferably, X denotes —CH$_2$—, —CH$_2$—CH$_2$—, —CH$_2$—CH$_2$—CH$_2$— or —CH$_2$—CH$_2$—NR$^4$—CO— and if the group Y is linked to X via a C atom, it also denotes —CH$_2$—CH═CH—, —CH$_2$—C≡C—, —CH$_2$—CH$_2$—O—, —CH$_2$—CH$_2$—CH$_2$—or —CH$_2$—CH$_2$—NR$^4$— or —CH$_2$—CH$_2$—CH$_2$—NR$^4$—, while R$^4$ and Y may be joined together, forming a heterocyclic ring system, while the bridge X may be connected to R' including the N atom attached to R$^1$ and X, forming a heterocyclic group, and in X a C atom may be substituted by R$^{10}$, preferably a hydroxy, ω-hydroxy-C$_{1-3}$-alkyl, ω-(C$_{1-4}$-alkoxy)-C$_{1-3}$-alkyl and/or C$_{1-4}$-alkoxy group, and/or one or two C atoms independently of one another may each be substituted by one or two identical or different C$_{1-4}$-alkyl groups, while two alkyl groups may be joined together, forming a carbocyclic ring system, and in each case one or more C atoms may be mono- or polysubstituted by F and/or in each case one or two C atoms may independently of one another be monosubstituted by Cl or Br.

Most particularly preferably, if the group Y is linked to X via a C atom, X denotes —CH$_2$—CH$_2$—O—, which may be substituted as specified hereinbefore.

If R$^4$ is linked to Y forming a heterocyclic ring system, Y preferably has the meaning phenyl and R$^4$ preferably has the meaning C$_{2-6}$-alkyl or C$_{2-6}$-alkenyl. Preferred heterocyclic ring systems are indole, dihydroindole, dihydroquinoline and tetrahydroquinoline.

The group R$^4$ preferably only represents vinyl if R$^4$ is attached to Y, forming a heterocyclic ring system.

The group X preferably has no carbonyl group.

Advantageously, the group X with the meaning C$_{2-4}$-alkyleneoxy, particularly —CH$_2$—CH$_2$—CH$_2$—O—, has no hydroxy substituents.

If a C atom is substituted in X, X' or X", the preferred substituents are selected from among the C$_{1-4}$-alkyl, C$_{2-4}$-alkenyl, C$_{2-4}$-alkynyl, C$_{3-7}$-cycloalkyl, C$_{3-7}$—cycloalkyl-C$_{1-3}$-alkyl, hydroxy, ω-hydroxy-C$_{1-3}$-alkyl, ω-(C$_{1-4}$-alkoxy)-C$_{1-3}$-alkyl- and C$_{1-4}$-alkoxy groups. Moreover, in X, X' or X", a C atom may be disubstituted and/or one or two C atoms may be mono- or disubstituted, while preferred substituents are selected from among C$_{1-4}$-alkyl, C$_{2-4}$-alkenyl, C$_{2-4}$-alkynyl, C$_{3-7}$-cycloalkyl and C$_{3-7}$-cycloalkyl-C$_{1-3}$- alkyl, and two C$_{1-4}$-alkyl and/or C$_{2-4}$-alkenyl substituents may also be joined together forming a saturated or monounsaturated carbocyclic ring.

Most particularly preferred substituents for one or two C atoms in X, X' or X" are selected from methyl, ethyl, n-propyl, i-propyl, cyclopropyl, cyclopropylmethyl, while two alkyl substituents on a C atom may also be joined together, forming a carbocyclic ring.

If Y denotes a fused bicyclic ring system, a preferred definition of the group X is —CH$_2$—, —CH$_2$—CH$_2$— and —CH$_2$—CH$_2$—CH$_2$—, particularly —CH$_2$— or -CH$_2$-CH$_2$—, which may be substituted as specified.

If in the group X, X' or X" one or more C atoms is or are substituted by a hydroxy and/or C$_{1-4}$-alkoxy group, the substituted C atom is preferably not directly adjacent to another heteroatom.

Preferably Z is a single bond, —CH$_2$— or —CH$_2$—CH$_2$—, while one or two C atoms independently of one another may be mono- or disubstituted by F, CH$_3$ or CF$_3$ and/or monosubstituted by Cl.

Particularly preferred definitions of the group Z are a single bond, —CH$_2$— or —CH$_2$—CH$_2$—, particularly a single bond.

According to a first embodiment the compounds according to the invention have a bridge W, which is selected from the group —CR$^{6a}$R$^{6b}$—O—, —CR$^{6a}$R$^{6b}$—NR$^8$—, —CR$^{7a}$R$^{7b}$—CR$^{7c}$R$^{7d}$— and —NR$^8$—, CR$^{6a}$R$^{6b}$—.

According to a second embodiment the compounds according to the invention have a bridge W, which denotes —CR$^{7a}$═CR$^{7c}$—.

W preferably denotes —CH$_2$—O, —CH$_2$—NR$^8$—, —CH$_2$—CH$_2$—or —CH═CH—, while in the last two meanings in each case one or two C atoms may be substituted independently of one another by F, Cl, CH$_3$ or CF$_3$. In the above definitions —CH$_2$—O— and —CH$_2$—NR$^8$— the group A is advantageously attached to the bridge W via a C atom.

Preferred definitions of the substituent R$^8$ are H and methyl.

Particularly preferred definitions of the group W are —CH$_2$—O—, —CH$_2$—NH—, —CH$_2$—NCH$_3$— and —CH$_2$—CH$_2$, particularly —CH$_2$—O—.

If the group W has the above meaning of an optionally substituted —CH═CH— bridge, the group Z is preferably a single bond.

Preferred embodiments of this invention therefore comprise compounds which may each be described by the following formulae Ia, Ib, Ic and Id:

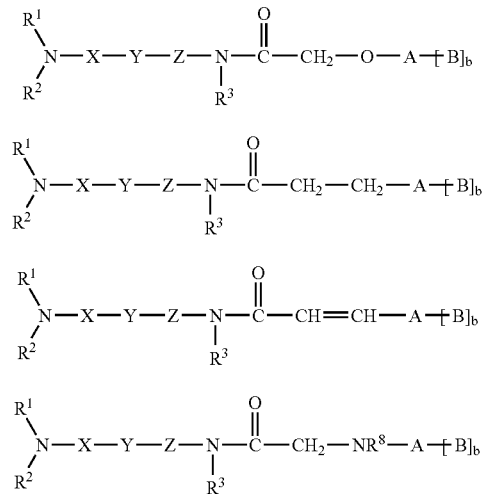

wherein $R^1$, $R^2$, X, Y, Z, $R^3$, $R^8$, A, B and b are defined as hereinbefore and hereinafter, particularly have the meanings given as being preferred, while $R^8$ preferably denotes H or methyl.

The group Y preferably has a meanings selected from among the bivalent cyclic groups phenyl, pyridinyl, naphthyl, tetrahydronaphthyl, indolyl, dihydroindolyl, quinolinyl, dihydroquinolinyl, tetrahydroquinolinyl, isoquinolinyl, dihydroisoquinolinyl or tetrahydro-isoquinolinyl, while the above-mentioned cyclic groups may be mono- or polysubstituted by $R^{20}$ at one or more C atoms and in the case of a phenyl group may also additionally be monosubstituted by nitro, and/or by $R^{21}$ at one or more N atoms. $R^1$ may be attached to Y and/or X may be attached to Y as specified hereinbefore.

particularly preferably, one definition of the group Y is selected from the following bivalent cyclic groups

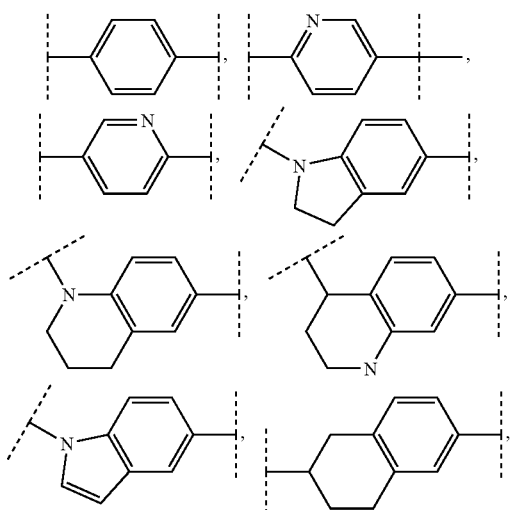

and particularly Y has one of the following definitions:

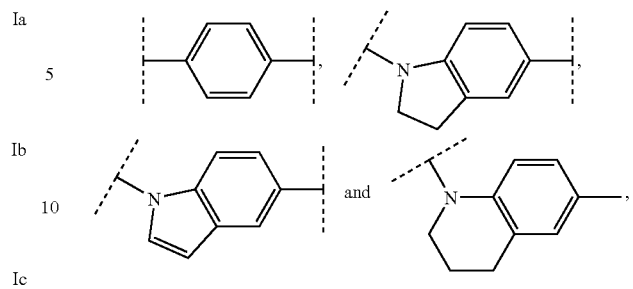

while the cyclic groups listed above may be mono- or polysubstituted by $R^{20}$ at one or more C atoms, and in the case of a phenyl group may also additionally be monosubstituted by nitro, and/or one or more NH groups may be substituted by $R^{21}$.

The group Y is preferably unsubstituted or mono- or disubstituted.

Particularly preferred substituents $R^{20}$ of the group Y are selected from among fluorine, chlorine, bromine, cyano, nitro, $C_{1-4}$-alkyl, $C_{2-6}$-alkenyl, hydroxy, $\omega$-hydroxy-$C_{1-3}$-alkyl, $C_{1-4}$-alkoxy, trifluoromethyl, trifluoromethoxy, $C_{2-4}$-alkynyl, $C_{1-4}$-alkoxycarbonyl, $\omega$-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, aminocarbonyl, $C_{1-4}$-alkyl-amino-carbonyl, di-($C_{1-4}$-alkyl)-amino-carbonyl, —CH=N—OH and —CH=N—O—$C_{1-4}$-alkyl.

Most particularly preferred substituents $R^{20}$ of the group Y are selected from among fluorine, chlorine, bromine, cyano, $C_{1-3}$-alkyl, $C_{1-3}$-alkoxy, trifluoromethyl, trifluoromethoxy, and, in the case of a phenyl ring, nitro as well.

If Y is a phenyl or pyridinyl group, the phenyl or pyridinyl group is at least monosubstituted, particularly if the group W denotes optionally substituted —CH=CH— or —CH$_2$—CH$_2$—.

Most particularly preferably, the group Y denotes substituted phenylene of the partial formula,

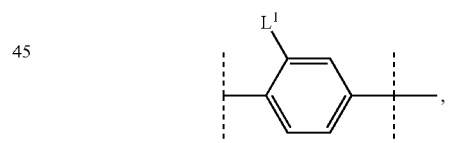

wherein $L^1$ has one of the meanings given hereinbefore for $R^{20}$, preferably F, Cl, Br, I, CH$_3$, CF$_3$, OCH$_3$, OCF$_3$, CN or NO$_2$, or denotes H.

The group Y preferably denotes monosubstituted phenylene according to the above partial formula, if the bridge W denotes —CH=CH—.

A preferred meaning of the group A is aryl or heteroaryl.

Preferably the group A is selected from among the cyclic groups phenyl, pyridinyl or naphthyl, which may be mono- or polysubstituted by $R^{20}$ at one or more C atoms, in the case of a phenyl ring may also additionally be monosubstituted by nitro.

If b has the value 0, the group A is preferably mono-, di or trisubstituted.

If b has the value 1, the group A is preferably unsubstituted or mono- or disubstituted.

Most particularly preferably, A is one of the following groups

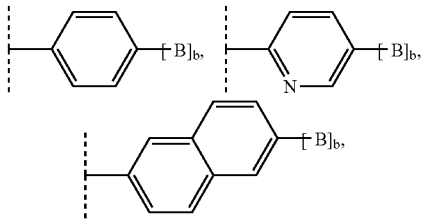

while the groups listed may be mono- or polysubstituted by $R^{20}$ as specified. The definitions phenyl and pyridyl given for the group A are preferred when b has the value 1.

Particularly preferred substituents $R^{20}$ for the group A are selected from among fluorine, chlorine, bromine, cyano, $C_{1-4}$-alkyl, $C_{2-6}$-alkenyl, —CHO, hydroxy, ω-hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, ω-($C_{1-4}$-alkoxy)-$C_{1-3}$- alkyl, $C_{1-4}$-alkoxy-carbonylamino, amino, $C_{1-4}$-alkyl-amino, di-($C_{1-4}$-alkyl)-amino, cyclo-$C_{3-6}$-alkyleneimino, aminocarbonyl, $C_{1-4}$-alkyl-amino-carbonyl, di-($C_{1-4}$-alkyl)-amino-carbonyl, —CH=N—OH and —CH=N—O—$C_{1-4}$- alkyl.

Most particularly preferred substituents $R^{20}$ for the group A are selected from among fluorine, chlorine, bromine, cyano, $C_{1-4}$-alkyl, $C_{1-4}$-alkoxy, trifluoromethyl, trifluoromethoxy, carboxy, $C_{1-4}$-alkoxycarbonyl, $C_{1-4}$-alkyl-amino, di-($C_{1-4}$-alkyl)-amino, If b has the value 0, a particularly preferred meaning of the group A is substituted phenyl of the partial formula

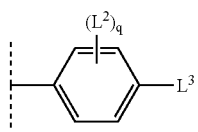

wherein $L^2$ has one of the meanings given for $R^{20}$ or denotes H, preferably F, Cl, Br, I, $CH_3$, $CF_3$, $OCH_3$, $OCF_3$, CN or $NO_2$, $L^3$ has one of the meanings given for $R^{20}$ or denotes H, preferably F, Cl, Br, I, $CF_3$, $OCF_3$, CN, $NO_2$, $C_{1-4}$-alkyl, $C_{3-7}$-cycloalkyl, $C_{3-7}$-cycloalkyl-$C_{1-3}$-alkyl, $C_{1-4}$-alkoxy, $C_{3-7}$-cycloalkyl-O, $C_{3-7}$-cycloalkyl-$C_{1-3}$-alkoxy, —COO— $C_{1-4}$-alkyl or —COOH, q has the value 0, 1 or 2, with the proviso that the phenyl and naphthyl group may be at most only monosubstituted by nitro.

Particularly preferably, A is substituted phenyl according to the above partial formula in which q denotes 1 or 2 and/or at least one substituent $L^2$ is in the meta position to the substituent $L^3$.

The group A preferably denotes substituted phenyl according to the above partial formula, while q has the value 1 or 2 if the bridge W represents —CH=CH, the group Y denotes phenyl and b has the value 0.

Another preferred partial formula for A, particularly if b has the value 0, is

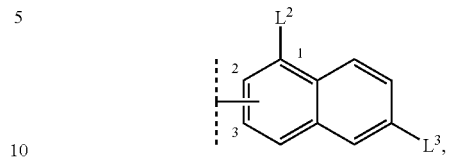

wherein the bond to the group W is made via the C atom with position number 2 or 3.

If b has the value 1, a preferred meaning for the group B is aryl or heteroaryl, which may be substituted as specified.

Preferred definitions of the group B are selected from among phenyl, pyridyl, thienyl and furanyl. Particularly preferably, the group B denotes phenyl. The group B with the meanings given above may be mono- or polysubstituted by $R^{20}$, and a phenyl group may additionally also be monosubstituted by nitro. Preferably the group B is mono-, di- or trisubstituted, particularly mono- or disubstituted. In the event of a monosubstitution the substituent is preferably in the para position to the group A.

Particularly preferred substituents $R^{20}$ for the group B are selected from among fluorine, chlorine, bromine, cyano, nitro, $C_{1-4}$-alkyl, hydroxy, ω-hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxy-carbonyl, ω-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, cyclo-$C_{3-6}$-alkyleneimino, aminocarbonyl, $C_{1-4}$-alkyl-amino-carbonyl- and di-($C_{1-4}$-alkyl )-amino-carbonyl.

Most particularly preferred substituents $R^{20}$ for the group B are selected from among fluorine, chlorine, bromine, cyano, $CF_3$, $C_{1-3}$-alkyl, $C_{1-4}$-alkoxy and trifluoromethoxy.

The group B preferably denotes an at least monosubstituted phenyl ring, if the bridge W denotes —CH=CH—, the group Y denotes phenyl and b has the value 1.

$R^4$ has one of the meanings given for $R^{17}$, preferably one of the meanings given for $R^{16}$.

Particularly preferred meanings of the substituent $R^4$ are H, $C_{1-6}$-alkyl and $C_{3-6}$-alkenyl. If $R^4$ is attached to Y, forming a heterocyclic ring system, particularly preferred meanings for $R^4$ are $C_{2-6}$-alkyl and $C_{2-6}$-alkenyl.

The groups $R^{6a}$, $R^{6b}$ represent H, $C_{1-4}$-alkyl or $CF_3$, preferably H or methyl, particularly H.

The groups $R^{7a}$, $R^{7b}$, $R^{7c}$, $R^{7d}$ represent H, F, $C_{1-4}$-alkyl or $CF_3$, preferably H or methyl, particularly H.

The group $R^8$ preferably denotes H or methyl.

If $R^{11}$ is a $C_{2-6}$-alkenyl or $C_{2-6}$-alkynyl group, the definitions —CH=$CH_2$, —CH=CH($CH_3$), —CH=C($CH_3$)$_2$ and —C≡CH, —C≡C—$CH_3$ are preferred.

The substituent $R^{20}$ preferably has none of the following structural elements:

a) —CO-aryl or —CO-heteroaryl, particularly —CO-phenyl, wherein heteroaryl, aryl and phenyl may be substituted, b) —C(=NH)—NH—, wherein the H atoms may be substituted and/or c) —NH—CO—NH—, wherein the H atoms may be substituted.

Preferred definitions of the group $R^{20}$ are halogen, hydroxy, cyano, $C_{1-4}$-alkyl, $C_{3-7}$-cycloalkyl and $C_{1-4}$-alkoxy. Particularly preferably $R^{20}$ denotes F, Cl, Br, I, OH, cyano, methyl, difluoromethyl, trifluoromethyl, ethyl, n-propyl, iso-propyl, methoxy, difluoromethoxy, trifluoromethoxy, ethoxy, n-propoxy or iso-propoxy.

Preferred definitions of the group $R^{21}$ are $C_{1-4}$-alkyl, $C_{1-4}$-alkylcarbonyl, $C_{1-4}$-alkylsulphonyl, $-SO_2-NH_2$, $-SO_2-NH-C_{1-3}$-alkyl, $-SO_2-N(C_{1-3}\text{-alkyl})_2$ and cyclo-$C_{3-6}$-alkleneimino-sulphonyl.

Cy preferably denotes a $C_{3-7}$-cycloalkyl, particularly a $C_{5-7}$-cycloalkyl group, a $C_{5-7}$-cycloalkenyl group, pyrrolidinyl, piperidinyl, piperazinyl, morpholinyl, thiomorpholinyl, aryl or heteroaryl, while aryl or heteroaryl preferably denotes a monocyclic or fused bicyclic ring system, and the above-mentioned cyclic groups may be mono- or polysubstituted by $R^{20}$ at one or more C atoms, and in the case of a phenyl group may also additionally be monosubstituted by nitro, and/or one or more NH groups may be substituted by $R^{21}$.

Preferred compounds according to the invention are those wherein one or more of the groups, residues, substituents and/or indices have one of the meanings given as being preferred.

Particularly preferred compounds according to the invention are those wherein

Y denotes phenyl, 1H-indolyl, 2,3-dihydro-1H-indolyl or 1,2,3,4-tetrahydroquinoline according to the definition described above as being preferred, particularly with phenyl substituted by $L^1$ according to the partial formula given hereinbefore and/or A denotes phenyl substituted by $L^2$ and $L^3$ according to the partial formula given hereinbefore.

Most particularly preferred compounds according to the invention are those wherein A, X, Y, Z, $R^1$, $R^2$, $R^3$ and W independently of one another have one or more of the above-mentioned preferred meanings.

Preferred groups of compounds according to this invention can be described by the following formulae Ia.1
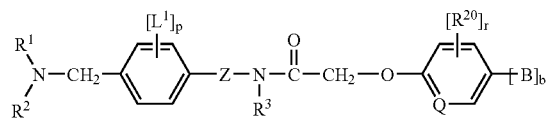

Ia.2
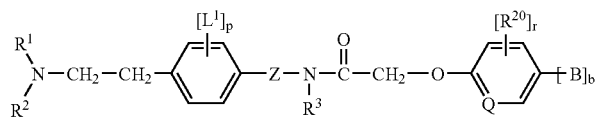

Ia.3
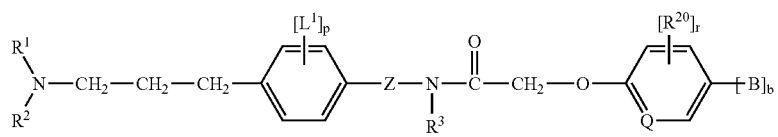

Ia.4
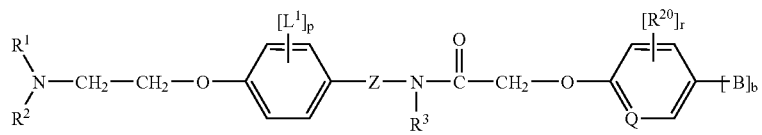

Ia.5
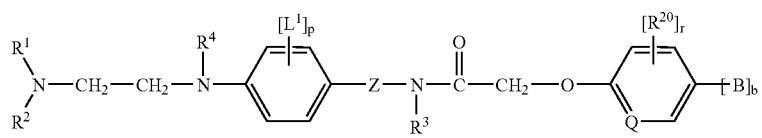

Ia.6
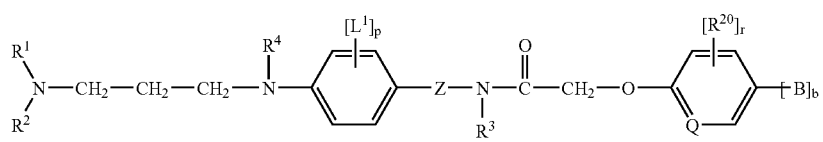

Ia.7
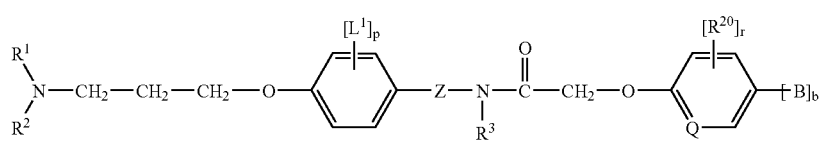

Ia.8
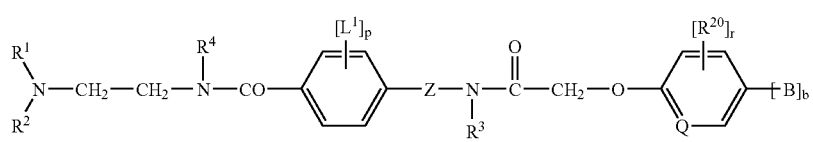

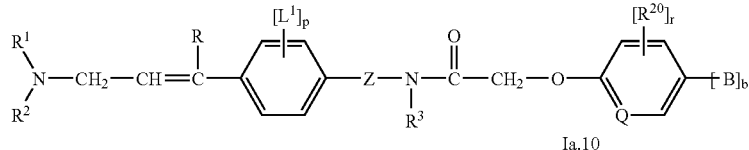

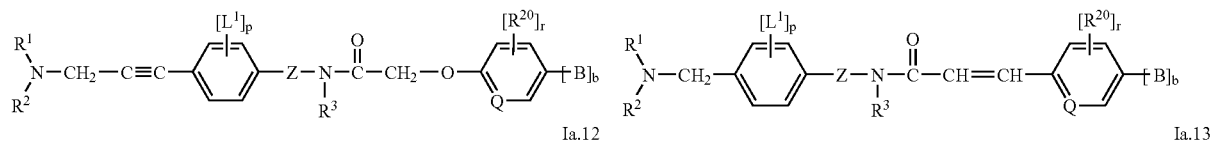

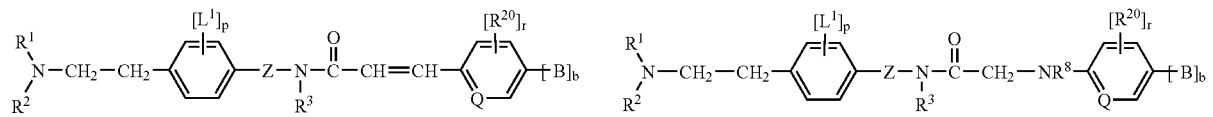

wherein $R^1$, $R^2$, Z, $R^3$, $R^4$, $R^8$, $R^{20}$, B and b have the meanings given hereinbefore and Z preferably denotes a single bond or —$CH_2$—$CH_2$—,
$R^3$ preferably denotes H or methyl,
$R^4$ preferably denotes H, $C_{1-6}$-alkyl or $C_{2-6}$-alkenyl, while $R^4$ may be attached to Y forming a heterocyclic ring system, particularly preferably forming an indole, dihydroindole, dihydroquinoline or tetrahydroquinoline group,
Q denotes CH or N, while CH may be substituted by $R^{20}$,
B preferably denotes aryl or heteroaryl, particularly preferably denotes phenyl, pyridyl, furanyl or thienyl, while B may be mono- or polysubstituted by $R^{20}$,
$L^1$ preferably denotes fluorine, chlorine, bromine, cyano, nitro, $C_{1-3}$-alkyl, $C_{1-3}$-alkoxy, trifluoromethyl, trifluoromethoxy or nitro,
p has the value 0 or 1,
$R^{20}$ preferably denotes fluorine, chlorine, bromine, cyano, $C_{1-4}$-alkyl, $C_{2-6}$-alkenyl, —CHO, hydroxy, ω-hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, ω-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, cyclo-$C_{3-6}$-alkyleneimino, aminocarbonyl, $C_{1-4}$-alkyl-aminocarbonyl, di-($C_{1-4}$-alkyl)-amino-carbonyl, —CH=N'OH and —CH=N—O— $C_{1-4}$-alkyl,
r has the value 1, 2 or 3 and, if b has the value 1, r may also denote 0 and the compounds according to provisos (M1), (M2) and (M3) are not included.

The following individual compounds are particularly preferred:

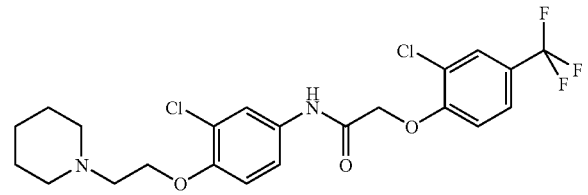

N-[3-chloro-4-(2-piperidin-1-yl-ethoxy)-phenyl]-2-(2-chloro-4-trifluoromethyl-phenoxy)-acetamide

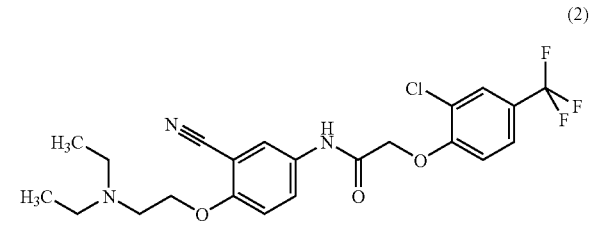

2-(2-chloro-4-trifluoromethyl-phenoxy)-N-[3-cyano-4-(2-diethylamino-ethoxy)-phenyl]-acetamide

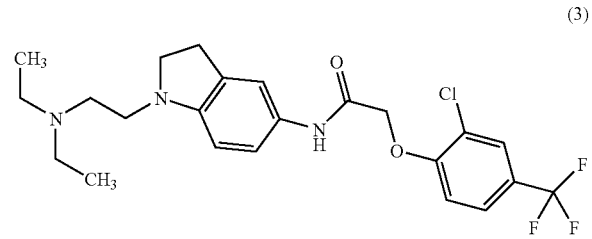

2-(2-chloro-4-trifluoromethyl-phenoxy)-N-[1-(2-diethylamino-ethyl)-2,3-dihydro-1H-indol-5-yl]-acetamide

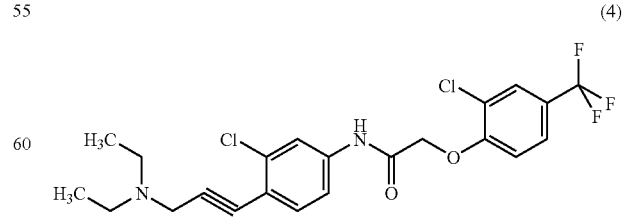

N-[3-chloro-4-(3-diethylamino-prop-1-ynyl)-phenyl]-2-(2-chloro-4-trifluoromethyl-phenoxy)-acetamide

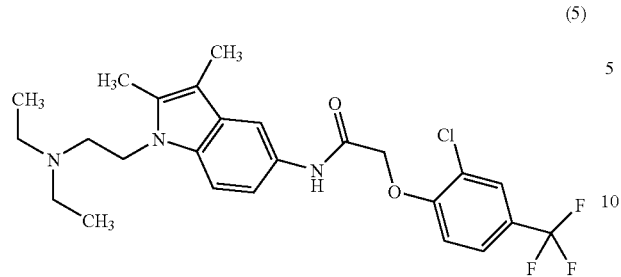

(5)

2-(2-chloro-4-trifluoromethyl-phenoxy)-N-[1-(2-diethylamino-ethyl)-2,3-dimethyl-1H-indol-5-yl]-acetamide

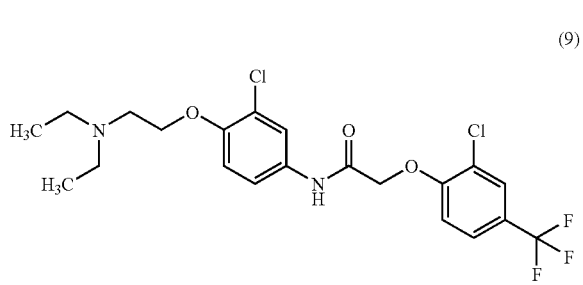

(9)

N-[3-chloro-4-(2-diethylamino-ethoxy)-phenyl]-2-(2-chloro-4-trifluoromethyl-phenoxy)-acetamide

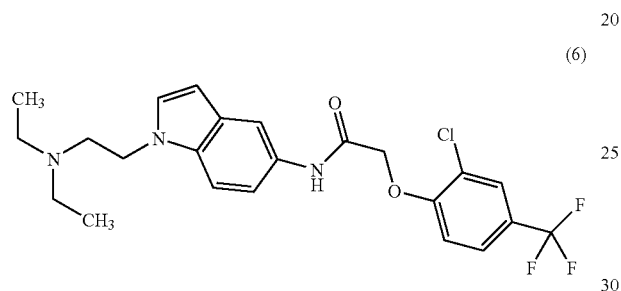

(6)

2-(2-chloro-4-trifluoromethyl-phenoxy)-N-[1-(2-diethylamino-ethyl)-1H-indol-5-yl]-acetamide

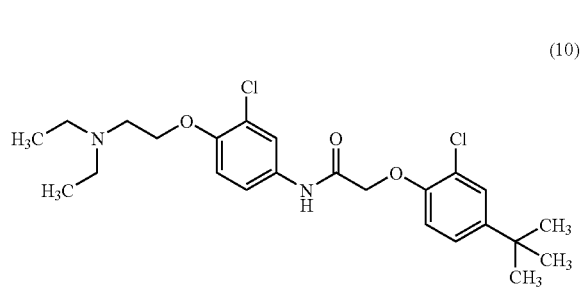

(10)

2-(4-tert.-butyl-2-chloro-phenoxy)-N-[3-chloro-4-(2-diethylamino-ethoxy)-phenyl]-acetamide

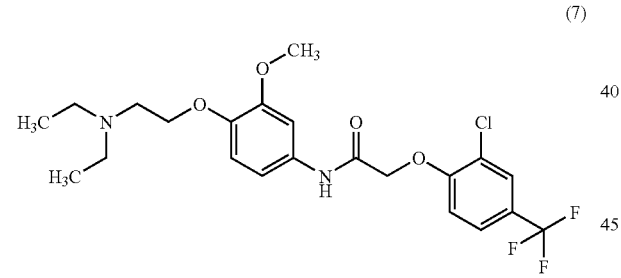

(7)

2-(2-chloro-4-trifluoromethyl-phenoxy)-N-[4-(2-diethylamino-ethoxy)-3-methoxy-phenyl]-acetamide

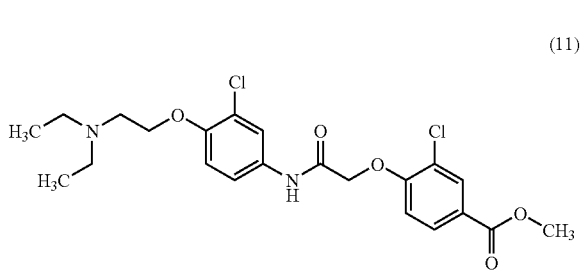

(11)

methyl 3-chloro-4-{[3-chloro-4-(2-diethylamino-ethoxy)-phenylcarbamoyl]-methoxy}-benzoate

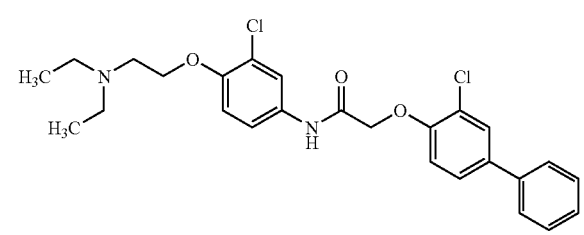

(8)

2-(3-chloro-biphenyl-4-yloxy)-N-[3-chloro-4-(2-diethylamino-ethoxy)-phenyl]-acetamide

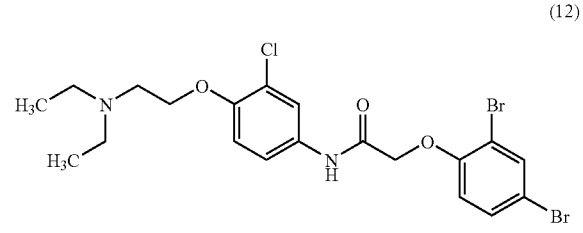

(12)

N-[3-chloro-4-(2-diethylamino-ethoxy)-phenyl]-2-(2,4-dibromo-phenoxy)-acetamide

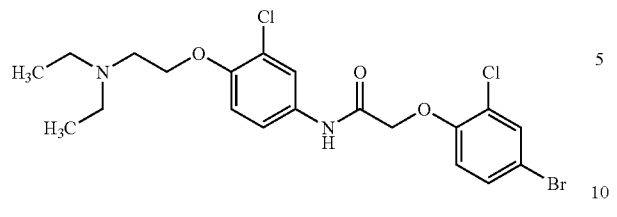

2-(4-bromo-2-chloro-phenoxy)-N-[3-chloro-4-(2-diethylamino-ethoxy)-phenyl]-acetamide (13)

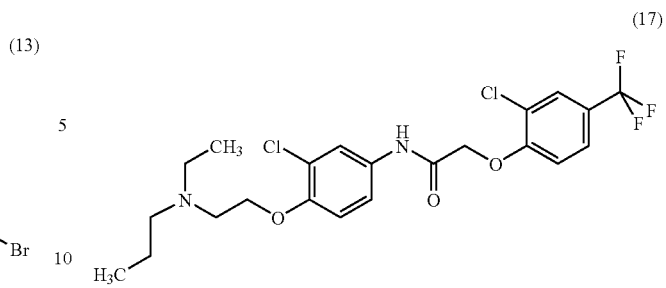

N-{3-chloro-4-[2-(ethyl-propyl-amino)-ethoxy]-phenyl}-2-(2-chloro-4-trifluoromethyl-phenoxy)-acetamide (17)

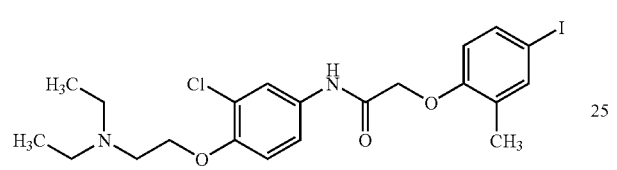

N-[3-chloro-4-(2-diethylamino-ethoxy)-phenyl]-2-(4-iodo-2-methyl-phenoxy)-acetamide (14)

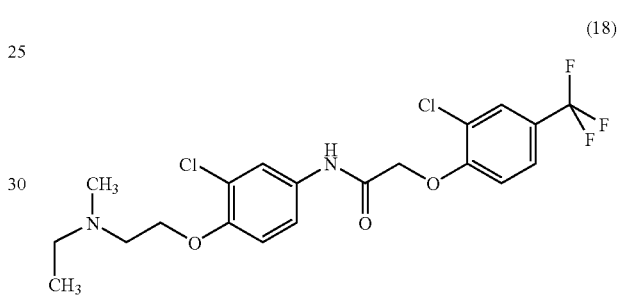

N-{3-chloro-4-[2-(ethyl-methyl-amino)-ethoxy]-phenyl}-2-(2-chloro-4-trifluoromethyl-phenoxy)-acetamide (18)

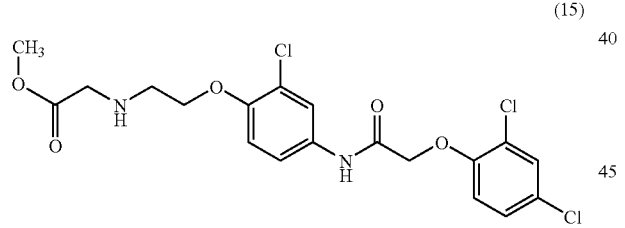

methyl (2-{2-chloro-4-[2-(2,4-dichloro-phenoxy)-acetylamino]-phenoxy}-ethylamino)-acetate (15)

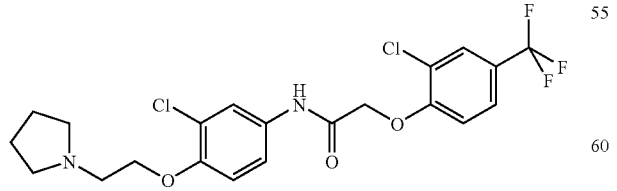

N-[3-chloro-4-(2-pyrrolidin-1-yl-ethoxy)-phenyl]-2-(2-chloro-4-trifluoromethyl-phenoxy)-acetamide (16)

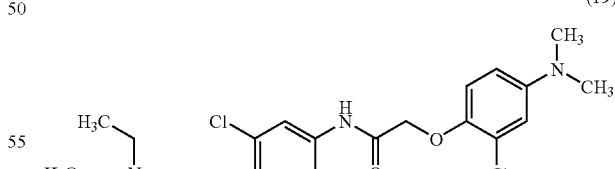

N-[3-chloro-4-(2-diethylamino-ethoxy)-phenyl]-2-(2-chloro-4-dimethylamino-phenoxy)-acetamide (19)

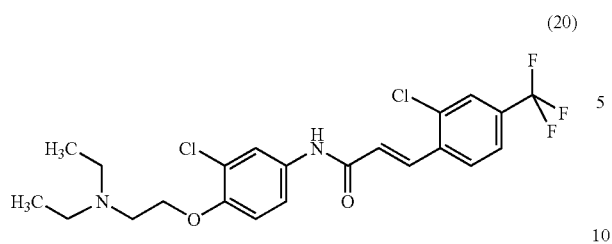

(E)-N-[3-chloro-4-(2-diethylamino-ethoxy)-phenyl]-
3-(2-chloro-4-trifluoromethyl-phenyl)-acrylamide

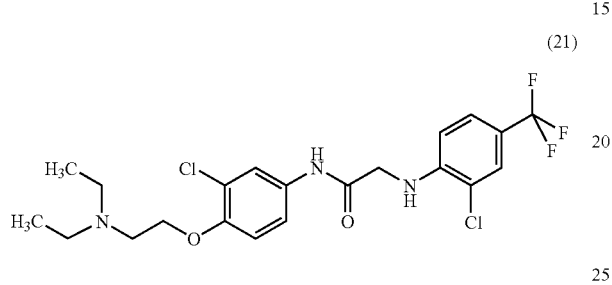

N-[3-chloro-4-(2-diethylamino-ethoxy)-phenyl]-2-
(2-chloro-4-trifluoromethyl-phenylamino)-acetamide

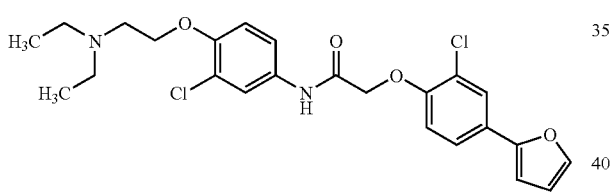

N-[3-chloro-4-(2-diethylamino-ethoxy)-phenyl]-2-
(2-chloro-4-furan-2-yl-phenoxy)-acetamide

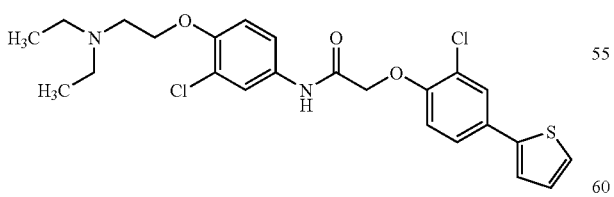

N-[3-chloro-4-(2-diethylamino-ethoxy)-phenyl]-2-
(2-chloro-4-thiophen-2-yl-phenoxy)-acetamide

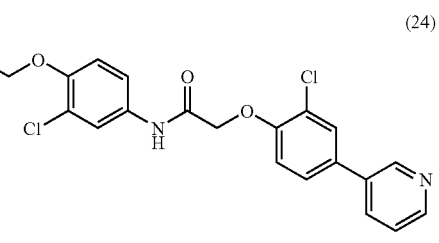

N-[3-chloro-4-(2-diethylamino-ethoxy)-phenyl]-2-
(2-chloro-4-pyridin-3-yl-phenoxy)-acetamide 2-(2-bromo-4-trifluoromethyl-phenoxy)-N-[3-
chloro-4-(2-diethylamino-ethoxy)-phenyl]-acetamide

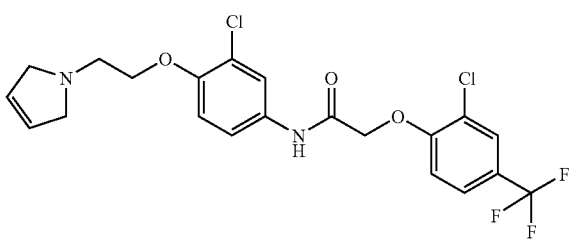

N-{3-chloro-4-[2-(2,5-dihydro-pyrrol-1-yl)-ethoxy]-
phenyl}-2-(2-chloro-4-trifluoromethyl-phenoxy)-
acetamide

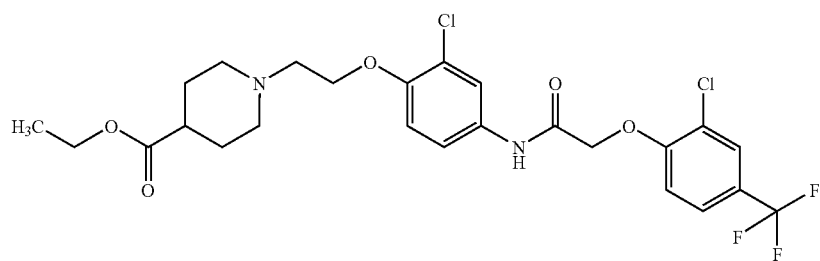

ethyl 1-(2-{2-chloro-4-[2-(2-chloro-4-trifluoromethyl-phenoxy)-acetylamino]-phenoxy}-ethyl)-piperidine-4-carboxylate (27)

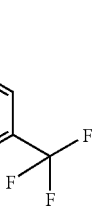

N-[3-chloro-4-(3-diethylamino-propoxy)-phenyl]-2-(2-chloro-4-trifluoromethyl-phenoxy)-acetamide (28)

N-[3-bromo-4-(2-diethylamino-ethoxy)-phenyl]-2-(2-chloro-4-trifluoromethyl-phenoxy)-acetamide (31)

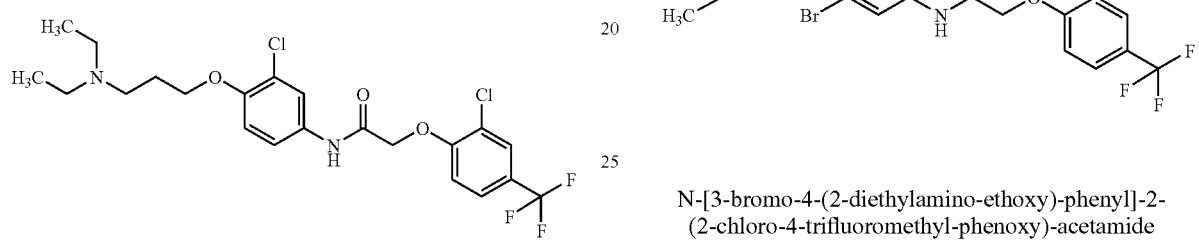

N-{4-[2-(2-aminomethyl-pyrrolidin-1-yl)-ethoxy]-3-chloro-phenyl}-2-(2-chloro-4-trifluoromethyl-phenoxy)-acetamide (29)

N-{3-chloro-4-[2-(4-methoxy-piperidin-1-yl)-ethoxy]-phenyl}-2-(2-chloro-4-trifluoromethyl-phenoxy)-acetamide (32)

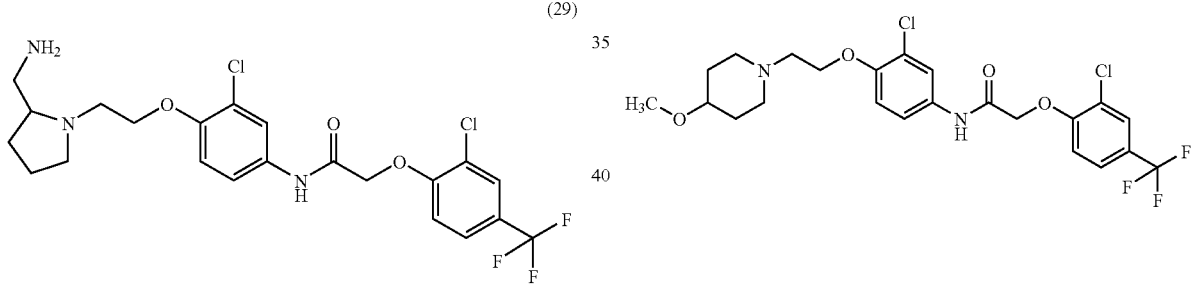

N-{3-chloro-4-[2-(2-dimethylaminomethyl-pyrrolidin-1-yl)-ethoxy]-phenyl}-2-(2-chloro-4-trifluoromethyl-phenoxy)-acetamide (30)

N-{3-chloro-4-[2-(4-hydroxy-piperidin-1-yl)-ethoxy]-phenyl}-2-(2-chloro-4-trifluoromethyl-phenoxy)-acetamide (33)

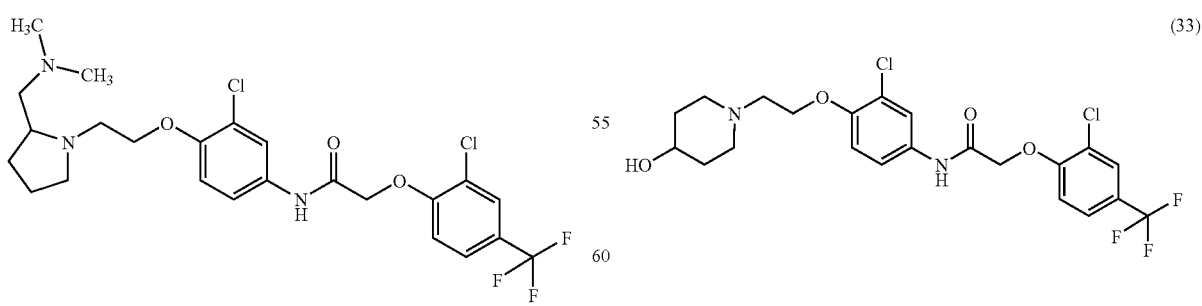

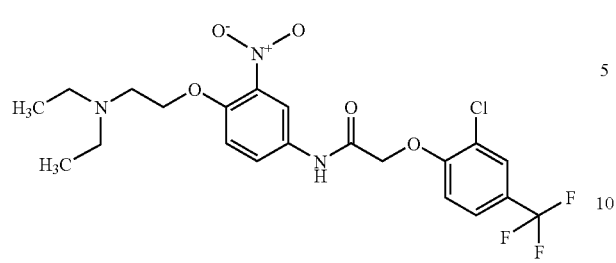

2-(2-chloro-4-trifluoromethyl-phenoxy)-N-[4-(2-diethylamino-ethoxy)-3-nitro-phenyl]-acetamide
(34)

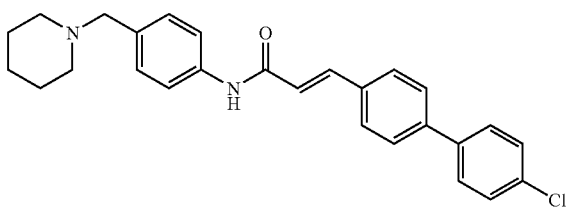

(E)-3-(4'-chloro-biphenyl-4-yl)-N-(4-piperidin-1-ylmethyl-phenyl)-acrylamide
(38)

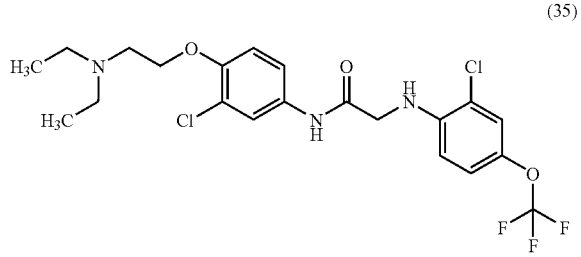

N-[3-chloro-4-(2-diethylamino-ethoxy)-phenyl]-2-(2-chloro-4-trifluoromethoxy-phenylamino)-acetamide
(35)

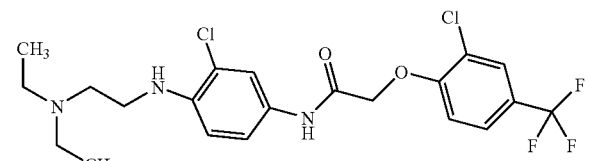

N-[3-chloro-4-(2-diethylamino-ethylamino)-phenyl]-2-(2-chloro-4-trifluoromethyl-phenoxy)-acetamide
(39)

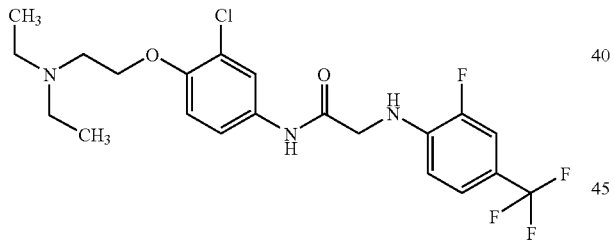

N-[3-chloro-4-(2-diethylamino-ethoxy)-phenyl]-2-(2-fluoro-4-trifluoromethyl-phenylamino)-acetamide
(36)

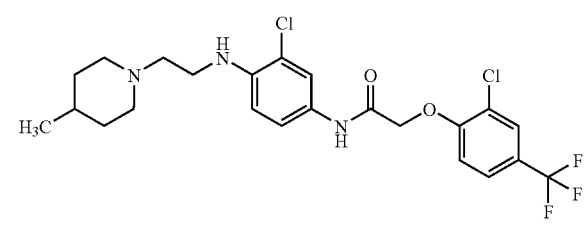

N-{3-chloro-4-[2-(4-methyl-piperidin-1-yl)-ethylamino]-phenyl}-2-(2-chloro-4-trifluoromethyl-phenoxy)-acetamide
(40)

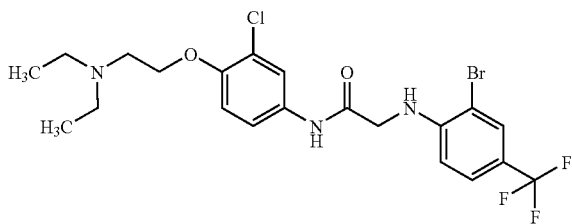

2-(2-bromo-4-trifluoromethyl-phenylamino)-N-[3-chloro-4-(2-diethylamino-ethoxy)-phenyl]-acetamide
(37)

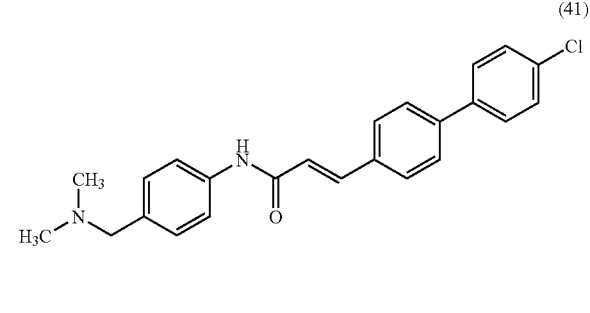

(E)-3-(4'-chloro-biphenyl-4-yl)-N-(4-dimethylaminomethyl-phenyl)-acrylamide
(41)

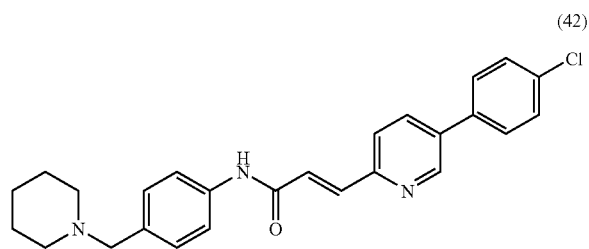

(E)-3-[5-(4-chloro-phenyl)-pyridin-2-yl]-N-(4-piperidin-1-ylmethyl-phenyl)-acrylamide

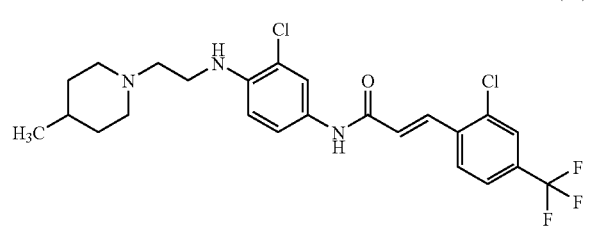

(E)-N-{3-chloro-4-[2-(4-methyl-piperidin-1-yl)-ethylamino]-phenyl}-3-(2-chloro-4-trifluoromethyl-phenyl)-acrylamide

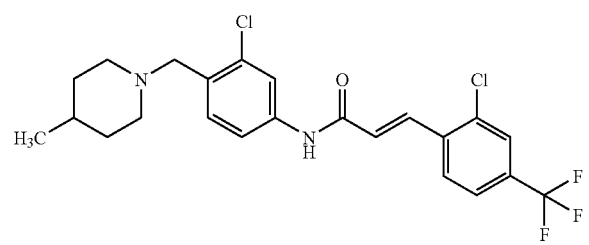

(E)-N-[3-chloro-4-(4-methyl-piperidin-1-ylmethyl)-phenyl]-3-(2-chloro-4-trifluoromethyl-phenyl)-acrylamide

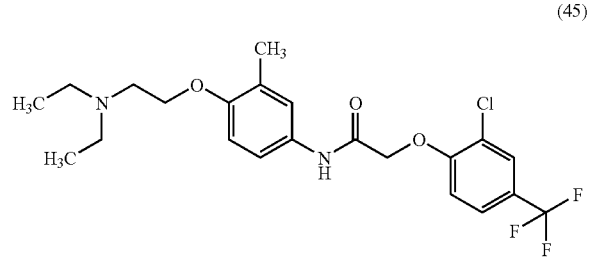

2-(2-chloro-4-trifluoromethyl-phenoxy)-N-[4-(2-diethylamino-ethoxy)-3-methyl-phenyl]-acetamide

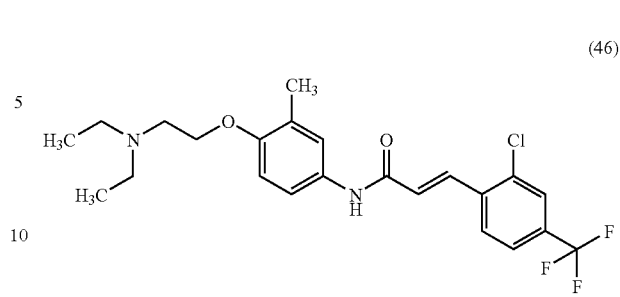

(E)-3-(2-chloro-4-trifluoromethyl-phenyl)-N-[4-(2-diethylamino-ethoxy)-3-methyl-phenyl]-acrylamide

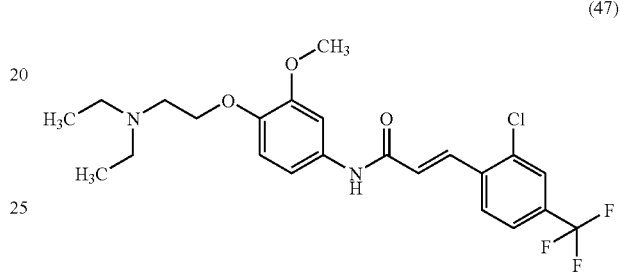

(E)-3-(2-chloro-4-trifluoromethyl-phenyl)-N-[4-(2-diethylamino-ethoxy)-3-methoxy-phenyl]-acrylamide

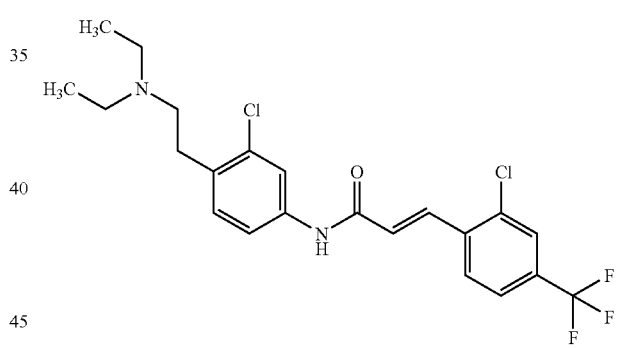

(E)-N-[3-chloro-4-(2-diethylamino-ethyl)-phenyl]-3-(2-chloro-4-trifluoromethyl-phenyl)-acrylamide

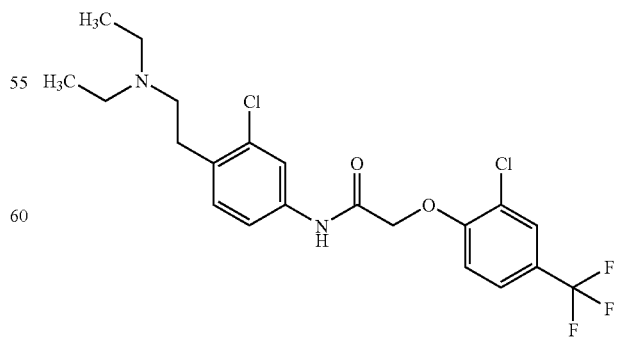

N-[3-chloro-4-(2-diethylamino-ethyl)-phenyl]-2-(2-chloro-4-trifluoromethyl-phenoxy)-acetamide

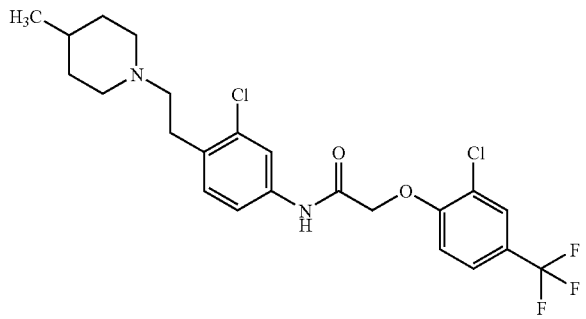

(50)

N-{3-chloro-4-[2-(4-methyl-piperidin-1-yl)-ethyl]-phenyl}-2-(2-chloro-4-trifluoromethyl-phenoxy)-acetamide including the salts thereof.

Some expressions used hereinbefore and below to describe the compounds according to the invention will now be defined more fully.

The term halogen denotes an atom selected from among F, Cl, Br and I, particularly F, Cl and Br.

The term $C_{1-n}$-alkyl, where n has a value of 3 to 8, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{1-n}$-alkylene, where n may have a value of 1 to 8, denotes a saturated, branched or unbranched hydrocarbon bridge with 1 to n C atoms. Examples of such groups include methylene (—$CH_2$—), ethylene (—$CH_2$—$CH_2$—), 1-methyl-ethylene (—CH($CH_3$)—$CH_2$—), 1,1-dimethyl-ethylene (—C($CH_3$)$_2$—$CH_2$—), n-prop-1,3-ylene (—$CH_2$—$CH_2$—$CH_2$—), 1-methylprop-1,3-ylene (—CH($CH_3$)—$CH_2$—$CH_2$—), 2-methylprop-1,3-ylene (—$CH_2$—CH($CH_3$)—$CH_2$—), etc., as well as the corresponding mirror-symmetrical forms.

The term $C_{2-n}$-alkenyl, where n has a value of 3 to 6, denotes a branched or unbranched hydrocarbon group with 2 to n C atoms and at least one C═C-double bond. Examples of such groups include vinyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, where n has a value of 3 to 6, denotes a branched or unbranched hydrocarbon group with 2 to n C atoms and a C≡C triple bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl etc.

The term $C_{1-n}$-alkoxy denotes a $C_{1-n}$-alkyl-O—group, wherein $C_{1-n}$-alkyl is defined as above. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylthio denotes a $C_{1-n}$-alkyl-S— group, wherein $C_{1-n}$-alkyl is defined as above. Examples of such groups include methylthio, ethylthio, n-propylthio, iso-propylthio, n-butylthio, iso-butylthio, sec-butylthio, tert-butylthio, n-pentylthio, iso-pentylthio, neo-pentylthio, tert-pentylthio, n-hexylthio, iso-hexylthio, etc.

The term $C_{1-n}$-alkylcarbonyl denotes a $C_{1-n}$-alkyl-C(═O)— group, wherein $C_{1-n}$-alkyl is defined as above. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

The term $C_{5-n}$-cycloalkenyl denotes a monounsaturated mono-, bi-, tri- or spirocarbocyclic group with 5 to n C atoms. Examples of such groups include cyclopentenyl, cyclohexenyl, cycloheptenyl, cyclooctenyl, cyclononenyl, etc.

The term $C_{3-n}$-cycloalkylcarbonyl denotes a $C_{3-n}$-cycloalkyl-C(═O) group, wherein $C_{3-n}$-cycloalkyl is defined as above.

The term aryl denotes a carbocyclic, aromatic ring system, such as for example phenyl, biphenyl, naphthyl, anthracenyl, phenanthrenyl, fluorenyl, indenyl, pentalenyl, azulenyl, biphenylenyl, etc. A particularly preferred meaning of "aryl" is phenyl.

The term cyclo-$C_{3-7}$-alkyleneimino denotes a 4- to 7-membered ring which has 3 to 7 methylene units as well as an imino group, the bond to the rest of the molecule being made via the imino group.

The term cyclo-$C_{3-7}$-alkyleneimino-carbonyl denotes a cyclo-$C_{3-7}$-alkyleneimino ring as defined hereinbefore which is linked to a carbonyl group via the imino group.

The term heteroaryl used in this application denotes a heterocyclic, aromatic ring system which comprises in addition to at least one C atom one or more heteroatoms selected from N, O and/or S. Examples of such groups are furanyl, thiophenyl, pyrrolyl, oxazolyl, thiazolyl, imidazolyl, isoxazolyl, isothiazolyl, 1,2,3-triazolyl, 1,3,5-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl,1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinozilinyl, quinolinyl, isoquinolinyl, quinoxalinyl, naphthyridinyl, pteridinyl, carbazolyl, azepinyl, diazepinyl, acridinyl, etc. The term heteroaryl also comprises the partially hydrogenated heterocyclic, aromatic ring systems, particularly those listed above. Examples of such partially hydrogenated heterocycles are 2,3-dihydrobenzofuranyl, pyrolinyl, pyrazolinyl, indolinyl, oxazolidinyl, oxazolinyl, oxazepinyl, etc. Particularly preferably, heteroaryl denotes a heteroaromatic mono- or bicyclic ring system.

Terms such as aryl-$C_{1-n}$-alkyl, heteroaryl-$C_{1-n}$-alkyl, etc. refer to $C_{1-n}$-alkyl, as defined above, which is substituted with an aryl or heteroaryl group.

Many of the terms given above may be used repeatedly in the definition of a formula or group and in each case have one of the meanings given above, independently of one another.

The term "unsaturated", e.g. in "unsaturated carbocyclic group" or "unsaturated heterocyclic group", as used particularly in the definition of the group Cy, comprises, in addition to the mono- or polyunsaturated groups, the corresponding totally unsaturated groups, but particularly the mono- and diunsaturated groups.

The term "optionally substituted" used in this application indicates that the group thus designated is either unsubstituted or mono- or polysubstituted by the substituents specified. If the group in question is polysubstituted, the substituents may be identical or different.

The H atom of any carboxy group present or an H atom (imino or amino group) bonded to an N atom may in each case be replaced by a group which can be cleaved in vivo. By a group which can be cleaved in vivo from an N atom is meant for example a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_e$CO—O—($R_fCR_g$)—O—CO group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom, a $C_{1-3}$-alkyl or $R_e$CO—O—($R_fCR_g$)—O group wherein $R_e$ to $R_g$ are as hereinbefore defined, while additionally the phthalimido group is a possibility for an amino group, and the above-mentioned ester groups may also be used as groups which can be converted into a carboxy group in vivo.

The residues and substituents described above may be mono- or polysubstituted by fluorine as described. Preferred fluorinated alkyl groups are fluoromethyl, difluoromethyl and trifluoromethyl. Preferred fluorinated alkoxy groups are fluoromethoxy, difluoromethoxy and trifluoromethoxy. Preferred fluorinated alkylsulphinyl and alkylsulphonyl groups are trifluoromethylsulphinyl and trifluoromethylsulphonyl.

The compounds of general formula I according to the invention may have acid groups, predominantly carboxyl groups, and/or basic groups such as e.g. amino functions. Compounds of general formula I may therefore be present as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alkaline earth metal hydroxides or carbonates, zinc or ammonium hydroxides or organic amines such as e.g. diethylamine, triethylamine, triethanolamine inter alia.

The compounds according to the invention may be obtained using methods of synthesis which are known in principle. Preferably the compounds are obtained analogously to the methods of preparation described more fully hereinafter, which are also a subject of this invention. Abbreviations used hereinafter are defined in the introduction to the experimental section or are familiar to those skilled in the art. The term alkyl used in reaction plans A, B and C denotes $C_{1-4}$-alkyl, unless otherwise stated.

If the starting materials or intermediate products listed below contain groups $R^1$, $R^2$, $R^3$, X, Y, Z, A or B with amine functions, these are preferably used in protected form, for example with a Boc, Fmoc or Cbz protective group, and liberated at the end of the reactions by standard methods.

According to general reaction plan A an alkyl haloacetate (A-1), preferably optionally substituted ethyl bromoacetate, is reacted with a hydroxy compound (A-2), for example a phenol, in a molar ratio of 1:1 to 2:1 in a suitable solvent in the presence of a suitable base. Suitable bases are particularly tertiary amines such as triethylamine or Hünig base as well as alkali metal carbonates, for example potassium carbonate. The reactions are carried out in a suitable solvent, while DMF is preferably used.

The reaction takes place in a period of from 4 to 24 hours in a temperature range from RT to 120° C., preferably from 60° C. to 100° C.

The alkyl aryloxy-acetates (A-3) thus obtained, after being purified, are hydrolysed to form the corresponding aryloxy-acetic acids (A-4). The reaction is preferably carried out in ethanol-water mixtures in the presence of an excess of alkali metal hydroxides, for example 2-5 equiv. sodium hydroxide. The reaction is carried out over a period of from 1 to 4 hours in a temperature range from RT to 80° C.

The aryloxy-acetic acids (A4) after purification are coupled with an aniline (A-5) to form the amide (A-6). The necessary activation of the acetic acid is preferably carried out using a mixed anhydride or using coupling reagents. The mixed anhydride of the relevant aryloxy-acetic acid (A-4) is preferably prepared by reacting the acetic acid with an excess of alkyl chloroformate, preferably isopropyl chloroformate, in a molar ratio of 1:1 to 1:1.2. The bases used are preferably tertiary amines, for example N-methylmorpholine, used in equimolar amounts to the alkyl chloroformate in question.

The reaction is carried out in a suitable solvent such as THF at temperatures between −10° C. and −5° C. and takes place over a period of 10 to 30 minutes.

The mixed anhydride thus obtained is preferably reacted with an amine compound (A-5), for example an aniline, without further purification. The aniline is used in excess relative to the particular acetic acid (A-4), preferably 5-10 mol %.

The reaction is carried out for example at RT over a period of 1 to 4 hours. Another preferred reaction yields the amide (A-6) by coupling the aniline (A-5) to the corresponding aryloxy-acetic acid (A-4) with the aid of peptide coupling reagents in a suitable solvent using a suitable base. The aryloxy-acetic acid (A-4) and an aniline (A-5) are preferably used in a molar ratio of from 1.5:1 to 1:1.5. The peptide coupling reagent used is TBTU, for example, used in an equimolar amount or in excess, preferably from equimolar to a 50 mol % excess. Alternatively, the reaction may also be carried out in the presence of an amount of HOBt equimolar to the TBTU. Preferred solvents are THF and DMF in a temperature range from RT to 80° C., preferably from RT to 40° C.

The bases used are preferably tertiary amines such as triethylamine or Hünig base.

Reaction plan A: (W representing —CH$_2$—O—)

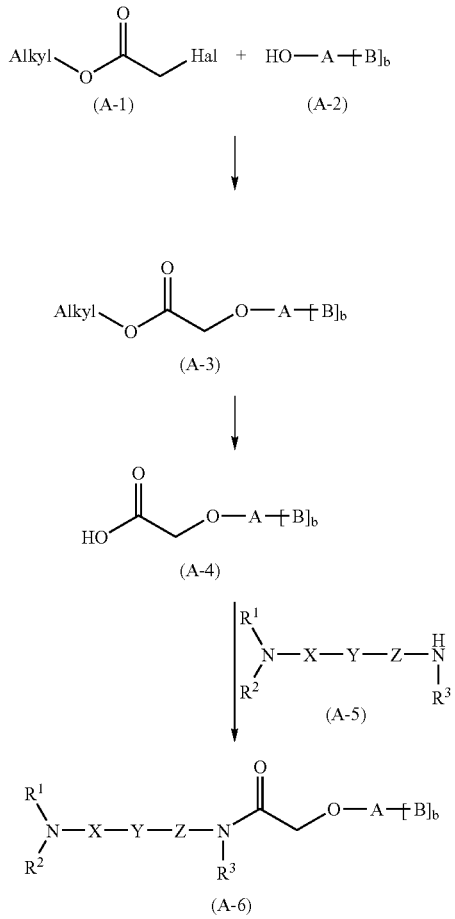

Reaction plan B: (W representing —CH$_2$—NR$^8$— with R$^8$ = H in this instance)

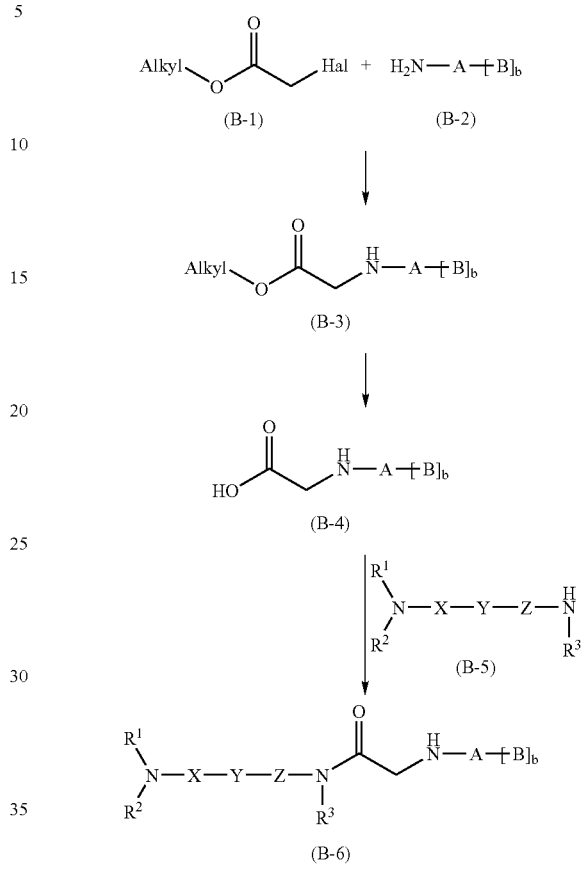

According to general reaction plan B an alkyl haloacetate (B-1), preferably ethyl bromoacetate, is reacted with an amine compound (B-2), for example an aniline, in an excess, preferably in a molar ratio of 1:1 to 1.2:1, in a suitable solvent in the presence of a suitable base. Suitable bases are, in particular, tertiary amines such as Hünig base.

The solvent used is preferably Hünig base, DMF or the mixtures thereof. The reaction is carried out over a period of 4 to 48 hours in a temperature range from 90° C. to 130° C. The further reaction of the ethyl arylamino-acetate (B-3) was carried out analogously to the general reaction plan A by hydrolysis to form the arylamino-acetic acid (B-4). The amide (B-6) is preferably prepared from the acetic acid (B-4) and the aniline (B-5) using TBTU and a suitable base in a suitable solvent. The aryloxy-acetic acid (B-4) and the aniline (B-5) are preferably used in a molar ratio of 1.5:1 to 1:1.5. The peptide coupling reagent used is TBTU, for example, which is used in an equimolar amount or in excess, preferably from equimolar to a 50 mol % excess. The preferred solvent is DMF in a temperature range from RT to 80° C., preferably from RT to 40° C. The bases used are preferably tertiary amines such as Hünig base.

According to reaction plan C an acrylic acid ester (C-3), e.g. an optionally substituted ethyl phenylacrylate, is prepared by palladium-catalysed reaction of an alkyl acrylate (C-1) and a (hetero)aryl halide (C-2). Preferably (hetero)arylbromide and (hetero)aryliodide (C-2) are added to the reaction in excess in relation to the acrylic acid, preferably in a molar ratio of 1:1 to 1:1.5. The solvent used may be for example acetonitrile at 80° C. The palladium catalyst used is preferably palladium(II)acetate (1 mol %) combined with tri-o-tolylphosphine (3 to 4 mol %). Suitable bases are tertiary amines such as triethylamine.

After purification, the acrylic acid ester (C-3) is hydrolysed to form the corresponding acrylic acid (C-4). The reaction is preferably carried out in ethanol-water mixtures in the presence of alkali metal hydroxides such as sodium hydroxide (200-300 mol %).

The reaction takes place over a period of 1 to 4 hours at ambient temperature.

After purification, the acrylic acid compound (C-4) is coupled to an amine compound (C-5), for example an aniline, to form the acrylamide (C-6). The necessary activation of the acrylic acid (C-4) takes place analogously to general reaction plan A, preferably via a mixed anhydride or using coupling reagents such as TBTU or TBTU in combination with HOBt.

Reaction plan C: (W representing —CH=CH—)

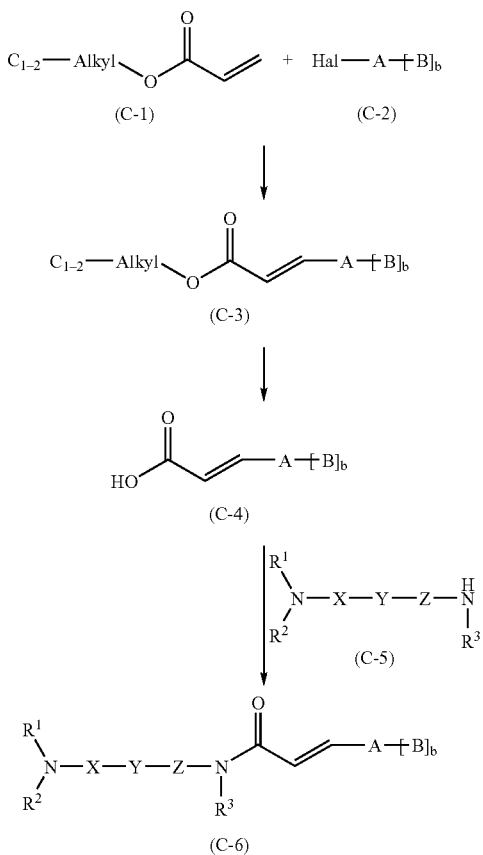

The compounds according to the invention may advantageously also be obtained using methods described in the following Examples, which may also be combined with methods known to the skilled man from the literature, for example.

Stereoisomeric compounds of formula (I) may be separated in principle by conventional methods. The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvents provided that they show sufficient differences in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

As already mentioned, the compounds of formula (I) may be converted into the salts thereof, particularly for pharmaceutical use into the physiologically and pharmacologically acceptable salts thereof. These salts may be present on the one hand as physiologically and pharmacologically acceptable acid addition salts of the compounds of formula (I) with inorganic or organic acids. On the other hand, in the case of acidically bound hydrogen, the compound of formula (I) may also be converted by reaction with inorganic bases into physiologically and pharmacologically acceptable salts with alkali or alkaline earth metal cations as counter-ion. The acid addition salts may be prepared, for example, using hydrochloric acid, hydrobromic acid, sulphuric acid, phosphoric acid, methanesulphonic acid, ethanesulphonic acid, toluenesulphonic acid, benzenesulphonic acid, acetic acid, fumaric acid, succinic acid, lactic acid, citric acid, tartaric acid or maleic acid. Moreover, mixtures of the above mentioned acids may be used. To prepare the alkali and alkaline earth metal salts of the compound of formula (I) with acidically bound hydrogen the alkali and alkaline earth metal hydroxides and hydrides are preferably used, while the hydroxides and hydrides of the alkali metals, particularly sodium and potassium are preferred and sodium and potassium hydroxide are most preferred.

The compounds according to the present invention, including the physiologically acceptable salts, are effective as antagonists of the MCH receptor, particularly the MCH-1 receptor, and exhibit good affinity in MCH receptor binding studies. Pharmacological test systems for MCH-antagonistic properties are described in the following experimental section.

As antagonists of the MCH receptor the compounds according to the invention are advantageously suitable as pharmaceutical active substances for the prevention and/or treatment of symptoms and/or diseases caused by MCH or causally connected with MCH in some other way. Generally the compounds according to the invention have low toxicity, they are well absorbed by oral route and have an intracerebral transitivity, particularly brain accessibility.

Therefore, MCH antagonists which contain at least one compound according to the invention, are particularly suitable in mammals, such as for example rats, mice, guinea pigs, hares, dogs, cats, sheep, horses, pigs, cattle, monkeys and also humans, for the treatment and/or prevention of symptoms and/or diseases which are caused by MCH or are otherwise causally connected with MCH.

Diseases caused by MCH or otherwise causally connected with MCH are particularly metabolic disorders, such as for example obesity, and eating disorders, such as for example bulimia, including bulimia nervosa. The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity. This range of indications also includes cachexia, anorexia and hyperphagia.

Compounds according to the invention may, in particular, be suitable for reducing hunger, curbing appetite, controlling eating behaviour and/or promoting a feeling of satiety.

In addition, the diseases caused by MCH or otherwise causally connected with MCH also include hyperlipidaemia, cellulitis, fat accumulation, malignant mastocytosis, systemic mastocytosis, emotional disorders, affectivity disorders, depression, anxiety states, sleep disoreders, reproductive disorders, sexual disorders, memory disorders, epilepsy, forms of dementia and hormonal disorders.

Compounds according to the invention are also suitable as active substances for the prevention and/or treatment of other illnesses and/or disorders, particularly those which accompany obesity, such as, for example, diabetes, diabetes mellitus, especially type II diabetes, hyperglycaemia, particularly chronic hyperglycaemia, complications of diabetes including diabetic retinopathy, diabetic neuropathy, diabetic nephropathy, etc., insulin resistance, pathological glucose tolerance, encephalorrhagia, cardiac insufficiency, cardiovascular diseases, particularly arteriosclerosis and high blood pressure, arthritis and gonitis.

MCH antagonists and formulations according to the invention may advantageously be used in combination with a dietary therapy, such as for example a dietary diabetes treatment, and exercise.

Another range of indications for which the compounds according to the invention are advantageously suitable is the prevention and/or treatment of urinary disorders, such as for example urinary incontinence, overactive bladder, urgency, nycturia and enuresis, while the Harninkontinenz, überaktiver Harnblase, Harndrang, Nykturie, Enuresis, while the overactive bladder and urgency may or may not be connected with benign prostatic hyperplasia.

The dosage required to achieve such an effect is conveniently, by intravenous or subcutaneous route, 0.001 to 30 mg/kg of body weight, preferably 0.01 to 5 mg/kg of body weight, and by oral or nasal route or by inhalation, 0.01 to 50 mg/kg of body weight, preferably 0.1 to 30 mg/kg of body weight, in each case once to three times a day.

For this purpose, the compounds of formula I prepared according to the invention may be formulated, optionally together with other active substances as described hereinafter, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, granules, solutions, emulsions, syrups, aerosols for inhalation, ointments or suppositories.

In addition to pharmaceutical compositions the invention also covers compositions containing at least one amide compound according to the invention and/or a salt according to the invention optionally together with one or more physiologically acceptable excipients. Such compositions may also be foods, for example, which may be solid or liquid, in which the compound according to the invention is incorporated.

For the above mentioned combinations it is possible to use as additional active substances particularly those which for example potentiate the therapeutic effect of an MCH antagonist according to the invention in terms of one of the indications mentioned above and/or which make it possible to reduce the dosage of an MCH antagonist according to the invention. Preferably one or more additional active substances are selected from among active substances for the treatment of diabetes,
active substances for the treatment of diabetic complications,
active substances for the treatment of obesity, preferably other than MCH antagonists,
active substances for the treatment of high blood pressure,
active substances for the treatment of hyperlipidaemia, including arteriosclerosis,
active substances for the treatment of arthritis,
active substances for the treatment of anxiety states,
active substances for the treatment of depression.

The above mentioned categories of active substances will now be explained in more detail by means of examples.

Examples of active substances for the treatment of diabetes are insulin sensitisers, insulin secretion accelerators, biguanides, insulins, α-glucosidase inhibitors, β3 adrenoreceptor agonists.

Insulin sensitisers include pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702, GW-1929.

Insulin secretion accelerators include sulphonylureas, such as for example tolbutamide, chloropropamide, tolzamide, acetohexamide, glyclopyramide and its ammonium salts, glibenclamide, gliclazide, glimepiride. Further examples of insulin secretion accelerators are repaglinide, nateglinide, mitiglinide (KAD-1229) and JTT-608.

Biguanides include mefformin, buformin and phenformin.

Insulins include those obtained from animals, particularly cattle or pigs, semisynthetic human insulins which are synthesised enzymatically from insulin obtained from animals, human insulin obtained by genetic engineering, e.g. from Escherichia coli or yeasts. Moreover, the term insulin also includes insulin-zinc (containing 0.45 to 0.9 percent by weight of zinc) and protamine-insulin-zinc obtainable from zinc chloride, protamine sulphate and insulin. Insulation may also be obtained from insulin fragments or derivatives (for example INS-1, etc.).

Insulin may also include different kinds, e.g. with regard to the onset time and duration of effect ("ultra immediate action type", "immediate action type", "two phase type", "intermediate type", "prolonged action type", etc.), which are selected depending on the pathological condition of the patient.

α-Glucosidase inhibitors include acarbose, voglibose, miglitol, emiglitate.

β3 Adreno receptor agonists include AJ-9677, BMS-1 96085, SB-226552, AZ40140.

Active substances for the treatment of diabetes other than those mentioned above include ergoset, pramlintide, leptin, BAY-27-9955 as well as glycogen phosphorylase inhibitors, sorbitol dehydrogenase inhibitors, protein tyrosine phosphatase 1B inhibitors, dipeptidyl protease inhibitors, glipizid, glyburide.

Active substances for the treatment of diabetic complications include for example aldose reductase inhibitors, glycation inhibitors and protein kinase C inhibitors.

Aldose reductase inhibitors are for example tolrestat, epalrestat, imirestat, zenarestat, SNK-860, zopolrestat, ARI-50i, AS-3201.

An example of a glycation inhibitor is pimagedine.

Protein Kinase C inhibitors are for example NGF, LY-333531.

Active substances other than those mentioned above for the treatment of diabetic complications include alprostadil, thiapride hydrochloride, cilostazol, mexiletine hydrochloride, ethyl eicosapentate, memantine, pimagedine (ALT-711).

Active substances for the treatment of obesity, preferably other than MCH antagonists, include lipase inhibitors and anorectics.

A preferred example of a lipase inhibitor is orlistat.

Examples of preferred anorectics are phentermine, mazindol, dexfenfluramine, fluoxetine, sibutramine, baiamine, (S)-sibutramine, SR-141716, NGD-95-1.

Active substances other than those mentioned above for the treatment of obesity include lipstatin.

Moreover for the purposes of this application the active substance group of anti-obesity active substances also includes the anorectics, of which the $\beta_3$ agonists, thyromimetic active substances and NPY antagonists should be emphasised. The scope of the anti-obesity or anorectic active substances which are preferred here is indicated by the following additional list, by way of example: phenylpropanolamine, ephedrine, pseudoephedrine, phentermine, a cholecystokinin-A (hereinafter referred to as CCK-A) agonist, a monoamine reuptake inhibitor (such as for example sibutramine), a sympathomimetic active substance, a serotonergic active substance (such as for example dexfenfluramine or fenfluramine), a dopamine antagonist (such as for example bromocriptine), a melanocyte-stimulating hormone receptor agonist or mimetic, an analogue of melanocyte-stimulating hormone, a cannabinoid receptor antagonist, an MCH antagonist, the OB protein (hereinafter referred to as leptin), a leptin analogue, a leptin receptor agonist, a galanine antagonist, a GI lipase inhibitor or reducer (such as for example orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as for example exendin and ciliary neurotrophic factors, such as for example axokine.

Active substances for the treatment of high blood pressure include inhibitors of angiotensin converting enzyme, calcium antagonists, potassium channel openers and angiotensin II antagonists.

Inhibitors of angiotensin converting enzyme include captopril, enalapril, alacepril, delapril (hydrochloride), lisinopril, imidapril, benazepril, cilazapril, temocapril, trandolapril, manidipine (hydrochloride).

Examples of calcium antagonists are nifedipine, amlodipine, efonidipine, nicardipine.

Potassium channel openers include levcromakalim, L-27152, AL0671, NIP-121.

Angiotensin II antagonists include telmisartan, losartan, candesartan cilexetil, valsartan, irbesartan, CS-866, E4177.

Active substances for the treatment of hyperlipidaemia, including arteriosclerosis, include HMG-CoA reductase inhibitors, fibrate compounds.

HMG-CoA reductase inhibitors include pravastatin, simvastatin, lovastatin, atorvastatin, fluvastatin, lipantil, cerivastatin, itavastatin, ZD-4522 and the salts thereof.

Fibrate compounds include bezafibrate, clinofibrate, clofibrate and simfibrate.

Active substances for the treatment of arthritis include ibuprofen.

Active substances for the treatment of anxiety states include chlordiazepoxide, diazepam, oxazolam, medazepam, cloxazolam, bromazepam, lorazepam, alprazolam, fludiazepam.

Active substances for the treatment of depression include fluoxetine, fluvoxamine, imipramine, paroxetine, sertraline.

The dosage for these active substances is conveniently ⅕ of the lowest normal recommended dose up to ¼ of the normal recommended dose.

In another embodiment the invention also relates to the use of at least one amide compound according to the invention and/or a salt according to the invention for influencing the eating behaviour of a mammal. This use is based particularly on the fact that compounds according to the invention may be suitable for reducing hunger, curbing appetite, controlling eating behaviour and/or promoting a feeling of satiety. The eating behaviour is advantageously influenced in such a way as to reduce food intake. Therefore, the compounds according to the invention are advantageously used for reducing body weight. A further use according to the invention is the prevention of increases in body weight, for example in people who have previously taken steps to reduce their weight and are then interested in maintaining their reduced body weight. According to this embodiment it is preferably a non-therapeutic use. Such a non-therapeutic use may be a cosmetic use, for example for altering the outer appearance, or an application for improving the general feeling of wellbeing. The compounds according to the invention are preferably used in a non-therapeutic capacity for mammals, particularly humans, who have no diagnosed disorders of eating behaviour, no diagnosed obesity, bulimia, diabetes and/or no diagnosed urinary problems, particularly urinary incontinence. Preferably the compounds according to the invention are suitable for non-therapeutic use in humans whose body mass index (BMI=body mass index), which is defined as the body weight measured in kilograms divided by the height (in metres) squared, is less than 30, particularly less than 25.

The Examples that follow are intended to illustrate the invention:

Preliminary Remarks:

As a rule, IR, $^1$H-NMR and/or mass spectra have been obtained for the compounds prepared. Unless otherwise stated the $R_f$ values are determined using ready-made silica gel 60 TLC plates $F_{254}$ (E. Merck, Darmstadt, Item no. 1.05714) without chamber saturation. The $R_f$ values obtained under the name Alox are determined using ready-made aluminium oxide 60 $F_{254}$ TLC plates (E. Merck, Darmstadt, Item no.1.05713) without chamber saturation. The ratios given for the eluants relate to units by volume of the solvent in question. The units by volume for $NH_3$ relate to a concentrated solution of $NH_3$ in water. Silica gel made by Millipore (MATREX™, 35-70 my) is used for chromatographic purification. Alox (E. Merck, Darmstadt, aluminium oxide 90 standardised, 63-200 μm, Item no. 1.01097.9050) is used for chromatographic purification. The HPLC data given are measured under the following parameters:

Analytical columns: Zorbax column (Agilent Technologies), SB (Stable Bond)—C18; 3.5 μm; 4.6×75 mm;

column temperature: 30° C.; flow: 0.8 mL/min; injection volume: 5 μL; detection at 254 nm (methods A and B) Symmetry 300 (Waters), 3.5 μm; 4.6×75 mm; column temperature: 30° C.; flow: 0.8 mL/min; injection volume: 5 μL; detection at 254 nm (method C)

method A: water:acetonitrile:formic acid 9:1:0.01 to 1:9:0.01 over 9 min method B: water:acetonitrile:formic acid 9:1:0.01 to 1:9:0.01 over 4 min, then 6 min 1:9:0.01 method C: water:acetonitrile:formic acid 9:1:0.01 to 1:9:0.01 over 4 min, then 6 min 1:9:0.01

Preparative column: Zorbax column (Agilent Technologies), SB (Stable Bond)—C18; 3.5 μm; 30×100 mm; column temperature: ambient temperature; flow: 30 mL/min; detection at 254 nm.

In preparative HPLC purifications, as a rule, the same gradients are used as were used to raise the analytical HPLC data.

The products are collected under mass control, the fractions containing product are combined and freeze-dried.

If there is no specific information as to the configuration, it is not clear whether there are pure enantiomers or whether partial or even total racemisation has taken place.

The following abbreviations are used above and hereinafter:

| abs. | absolute |
|---|---|
| Boc | tert-butoxycarbonyl |
| Cbz | benzyloxycarbonyl |
| CDI | N,N'-carbonyldiimidazole |
| CDT | 1,1'-carbonyldi(1,2,4-triazole) |
| DMF | N,N-dimethylformamide |
| ether | diethyl ether |
| EtOAc | ethyl acetate |
| EtOH | ethanol |
| Fmoc | 9-fluorenylmethoxycarbonyl |
| sat. | saturated |
| semiconc. | semiconcentrated |
| HCl | hydrochloric acid |
| HOAc | acetic acid |
| HOBt | 1-hydroxybenzotriazole-hydrate |
| Hünig base | N-ethyldiisopropylamine |
| HV | high vacuum |
| i.vac. | in vacuo (in vacuo) |
| KOH | potassium hydroxide |
| conc. | concentrated |
| MeOH | methanol |
| MTBE | methyl-tert-butylether |
| NaCl | sodium chloride |
| NaOH | sodium hydroxide |
| org. | organic |
| Ph | phenyl |
| RT | ambient temperature (ca. 20° C.) |
| TBTU | 2-(1H-benzotriazol-1-yl)-1,1,3,3-tetramethyluronium-tetrafluoroborate |
| TEBAC | triethylbenzylammonium chloride |
| TFA | trifluoroacetic acid |
| THF | tetrahydrofuran |
| →* | denotes the binding site of a group |

Synthesis of Intermediate Products
Intermediate Product 1:

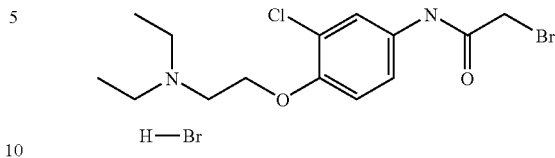

Z1a) [2-(2-chloro-4-nitro-phenoxy)-ethyl]-diethyl-amine-hydrobromide 40.00 g (1.00 mol) of potassium carbonate was added to a solution of 50.00 g (0.288 mol) of 2-chloro-4-nitro-phenol and 60.23 g (0.350 mol) of (2-chloro-ethyl)-diethyl-amine in 700 mL DMF and the mixture was stirred for 16 hours at 80° C. The reaction mixture was evaporated down i. vac., the residue was combined with water and the aqueous phase was exhaustively extracted with EtOAc. The combined org. extracts were washed with water, dried over magnesium sulphate and evaporated down i. vac. The crude product was recrystallised from EtOAc and the mother liquor evaporated down i. vac. Purification of the residue by column chromatography (silica gel, gradient dichloromethane/MeOH 10:0→9:1) yielded the desired product.

Yield: 29.00 g (37% of theory)
$C_{12}H_{17}ClN_2O_3$ (M=272.734)
Calc.: molpeak $(M+H)^+$: 273/275
Found: molpeak $(M+H)^+$: 273/275 (Cl)

Z1b) 3-chloro-4-(2-diethylamino-ethoxy)-phenylamine

A solution of 100 mL of conc. aqueous HCl in 100 mL EtOH was added dropwise to a suspension of 20.00 g (358 mmol) of iron powder and 20 g (73.33 mmol) of [2-(2-chloro-4-nitro-phenoxy)-ethyl]-diethyl-amine in 200 mL EtOH, while the temperature was kept below 20° C. by cooling with ice. The reaction mixture was stirred for 30 minutes, neutralised with 10% aqueous sodium bicarbonate solution and was exhaustively extracted with EtOAc. The combined org. extracts were dried over magnesium sulphate and evaporated down i. vac. The product was stored under a nitrogen atmosphere.

Yield: 17.40 g (98% of theory)
$C_{12}H_{19}ClN_2O$ (M=242.751)
Calc.: molpeak $(M+H)^+$: 243/245
Found: molpeak $(M+H)^+$: 243/245 (Cl)
$R_f$ value: 0.6 (silica gel, dichloromethane/MeOH/conc. aqueous ammonia 90:10:1)

Z1c) 2-bromo-N-[3-chloro-4-(2-diethylamino-ethoxy)-phenyl]-acetamide-hydrobromide A solution of 1.86 mL (21.00 mmol) of bromoacetylbromide in 10 mL of dichloromethane was added dropwise to a solution of 5.00 g (21.00 mmol) of 3-chloro-4-(2-diethylamino-ethoxy)-phenylamine. in 100 mL of dichloromethane at 0° C. and the mixture was stirred for 20 minutes at 0° C. The precipitate formed was filtered off, washed with dichloromethane and MTBE and dried i. vac. at 40° C.

Yield: 8.20 g (89 % of theory)
$C_{14}H_{21}BrClN_2O_2$ * Br (M=444.597)
Calc.: molpeak $(M+H)^+$: 363/365/367
Found: molpeak $(M+H)^+$: 363/365/367 (BrCl)
HPLC-MS: 4.2for 5 min. (Stable Bond Cl 8; 3.5 μm; water:acetonitrile:formic acid 9:1:0.01→1:9:0.01 over9 min)

Intermediate Product 2:

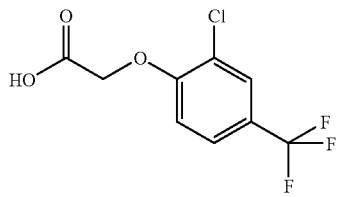

Z2a) ethyl (2-chloro-4-trifluoromethyl-phenoxy)-acetate 28.19 g (0.204 mol) of potassium carbonate was added to a solution of 20.00 g (0.102 mol) of 2-chloro-4-trifluoromethyl-phenol and 11.36 mL (0.102 mol) of ethyl bromoacetate in 300 mL of DMF and the mixture was stirred for 7 hours at 60° C. and for 16 hours at RT. The reaction mixture was evaporated down i. vac. and the residue combined with EtOAc. The org. phase was washed with water, dried over magnesium sulphate and evaporated down i. vac.

Yield: 23.79 g (83% of theory)
$C_{11}H_{10}ClF_3O_3$ (M=282.649)
Calc.: molpeak(M+Na)$^+$: 305/307
Found: molpeak (M+Na)$^+$: 305/307 (Cl)
$R_f$ value: 0.58 (silica gel, petroleum ether/EtOAc 4:1)

Z2b) (2-chloro-4-trifluoromethyl-phenoxy)-acetic acid 84 mL of 2 M aqueous NaOH was added to a solution of 23.97 g (0.084 mol) of ethyl (2-chloro-4-trifluoromethyl-phenoxy)-acetate in 200 mL EtOH and the mixture was refluxed for 1 hour. EtOH was concentrated by evaporation i. vac., the residue was diluted with ice water and acidified with 2 M aqueous HCl. The precipitate formed was filtered off, washed with water and dried at 70° C. i. vac.

Yield: 12.33 g (58% of theory)
$C_9H_6ClF_3O_3$ (M=254.595)
Calc.: molpeak(M–H)$^-$: 253/255
Found: molpeak (M–H)$^-$: 253/255 (Cl)
$R_f$ value: 0.04 (silica gel, petroleum ether/EtOAc 3:2)

Intermediate Product 3:

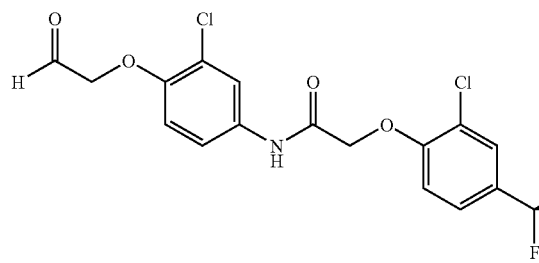

Z3a) 2-chloro-1-(2,2-diethoxy-ethoxy)4-nitrobenzene 26.56 g (0.150 mol) of 2-chloro-4-nitrophenol and 24.25 mL (0.150 mol) of 2-bromo-1,1-diethoxy-ethane was added to a suspension of 22.80 g (0.165 mol) of potassium carbonate in 250 mL DMF and the mixture was heated to 140° C. for 24 hours. The reaction mixture was diluted with 1 L water and exhaustively extracted with MTBE. The combined org. extracts were washed with water, dried over magnesium sulphate and evaporated down i. vac. Yield: 32.10 g (74% of theory) $C_{12}H_{16}ClNO_5$ (M=289.718) $R_f$ value: 0.7 (silica gel, dichloromethane/cyclohexane/EtOAc 1:4:1)

Z3b) 3-chloro-4-(2,2-diethoxy-ethoxy)-phenylamine 30 g (0.104 mol) of 2-chloro-1-(2,2-diethoxy-ethoxy)-4-nitrobenzene was added to a suspension of 1.50 g Pd/C (10%) in 500 mL EtOAc and the mixture was hydrogenated for 2 hours at 20 psi. The catalyst was filtered off and the filtrate evaporated down i. vac.

Yield: 27.00 g (quantitative yield)
$C_{12}H_{18}ClNO_3$ (M=259.735)
Calc.: molpeak (M+H)$^+$: 260/262
Found: molpeak (M+H)$^+$: 260/262 (Cl)
$R_f$ value: 0.75 (silica gel, dichloromethane/MeOH 9:1)

Z3c) N-[3-chloro-4-(2,2-diethoxy-ethoxy)-phenyl]-2-(2-chloro-4-trifluoromethyl-phenoxy)-acetamide 4.495 g (0.028 mol) of CDI was added to a solution of 6.365 g (0.025 mol) of (2-chloro-4-trifluoromethyl-phenoxy)-acetic acid (intermediate product 2b) in 100 mL abs. THF and the mixture was stirred for 30 minutes at 50° C. 6.494 g (0.025 mol) of 3-chloro-4-(2,2-diethoxy-ethoxy)-phenylamine was added and the mixture was stirred for 16 hours at RT. The reaction mixture was poured into ice water and stirred for 1 hour. The precipitate formed was filtered off, washed with water and dried at 50° C.

Yield: 11.40 g (92% of theory)
$C_{21}H_{22}Cl_2F_3NO_5$ (M=496.314)
Calc.: molpeak(M–H)$^-$: 494/496/498
Found: molpeak (M–H)$^-$: 494/496/498 (Cl$_2$)
$R_f$ value: 0.73 (silica gel, petroleum ether/EtOAc 3:2)

Z3d) N-[3-chloro-4-(2-oxo-ethoxy)-phenyl]-2-(2-chloro-4-trifluoromethyl-phenoxy)-acetamide 40 mL water and 130 mL TFA was added to a solution of 11.40 g (0.023 mol) of N-[3-chloro-4-(2,2-diethoxy-ethoxy)-phenyl]-2-(2-chloro-4-trifluoromethyl-phenoxy)-acetamide in 130 mL chloroform at 0° C. and the mixture was stirred for 3.5 hours at 0° C. and for 48 hours at RT. The reaction mixture was neutralised with sat. aqueous sodium carbonate solution and exhaustively extracted with dichloromethane. The combined org. extracts were washed with water, dried over magnesium sulphate and evaporated down i. vac.

Yield: 8.40g (86% of theory)
$C_{17}H_{12}Cl_2F_3NO_4$ (M=422.191)
Calc.: molpeak(M–H)$^-$: 421/423/425
Found: molpeak (M–H)$^-$: 421/423/425 (Cl$_2$)
$R_f$ value: 0.14 (silica gel, petroleum ether/EtOAc 3:2)

Intermediate Product 4:

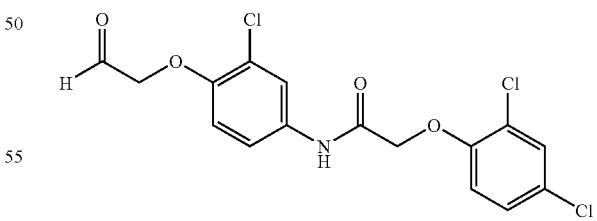

Z4a) N-[3-chloro-4-(2,2-diethoxy-ethoxy)-phenyl]-2-(2,4-dichloro-phenoxy)-acetamide At 0° C. a solution of 0.57 g (2.38 mmol) of (2,4-dichloro-phenoxy)-acetylchloride in 4 mL dichloromethane was added dropwise to a solution of 0.50 g (2.16 mmol) of 3-chloro-4-(2,2-diethoxy-ethoxy)-phenylamine (intermediate product Z3b) and 0.74 mL (4.32 mmol) of ethyldiisopropylamine in 10 mL dichloromethane and the mixture was stirred for 1 hour at 0° C. MeOH was added and the precipitated product was filtered off. The product was washed with MeOH and dried i. vac.

Yield: 0.74 g (79% of theory)

$C_{18}H_{18}Cl_3NO_5$ (M=434.70)

Calc.: molpeak(M−H)⁻: 432/434/436

Found: molpeak (M−H)⁻: 432/434/436 ($Cl_3$)

HPLC-MS: 5.00 Min. (Devosil RPAqueous; 30-100% water/acetonitrile 70:30→0:100 in for 5 min.)

Z4b) N-[3-chloro-4-(2-oxo-ethoxy)-phenyl]-2-(2,4-dichloro-phenoxy)-acetamide

At 0° C. 2 mL TFA and 0.15 mL water was added to a solution of 50 mg (0.011 mmol) of N-[3-chloro-4-(2,2-diethoxy-ethoxy)-phenyl]-2-(2,4-dichloro-phenoxy)-acetamide in 2 mL dichloromethane and the mixture was stirred for 3.5 hours. 200 ml of 2 M aqueous sodium carbonate solution was added and exhaustively extracted with dichloromethane. The combined org. extracts were dried over magnesium sulphate, evaporated down i. vac. and the residue was purified by column chromatography (silica gel, EtOAc/hexane 1:1).

Yield: 40 mg (89% of theory)

$C_{16}H_{12}C_{13}NO_4$ (M=388.63)

Calc.: molpeak(M−H)⁻: 386/388/390

Found: molpeak (M−H)⁻: 386/388/390 ($C_{13}$)

$R_f$ value: 0.25 (silica gel, hexane/EtOAc 3:2)

HPLC-MS: 4.56 Min. (Devosil RPAqueous; 5-100% water/acetonitrile 70:30→0:100 in for 5 min.)

Intermediate Product 5:

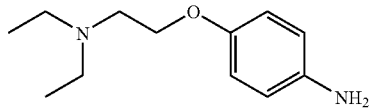

Z5a) Diethyl-[2-(4-nitro-phenoxy)-ethyl]-amine 2.07 g (15.0 mmol) of potassium carbonate was added to a solution of 1.04 g (7.5 mmol) of 4-nitrophenol in 20 mL DMF under an argon atmosphere and the mixture was stirred for 20 minutes at 80° C. 1.72 g (10.0 mmol) of (2-chloro-ethyl)-diethyl-amine-hydrochloride was added and the mixture was stirred for 8 hours at 90° C. 100 ml of 2 M aqueous sodium carbonate solution was added and exhaustively extracted with ether. The combined org. extracts were dried over magnesium sulphate and evaporated down i. vac. The crude product was used in the next reaction step without further purification.

Yield: 1.59 g (89% of theory)

$C_{12}H_{18}N_2O_3$ (M=238.28).

Calc.: molpeak (M+H)⁺: 239

Found: molpeak (M+H)⁺: 239

$R_f$ value: 0.2 (silica gel, EtOAc)

Z5b) 4-(2-Diethylamino-ethoxy)-phenylamine 2.6 g (10.9 mmol) of diethyl-[2-(4-nitro-phenoxy)-ethyl]-amine was added to a suspension of 130 mg Pd/C (10%) in 20 mL MeOH and the mixture was hydrogenated for 4 hours. The catalyst was filtered off and the filtrate evaporated down i. vac.

Yield: 2.19 g (96% of theory)

$C_{12}H_{20}N_2O$ (M=208.30)

Calc.: molpeak (M+H)⁺: 209

Found: molpeak (M+H)⁺: 209

$R_f$ value: 0.2 (silica gel, dichloromethane/MeOH 9:1)

Intermediate Product 6:

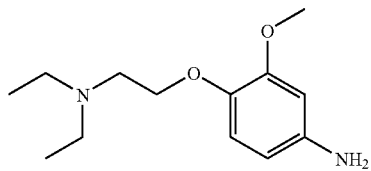

Z6a) Diethyl-[2-(2-methoxy-4-nitro-phenoxy)-ethyl]-amine

The product was obtained analogously to intermediate product Z5a starting from 1.27 g (7.5 mmol) of 2-methoxy-4-nitro-phenol and 1.72 g (10.0 mmol) of (2-chloro-ethyl)-diethyl-amine-hydrochloride.

Yield: 1.01 g (50% of theory)

$C_{13}H_{20}N_2O_4$ (M=268.31)

Calc.: molpeak (M+H)⁺: 269

Found: molpeak (M+H)⁺: 269

$R_f$ value: 0.2 (silica gel, EtOAc)

Z6b) 4-(2-Diethylamino-ethoxy)-3-methoxy-phenylamine 0.77 g (2.87 mmol) of diethyl-[2-(2-methoxy-4-nitro-phenoxy)-ethyl]-amine was added to a suspension of 1.00 g (17.9 mmol) of iron powder in 7 mL EtOH and the mixture was stirred for 10 minutes at RT. 6.6 mL of conc. aqueous HCl was added dropwise within 15 minutes and the mixture was stirred for 1 hour. 100 ml of 2 M sodium carbonate solution was added and the mixture was exhaustively extracted with EtOAc. The combined org. extracts were dried over magnesium sulphate and evaporated down i. vac.

Yield: 0.62 g (92% of theory)

$C_{13}H_{22}N_2O_2$ (M=238.33)

Calc.: molpeak (M+H)⁺: 269

Found: molpeak (M+H)⁺: 269

$R_f$ value: 0.05 (silica gel, dichloromethane/MeOH 9:1)

Intermediate Product 7:

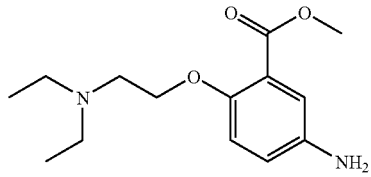

Z7a) methyl 2-(2-diethylamino-ethoxy)-5-nitro-benzoate

The product was obtained analogously to intermediate product Z5a starting from 1.48 g (7.5 mmol) of methyl 2-hydroxy-5-nitro-benzoate and 1.72 g (10.0 mmol) of (2-chloro-ethyl)-diethyl-amine-hydrochloride.

Yield: 0.81 g (40% of theory)

$C_{14}H_{20}N_2O_5$ (M=296.32)

Calc.: molpeak (M+H)⁺: 297

Found: molpeak (M+H)⁺: 297

$R_f$ value: 0.1 (silica gel, EtOAc/MeOH 9:1)

Z7b) methyl 5-amino-2-(2-diethylamino-ethoxy)-benzoate

The product was obtained analogously to intermediate product Z5b starting from 400 mg (1.35 mmol) of methyl 2-(2-diethylamino-ethoxy)-5-nitro-benzoate.

Yield: 0.35 g (97% of theory)
$C_{14}H_{22}N_2O_3$ (M=266.34)
Calc.: molpeak (M+H)$^+$: 267
Found: molpeak (M+H)$^+$: 267
$R_f$ value: 0.2 (silica gel, EtOAc/MeOH 9:1)

Intermediate Product 8:

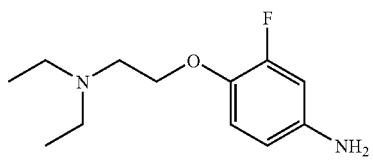

Z8a) diethyl-[2-(2-fluoro-4-nitro-phenoxy)-ethyl]-amine

The product was obtained analogously to intermediate product Z5a starting from 1.18 g (7.5 mmol) of 2-fluoro-4-nitro-phenol and 1.72 g (10.0 mmol) of (2-chloro-ethyl)-diethyl-amine-hydrochloride obtained.

Yield: 1.65 g (86% of theory)
$C_{12}H_{17}FN_2O_3$ (M=256.27)
Calc.: molpeak (M+H)$^+$: 257.
Found: molpeak (M+H)$^+$: 257.

$R_f$ value: 0.1 (silica gel, EtOAc)

Z8b) 4-(2-diethylamino-ethoxy)-3-fluoro-phenylamine

The product was obtained analogously to intermediate product Z6b starting from 0.68 g (2.65 mmol) of diethyl-[2-(2-fluoro-4-nitro-phenoxy)-ethyl]-amine.

Yield: 0.60 g (quantitative yield)
$C_{12}H_{19}FN_2O$ (M=226.29)
Calc.: molpeak (M+H)$^-$: 227.
Found: molpeak (M+H)+: 227.

$R_f$ value: 0.1 (silica gel, dichloromethane/MeOH 9:1)

Intermediate Product 9:

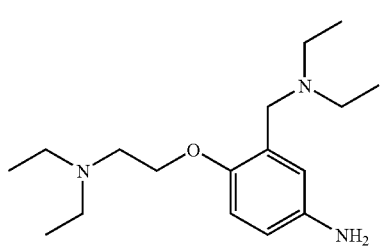

Z9a) tert.butyl (3-diethylaminomethyl-4-hydroxy-phenyl)-carbaminate

At 80° C. a solution of 0.90 g (4.11 mmol) of Boc-anhydride in 20 mL THF was added to a solution of 1.00 g (3.74 mmol) of 4-amino-2-diethylaminomethyl-phenol and 0.52 mL (3.74 mmol) of triethylamine in 20 mL abs. THF and the mixture was refluxed for 24 hours. 100 ml of 2 M aqueous sodium carbonate solution was added and the mixture was exhaustively extracted with ether. The combined org. extracts were dried over magnesium sulphate, evaporated down i. vac. and the residue was purified by column chromatography (silica gel, EtOAc).

Yield: 1.03 g (94% of theory)
$C_{16}H_{26}N_2O_3$ (M=294.39)
Calc.: molpeak (M+H)$^-$: 295
Found: molpeak (M+H)$^+$: 295
$R_f$ value: 0.3 (silica gel, EtOAc)

Z9b) tert.butyl [4-(2-diethylamino-ethoxy)-3-diethylaminomethyl-phenyl]-carbaminate The product was obtained analogously to intermediate product Z5a starting from 2.21 g (7.5 mmol) of tert.butyl (3-diethylaminomethyl-4-hydroxy-phenyl)-carbaminate and 1.72 g (10.0 mmol) of (2-chloro-ethyl)-diethyl-amine-hydrochloride.

Yield: 0.88 g (30% of theory)
$C_{22}H_{39}N_3O_3$ (M=393.56)
Calc.: molpeak (M+H)$^+$: 394
Found: molpeak (M+H)$^+$: 394
$R_f$ value: 0.05 (silica gel, dichloromethane/MeOH 9:1)

Z9c) 4-(2-diethylamino-ethoxy)-3-diethylaminomethyl-phenylamine 5 mL TFA was added to a solution of 0.18 g (0.457 mmol) of tert.butyl [4-(2-diethylamino-ethoxy)-3-diethylaminomethyl-phenyl]-carbaminate in 5 mL chloroform and the mixture was stirred for 1 hour at RT. 100 ml of 2 M aqueous sodium carbonate solution was added and exhaustively extracted with ether. The combined org. extracts were dried over magnesium sulphate and evaporated down i. vac.

Yield: 0.13 g (97% of theory)
$C_{17}H_{31}N_3O$ (M=293.45)
Calc.: molpeak (M+H)$^+$: 294
Found: molpeak (M+H)$^+$: 294
$R_f$ value: 0.05 (silica gel, dichloromethane/MeOH 4:1)

Intermediate Product 10:

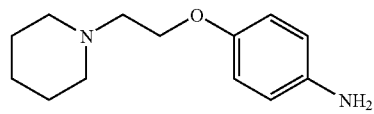

Z10) 4-(2-piperidin-1-yl-ethoxy)-phenylamine 15.4 g (111.00 mmol) of potassium carbonate was added to a solution of 4.0 g (27.86 mmol) of 4-amino-2-chlorophenol and 5.1 g (27.86 mmol) of 1-(2-chloro-ethyl)-piperidine in 50 mL acetonitrile and the mixture was stirred for 48 hours at RT. The solvent was evaporated off i. vac., the residue was combined with water and the aqueous phase was exhaustively extracted with EtOAc. The combined org. extracts were washed with water, dried over magnesium sulphate, evaporated down i. vac. and the residue was purified by column chromatography (silica gel, dichloromethane/MeOH/conc. aqueous ammonia 90:10:1).

Yield: 77 mg (61% of theory)
$C_{13}H_{19}ClN_2O$ (M=254.762)
Calc.: molpeak (M+H)$^+$: 255/257.

Found: molpeak (M+H)⁺: 255/257 (Cl).

Intermediate Product 11:

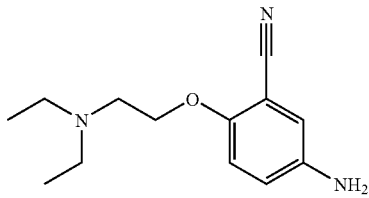

Z11a) 2-hydroxy-5-nitro-benzonitrile

At 45-50° C. a solution of 36.0 mL of 65% aqueous nitric acid in 50 mL conc. acetic acid was added dropwise to a solution of 50 g (0.416 mol) of 2-hydroxy-benzonitrile in 150 mL conc. acetic acid and the mixture was stirred for 1 hour at 50° C. The reaction mixture was cooled to RT, diluted with 400 mL water and the precipitate formed was filtered off (mixture of o- and p-substituted product). The mother liquor was diluted with 1 L ice water and the precipitate formed was filtered off (product). The product mixture was dissolved in dichloromethane/MeOH and purified by column chromatography (silica gel, gradient dichloromethane/MeOH 10:0→4:1).

Yield: 25.22 g (37% of theory)
$C_7H_4N_2O_3$ (M=164.122)
Calc.: molpeak (M−H)⁻: 163
Found: molpeak (M−H)⁻: 163
$R_f$ value: 0.35 (silica gel, dichloromethane/MeOH 9:1)

Z11b) 5-amino-2-hydroxy-benzonitrile 4.50 g (27.00 mmol) of 2-hydroxy-5-nitro-benzonitrile was added to a suspension of 0.45 g Pd/C (10%) in 45 mL EtOAc and the mixture was hydrogenated for 1.5 hours under 3 bar $H_2$ atmosphere. The catalyst was filtered off and the residue dried i. vac.

Yield: 3.40 g (94% of theory)
$C_7H_6N_2O$ (M=134.139)
Calc.: molpeak (M−H)⁻: 133.
Found: molpeak (M−H)⁻: 133.
$R_f$ value: 0.3 (silica gel, dichloromethane/MeOH 9:1)

Z11c) 5-amino-2-(2-diethylamino-ethoxy)-benzonitrile 11.06 g (0.080 mol) of potassium carbonate was added to a solution of 2.683 g (0.020 mol) of 5-amino-2-hydroxy-benzonitrile and 3.786 g (0.022 mol) of N,N-diethylamino-ethylchoride-hydrochlor in 100 mL abs. acetonitrile and the mixture was stirred for 48 hours at RT. The solvent was evaporated off i. vac. and the residue was combined with water. The aqueous phase was exhaustively extracted with EtOAc, the combined org. extracts were washed with water, dried over magnesium sulphate and evaporated down i. vac. The residue was purified by column chromatography (silica gel, dichloromethane/MeOH/conc. aqueous ammonia 90:10:1).

Yield: 0.80 g (17% of theory)
$C_{13}H_{19}N_3O$ (M=233.316)
Calc.: molpeak (M+H)⁺: 234
Found: molpeak (M+H)⁺: 234
$R_f$ value: 0.15 (silica gel, dichloromethane/MeOH/conc. aqueous ammonia 90:10:1)

Intermediate Product 12:

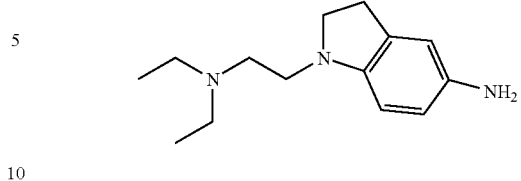

Z12a) diethyl-[2-(5-nitro-2,3-dihydro-indol-1-yl)-ethyl]-amine 1.00 g (7.262 mmol) of potassium carbonate was added to a solution of 0.477 g (2.905 mmol) of 5-nitro-2,3-dihydro-1H-indole and 0.500 g (2.905 mmol) of N,N-diethylamino-ethylchloride-hydrochloride in 5 mL DMF and the mixture was stirred for 16 hours at 90° C. The reaction mixture was diluted with water and exhaustively extracted with EtOAc. The combined org. phases were dried over magnesium sulphate and evaporated down i. vac. The residue was purified by column chromatography (silica gel, EtOAc).

Yield: 0.14 g (18% of theory)
$C_{14}H_{21}N_3O_2$ (M=263.342)
Calc.: molpeak (M+H)⁺: 264
Found: molpeak (M+H)⁺: 264
$R_f$ value: 0.26 (silica gel, EtOAc/MeOH 9:1)

Z12b) 1-(2-diethylamino-ethyl)-2,3-dihydro-1H-indol-5-ylamine 140 mg (0.532 mmol) of diethyl-[2-(5-nitro-2,3-dihydro-indol-1-yl)-ethyl]-amine was added to a suspension of 50 mg of Raney-Ni in 5 mL MeOH and the mixture was hydrogenated for 1 hour at RT under 20 psi of $H_2$ atmosphere. The catalyst was filtered off and the filtrate evaporated down i. vac. The crude product was reacted immediately without any further purification (cf. Example 12).

Yield: 80 mg (64% of theory)

Intermediate Product 13:

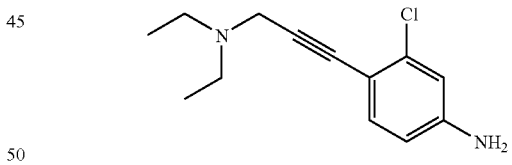

Z13a) [3-(2-chloro-4-nitro-phenyl)-prop-2-ynyl]-diethyl-amine

Under a nitrogen atmosphere 12.5 mL (0.090 mol) of 3-N,N-diethylamino-propyne was added to 25.00 g (0.106 mol) of 4-bromo-3-chloro-nitrobenzene, 43.7 mL (0.315 mol) of triethylamine, 10.40 g (0.009 mol) of tetrakis[triphenylphosphine]-palladium(II) and 1.71 g (0.009 mol) of copper(I)-iodide in 250 mL acetonitrile and the mixture was refluxed for 18 hours. The reaction mixture was evaporated down i. vac., combined with EtOAc and the organic phase was washed with water. The org. phase was evaporated down i. vac. and the residue was purified by column chromatography (silica gel, petroleum ether/EtOAc 10:0→4:1) followed by column chromatography (silica gel, dichloromethane).

Yield: 15.0 g (62% of theory)
$C_{13}H_{15}ClN_2O_2$ (M=266.730)
Calc.: molpeak (M+H)$^+$: 267/269
Found: molpeak (M+H)$^+$: 267/269 (Cl)

Z13b) 3-chloro-4-(3-diethylamino-prop-1-ynyl)-phenylamine

A solution of 15 mL of conc. aqueous HCl in 15 mL EtOH was added to a suspension of 4.189 g (75.00 mmol) of iron powder and 2.00 g (7.50 mmol) of [3-(2-chloro-4-nitro-phenyl)-prop-2-ynyl]-diethyl-amine in 20 mL of EtOH with vigorous stirring and the mixture was stirred for 30 minutes. The reaction mixture was neutralised with 200 mL of 10% aqueous sodium carbonate solution and exhaustively extracted with EtOAc. The combined org. phases were dried over magnesium sulphate, evaporated down i. vac. and the residue was purified by column chromatography (silica gel, gradient dichloromethane /10% conc. aqueous ammonia in MeOH 100:0→5:95).

Yield: 0.45 g (25% of theory)
$C_{13}H_{17}ClN_2$ (M=236.747)
Calc.: molpeak (M+H)$^+$: 237/239
Found: molpeak (M+H)$^+$: 237/239 (Cl)

Intermediate Product 14:

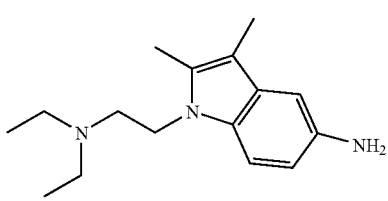

Z14a) [2-(2,3-dimethyl-5-nitro-indol-1-yl)-ethyl]-diethyl-amine 1.00 g (7.262 mmol) of potassium carbonate was added to a solution of 0.553 g (2.905 mmol) of 2,3-dimethyl-5-nitro-1H-indole and 0.500 g (2.905 mmol) of N,N-diethylamino-ethylchloride-hydrochloride in 5 mL DMF and the mixture was stirred for 16 hours at 90° C. The reaction mixture was diluted with water and exhaustively extracted with EtOAc. The combined org. phases were dried over magnesium sulphate and evaporated down i. vac. The residue was purified by column chromatography (silica gel, EtOAc/MeOH 9:1).

Yield: 0.15 g (18% of theory)
$C_{16}H_{23}N_3O_2$ (M=289.3812)
Calc.: molpeak(M+H)$^+$: 290
Found: molpeak (M+H)$^+$: 290
$R_f$ value: 0.54 (silica gel, EtOAc/MeOH 9:1)

Z14b) 1-(2-diethylamino-ethyl)-2,3-dimethyl-1H-indol-5-ylamine 150 mg (0.518 mmol) of [2-(2,3-dimethyl-5-nitro-indol-1-yl)-ethyl]-diethyl-amine was added to a suspension of 100 mg of Raney-Ni in 5 mL MeOH and the mixture was hydrogenated for 1 hour at RT under 20 psi H$_2$ atmosphere. The catalyst was filtered off and the filtrate evaporated down i. vac. The crude product was reacted immediately without further purification (see Example 5).

Yield: 100 mg (74% of theory)

Intermediate Product 15:

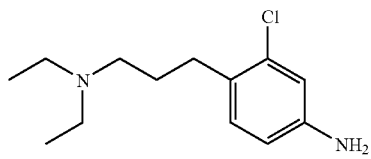

Z15) 3-chloro-4-(3-diethylamino-propyl)-phenylamine 2.00 g (7.498 mmol) of 3-chloro-4-(3-diethylamino-prop-1-ynyl)-phenylamine (intermediate product Z13b) was added to a suspension of 0.50 g Raney-Ni in 50 mL abs. MeOH and the mixture was hydrogenated for 2.5 hours at RT and 50 psi H$_2$ atmosphere. The catalyst was filtered off, the filtrate evaporated down i. vac. and the residue was purified by column chromatography (silica gel, gradient dichloromethane/10% conc. aqueous ammonia in MeOH 100:0→5:95).

Yield: 0.90 g (50% of theory)
$C_{13}H_{21}ClN$ (M=240.779)
Calc.: molpeak(M+H)$^+$: 241/243
Found: molpeak (M+H)$^+$: 241/243 (Cl)

Intermediate Product 16:

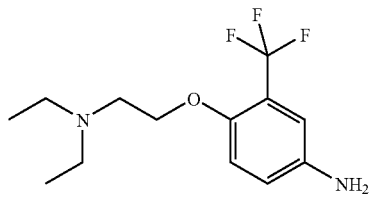

Z16a) diethyl-[2-(4-nitro-2-trifluoromethyl-phenoxy)-ethyl]-amine 5.60 g (40.00 mmol) of potassium carbonate was added to a solution of 4.10 g (20.00 mmol) of 4-nitro-2-trifluoromethyl-phenol (J. Org. Chem. 1962, 27, 4660-4662.) in 40 mL DMF and the mixture was heated to 80° C. A solution of 3.5 g (20.00 mmol) of N,N-diethylamino-ethylchloride-hydrochloride in 10 mL DMF was added dropwise and the mixture was stirred for a further 3 hours at 80° C. The reaction mixture was diluted with 100 mL sat. aqueous NaCl solution and exhaustively extracted with EtOAc. The combined org. extracts were washed with 10% aqueous sodium carbonate solution, dried over magnesium sulphate and evaporated down i. vac.

Yield: 7.5 g (80% of theory)
$C_{13}H_{17}F_3N_2O_3$ (M=306.287)
Calc.: molpeak(M+H)$^+$: 307
Found: molpeak (M+H)$^+$: 307

Z16b) 4-(2-diethylamino-ethoxy)-3-trifluoromethyl-phenylamine 7.0 g (22.854 mmol) of 4-(2-diethylamino-ethoxy)-3-trifluoromethyl-phenylamine was added to a suspension of 0.50 g Pd/C (10%) in EtOAc and the mixture was hydrogenated for 6 hours at 50° C. and 50 psi H$_2$ atmosphere. The catalyst was filtered off and the filtrate evaporated down i. vac. MTBE was added and the org. phase was washed several times with water, dried over magnesium sulphate, filtered through activated charcoal and evaporated down i. vac.

Yield: 4.40 g (70% of theory)
$C_{13}H_{19}F_3N_2O$ (M=276.304)
Calc.: molpeak(M+H)$^+$: 277
Found: molpeak (M+H)$^+$: 277

Intermediate Product 17:

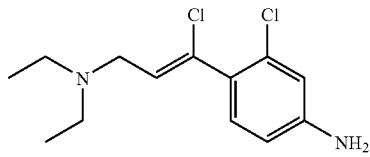

Z17) 3-chloro-4-((Z)-1-chloro-3-diethylamino-propenyl)-phenylamine

A solution of 15 mL conc. aqueous HCl in 15 mL EtOH was added to a suspension of 2.20 g (75.00 mmol) of iron powder and 2.20 g (8.25 mmol) of [3-(2-chloro-4-nitro-phenyl)-prop-2-ynyl]-diethyl-amine (intermediate product Z13a) in 20 mL EtOH with vigorous stirring and the mixture was stirred for 2 hours at 80° C. The reaction mixture was neutralised with 200 mL 10% aqueous sodium carbonate solution and exhaustively extracted with EtOAc. The combined org. phases were dried over magnesium sulphate and evaporated down i. vac.

Yield: 1.70 g (75% of theory)
$C_{13}H_{18}Cl_2N_2$ (M=273.208)
Calc.: molpeak(M+H)$^+$: 273/275/277
Found: molpeak (M+H)$^+$: 273/275/277 (Cl$_2$)
$R_f$ value: 0.71 (silica gel, EtOAc/MeOH/conc. aqueous ammonia 90:10:1)

Intermediate Product 18:

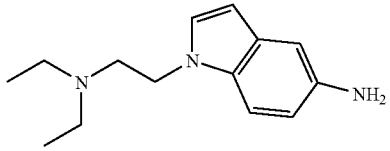

Z18a) diethyl-[2-(5-nitro-indol-1-yl)-ethyl]-amine 1.00 g (7.262 mmol) of potassium carbonate was added to a solution of 0.47 g (2.905 mmol) of 5-nitro-1H-indole and 0.50 g (2.905 mmol) of N,N-diethylamino-ethylchoride-hydrochloride in 5 mL DMF and the mixture was stirred for 3 hours at 80° C. The reaction mixture was diluted with water and exhaustively extracted with EtOAc. The combined org. phases were dried over magnesium sulphate and evaporated down i. vac.

Yield: 0.65 g (86% of theory)
$C_{14}H_{19}N_3O_2$ (M=261.326)
Calc.: molpeak(M+H)$^+$: 262
Found: molpeak (M+H)$^+$: 264

Z18b) 1-(2-diethylamino-ethyl)-1H-indol-5-ylamine 650 mg (2.487 mmol) of diethyl-[2-(5-nitro-indol-1-yl)-ethyl]-amine was added to a suspension of 200 mg Raney-Ni in 10 mL MeOH and the mixture was hydrogenated for 2 hours at RT under 20 psi H$_2$ atmosphere. The catalyst was filtered off and the filtrate evaporated down i. vac.

Yield: 520 mg (90% of theory)
$C_{14}H_{21}N_3$ (M=231.344)
Calc.: molpeak(M+H)$^+$: 232
Found: molpeak (M+H)$^+$: 232

Intermediate Product 19:

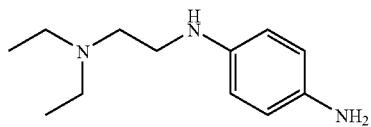

Z19a) N'-(2-chloro-4-nitro-phenyl)-N,N-diethyl-ethane-1,2-diamine 25 mL of 50% aqueous KOH solution was added to a solution of 1.00 g (5.795 mmol) of 2-chloro-4-nitro-phenylamine, 2.995 g (17.384 mmol) of (2-chloro-ethyl)-diethyl-amine and 0.66 g (2.898 mmol) of TEBAC in 50 mL toluene and the mixture was refluxed for 5 days. The reaction mixture was cooled to RT and exhaustively extracted with EtOAc. The combined org. phases were dried over magnesium sulphate, evaporated down i. vac. and the residue was purified by column chromatography (silica gel, dichloromethane/MeOH 4:1).

Yield: 1.2 g (76% of theory)
$C_{12}H_{18}ClN_3O_2$ (M=271.749)
Calc.: molpeak(M+H)$^+$: 272/274
Found: molpeak (M+H)$^+$: 272/274 (Cl)

Z19b) N-(2-diethylamino-ethyl)-benzene-1,4-diamine 1.20 mg (4.416 mmol) of N'-(2-chloro-4-nitro-phenyl)-N,N-diethyl-ethane-1,2-diamine was added to a suspension of 200 mg Raney-Ni in 20 mL MeOH and the mixture was hydrogenated for 2 hours at RT under 20 psi H$_2$ atmosphere. The catalyst was filtered off and the filtrate evaporated down i. vac.

Yield: 800 mg (87% of theory)
$C_{12}H_{21}N_3$ (M=207.321)
Calc.: molpeak(M+H)$^+$: 207
Found: molpeak (M+H)$^+$: 207

Intermediate Product 20:

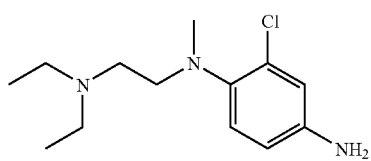

Z20a) N-(2-chloro-4-nitro-phenyl)-N',N'-diethyl-N-methyl-ethane-1,2-diamine 1.00 mL (6.181 mmol) of N,N-diethyl-N'-methyl-ethane-1,2-diamine was added to a solution of 1.085 g (6.181 mmol) of 2-chloro-1-fluoro-4-nitrobenzene and 1.03 mL (7.417 mmol) of triethylamine in 20 mL THF and the mixture was stirred for 48 hours at RT. The reaction mixture was combined with sat. aqueous sodium bicarbonate solution and exhaustively extracted with EtOAc. The combined org. extracts were dried over magnesium sulphate and evaporated down i. vac.

Yield: 1.60 mg (91% of theory)

$C_{13}H_{20}ClN_3O_2$ (M=285.776)

Calc.: molpeak(M+H)$^+$: 286/288

Found: molpeak (M+H)$^+$: 286/288 (Cl).

Z20b) 2-chloro-N'-(2-diethylamino-ethyl)-N'-methyl-benzene-1,4-diamine 1.60 mg (5.599 mmol) of N-(2-chloro-4-nitro-phenyl)-N',N'-diethyl-N-methyl-ethane-1,2-diamine was added to a suspension of 200 mg Raney-Ni in 20 mL MeOH and the mixture was hydrogenated for 2 hours at RT under 20 psi H$_2$ atmosphere. The catalyst was filtered off and the filtrate evaporated down i. vac.

Yield: 1.30 mg (91% of theory)

$C_{13}H_{22}ClN_3$ (M=255.793)

Calc.: molpeak(M+H)$^+$: 256/258

Found: molpeak (M+H)$^+$: 256/258

Intermediate Product 21:

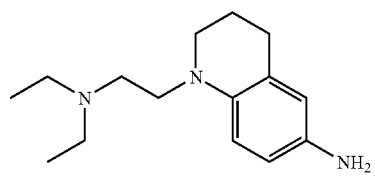

Z21a) N-[1-(2-diethylamino-ethyl)-1,2,3,4-tetrahydroquinolin-6-yl]-2,2,2-trifluoro-acetamide 50 mL of 50% aqueous KOH solution was added to a solution of 3.00 g (12.284 mmol) of 6-nitro-1,2,3,4-tetrahydro-quinoline, 6.342 g (36.852 mmol) of (2-chloro-ethyl)-diethyl-amine and 1.68 g (7.370 mmol) of TEBAC in 100 mL toluene and the mixture was stirred for 1 hour at 80° C. The reaction mixture was cooled to RT and exhaustively extracted with EtOAc. The combined org. phases were dried over magnesium sulphate, evaporated down i. vac. and the residue was purified by column chromatography (silica gel, EtOAc/MeOH 9:1).

Yield: 0.75 g (18% of theory)

$C_{17}H_{24}F_3N_3O$ (M=343.396)

Calc.: molpeak(M+H)$^+$: 344

Found: molpeak (M+H)$^+$: 344

Z21b) 1-(2-diethylamino-ethyl)-1,2,3,4-tetrahydro-quinolin-6-ylamine 1.1 mL 6 M aqueous NaOH solution was added to a solution of 0.75 g (2.184 mmol) of N-[1-(2-diethylamino-ethyl)-1,2,3,4-tetrahydro-quinolin-6-yl]-2,2,2-trifluoro-acetamide in 5 mL MeOH at 0° C. and the mixture was stirred for 15 minutes at 0° C. and for 1 hour at RT. The reaction mixture was evaporated down i. vac., sat. aqueous sodium bicarbonate solution was added and the mixture was exhaustively extracted with EtOAc. The combined org. extracts were dried over magnesium sulphate, evaporated down i. vac. and the residue was purified by column chromatography (silica gel, dichloromethane/MeOH/conc. aqueous ammonia 90:10:1).

Yield: 220 mg (41% of theory)

$C_{15}H_{25}N_3$ (M=247.387)

Calc.: molpeak(M+H)$^+$: 248

Found: molpeak (M+H)$^+$: 248

Intermediate Product 22:

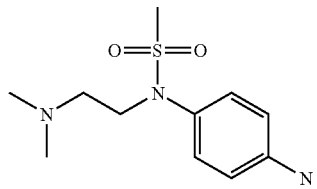

Z22a) N-(4-nitro-phenyl)-methanesulphonic acid amide 27.60 g (0.20 mol) of 4-nitroaniline was dissolved in 100 mL pyridine. At 0° C. 16.3 mL (0.21 mol) of methanesulphonic acid chloride were added dropwise so that the reaction temperature did not exceed 20-25° C. Then the mixture was stirred for 2.5 hours at RT. The reaction mixture was added to 800 mL ice water with stirring and stirred for 30 minutes. The precipitated solid was filtered off, washed with 500 mL water and 100 mL EtOH and dried.

Yield: 41.00 g (95% of theory)

melting point: 183-184° C.

$R_f$ value: 0.50 (silica gel, dichloromethane/EtOAc=90:10)

Z22b) N-(2-dimethylamino-ethyl)-N-(4-nitro-phenyl)-methanesulphonic acid amide 36.00 g (0.166 mol) of N-(4-nitro-phenyl)-methanesulphonic acid amide was dissolved in 2000 mL acetone. The solution was combined with 47.8 g (0.332 mol) of 1-chloro-2-dimethylaminoethane * HCl, 68.8 g (0.498 mol) of potassium carbonate, 5.0 g (0.033 mol) of sodium iodide and 50 mL water. It was refluxed for 16 hours with stirring. After the addition of another 23.9 g (0.166 mol) of 1-chloro-2-dimethylaminoethane * HCl, 45.9 g (0.332 mol) of potassium carbonate and 5.0 g (0.033 mol) of sodiumiodide, the mixture was refluxed for 5 hours with stirring. At RT the inorganic salts were filtered off. The filtrate was evaporated down i. vac. and the residue dissolved in EtOAc. The org. phase was washed 2× with semisat. aqueous sodium chloride solution, dried over magnesium sulphate, filtered and evaporated down i. vac.

Yield: 30.57 g (64% of theory)

$C_{11}H_{17}N_3O_4S$ (M=287.340)

Calc.: molpeak(M+H)$^+$: 288

Found: molpeak (M+H)$^+$: 288

$R_f$ value: 0.60 (silica gel, dichloromethane/MeOH/conc. aqueous ammonia=90:10:1)

Z22c) N-(4-amino-phenyl)-N-(2-dimethylamino-ethyl)-methanesulphonic acid amide 9.00 g (31.3 mmol) of N-(2-dimethylamino-ethyl)-N-(4-nitro-phenyl)-methanesulphonic acid amide were dissolved in 120 mL MeOH. After the addition of 1.0 g of 10% palladium/charcoal the mixture was hydrogenated for 1 hour at RT and 50 psi H$_2$ atmosphere. The reaction mixture was filtered and the filtrate evaporated down i. vac. The residue was stirred with ether/petroleum ether=1:1. The solid was filtered off, washed with ether/petroleum ether=1:1 and dried.

Yield: 7.65 g (95% of theory)

melting point: 151-152° C.

$R_f$ value: 0.40 (silica gel, dichloromethane/MeOH/conc. aqueous ammonia=90:10:1)

Intermediate Product 23:

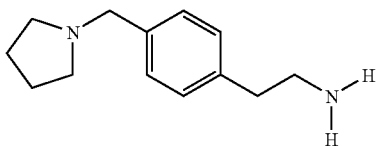

Z23a) ethyl 4-cyanomethyl-benzoate

A solution of 500 g (2.057 mol) of ethyl 4-bromomethyl-benzoate in 1000 ml of ethanol is added dropwise to a solution of 147.5 g (2.263 mol) of potassium cyanide in 250 mL of hot water. The reaction mixture is refluxed for one hour and stirred for 12 hours at RT. A further 73.7 g (0.5 mol) of potassium cyanide are added and the mixture is refluxed for two hours. The solid present in the reaction mixture is filtered off and the filtrate is filtered through a mixture of silica gel and activated charcoal. The filtrate obtained is evaporated down and the residue is poured onto 1000 mL of water. The aqueous solution is extracted with MTBE and the organic phase is extracted three times with water. Then the organic phase is dried over magnesium sulphate and the solvent is distilled off using the rotary evaporator. The product is purified by column chromatography on silica gel (petroleum ether/ethyl acetate 8:2).

Yield: 164.46 g (42.2% of theory)
$C_{11}H_{11}NO_2$ (M=189.216)
Calc.: molpeak (M+H)$^+$: 190
Found: molpeak (M+H)+: 190
$R_f$ value: 0.3 (silica gel, petroleum ether/EtOAc 8:2)

Z23b) 4-cyanomethyl-benzoic acid

A solution of 10 g (53 mol) of ethyl 4-cyanomethyl-benzoate and 2.02 mL of a 1 M sodium hydroxide solution in 100 mL of ethanol is refluxed for one hour. Then the reaction solution is evaporated down and the residue is combined with ice water. Concentrated hydrochloric acid is added dropwise to the reaction solution until no more precipitate is formed. The precipitate is filtered off, washed twice with water and dried.

Yield: 4.7 g (55% of theory)
$C_9H_7NO_2$ (M=161,162)
Calc.: molpeak (M–H)$^-$: 160
Found: molpeak (M–H)$^-$: 160

Z23c) (4-hydroxymethyl-phenyl)-acetonitrile 5.17 g (32 mol) of CDI are added to a solution of 4.7 g (29 mol) of 4-cyanomethyl-benzoic acid in 250 mL of tetrahydrofuran and stirred until no more gas is given off. This reaction mixture is added dropwise to a solution of 3.29 g (87 mol) of sodium borohydride in 200 mL of water in such a way that the temperature does not exceed 30° C. The mixture is stirred for two hours and the reaction mixture is adjusted to pH 3-4 with potassium hydrogen sulphate solution. Then it is extracted with EtOAc, the organic phase is dried over magnesium sulphate and the solvent is separated off using the rotary evaporator.

Yield: 2.6 g (60.9% of theory)
$C_9H_9NO$ (M=147.178)
Calc.: molpeak(M–H)$^-$: 146
Found: molpeak (M–H)$^-$: 146

Z23d) (4-bromomethyl-phenyl)-acetonitrile 0.86 mL (9 mmol) of phosphorus tribromide are added dropwise to a solution of 2.6 g (17.66 mmol) of (4-hydroxymethyl-phenyl)-acetonitrile in 25 mL MTBE at 0° C. After the reaction has ended the reaction mixture is combined with water at RT, the organic phase is separated off and these are extracted successively with sodium hydrogen carbonate solution and water. The organic phase is dried over magnesium sulphate and the solvent is distilled off using the rotary evaporator.

Yield: 2.9 g (78.1% of theory)
$C_9H_8BrN$ (M=210.075)
Calc.: molpeak(M+H)$^+$: 209/211
Found: molpeak (M+H)$^+$: 209/211

Z23e) (4-pyrrolidin-1-ylmethyl-phenyl)-acetonitrile 0.446 mL (5.44 mmol) of pyrrolidine and 1.366 g (9.882 mmol) of potassium carbonate are added to 20 mL of dimethylformamide. 1.038 g (4.941 mmol) of (4-bromomethyl-phenyl)-acetonitrile are added with stirring and the mixture is stirred for 12 hours at RT. The reaction mixture is evaporated down in the rotary evaporator and the residue is extracted with EtOAc and water. The organic phase is dried over magnesium sulphate and the solvent is removed using the rotary evaporator.

Yield: 0.732 g (74% of theory)
$C_{13}H_{16}N_2$ (M=200,286)
Calc.: molpeak(M+H)$^+$: 201
Found: molpeak (M+H)$^+$: 201
$R_f$ value: 0.5 (silica gel, dichloromethane/MeOH/conc. aqueous ammonia 90:10:1)

Z23f) 2-(4-pyrrolidin-1-ylmethyl-phenyl)-ethylamine

A reaction mixture of 0.73 g (3.66 mmol) of (4-pyrrolidin-1-ylmethyl-phenyl)-acetonitrile and 0.1 g Raney nickel in 25 mL of methanolic ammonia solution is hydrogenated for 9 hours at 50° C. under 3 bar hydrogen.

Yield: 0.72 g (96.4% of theory)
$C_{13}H_{20}N_2$ (M=204.31)
Calc.: molpeak(M+H)$^+$: 205
Found: molpeak (M+H)$^+$: 205
$R_f$ value: 0.23 (silica gel, dichloromethane/MeOH/conc. aqueous ammonia 90:10:1)

Intermediate Product 24

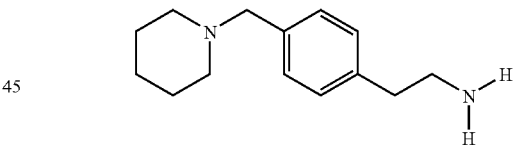

Z24a) (4-piperidin-1-ylmethyl-phenyl)-acetonitrile

Prepared analogously to Example Z23e from piperidine and (4-bromomethyl-phenyl)-acetonitrile.

Yield: 1.6 g (39% of theory)
$C_{14}H_{18}N_2$ (M=214.31)
Calc.: molpeak(M+H)$^+$: 215
Found: molpeak (M+H)$^+$: 215
$R_f$ value: 0.4 (silica gel, cyclohexane/EtOAc 1:1)

Z24b) 2-(4-piperidin-1-ylmethyl-phenyl)-ethylamine

Prepared analogously to Example Z23f from (4-piperidin-1-ylmethyl-phenyl)-acetonitrile Yield: 1.4 g (85.9% of theory)
$C_{14}H_{22}N_2$ (M=218.34)
Calc.: molpeak(M+H)$^+$: 219
Found: molpeak (M+H)$^+$: 219
$R_f$ value: 0.2 (silica gel, dichloromethane/ethanol/ammonia 20:1:0.1)

Intermediate Product 25:

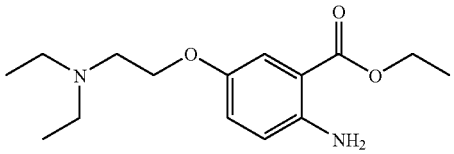

Z25a) Ethyl 5-hydroxy-2-nitrobenzoate

A solution of 5.00 g (27.304 mmol) 5-hydroxy-2-nitrobenzoic acid was refluxed in 200 mL ethanolic HCl for 5 h and then stirred for 48 h at RT. The reaction mixture was evaporated down i. vac. and diluted with EtOAc. The org. phase was washed with water, dried over magnesium sulphate and evaporated down i. vac. The crude product was used in the next reaction step without any further purification.

Yield: 5.00 g (87% of theory)
$C_9H_9NO_5$ (M=211,176)
Calc.: molpeak (M−H)⁻: 210
Found: molpeak (M−H)⁻: 210

Z25b) Ethyl 2-nitro-5-(2-diethylamino-ethoxy)-benzoate

Prepared analogously to intermediate product Z5a from ethyl 5-hydroxy-2-nitrobenzoate and (2-chloroethyl)-diethyl-amine-hydrochloride Yield: 6.30 g (85% of theory)
$C_{15}H_{22}N_2O_5$ (M=310,353)
Calc.: molpeak (M+H)⁺: 311
Found: molpeak (M+H)⁺: 311

Z25c) ethyl 2-amino-5-(2-diethylamino-ethoxy)-benzoate

Prepared analogously to intermediate product Z5b from ethyl 2-nitro-5-(2-diethylamino-ethoxy)-benzoate. Column chromatography (silica gel, EtOAc/MeOH/ammonia 90:10:1) yielded the product.

Yield: 4.00 g (71% of theory)
$C_{15}H_{24}N_2O_3$ (M=280,370)
Calc.: molpeak (M+H)⁺: 281
Found: molpeak (M+H)⁺: 281

Intermediate Product 26:
ethyl (4-bromo-2-chloro-phenoxy)-acetate

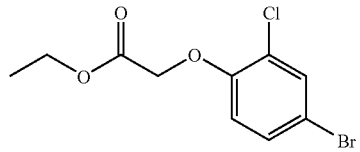

Z26) 14.5 mL (83.242 mmol) Hünig base was added to a solution of 7.800 g (37.222 mmol) 4-bromo-2-chlorophenol and 4.70 mL (41.537 mmol) ethyl bromoacetate in 100 mL DMF and the mixture was stirred for 4 h at 100° C. The reaction mixture was combined with water and exhaustively extracted with EtOAc. The combined org. phases were washed with saturated aqueous sodium bicarbonate, water and saturated aqueous NaCl, dried over sodium sulphate and evaporated down i. vac. The crude product was used in the next reaction step without any further purification.

Yield: 11.36 g (quant. yield)
$C_{10}H_{10}BrClO_3$ (M=293.546)
$R_f$ value: 0.65 (silica gel, dichloromethane)

Intermediate Product 27:

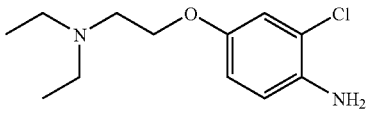

Z27a) [2-(3-chloro-4-nitro-phenoxy)-ethyl]-diethyl-amine

Prepared analogously to intermediate product Z5a starting from 3-chloro-4-nitro-phenol and (2-chloro-ethyl)-diethyl-amine.

Yield: 1.25 g (79% of theory)
$C_{12}H_{17}ClN_2O_3$ (M=272.734)
Calc.: molpeak (M+H)⁺: 273/275
Found: molpeak (M+H)⁺: 273/275 (Cl)
$R_f$ value: 0.44 (silica gel, dichloromethane/MeOH 9:1).

Z27b) 2-chloro-4-(2-diethylamino-ethoxy)-phenylamine

A suspension of 1.24 g (4.547 mmol) [2-(3-chloro-4-nitro-phenoxy)-ethyl]diethyl-amine (Z27a) and 300 mg Raney nickel in EtOAc was hydrogenated at RT and 3 bar. The catalyst was filtered off and the filtrate evaporated down i. vac.

Yield: 1.10 g (quant. yield)
$C_{12}H_{19}ClN_2O$ (M=242.751)
Calc.: molpeak (M+H)⁺: 243/245
Found: molpeak (M+H)⁺: 243/245 (Cl)
$R_f$ value: 0.41 (silica gel, dichloromethane/MeOH 9:1).

Intermediate Product 28:

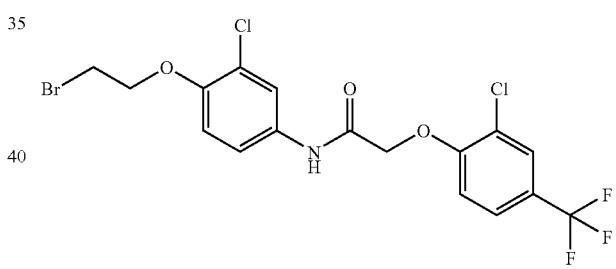

Z28a) N-(3-chloro-4-hydroxy-phenyl)-2-(2-chloro-4-trifluoromethyl-phenoxy)-acetamide 17.31 mL (98.510 mmol) Hünig base was added at RT to a solution of 7.600 g (29.850 mmol) (2-chloro-4-trifluoromethyl-phenoxy)-acetic acid (Z2b), 4.370 g (29.850 mmol) 4-amino-2-chloro-phenol and 10.56 g (32.840 mmol) TBTU in 550 mL as. THF and the mixture was stirred for 48 h. The reaction mixture was evaporated down i. vac. and diluted with EtOAc. The org. phase was washed with water, saturated aqueous sodium bicarbonate and saturated aqueous NaCl, dried over sodium sulphate and evaporated down i. vac. Column chromatography (silica gel, gradient dichloromethane/MeOH 99:1→19:1) yielded the product.

Yield: 4.200 g (37% of theory)
$C_{15}H_{10}Cl_2F_3NO_3$ (M=380.153)
Calc.: molpeak (M+H)⁺: 380/382/384
Found: molpeak (M+H)⁺: 380/382/384 (Cl₂)
$R_f$ value: 0.58 (silica gel, dichloromethane/MeOH 19:1).

Z28b) N-[4-(2-bromo-ethoxy)-3-chloro-phenyl]-2-(2-chloro-4-trifluoromethyl-phenoxy)-acetamide A solution of 3.66 mL (41.56 mmol) 1,2-dibromoethane in 5 mL DMF was slowly added at RT to a suspension of 1.580 g (4.156 mmol) N-(3-chloro-4-hydroxy-phenyl)-2-(2-chloro-4-trifluoromethyl-phenoxy)-acetamide and 2.880 g (8.310 mmol) potassium carbonate in 20 mL DMF and the mixture was stirred for 2.5 h. The reaction mixture was evaporated down i. vac. and diluted with EtOAc . The org. phase was washed with water and saturated aqueous NaCl, dried over magnesium sulphate and evaporated down i. vac. Column chromatography (silica gel, petroleum ether→dichloromethane) yielded the product.

Yield: 1.120 g (55% of theory)
$C_{17}H_{13}BrCl_2F_3NO_3$ (M=487.103)
Calc.: molpeak $(M+H)^+$: 486/488/490/492
Found: molpeak $(M+H)^+$: 486/488/490/492 ($BrCl_2$)
$R_f$ value: 0.72 (silica gel, dichloromethane/MeOH 49:1).

Intermediate Product 29:

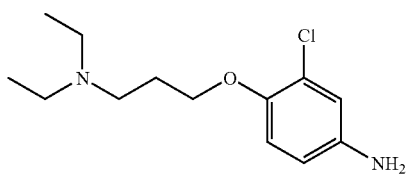

Z29a) [2-(2-chloro-4-nitro-phenoxy)-propyl]-diethyl-amine

At 0° C. 1.60 g (33.000 mmol) NaH (50% in oil) was added to a solution of 5.30 g (30.000 mmol) 3-chloro-4-fluoro-nitrobenzene and 4.30 g (33.000 mmol) 3-diethylamino-propanol in 50 mL abs. DMF and the mixture was stirred for 2 h at 0° C. and for 1 h at RT. The reaction mixture was evaporated down i. vac. and diluted with EtOAc . The org. phase was washed with water, dried over sodium sulphate and evaporated down i. vac. Column chromatography (silica gel, dichloromethane/EtOH/conc. aqueous ammonia 90:10:0.1) yielded the product.

Yield: 8.00 g (93% of theory)
$C_{13}H_{19}ClN_2O_3$ (M=286.761)
$R_f$ value: 0.30 (silica gel, dichloromethane/MeOH/conc. aqueous ammonia 90:10:0.1).

Z29b) 3-chloro-4-(3-diethylamino-propoxy)-phenylamine

A suspension of 8.00 g (27.900 mmol) [2-(2-chloro-4-nitro-phenoxy)-propyl]-diethyl-amine (Z29a) and 0.80 g Raney nickel in 170 mL MeOH was hydrogenated for 8 h at RT and 50 psi. The catalyst was filtered off and the filtrate evaporated down i. vac.

Yield: 6.70 g (93% of theory)
$C_{13}H_{21}ClN_2O$ (M=256.778)
Calc.: molpeak $(M+H)^+$: 257/259
Found: molpeak $(M+H)^+$: 257/259 (Cl)
$R_f$ value: 0.40 (silica gel, dichloromethane/MeOH/conc. aqueous ammonia 50:10:0.1).

Intermediate Product 30:

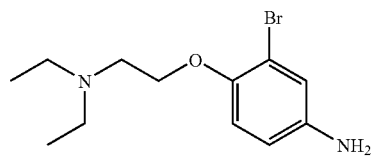

Z30a) [2-(2-bromo-4-nitro-phenoxy)-ethyl]-diethyl-amine

Prepared analogously to Intermediate product Z29a starting from 2-bromo-1-fluoro-4-nitro-benzene and 2-diethylamino-ethanol.

Yield: 0.790 g (83% of theory)
$C_{12}H_{17}BrN_2O_3$ (M=317.185)
Calc.: molpeak $(M+H)^+$: 317/319
Found: molpeak $(M+H)^+$: 317/319 (Br)
$R_f$ value: 0.48 (silica gel, dichloromethane/MeOH 9:1).

Z30b) 3-bromo-4-(2-diethylamino-ethoxy)-phenylamine

Prepared analogously to Intermediate product Z29b starting from [2-(2-bromo-4-nitro-phenoxy)-ethyl]-diethylamine (Z30a).

Yield: 0.670 g (96% of theory)
$C_{12}H_{19}BrN_2O$ (M=287.202)
Calc.: molpeak $(M+H)^+$: 287/289
Found: molpeak $(M+H)^+$: 287/289 (Br)
$R_f$ value: 0.30 (silica gel, dichloromethane/MeOH 9:1).

Intermediate Product 31:

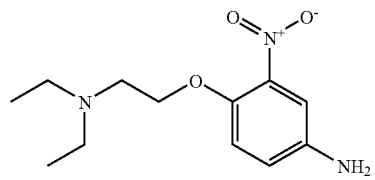

Z31 a) N-[4-(2-diethylamino-ethoxy)-3-nitro-phenyl]-acetamide 0.737 g (7.286 mmol) potassium nitrate was added batchwise at −10° C. to a solution of 1.520 g (6.072 mmol) N-[4-(2-diethylamino-ethoxy)-phenyl]-acetamide in 25 mL conc. sulphuric acid and the mixture was stirred for 1 h at −10° C. The reaction mixture was poured onto a mixture of ice and conc. aqueous ammonia and the aqueous phase was exhaustively extracted with EtOAc. The combined org. phases were dried over sodium sulphate and evaporated down i. vac.

Yield: 1.8 g (quant. yield)
$C_{14}H_{21}N_3O_4$ (M=295.341)
Calc.: molpeak $(M+H)^+$: 296
Found: molpeak $(M+H)^+$: 296
$R_f$ value: 0.51 (Alox, dichloromethane/MeOH 39:1).

Z31b) 4-(2-diethylamino-ethoxy)-3-nitro-phenylamine

A solution of 1.85 g (6.264 mmol) N-[4-(2-diethylaminoethoxy)-3-nitro-phenyl]-acetamide (Z31a) in semiconc. aqueous HCl was stirred for 2 h at 100° C., cooled to RT, made basic with ice and conc. aqueous ammonia and the aqueous phase was exhaustively extracted with EtOAc. The combined org. phases were washed with water and dried over sodium sulphate.

Yield: 1.38 g (87% of theory)
$C_{12}H_{19}N_3O_3$ (M=253.304)
Calc.: molpeak $(M+H)^+$: 254
Found: molpeak $(M+H)^+$: 254
$R_f$ value: 0.68 (Alox, dichloromethane/MeOH 39:1).

Intermediate Product 32:

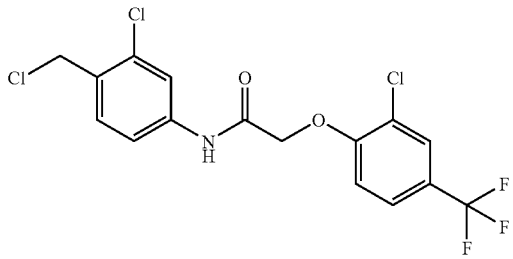

Z32a) N-(3-chloro-4-hydroxymethyl-phenyl)-2-(2-chloro-4-trifluoromethyl-phenoxy)-acetamide 0.55 mL (4.200 mmol) of isopropyl chloroformate was slowly added dropwise at −5° C. to a solution of 1.018 g (4.000 mmol) of (2-chloro-4-trifluoromethyl-phenoxy)-acetic acid (Z2b) and 0.46 mL (4.200 mmol) N-methylmorpholine in 5 mL abs. DMF and the mixture was stirred for another 5 min. 0.662 g (4.200 mmol) (4-amino-2-chlorophenyl)-methanol was added at −5° C., the mixture was stirred for 2 h at RT and then the reaction mixture was poured onto ice water. The precipitate was filtered off, washed with water and dried in HV.

Yield: 1.360 g (83% of theory)
$C_{16}H_{12}Cl_2F_3NO_3$ (M=394.180)
$R_f$ value: 0.50 (silica gel, dichloromethane/MeOH 19:1).

Z32b) N-(3-chloro-4-chloromethyl-phenyl)-2-(2-chloro-4-trifluoromethyl-phenoxy)-acetamide 1.12 mL (16.440 mmol) thionyl chloride was added to a solution of 1.620 g (4.110 mmol) N-(3-chloro-4-hydroxymethyl-phenyl)-2-(2-chloro-4-trifluoromethyl-phenoxy)-acetamide (Z32a) in 30 mL toluene and the mixture was stirred for 2 h at 80° C. The reaction mixture was evaporated down i. vac. and the residue recrystallised from ether/petroleum ether. The precipitate was filtered off, washed with petroleum ether and dried in a HV.

Yield: 1.100 g (65% of theory)
$C_{16}H_{11}Cl_3F_3NO_2$ (M=412.626)
Calc.: molpeak (M+H)⁺: 412/414/416/418
Found: molpeak (M+H)⁺: 412/414/416/418 (Cl₃)
$R_f$ value: 0.69 (silica gel, petroleum ether/EtOAc 3:1).

Intermediate Product 33:

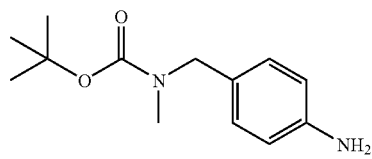

Z33a) tert-butyl methyl-(4-nitro-benzyl)-carbaminate 17.68 g (81.00 mmol) Boc-anhydride was slowly added at 0° C. to a solution of 13.40 g (81.00 mmol) methyl-(4-nitrobenzyl)-amine in 25 mL EtOAc and the mixture was stirred for 3 h at RT. The org. phase was washed with water, dried over sodium sulphate and evaporated down i. vac.

Yield: 21.36 g (99% of theory)
$C_{13}H_{18}N_2O_4$ (M=266.299)
$R_f$ value: 0.60 (silica gel, petroleum ether/EtOAc 3:7).

Z33b) tert-butyl (4-amino-benzyl)-methyl-carbaminate

A suspension of 23.00 g (86.00 mmol) tert-butyl methyl-(4-nitro-benzyl)-carbaminate (Intermediate product Z33a) and 2.30 g Raney nickel in 460 mL EtOH/EtOAc (1:1) was hydrogenated at RT and 3 bar. The catalyst was filtered off, the filtrate evaporated down i. vac. and the residue purified by column chromatography (silica gel, petroleum ether/EtOAc 1:1).

Yield: 9.23 g (45% of theory)
$C_{13}H_{20}N_2O_2$ (M=236.317)
Calc.: molpeak (M+H)⁺: 237
Found: molpeak (M+H)⁺: 237
$R_f$ value: 0.40 (silica gel, petroleum ether/EtOAc 1:1).

Intermediate Product 34:

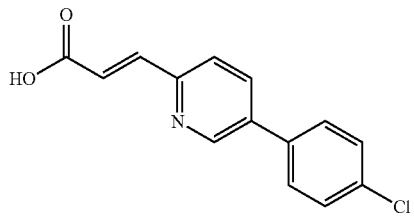

Z34a) ethyl (E)-3-[5-(4-chloro-phenyl)-pyridin-2-yl]-acrylate 2.000 g (5.560 mmol) (ethoxycarbonylmethylene)-triphenylphosphorane was added at RT to a solution of 1.100 g (5.050 mmol) 5-(4-chloro-phenyl)-pyridine-2-carbaldehyde in 50 mL abs. THF and the mixture was stirred for 4 h at RT. The reaction mixture was evaporated down i. vac. and the residue purified by column chromatography (Alox, neutral, act. II-III, petroleum ether/EtOAc 5:1). Recrystallisation from petroleum ether yielded the product.

Yield: 1.200 g (83% of theory)
$C_{16}H_{14}ClNO_2$ (M=287.748)
Calc.: molpeak (M+H)⁺: 288/290
Found: molpeak (M+H)⁺: 288/290 (Cl)
$R_f$ value: 0.60 (silica gel, petroleum ether/EtOAc 5:1).

Z34b) (E)-3-[5-(4-chloro-phenyl)-pyridin-2-yl]-acrylic acid 12.6 mL aqueous NaOH (1 M) was added at RT to a suspension of 1.200 g (4.200 mmol) ethyl (E)-3-[5-(4-chloro-phenyl)-pyridin-2-yl]-acrylate (Z34a) in 50 mL EtOH and the mixture was stirred for 1 h . 12.6 mL aqueous HCl (1 M) was added at 0° C. The precipitate formed was filtered off, washed with water and dried i. vac. at 100° C.

Yield: 1.000 g (92% of theory)
$C_{14}H_{10}ClNO_2$ (M=259.694)
Calc.: molpeak (M+H)⁺: 260/262
Found: molpeak (M+H)⁺: 260/262 (Cl)
$R_f$ value: 0.40 (silica gel, dichloromethane/MeOH 9:1).

Intermediate Product 35:

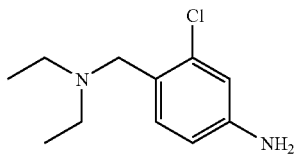

Z35a) (2-chloro-4-nitro-benzyl)-diethyl-amine 0.80 g (3.883 mmol) 2-chloro-1-chloromethyl-4-nitrobenzene was added to a solution of 2.60 mL (25.000 mmol) diethylamine in 50 mL THF and the mixture was refluxed for 8 h. The reaction mixture was evaporated down i. vac. and the residue was taken up in EtOAc. The org. phase was washed with water, dried over sodium sulphate and evaporated down i. vac.

Yield: 0.750 g (80% of theory)
$C_{11}H_{15}ClN_2O_2$ (M=242.707)
Calc.: molpeak (M+H)$^+$: 243/245
Found: molpeak (M+H)$^+$: 243/245 (Cl)
$R_f$ value: 0.50 (Alox, petroleum ether).

Z35b) 3-chloro-4-diethylaminomethyl-phenylamine

A suspension of 0.700 g (2.884 mmol) (2-chloro-4-nitro-benzyl)-diethyl-amine (Z35a) and 0.400 g Raney nickel in 20 mL THF was hydrogenated for 7.5 h at RT and 25 psi. The catalyst was filtered off and the filtrate was evaporated down i. vac. The crude product was purified by column chromatography (Alox, neutral, act. II-III, petroleum ether/EtOAc 4:1).

Yield: 0.510 g (83% of theory)
$C_{11}H_{17}ClN_2$ (M=212.725)
Calc.: molpeak (M+H)$^+$: 213/215
Found: molpeak (M+H)$^+$: 213/215 (Cl)
$R_f$ value: 0.58 (Alox, petroleum ether/EtOAc 3:1).

Intermediate Product 36:

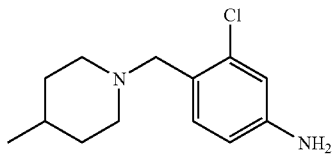

Z36a) 1-(2-chloro-4-nitro-benzyl)-4-methyl-piperidine 1.00 g (4.854 mmol) 2-chloro-1-chloromethyl-4-nitrobenzene was slowly added at RT to 2.00 mL (16.223 mmol) 4-methylpiperidine and the mixture was stirred for a further 15 min. EtOAc was added, the org. phase was washed with water, dried over sodium sulphate and evaporated down i. vac.

$C_{13}H_{17}ClN_2O_2$ (M=268.746)
Calc.: molpeak (M+H)$^+$: 269/271
Found: molpeak (M+H)$^+$: 269/271 (Cl)
$R_f$ value: 0.40 (Alox, petroleum ether).

Z36b) 3-chloro-4-(4-methyl-piperidin-1-ylmethyl)-phenylamine

Prepared analogously to Intermediate product Z35b starting from 1-(2-chloro-4-nitro-benzyl)-4-methyl-piperidine (Z36a). The crude product was purified by column chromatography (Alox, neutral, act. II-III, gradient petroleum ether/EtOAc 6:1→3:1).

Yield: 0.930 g (80% of theory)
$C_{13}H_{19}ClN_2$ (M=238.763)
Calc.: molpeak (M+H)$^+$: 239/241
Found: molpeak (M+H)$^+$: 239/241 (Cl)
$R_f$ value: 0.58 (Alox, petroleum ether/EtOAc 3:1)

Intermediate Product 37:

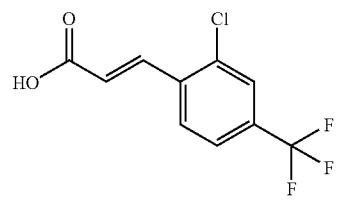

Z37a) ethyl (E)-3-(2-chloro-4-trifluoromethyl-phenyl)-acrylate 0.157 g (0.686 mmol) palladium(II)acetate, 0.800 g (2.550 mmol) tri-o-tolylphosphine and 23.94 mL (171.73 mmol) triethylamine was added to 21.48 g (68.69 mmol) 2-chloro-1-iodo-4-trifluoromethyl-benzene and 10.45 mL (96.17 mmol) ethyl acrylate in 100 mL acetonitrile and the mixture was refluxed for 6 h. The reaction mixture was evaporated down i. vac. and the residue triturated with EtOAc. The precipitate was filtered off and dried in a HV. The crude product was used in the next reaction step without any further purification.

Yield: 19.1 g (quant. yield)
$C_{12}H_{10}ClF_3O_2$ (M=278.661)
$R_f$ value: 0.65 (silica gel, petroleum ether/EtOAc 6:1).

Z37b) (E)-3-(2-chloro-4-trifluoromethyl-phenyl)-acrylic acid

A solution of 5.80 g (145.00 mmol) NaOH in 30 mL water was slowly added to a solution of 19.1 g (68.61 mmol) (E)-3-(2-chloro-4-trifluoromethyl-phenyl)-acrylate ethyl (Z37a) in 100 mL EtOH and the mixture was stirred for 1 h at RT. EtOH was concentrated by evaporation i. vac., the aqueous phase was washed with EtOAc and acidified to pH 1 with semiconc. aqueous HCl. The precipitate was filtered off, washed with water and dried in a HV.

Yield: 15.80 g (92% of theory)
$C_{10}H_6ClF_3O_2$ (M=250.606)
Calc.: molpeak (M+H)$^+$: 249/250
Found: molpeak (M+H)$^+$: 249/250 (Cl)
$R_f$ value: 0.50 (silica gel, petroleum ether/EtOAc 3:1).

Intermediate Product 38:

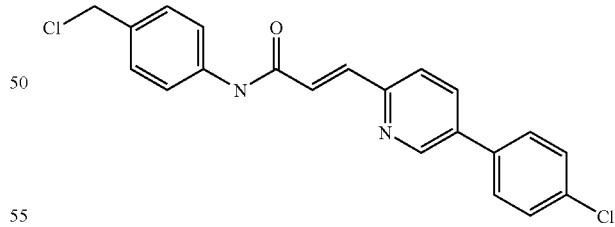

Z38a) (E)-3-[5-(4-chloro-phenyl)-pyridin-2-yl]-N-(4-hydroxymethyl-phenyl)-acrylamide 90 μL (0.720 mmol) isobutyl chloroformate was added dropwise at −6° C. to a solution of 0.180 g (0.690 mmol) (E)-3-[5-(4-chloro-phenyl)-pyridin-2-yl]-acrylic acid (Z34b) and 80 μL (0.720 mmol) N-methylmorpholine in 5 mL abs. DMF and the mixture was stirred for 5 min. 90 mg (0.720 mmol) 4-amino-benzylalcohol was added and the mixture was stirred for 2 h. The reaction mixture was poured onto water and the precipitate was filtered off. The precipitate was suspended in toluene, concentrated by evaporation i. vac., then stirred with ether and dried i. vac. at 80° C.

Yield: 0.210 g (83% of theory)
$C_{21}H_{17}ClN_2O_2$ (M=364.835)
Calc.: molpeak (M+H)$^+$: 365/367
Found: molpeak (M+H)$^+$: 365/367 (Cl)
$R_f$ value: 0.30 (silica gel, dichloromethane/MeOH/HOAC 90:10:0.1).

Z38b) (E)-N-(4-chloromethyl-phenyl)-3-[5-(4-chloro-phenyl)-pyridin-2-yl]-acrylamide 50 µL (0.680 mmol) thionyl chloride was added to a suspension of 0.190 g (0.520 mmol) (E)-3-[5-(4-chloro-phenyl)-pyridin-2-yl]-N-(4-hydroxymethyl-phenyl)-acrylamide (Z38a) in 20 mL dichloromethane and the mixture was stirred for 2 h at RT. Another 50 µL thionyl chloride were added and the mixture was again stirred for 3 h. The solvent was concentrated by evaporation i. vac., the residue taken up twice in toluene and concentrated by evaporation i. vac. The crude product was obtained as the HCl salt and used in the next reaction step without any further purification.

Yield: 0.132 g (60% of theory)
$C_{21}H_{16}Cl_2N_2O$ * HCl (M=419.741)
Calc.: molpeak (M+H)$^+$: 383/385/387
Found: molpeak (M+H)$^+$: 383/385/387 (Cl$_2$)
$R_f$ value: 0.90 (silica gel, dichloromethane/MeOH/conc. aqueous ammonia 90:10:0.1).

Intermediate Product 39:

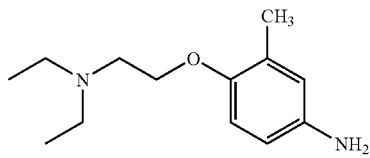

Z39a) diethyl-[2-(2-methyl-4-nitro-phenoxy)-ethyl]-amine

At 0° C. 0.92 g (19.2 mmol) sodium hydride (50% in oil) was added to a solution of 2.70 g (17.4 mmol) 2-fluoro-5-nitro-toluene and 2.54 mL (19.2 mmol) 2-diethylaminoethanol in 50 mL DMF under an argon atmosphere and the mixture was stirred for 2 hours at 0° C. and for 1 hour at ambient temperature. The solvent was removed, the residue was taken up in ethyl acetate and extracted with water. The organic phase was dried over sodium sulphate and evaporated down i. vac. Then it was purified by silica gel column chromatography with dichloromethane/methanol 9:1 as eluant.

Yield: 3.1 g (71% of theory)
$C_{13}H_{20}N_2O_3$ (M=252.31)
Calc.: molpeak (M+H)$^+$: 253
Found: molpeak (M+H)$^+$: 253
$R_f$ value: 0.60 (silica gel, dichloromethane/MeOH 9:1)

Z39b) 4-(2-diethylamino-ethoxy)-3-methyl-phenylamine 3.10 g (12.3 mmol) diethyl-[2-(2-methyl-4-nitro-phenoxy)-ethyl]-amine were dissolved in 250 mL ethyl acetate, 0.55 g Raney nickel was added and the mixture was hydrogenated for 36 hours at 50 psi and ambient temperature. The catalyst was filtered off and the filtrate evaporated down i. vac.

Yield: 2.70 g (99% of theory)
$C_{13}H_{22}N_2O$ (M=222.33)
Calc.: molpeak (M+H)$^+$: 223
Found: molpeak (M+H)$^+$: 223

$R_f$ value: 0.35 (silica gel, dichloromethane/methanol 9:1)

Intermediate Product 40:

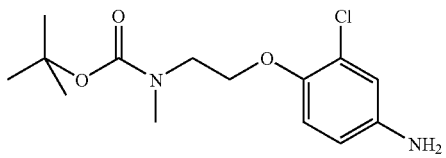

Z40a) N-tert.butoxycarbonyl-N-methyl-[2-(2-chloro-4-nitro-phenoxy)-ethyl]-amine

The product was obtained analogously to Intermediate product 29a starting from 2.00 g (11.4 mmol) 3-chloro-4-fluoro-nitrobenzene, 2.10 g (12.0 mmol) N-tert.butoxycarbonyl-N-methyl-aminoethanol and 820 mg (17.1 mmol) sodium hydride (50% in oil).

Yield: 3.77 g (100% of theory)
$C_{14}H_{19}ClN_2O_5$ (M=330.77)
$R_f$ value: 0.35 (silica gel, petroleum ether/ethyl acetate 4:1)

Z40b) 4-(N-tert.butoxycarbonyl-2-methylamino-ethoxy)-3-chloro-phenylamine

The product was obtained analogously to Intermediate product 29b starting from 4.19 g (12.7 mmol) N-tert.butoxycarbonyl-N-methyl-[2-(2-chloro-4-nitro-phenoxy)-ethyl]-amine by hydrogenation with 500 mg Raney nickel at 3 bar.

Yield: 3.68 g (94% of theory)
$C_{14}H_{21}ClN_2O_3$ (M=300.78)
Calc.: molpeak (M+H)$^+$: 301/303
Found: molpeak (M+H)$^+$: 301/303
$R_f$ value: 0.60 (silica gel, dichloromethane/methanol 19:1)

Intermediate Product 41:

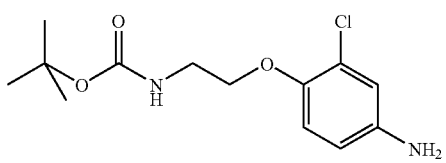

Z41 a) N-tert. butoxycarbonyl-[2-(2-chloro-4-nitro-phenoxy)-ethyl]-amine

The product was obtained analogously to Intermediate product 29a starting from 2.00 g (11.4 mmol) 3-chloro-4-fluoro-nitrobenzene, 1.85 mL (12.0 mmol) N-tert.butoxycarbonyl-aminoethanol and 820 mg (17.1 mmol) sodium hydride (50% in oil).

Yield: 2.25 g (62% of theory)
$C_{13}H_{17}ClN_2O_5$ (M=316.74)
Calc.: molpeak (M−H)$^-$: 315/317
Found: molpeak (M−H)$^-$: 315/317
$R_f$ value: 0.45 (silica gel, petroleum ether/ethyl acetate 4:1)

Z41 b) 4-(N-tert. butoxycarbonyl-2-amino-ethoxy)-3-chloro-phenylamine

The product was obtained analogously to Intermediate product 29b starting from 2.25 g (7.10 mmol) N-tert.butoxycarbonyl-[2-(2-chloro-4-nitro-phenoxy)-ethyl]-amine by hydrogenation with 500 mg Raney nickel at 3 bar.

Yield: 1.95 g (81% of theory)
C$_{13}$H$_{19}$ClN$_2$O$_3$ (M=286.76)
Calc.: molpeak (M+H)$^+$: 287/289
Found: molpeak (M+H)$^+$: 287/289
R$_f$ value: 0.55 (silica gel, dichloromethane/methanol 19:1)

Intermediate Product 42:

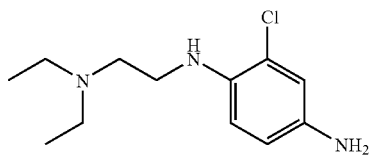

Z42a) N'-(2-chloro-4-nitro-phenyl)-N,N-diethyl-ethane-1,2-diamine 9.440 g (34.120 mmol) potassium carbonate was added to a solution of 4.96 mL (34.160 mmol) N',N'diethyl-ethane-1,2-diamine in 64 mL DMF and the mixture was stirred for 15 min. at RT. 6.120 g (68.240 mmol) 2-chloro-1-fluoro-4-nitro-benzene was added and the resulting mixture was stirred for 16 h at RT. The reaction mixture was poured onto ice water, the precipitate was filtered off and purified by column chromatography (Alox, neutral, act. II-III, dichloromethane/MeOH 49:1).

Yield: 9.20 g (99% of theory)
C$_{12}$H$_{18}$ClN$_3$O$_2$ (M=271.749)
Calc.: molpeak (M+H)$^+$: 272/274
Found: molpeak (M+H)$^+$: 272/274
R$_f$ value: 0.72 (Alox, dichloromethane/methanol 49:1)

Z42b) 2-chloro-N'-(2-diethylamino-ethyl)-benzene-1,4-diamine

A suspension of 8.850 g (32.570 mmol) N'-(2-chloro-4-nitro-phenyl)-N,N-diethyl-ethane-1,2-diamine and 4.00 g Raney nickel in 200 mL THF was hydrogenated for 7 h at 20 psi hydrogen pressure. The catalyst was filtered off, the filtrate evaporated down i. vac. and the residue purified by column chromatography (Alox, neutral, act. II-III, gradient dichloromethane/MeOH 100:0→24:1).

Yield: 6.150 g (78% of theory)
C$_{12}$H$_{20}$ClN$_3$ (M=241.766)
Calc.: molpeak (M+H)$^+$: 242/244
Found: molpeak (M+H)$^+$: 242/244
R$_f$ value: 0.62 (Alox, dichloromethane/methanol 49:1)

Intermediate Product 43:

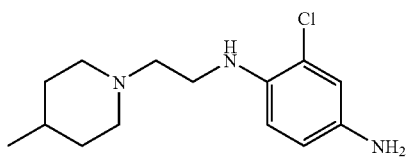

Z43a) tert-butyl [2-(4-methyl-piperidin-1-yl)-ethyl]-carbaminate

A solution of 10.00 g (43.280 mmol) tert-butyl (2-bromoethyl)-carbaminate and 11.60 mL (96.000 mmol) 4-methyl-piperidine in 100 mL dichloromethane was stirred for 16 h at RT. The crude product was filtered through Alox (neutral, act. II-III, dichloromethane/MeOH 49:1) and the filtrate was evaporated down i. vac.

Yield: 6.150 g (78% of theory)
C$_{13}$H$_{26}$N$_2$O$_2$ (M=242.364)
Calc.: molpeak (M+H)$^+$: 243
Found: molpeak (M+H)$^+$: 243
R$_f$ value: 0.65 (Alox, dichloromethane/methanol 19:1)

Z43b) 2-(4-methyl-piperidin-1-yl)-ethylamine-bis-trifluoroacetate 11.56 mL (150 mmol) TFA was added at RT to a solution of 8.500 g (35.070 mmol) tert-butyl [2-(4-methyl-piperidin-1-yl)-ethyl]-carbaminate in 100 mL dichloromethane and the mixture was stirred for 16 h at RT. The reaction mixture was evaporated down i. vac. and the residue stirred with ether. The precipitate was filtered off, washed with ether and dried in a HV. The product was obtained as the bis-trifluoroacetate salt.

Yield: 12.10 g (93% of theory)
C$_8$H$_{18}$N$_2$*2 C$_2$HF$_3$O$_2$ (M=370.295)
Calc.: molpeak (M+H)$^+$: 143
Found: molpeak (M+H)$^+$: 143

Z43c) (2-chloro-4-nitro-phenyl)-[2-(4-methyl-piperidin-1-yl)-ethyl]-amine

Prepared analogously to Intermediate product Z42a starting from 12.02 g (32.450 mmol) 2-(4-methyl-piperidin-1-yl)-ethylamine-bis-trifluoroacetate, 5.810 g (32.450 mmol) 2-chloro-1-fluoro-4-nitro-benzene and 17.94 g (129.64 mmol) potassium carbonate.

Yield: 8.85 g (92% of theory)
C$_{14}$H$_{20}$ClN$_3$O$_2$ (M=297.787)
Calc.: molpeak (M+H)$^+$: 298/300
Found: molpeak (M+H)$^+$: 298/300

Z43d) 2-chloro-N'-[2-(4-methyl-piperidin-1-yl)-ethyl]-benzene-1,4-diamine

Prepared analogously to Intermediate product Z42b starting from 8.715 g (29.270 mmol) (2-chloro-4-nitro-phenyl)-[2-(4-methyl-piperidin-1-yl)-ethyl]-amine.

Yield: 7.00 g (89% of theory)
C$_{14}$H$_{22}$ClN$_3$ (M=267.805)
Calc.: molpeak (M+H)$^+$: 268/280
Found: molpeak (M+H)$^+$: 268/280 (Cl)
R$_f$ value: 0.60 (Alox, dichloromethane/methanol 49:1)

Intermediate Product 44:

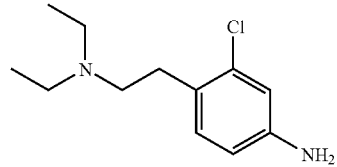

Z44a) (2-chloro-4-nitro-phenyl)-acetyl-chloride

A suspension of 8.100 g (37.571 mmol) (2-chloro-4-nitro-phenyl)-acetic acid in 40 mL thionyl chloride was refluxed for 2 h, cooled to RT and evaporated down i. vac. The crude product was used in the next reaction step without any further purification.

Yield: 8.80 g (quant. yield)
C$_8$H$_5$Cl$_2$NO$_3$ (M=234.040)

Z44b) 2-(2-chloro-4-nitro-phenyl)-N,N-diethyl-acetamide

At 0° C. a solution of 3.20 g (13.673 mmol) (2-chloro-4-nitro-phenyl)-acetyl-chloride in 50 mL EtOAc was slowly added dropwise to a solution of 5.67 mL (54.000 mmol) diethylamine in 50 mL EtOAc, then the cooling bath was removed and the mixture was stirred for 2 h at RT . The reaction mixture was diluted with EtOAc, the org. phase was washed with water and saturated aqueous NaCl solution, dried over sodium sulphate and evaporated down i. vac.

Yield: 3.70 g (quant. yield)
$C_{12}H_{15}ClN_2O_3$ (M=270.718)
Calc.: molpeak (M+H)$^+$: 271/273
Found: molpeak (M+H)$^+$: 271/273 (Cl)
$R_f$ value: 0.45 (silica gel, petroleum ether/EtOAc 1:1)

Z44c) [2-(2-chloro-4-nitro-phenyl)-ethyl]-diethyl-amine 65 mL (65.000 mmol) borane (1 M in THF) was added at RT to a solution of 3.702 g (13.673 mmol) 2-(2-chloro-4-nitro-phenyl)-N,N-diethyl-acetamide in 130 mL THF and the mixture was stirred for 4 h . The reaction mixture was evaporated down i. vac., the residue was combined with 15 mL MeOH and 15 mL semiconc. aqueous HCl and heated to 100° C. for 15 min. Water was added, the mixture was made basic with aqueous sodium carbonate solution and the aqueous phase was extracted with EtOAc. The combined org. phases were washed with water and saturated aqueous NaCl solution, dried over sodium sulphate and evaporated down i. vac. The crude product was purified by column chromatography (Alox, neutral, act. II-III, gradient petroleum ether/EtOAc 8:1→4:1).

Yield: 2.10 g (60% of theory)
$C_{12}H_{17}ClN_2O_2$ (M=256.734)
$R_f$ value: 0.63 (Alox, petroleum ether/EtOAc 3:1)

Z44d) 3-chloro-4-(2-diethylamino-ethyl)-phenylamine

A suspension of 2.00 g (7.790 mmol) [2-(2-chloro-4-nitro-phenyl)-ethyl]-diethyl-amine and 0.80 g Raney nickel in THF was hydrogenated for 2.5 h at RT and 25 psi hydrogen pressure. The catalyst was filtered off and the filtrate evaporated down i. vac.

Yield: 3.70 g (quant. yield)
$C_{12}H_{19}ClN_2$ (M=226.752)
Calc.: molpeak (M+H)$^+$: 227/229
Found: molpeak (M+H)$^+$: 227/229 (Cl)

Intermediate Product 45:

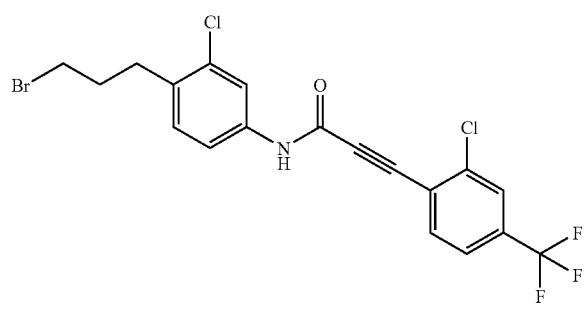

Z45a) 3-(2-chloro-4-nitro-phenyl)-prop-2-yn-1-ol 1.059 mL (18.000 mmol) propargylalcohol was added under argon to 5.013 g (21.200 mmol) 4-bromo-3-chloronitrobenzene, 8.72 mL (63.000 mmol) triethylamine, 1.265 g (1.800 mmol) bis(triphenylphosphine)-palladium(II)dichloride and 0.343 g (1.800 mmol) copper(I)iodide in 50 mL acetonitrile and the mixture was refluxed for 4 h. The reaction mixture was filtered through Celite and the filtrate was evaporated down i. vac. The residue was dissolved in EtOAc, the org. phase was washed with water, dried over sodium sulphate and evaporated down i. vac. The crude product was purified by column chromatography (silica gel, petroleum ether/EtOAc 3:1) and by trituration with petroleum ether.

Yield: 2.550 g (67% of theory)
$C_9H_6ClNO_3$ (M=211.606)
Calc.: molpeak (M+H)$^+$: 211/213
Found: molpeak (M+H)$^+$: 211/213 (Cl)
$R_f$ value: 0.38 (silica gel, dichloromethane/MeOH 50:1)

Z45b) 3-(2-chloro-4-nitro-phenyl)-propan-1-ol

A suspension of 1.25 g (6.808 mmol) 3-(2-chloro-4-nitro-phenyl)-prop-2-yn-1-ol and 1.00 g Raney nickel in 50 mL THF was hydrogenated for 12 h at RT and 25 psi hydrogen pressure. The catalyst was filtered off and the filtrate was evaporated down i. vac.

Yield: 1.26 g (quant. yield)
$C_9H_{12}ClNO$ (M=185.655)
Calc.: molpeak (M+H)$^+$: 186/188
Found: molpeak (M+H)$^+$: 186/188 (Cl)
$R_f$ value: 0.33 (silica gel, dichloromethane/MeOH 19:1)

Z45c) (E)-N-[3-chloro-4-(3-hydroxy-propyl)-phenyl]-3-(2-chloro-4-trifluoromethyl-phenyl)-acrylamide Prepared analogously to Intermediate product Z32a starting from (E)-3-(2-chloro-4-trifluoromethyl-phenyl)-acrylic acid (Z37b) and 3-(2-chloro-4-nitro-phenyl)-propan-1-ol. The crude product was purified by column chromatography (silica gel, petroleum ether/EtOAc 1:1).

Yield: 1.800 g (63% of theory)
$C_{19}H_{16}Cl_2F_3NO_2$ (M=418.246)
Calc.: molpeak (M+H)$^+$: 418/420/422
Found: molpeak (M+H)$^+$: 418/420/422 (Cl$_2$)

Z45d) (E)-N-[4-(3-bromo-propyl)-3-chloro-phenyl]-3-(2-chloro-4-trifluoromethyl-phenyl)-acrylamide 0.577 g (2.200 mmol) triphenylphosphine was added batchwise to a suspension of 0.836 g (2.000 mmol) (E)-N-[3-chloro-4-(3-hydroxy-propyl)-phenyl]-3-(2-chloro-4-trifluoromethyl-phenyl)-acrylamide and 0.730 g (2.200 mmol) tetrabromomethane in 10 mL dichloromethane and the mixture was stirred for 48 h at RT. The reaction mixture was purified by column chromatography (silica gel, dichloromethane) and the residue was triturated with petroleum ether.

Yield: 0.620 g (64% of theory)
$C_{19}H_{15}BrCl_2F_3NO$ (M=481.143)
Calc.: molpeak (M+H)$^+$: 480/482/484/486
Found: molpeak (M+H)$^+$: 480/482/484/486 (BrCl$_2$)
$R_f$ value: 0.81 (silica gel, dichloromethane)

Intermediate Product 46:

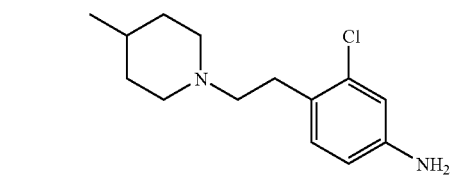

Z46a) 2-(2-chloro-4-nitro-phenyl)-1-(4-methyl-piperidin-1-yl)-ethanone

Prepared analogously to Intermediate product Z44b starting from (2-chloro-4-nitro-phenyl)-acetyl-chloride (Z44a) and 4-methylpiperidine.

Yield: 1.050 g (77% of theory)
$C_{14}H_{17}ClN_2O_3$ (M=296.756)

$R_f$ value: 0.51 (silica gel, petroleum ether/EtOAc 1:1)

Z46b) 1-[2-(2-chloro-4-nitro-phenyl)-ethyl]-4-methyl-piperidine

Prepared analogously to Intermediate product Z44c starting from (2-chloro-4-nitro-phenyl)-1-(4-methyl-piperidin-1-yl)-ethanone. The crude product was purified by column chromatography (Alox, neutral, act. II-III, gradient petroleum ether/EtOAc 8:1→6:1).

Yield: 0.820 g (57% of theory)
$C_{14}H_{19}ClN_2O_2$ (M=282.773)
$R_f$ value: 0.73 (silica gel, petroleum ether/EtOAc 2:1)

Z46c) 3-chloro-4-[2-(4-methyl-piperidin-1-yl)-ethyl]-phenylamine

Prepared analogously to Intermediate product Z44d starting from 1-[2-(2-chloro-4-nitro-phenyl)-ethyl]-4-methyl-piperidine.

Yield: 0.820 g (57% of theory)
$C_{14}H_{21}ClN_2$ (M=252.790)
Calc.: molpeak $(M+H)^+$: 253/255
Found: molpeak $(M+H)^+$: 253/255 (Cl)

General Working Method I (TBTU Coupling):

Triethylamine (1.5 eq.) or N-ethyldiisopropylamine (1.5eq.) and TBTU (1.0-1.5 eq.) are added successively to a solution of carboxylic acid (1.0 eq.) in THF or DMF. Depending on the carboxylic acid the mixture is stirred for 10 minutes-12 hours between ambient temperature and 40° C. before the amine (1.0 eq.) is added. The reaction is stirred for 30 minutes-24 hours between ambient temperature and 40° C., before semisaturated $NaHCO_3$ solution is added.

After extraction of the aqueous phase with EtOAc the organic phase is dried over magnesium sulphate. The solvent is removed using the rotary evaporator; further purification is carried out by column chromatography or crystallisation. The reaction may also be carried out in a Chemspeed automatic synthesiser.

The following compounds were prepared according to general working method I:

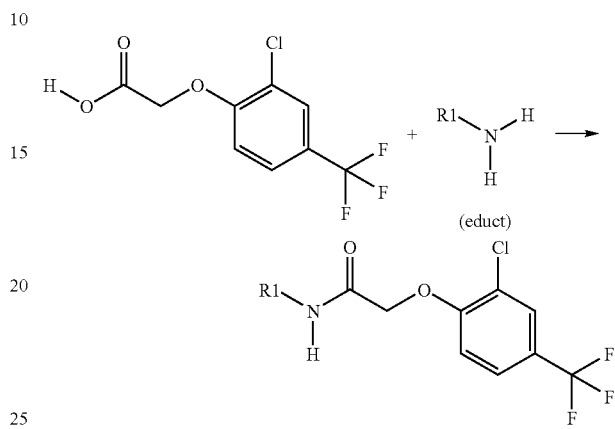

while in the Table that follows the products are defined by the partial formula $R^1$—NH— and the associated carboxylic acid educts are defined by reference to the corresponding Example number of the intermediate product.

| Example | $R^1$NH— | Educt | Empirical formula | Mass spectrum | $R_f$ value | Yield (%) |
|---|---|---|---|---|---|---|
| 1 | (piperidinyl-ethoxy-chlorophenyl-NH*) | Z10 | $C_{22}H_{23}Cl_2F_3N_2O_3$ | 491/493$[M + H]^+$ | 0.45(A) | 44 |
| 2 | (diethylamino-ethoxy-cyanophenyl-NH*) | Z11b | $C_{22}H_{23}ClF_3N_3O_3$ | 470/472$[M + H]^+$ | 0.36(A) | 64 |
| 3 | (diethylamino-ethyl-indolinyl-NH*) | Z12b | $C_{23}H_{27}ClF_3N_3O_2$ | 470/472$[M + H]^+$ | 0.22(A) | 44 |

-continued

| Example | R¹NH— | Educt | Empirical formula | Mass spectrum | R_f value | Yield (%) |
|---|---|---|---|---|---|---|
| 4 | | Z13b | $C_{22}H_{21}Cl_2F_3N_2O_2$ | 473/475/477[M + H]⁺ | 0.42(A) | 21 |
| 5 | | Z14b | $C_{25}H_{29}ClF_3N_3O_2$ | 496/498[M + H]⁺ | 0.30(A) | 48 |
| 6 | | Lit. | $C_{21}H_{24}ClF_3N_2O_2$ | 429/431[M + H]⁺ | 0.33(A) | 36 |
| 7 | | Z24b | $C_{23}H_{26}ClF_3N_2O_2$ | 455/457[M + H]⁺ | 0.46(A) | 50 |
| 8 | | Z23f | $C_{22}H_{24}ClF_3N_2O_2$ | 441/443[M + H]⁺ | 0.37(A) | 46 |
| 9 | | Z15 | $C_{22}H_{25}Cl_2F_3N_2O_2$ | 477/479/481[M + H]⁺ | 0.22(A) | 31 |
| 10 | | Z16b | $C_{22}H_{23}ClF_6N_2O_3$ | 513/515[M + H]⁺ | 0.27(A) | 39 |

-continued

| Example | R¹NH— | Educt | Empirical formula | Mass spectrum | $R_f$ value | Yield (%) |
|---|---|---|---|---|---|---|
| 11 | (diethylamino-propenyl with Cl,Cl-substituted phenyl-NH*) | Z17 | $C_{22}H_{22}Cl_3F_3N_2O_2$ | 509/11/13/15[M + H]⁺ | 0.48(A) | 1 |
| 12 | (diethylaminoethyl-indole-NH*) | Z18b | $C_{23}H_{25}ClF_3N_3O_2$ | 468/470[M + H]⁺ | 0.63(A) | 1 |
| 13 | (diethylaminoethyl-N-phenyl-NH*) | Z19b | $C_{21}H_{25}ClF_3N_3O_2$ | 444/446[M + H]⁺ | 0.35(A) | 35 |
| 14 | (diethylaminoethyl-N-methyl-chlorophenyl-NH*) | Z20b | $C_{22}H_{26}Cl_2F_3N_3O_2$ | 492/494/496[M + H]⁺ | 0.46(A) | 49 |
| 15 | (diethylaminoethyl-tetrahydroquinoline-NH*) | Z21b | $C_{24}H_{29}ClF_3N_3O_2$ | 484/486[M + H]⁺ | 0.86(B) | 42 |

Lit.: known from the literature

Eluant:

(A) dichloromethane/MeOH/conc. aqueous ammonia = 90:10:1

(B) EtOAc/MeOH/conc. aqueous ammonia = 90:10:1

General Working Method II:

A solution of 1.0 eq. acid chloride in THF is slowly added dropwise to a solution of 1.0 eq. of 3-chloro-4-(2-diethylamino-ethoxy)-phenylamine and 4.5-6.0 eq. of triethylamine in THF at 5° C. The reaction mixture is stirred for 3 hours at 25-30° C., filtered off and washed with THF. The filtrate is evaporated down i. vac. and the residue purified by column chromatography. The intermediate product is dissolved in acetonitrile, acidified with ethereal HCl and precipitated with ether. Further purification is carried out by recrystallisation.

According to general working method II the following compounds were prepared:

while in the Table that follows the products are defined by means of the group $R^1$—. The associated amino educts are commercially available and/or known from the literature.

while in the Table that follows the products are defined by means of the group $R^1$—. The associated amino educts are commercially available and/or known from the literature.

| Example | $R^1$ | Empirical formula | Melting point | Yield (%) |
|---|---|---|---|---|
| 16 | 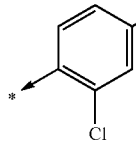 | $C_{20}H_{23}Cl_3N_2O_3 \times HCl$ | 186-188° C. | 63 |
| 17 | 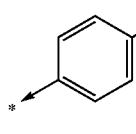 | $C_{20}H_{24}Cl_3N_2O_3 \times HCl$ | 171-172° C. | 62 |
| 18 | 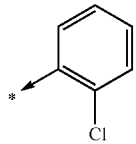 | $C_{20}H_{24}Cl_2N_2O_3 \times HCl$ | 183-185° C. | 63 |

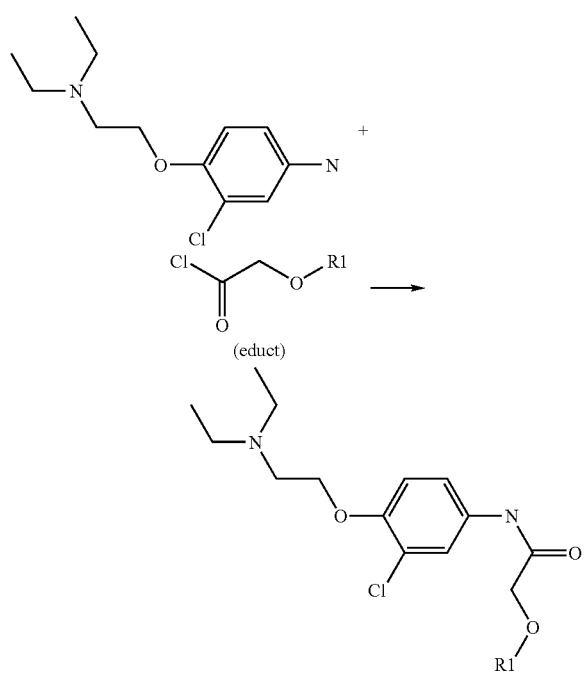

EXAMPLE 19

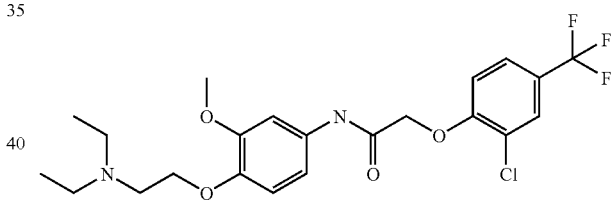

19) 2-(2-chloro-4-trifluoromethyl-phenoxy)-N-[4-(2-diethylamino-ethoxy)-3-methoxy-phenyl]-acetamide 171 mg (0.82 mmol) of CDI was added to a solution of 185 mg (0.73 mmol) of (2-chloro-4-trifluoromethyl-phenoxy)-acetic acid (cf intermediate product Z2b) in 5 mL tetrahydrofuran and the reaction mixture was stirred for 30 minutes at 50° C. Then 0.1 mL (0.73 mmol) of triethylamine and 200 mg (0.73 mmol) of 4-(2-diethylamino-ethoxy)-3-methoxy-phenylamine (see intermediate product Z6b) were added and the solution was stirred for 16 hours at RT. The reaction solution was added to water and stirred for 45 minutes at RT. After filtration the residue was dried in the circulating air dryer.

Yield: 170 mg (49% of theory)

$C_{22}H_{26}ClF_3N_2O_4$ (M=474.912)

Calc.: Molpeak(M+H)$^+$: 475/477

Found: Molpeak (M+H)$^+$: 475/477 (Cl)

$R_f$ value: 0.30 (silica gel, dichloromethane/MeOH/conc. aqueous ammonia 90:10:1).

EXAMPLE 20

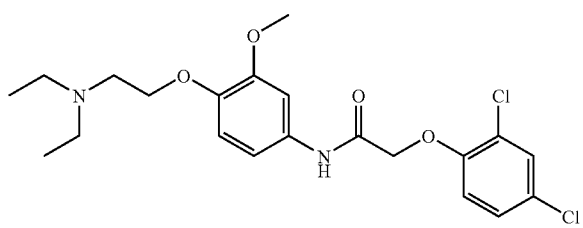

20) 2-(2,4-dichloro-phenoxy)-N-[4-(2-diethylamino-ethoxy)-3-methoxy-phenyl]-acetamide A solution of 70 mg (0.290 mmol) of (2,4-dichloro-phenoxy)-acetylchloride in 0.5 mL dichloromethane was added to a solution of 66 mg (0.278 mmol) of 4-(2-diethylamino-ethoxy)-3-methoxy-phenylamine (intermediate product Z6b) and 96 µL (0.56 mmol) of ethyl-diisopropylamine in 1.5 mL abs. dichloromethane and the mixture was stirred for 15 hours at RT. The reaction mixture was evaporated down i. vac. and the residue was purified by column chromatography (silica gel, dichloromethane/MeOH 9:1).

Yield: 77 mg (61% of theory)
$C_{21}H_{26}Cl_2N_2O_4$ (M=441.358)
Calc.: Molpeak(M+H)$^+$: 441/443/445
Found: Molpeak (M+H)$^+$: 441/443/445
$R_f$ value: 0.32 (silica gel, dichloromethane/MeOH 9:1)

The following compounds were prepared analogously to Example 20:

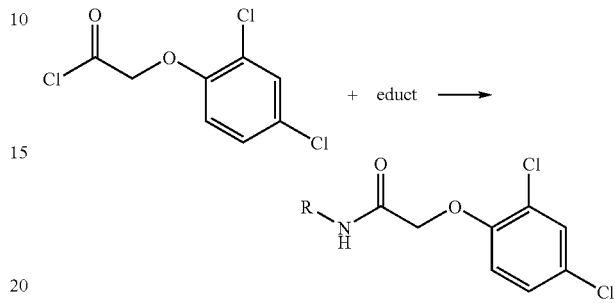

while in the Table that follows the products are defined by means of the group R and the associated educts are defined by reference to the corresponding Example number of the intermediate product or are given as known from the literature (Lit.).

| Example | R | Educt | Empirical formula | Mass spectrum | $R_f$ value | Yield (%) |
|---|---|---|---|---|---|---|
| 21 | ![R21] | Lit. | $C_{22}H_{27}Cl_2N_3O_3$ | 452/454/457[M + H]$^+$ | 0.12 (A) | 65% |
| 22 | ![R22] | Lit. | $C_{20}H_{24}Cl_2N_2O_2$ | 395/397/399[M + H]$^+$ | 0.38 (A) | 46% |
| 23 | ![R23] | Lit. | $C_{21}H_{26}Cl_2N_2O_3$ | 425/427/429[M + H]$^+$ | 0.31 (A) | 69% |

-continued

| Example | R | Educt | Empirical formula | Mass spectrum | $R_f$ value | Yield (%) |
|---|---|---|---|---|---|---|
| 24 | [diethylaminoethoxy-3-fluorophenyl] | Z8b | $C_{20}H_{23}Cl_2FN_2O_3$ | 429/431/433[M + H]$^+$ | 0.34 (A) | 66% |
| 25 | [diethylaminoethoxy-methyl benzoate] | Z7b | $C_{22}H_{26}Cl_2N_2O_5$ | 469/471/473[M + H]$^+$ | 0.30 (A) | 40% |
| 26 | [diethylaminoethoxy-phenyl] | Z5b | $C_{20}H_{24}Cl_2N_2O_3$ | 411/413/415[M + H]$^+$ | 0.33 (A) | 89% |
| 27 | [diethylaminoethyl-benzamide] | Lit. | $C_{21}H_{25}Cl_2N_3O_3$ | 438/440/442[M + H]$^+$ | 0.28 (A) | 52% |
| 28 | [dimethylamino-ethyl-methanesulfonamide-phenyl] | Z23c | $C_{19}H_{23}Cl_2N_3O_4S$ | 460/462[M + H]$^+$ | 0.40 (A) | 36% |
| 29 | [bis-diethylaminomethyl-phenoxy-ethyl] | Z9c | $C_{25}H_{39}Cl_2N_3O_3$ | 496/498/500[M + H]$^+$ | 0.21 (A) | 84% |
| 30 | [diethylaminomethyl-phenyl] | Lit. | $C_{19}H_{22}Cl_2N_2O_2$ | 381/383[M + H]$^+$ | 0.48 (A) | 35% |
| 31 | [4-methylpiperazinylmethyl-phenyl] | Lit. | $C_{20}H_{23}Cl_2N_3O_2$ | 408/410/412[M + H]$^+$ | 0.35 (A) | 40% |

$R_f$ value:
(A) = (silica gel, dichloromethane/MeOH 9:1)
(B) = (silica gel, EtOAc)

EXAMPLE 32

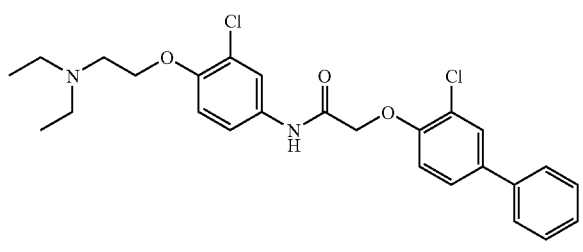

32) 2-(3-chloro-biphenyl-4-yloxy)-N-[3-chloro-4-(2-diethylamino-ethoxy)-phenyl]-acetamide 65 mg (0.47 mmol) of potassium carbonate was added to a solution of 70 mg (0.159 mmol) of 2-bromo-N-[3-chloro-4-(2-diethylamino-ethoxy)-phenyl]-acetamide-hydrobromide (intermediate product Z1c) and 64 mg (0.314 mmol) of 3-chloro-biphenyl-4-ol in 1 mL of abs. DMF and the mixture was stirred for 1 hour at 40° C. and for 15 hours at RT. The reaction mixture was diluted with dichloromethane, the org. phase was washed with sat. aqueous sodium bicarbonate solution and water and dried over magnesium sulphate. Column chromatography (silica gel, dichloromethane/MeOH 9:1) yielded the product.

Yield: 51 mg (67% of theory)
$C_{26}H_{28}Cl_2N_2O_3$ (M=487.431)
Calc.: Molpeak(M+H)$^+$: 487/489/491
Found: Molpeak (M+H)$^+$: 487/489/491 (Cl$_2$)
$R_f$ value: 0.43 (silica gel, dichloromethane/MeOH 9:1)

The following compounds were prepared analogously to Example 32:

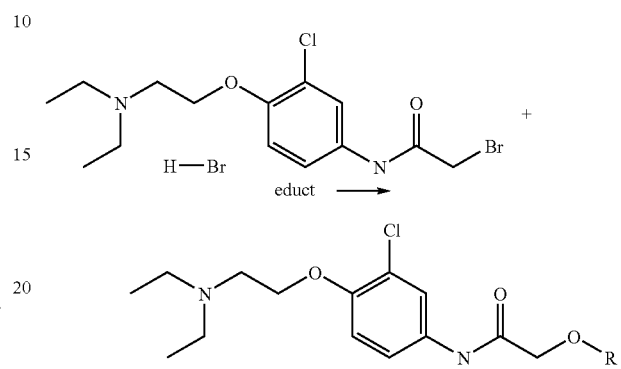

while in the Table that follows the products are defined by means of the group R and the associated educts are commercially available.

| Example | R | Empirical formula | Mass spectrum | $R_f$ value | Yield (%) |
|---|---|---|---|---|---|
| 33 | *-C6H3(Cl)(CF3) | $C_{21}H_{23}Cl_2F_3N_2O_3$ | 479/481/483[M + H]$^+$ | 0.34 (A) | 67% |
| 34 | *-C6H3(Cl)(tBu) | $C_{24}H_{32}Cl_2N_2O_3$ | 467/469/471[M + H]$^+$ | 0.31 (A) | 63% |
| 35 | *-C6H3(Cl)(CO2Me) | $C_{22}H_{26}Cl_2N_2O_5$ | 469/471/473[M + H]$^+$ | 0.30 (A) | 80% |
| 36 | *-C6H3(Br)(Br) | $C_{20}H_{23}Br_2ClN_2O_3$ | 533/535/537[M + H]$^+$ | 0.31 (A) | 82% |

-continued
| Example | R | Empirical formula | Mass spectrum | $R_f$ value | Yield (%) |
|---|---|---|---|---|---|
| 37 | 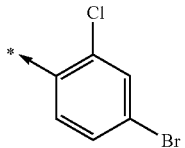 | $C_{20}H_{23}BrCl_2N_2O_3$ | 489/491/495/495[M + H]$^+$ | 0.25 (A) | 74% |
| 38 | 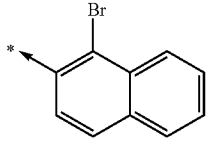 | $C_{24}H_{26}BrClN_2O_3$ | 505/507/509[M + H]$^+$ | 0.36 (A) | 80% |
| 39 | 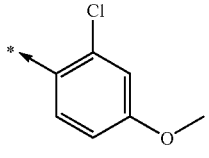 | $C_{21}H_{26}Cl_2N_2O_4$ | 441/443/445[M + H]$^+$ | 0.38 (A) | 60% |
| 40 | 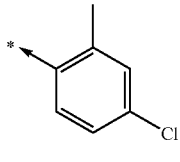 | $C_{21}H_{26}Cl_2N_2O_3$ | 425/427/429[M + H]$^+$ | 0.31 (A) | 85% |
| 41 | 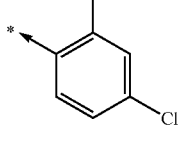 | $C_{20}H_{23}BrCl_2N_2O_3$ | 489/491/493/495[M + H]$^+$ | 0.32 (A) | 57% |
| 42 | 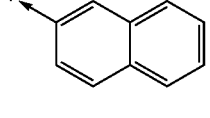 | $C_{24}H_{27}ClN_2O_3$ | 427/429[M + H]$^+$ | 0.31 (A) | 78% |
| 43 | 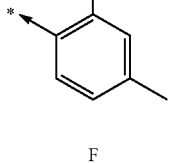 | $C_{22}H_{29}ClN_2O_3$ | 405/407[M + H]$^+$ | 0.30 (A) | 73% |
| 44 | 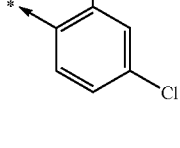 | $C_{20}H_{23}Cl_2FN_2O_3$ | 429/431/433[M + H]$^+$ | 0.26 (A) | 74% |
| 45 | 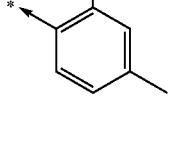 | $C_{21}H_{26}Cl_2N_2O_3$ | 425/427/429[M + H]$^+$ | 0.19 (A) | 54% |

-continued

| Example | R | Empirical formula | Mass spectrum | $R_f$ value | Yield (%) |
|---|---|---|---|---|---|
| 46 | 2-cyclohexyl-4-chlorophenyl | $C_{26}H_{34}Cl_2N_2O_3$ | 493/495/497[M + H]$^+$ | 0.24 (A) | 62% |
| 47 | 2-(methoxycarbonyl)-4-chlorophenyl | $C_{22}H_{26}Cl_2N_2O_5$ | 469/471/473[M + H]$^+$ | 0.25 (A) | 68% |
| 48 | 2-methoxy-4-chlorophenyl | $C_{21}H_{26}Cl_2N_2O_4$ | 441/443/445[M + H]$^+$ | 0.31 (A) | 80% |
| 49 | 3,4-dichlorophenyl | $C_{20}H_{23}Cl_3N_2O_3$ | 445/447/449/451[M + H]$^+$ | 0.26 (A) | 66% |
| 50 | 2-benzyl-4-chlorophenyl | $C_{27}H_{30}Cl_2N_2O_3$ | 501/503/505[M + H]$^+$ | 0.36 (A) | 93% |
| 51 | 2-phenyl-4-chlorophenyl | $C_{26}H_{28}Cl_2N_2O_3$ | 487/489/491[M + H]$^+$ | 0.36 (A) | 83% |
| 52 | 2-chloro-4-fluorophenyl | $C_{20}H_{23}Cl_2FN_2O_3$ | 429/431/433[M + H]$^+$ | 0.36 (A) | 64% |
| 53 | 1-naphthyl | $C_{24}H_{27}ClN_2O_3$ | 427/429[M + H]$^+$ | 0.32 (A) | 84% |

| Example | R | Empirical formula | Mass spectrum | $R_f$ value | Yield (%) |
|---|---|---|---|---|---|
| 54 | 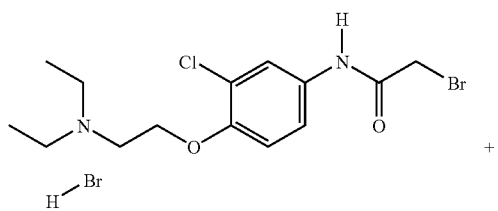 | $C_{21}H_{25}Cl_2N_3O_4$ | 454/456/458[M + H]$^+$ | 0.08 (A) | 72% |
| 55 | 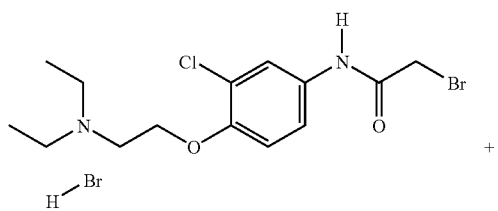 | $C_{27}H_{29}Cl_2N_3O_4$ | 530/532/534[M + H]$^+$ | 0.23 (A) | 48% |

$R_f$ value: (A) = (silica gel, dichloromethane/MeOH 9:1)

General Working Method III (Phenol Alkylation I):

Phenol (2.0 eq.) and potassium carbonate (3.0-5.0 eq.) are added successively to a solution of the alkyl bromide (see intermediate product Z1c) (1.0 eq.) in DMF. The mixture is stirred for 48-72 hours at RT under a nitrogen atmosphere, before being added to water. After extraction of the aqueous phase with EtOAc the organic phase is dried over magnesium sulphate. The solvent is removed using the rotary evaporator; further purification is carried out by column chromatography or crystallisation.

According to general working method III the following compounds were prepared:

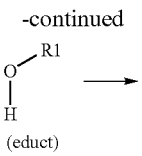

+

-continued

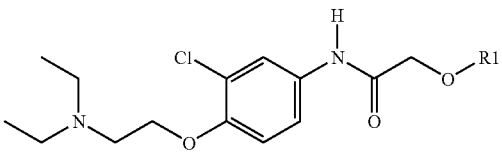

while in the Table that follows the products are defined by means of the group R1 and the associated educts are commercially available.

| Example | R1 | Empirical formula | Mass spectrum | $R_f$ value | Yield (%) |
|---|---|---|---|---|---|
| 56 | 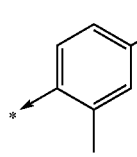 | $C_{21}H_{26}ClIN_2O_3$ | 517/519[M + H]$^+$ | 0.32 (A) | 47 |
| 57 | 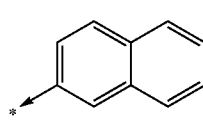 | $C_{24}H_{26}BrClN_2O_3$ | 505/507/509[M + H]$^+$ | 0.42 (A) | 20 |

-continued
| Example | R1 | Empirical formula | Mass spectrum | $R_f$ value | Yield (%) |
|---|---|---|---|---|---|
| 58 |  | $C_{21}H_{27}BrClN_2O_3$ | 469/471/473[M + H]$^+$ | 0.33 (A) | 49 |
| 59 | 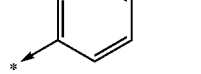 | $C_{21}H_{24}ClF_3N_2O_3$ | 445/447[M + H]$^+$ | 0.32 (A) | 56 |
| 60 |  | $C_{23}H_{29}ClN_2O_4$ | 433/435[M + H]$^+$ | 0.37 (A) | 23 |
| 61 |  | $C_{21}H_{26}Cl_2N_2O_3$ | 425/427/429[M + H]$^+$ | 0.42 (A) | 24 |
| 62 |  | $C_{22}H_{27}Cl_2N_3O_4$ | 468/470/472[M + H]$^+$ | 0.26 (A) | 21 |
| 63 |  | $C_{22}H_{28}BrClN_2O_3$ | 483/485/487[M + H]$^+$ | 0.32 (A) | 48 |
| 64 | 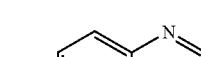 | $C_{23}H_{26}ClN_3O_3$ | 428/430[M + H]$^+$ | 0.23 (A) | 12 |
Eluant: (A) dichloromethane/MeOH/ammonia = 90:10:1

General Working Method IV (Phenolalkylation II):

Bromoacetylbromide (1.0 eq.) in dioxane is added dropwise to a solution of the aniline (see intermediate product Z1b) (1.0 eq.) in DMF at −10° C. Then the mixture is heated to RT and phenol (1.0 eq.) in DMF and potassium-tert-butoxide (2.0 eq.) in tert-butanol are added successively. The mixture is heated to 80° C. for 4 hours. DMF is eliminated in vacuo and the residue is dissolved in EtOAc. The ethyl acetate solution is washed 1× with 10% $K_2CO_3$ solution, then 2× with water. The EtOAc is eliminated in vacuo. Further purification is carried out by column chromatography.

According to general working method IV the following compounds were prepared:

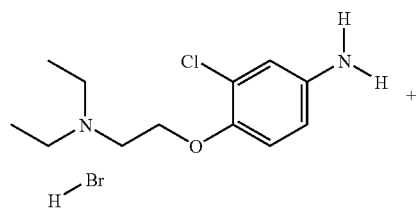

-continued

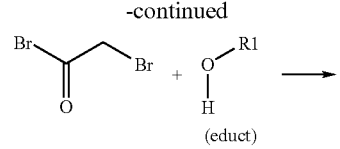
(educt)

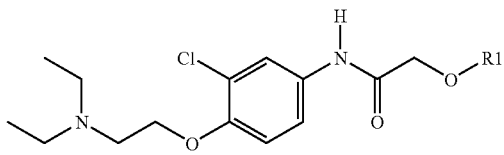

while in the Table that follows the products are defined by means of the group R1 and the associated educts are commercially available.

| Example | R1 | Empirical formula | Mass spectrum | $R_f$ value | Yield (%) |
|---|---|---|---|---|---|
| 65 | | $C_{21}H_{23}ClF_3N_3O_5$ | 490/492[M + H]$^+$ | 0.24 (A) | 6 |
| 66 | | $C_{20}H_{23}Cl_2N_3O_5$ | 456/458/460[M + H]$^+$ | 0.28 (A) | 7 |
| 67 | | $C_{24}H_{25}Br_2ClN_2O_5$ | 583/85/87/89[M + H]$^+$ | 0.50 (A) | 7 |
| 68 | | $C_{25}H_{29}ClN_2O_4$ | 455/457[M + H]$^+$ | 0.24 (A) | 13 |
| 69 | | $C_{20}H_{22}Cl_4N_2O_3$ | 479/81/83/85/87[M + H]$^+$ | 0.28 (A) | 10 |

-continued

| Example | R1 | Empirical formula | Mass spectrum | $R_f$ value | Yield (%) |
|---|---|---|---|---|---|
| 70 | 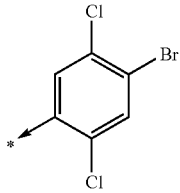 | $C_{20}H_{22}BrCl_3N_2O_3$ | 521/23/25/27[M + H]$^+$ | 0.28 (A) | 10 |
| 71 | 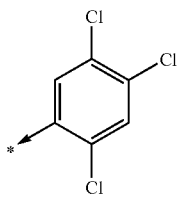 | $C_{20}H_{22}Cl_4N_2O_3$ | 477/79/81/83[M + H]$^+$ | 0.23 (A) | 8 |
| 72 | 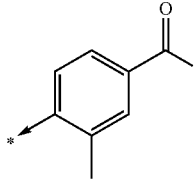 | $C_{22}H_{27}ClN_2O_4$ | 419/421[M + H]$^+$ | 0.25 (A) | 5 |
| 73 | 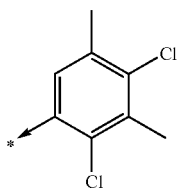 | $C_{22}H_{27}Cl_3N_2O_3$ | 473/75/77/79[M + H]$^+$ | 0.31 (A) | 8 |
| 74 | 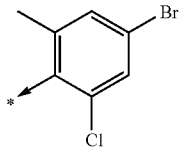 | $C_{21}H_{25}BrCl_2N_2O_3$ | 503/05/07/09[M + H]$^+$ | 0.28 (A) | 8 |

Eluant: (A) dichloromethane/MeOH/ammonia = 90:10:1

EXAMPLE 75

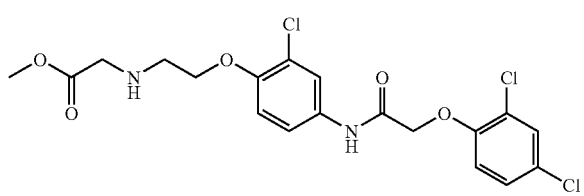

75) methyl (2-{2-chloro-4-[2-(2,4-dichloro-phenoxy)-acetylamino]-phenoxy}-ethylamino)-acetate 75 μL (0.54 mmol) of triethylamine and 70 mg (0.18 mmol) of N-[3-chloro-4-(2-oxo-ethoxy)-phenyl]-2-(2,4-dichloro-phenoxy)-acetamide was added to a suspension of 45 mg (0.36 mmol) of methyl amino-acetate hydrochloride in 2 mL dichloromethane/THF (1:1). 114 mg (0.54 mmol) of sodium triacetoxyborohydride was added and the mixture was stirred for 3 hours at RT. 100 mL of 2 N aqueous sodium carbonate solution was added and the aqueous phase was exhaustively extracted with chloroform. The combined org. extracts were dried over magnesium sulphate, evaporated down i. vac. and purified by column chromatography (silica gel, EtOAc/MeOH 9:1).

Yield: 71 mg (78% of theory)
$C_{19}H_{19}Cl_3N_2O_5$ (M=461.733)
Calc.: Molpeak(M+H)$^+$: 461/463/465/467
Found: Molpeak (M+H)$^+$: 461/463/465/467 (Cl$_3$)
$R_f$ value: 0.32 (silica gel, EtOAc)

The following compounds were prepared analogously to Example 75:

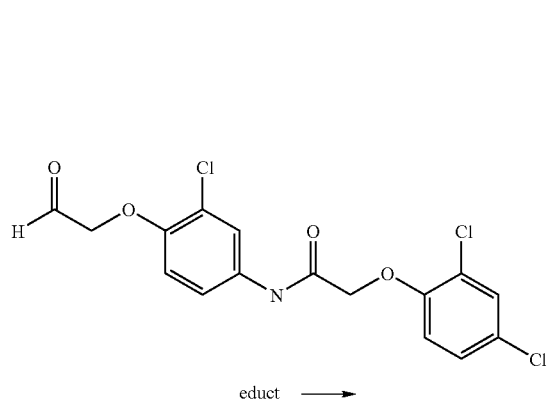

educt ⟶

-continued

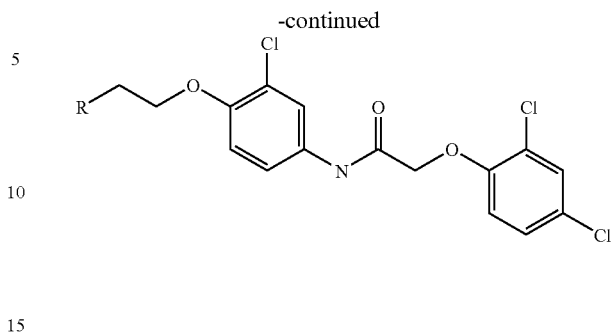

while in the Table that follows the products are defined by means of the group R and the associated educts are commercially available.

| Example | R | Empirical formula | Mass spectrum | $R_f$ value | Yield (%) |
|---------|---|-------------------|---------------|-------------|-----------|
| 76 | piperidinyl | $C_{21}H_{23}Cl_3N_2O_3$ | 457/459/461/463[M + H]$^+$ | 0.30 (A) | 66% |
| 77 | pyrrolidinyl | $C_{20}H_{21}Cl_3N_2O_3$ | 443/445/447/449[M + H]$^+$ | 0.28 (A) | 70% |
| 78 | morpholinyl | $C_{20}H_{21}Cl_3N_2O_4$ | 459/461/463/465[M + H]$^+$ | 0.18 (B) | 72% |
| 79 | 4-(p-tolyl)piperidinyl | $C_{28}H_{29}Cl_3N_2O_3$ | 547/549/551/553[M + H]$^+$ | 0.19 (B) | 52% |
| 80 | 4-methylpiperazinyl | $C_{21}H_{24}Cl_3N_3O_3$ | 472/474/476/478[M + H]$^+$ | 0.31 (A) | 66% |
| 81 | N,N-dimethylaminoethylamino | $C_{20}H_{24}Cl_3N_3O_3$ | 460/462/464/466[M + H]$^+$ | 0.19 (A) | 42% |
| 82 | 1,2,3,4-tetrahydroisoquinolinyl | $C_{25}H_{23}Cl_3N_2O_3$ | 505/507/509/511[M + H]$^+$ | 0.61 (B) | 78% |
| 83 | cyclohexylamino | $C_{22}H_{25}Cl_3N_2O_3$ | 471/473/475/477[M + H]$^+$ | 0.41 (B) | 64% |

-continued

| Example | R | Empirical formula | Mass spectrum | $R_f$ value | Yield (%) |
|---|---|---|---|---|---|
| 84 | 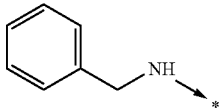 | $C_{23}H_{21}Cl_3N_2O_3$ | 479/481/483/485[M + H]$^+$ | 0.16 (B) | 69% |
| 85 | 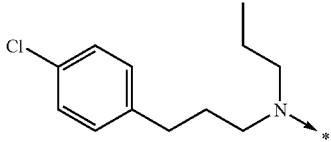 | $C_{28}H_{30}Cl_3N_2O_3$ | 583/585/587/589[M + H]$^+$ | 0.51 (B) | 56% |
| 86 | 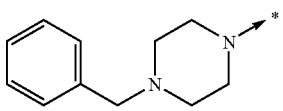 | $C_{27}H_{28}Cl_3N_3O_3$ | 548/550/552/554[M + H]$^+$ | 0.10 (B) | 82% |
| 87 | 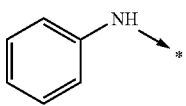 | $C_{22}H_{19}Cl_3N_2O_3$ | 465/467/469/471[M + H]$^+$ | 0.51 (C) | 58% |

$R_f$ value:
(A) = (silica gel, dichloromethane/MeOH 9:1)
(B) = (silica gel, EtOAc)
(C) = (silica gel, EtOAc/hexane 1:1)

General Working Method V (Reductive Amination):

Conc. hydrochloric acid (2.0 eq.) is added to a solution of the aldehyde (see intermediate product Z3d) (1.0 eq.) and amine (2.0 eq.) in THF or the pH is adjusted to between 4-6 with glacial acetic acid. The mixture is stirred for 10 minutes at RT and then sodium cyanoborohydride (2.0 eq.) in THF or sodium triacetoxyborohydride (2.0 eq.) is added. The reaction mixture is stirred for 30 minutes—24 hours at RT to 60° C., depending on the amine, before adding sat. aqueous sodium bicarbonate solution. After extraction of the aqueous phase with ether the organic phase is dried over magnesium sulphate. The solvent is removed using the rotary evaporator; further purification is carried out by column chromatography or crystallisation.

According to general working method V the following compounds were prepared:

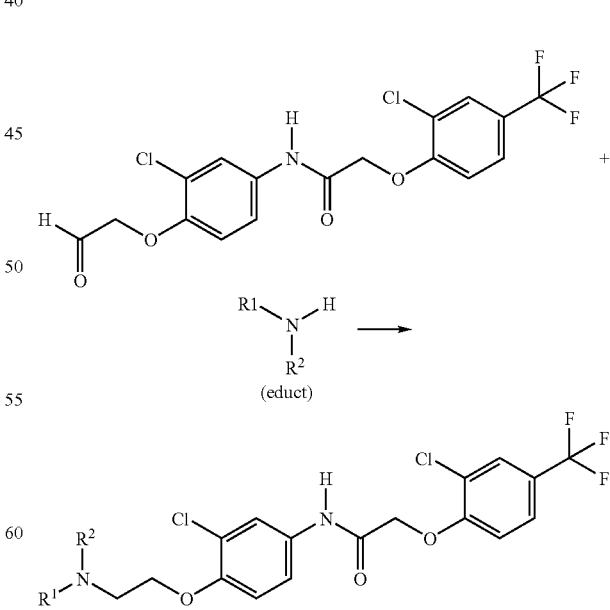

while in the Table that follows the products are defined by means of the group $R^1R^2N$— and the associated educts are commercially available or known from the literature.

| Example | R¹R²N— | Empirical formula | Mass spectrum | $R_f$ value | Yield (%) |
|---|---|---|---|---|---|
| 88 | pyrrolidinyl | $C_{21}H_{21}Cl_2F_3N_2O_3$ | 477/479/481[M + H]$^+$ | 0.13 (A) | 27 |
| 89 | N-ethyl-propyl | $C_{22}H_{25}Cl_2F_3N_2O_3$ | 493/495/497[M + H]$^+$ | 0.26 (B) | 8 |
| 90 | N-methyl-ethyl | $C_{20}H_{21}Cl_2F_3N_2O_3$ | 465/67/69[M + H]$^+$ | 0.25 (B) | 4 |
| 91 | 4-dimethylamino-piperidinyl | $C_{24}H_{28}Cl_2F_3N_3O_3$ | 534/536[M + H]$^+$ | 0.10 (B) | 30 |
| 92 | isopropyl-NH | $C_{20}H_{21}Cl_2F_3N_2O_3$ | 465/467/469[M + H]$^+$ | 0.28 (B) | 9 |
| 93 | N-benzyl-ethyl | $C_{26}H_{25}Cl_2F_3N_2O_3$ | 541/543/545[M + H]$^+$ | 0.80 (B) | 10 |
| 94 | tetrahydroisoquinolinyl | $C_{26}H_{23}Cl_2F_3N_2O_3$ | 539/541/543[M + H]$^+$ | 0.35 (B) | 19 |
| 95 | N-(2-methoxyethyl)-ethyl | $C_{22}H_{25}Cl_2F_3N_2O_4$ | 509/511/513[M + H]$^+$ | 0.37 (B) | 7 |
| 96 | N-(2-dimethylaminoethyl)-ethyl | $C_{23}H_{28}Cl_2F_3N_3O_3$ | 522/524/526[M + H]$^+$ | 0.18 (B) | 8 |
| 97 | N-ethyl-(1-Boc-piperidin-4-yl) | $C_{29}H_{36}Cl_2F_3N_3O_5$ | 634/636/638[M + H]$^+$ | 0.32 (B) | 6 |
| 98 | benzyl-NH | $C_{24}H_{21}Cl_2F_3N_2O_3$ | 513/515/517[M + H]$^+$ | 0.47 (C) | 27 |

| Example | R¹R²N— | Empirical formula | Mass spectrum | $R_f$ value | Yield (%) |
|---|---|---|---|---|---|
| 99 | | $C_{25}H_{29}Cl_2F_3N_2O_3$ | 533/535/537[M + H]⁺ | 0.37 (C) | 1 |
| 100 | | $C_{21}H_{21}Cl_2F_3N_2O_4$ | 493/495[M + H]⁺ | 0.33 (B) | 13 |
| 101 | | $C_{25}H_{24}Cl_2F_3N_3O_3$ | 542/544/546[M + H]⁺ | 0.35 (B) | 10 |
| 102 | | $C_{22}H_{24}Cl_2F_3N_3O_3$ | 506/508/510[M + H]⁺ | 0.15 (B) | 1 |
| 103 | | $C_{26}H_{30}Cl_2F_3N_3O_5$ | 592/594/596[M + H]⁺ | 0.55 (B) | 21 |
| 104 | | $C_{29}H_{29}Cl_2F_3N_2O_3$ | 581/583/585[M + H]⁺ | 0.55 (B) | 18 |
| 105 | | $C_{23}H_{27}Cl_2F_3N_2O_3$ | 507/509/511[M + H]⁺ | 0.65 (B) | 6 |

Eluant:
(A) dichloromethane/MeOH/conc. aqueous ammonia = 95:5:0.5
(B) dichloromethane/MeOH/conc. aqueous ammonia = 90:10:1
(C) dichloromethane/MeOH = 9:1

EXAMPLE 106

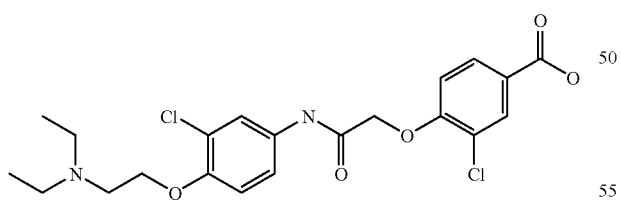

106) 3-chloro-4-{[3-chloro-4-(2-diethylamino-ethoxy)-phenylcarbamoyl]-methoxy}-benzoic acid A solution of 1.8 g (3.835 mmol) of methyl 3-chloro-4-{[3-chloro-4-(2-diethylamino -ethoxy)-phenylcarbamoyl]-methoxy}-benzoate (from Example 35) and 2 ml of 2 M aqueous NaOH solution in 20 mL MeOH was refluxed for 1 hour. The reaction solution was evaporated down i. vac., diluted with water and acidified weakly with HCl. After 3 days at RT the solution was evaporated down i. vac. The residue was triturated with cold EtOH and the precipitate was filtered off.

Yield: 230 mg (13% of theory)
$C_{21}H_{24}Cl_2N_2O_5$ (M=455.342)
Calc.: Molpeak(M+H)⁺: 454/456/458
Found: Molpeak (M+H)⁺: 454/456/458 (Cl₂)

$R_f$ value: 0.05 (silica gel, dichloromethane/MeOH/conc. aqueous ammonia 90:10:1).

General Working Method VI:
A solution of 1.0 eq. of 3-chloro-4-{[3-chloro-4-(2-diethylamino-ethoxy)-phenylcarbamoyl]-methoxy}-benzoic acid (from Example 106) and 1.07 eq. of TBTU in DMF is placed at RT. After the addition of 1.07 eq. triethylamine the mixture is stirred for 10 minutes. Then 7.0 eq. amine are added and the mixture is stirred for 16 hours at RT. The reaction mixture is combined with water or 5% sodium carbonate solution. The precipitated solid is filtered off, washed with water and dried i. vac.

According to general working method VI the following compounds were prepared:

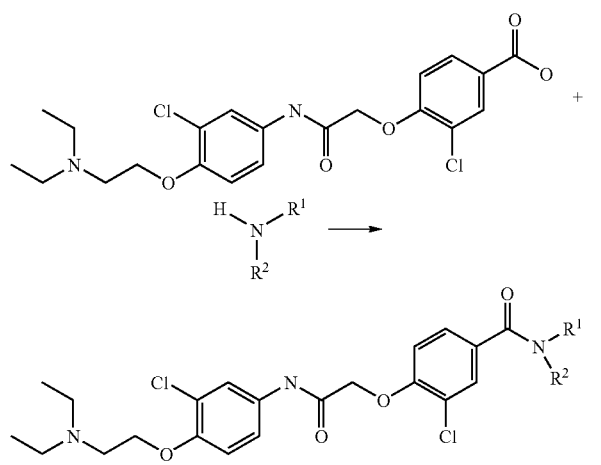

while in the Table that follows the products are defined by means of the group R¹R²N- and the associated educts are commercially available or known from the literature.

80° C. The reaction solution is combined with 10% aqueous Na₂CO₃ solution and the aqueous phase is extracted with EtOAc. The organic phases are combined and the solvent is eliminated in vacuo. Further purification is carried out by column chromatography.

According to general working method VII the following compounds were prepared:

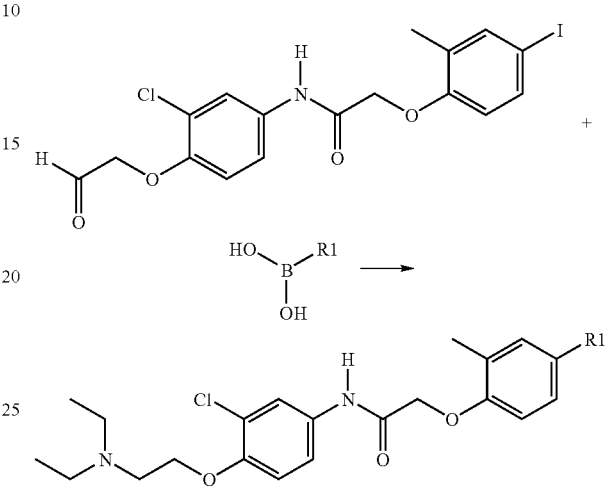

| Example | R¹R²N— | Empirical formula | Mass spectrum | $R_f$ value | Yield (%) |
|---|---|---|---|---|---|
| 107 | H\N\H * aus (NH₄)₂CO₃ | $C_{21}H_{25}Cl_2F_3N_3O_4$ | 454/456/458[M + H]⁺ | 0.37 (A) | 59 |
| 108 | H\N\* | $C_{22}H_{27}Cl_2F_3N_3O_4$ | 468/470/472[M + H]⁺ | 0.38 (A) | 57 |
| 109 | \N\* | $C_{23}H_{29}Cl_2F_3N_3O_4$ | 482/484/486[M + H]⁺ | 0.38 (A) | 55 |

Eluant: (A) dichloromethane/MeOH/conc. aqueous ammonia = 90:10:1

General Working Method VII (Suzuki Coupling):

Boric acid (2.0 eq.) and tetrakis-(triphenylphosphine)-palladium (0.1 eq.) are added successively to a solution of the iodide (1.0 eq.; see Example 56) in toluene and 2M sodium carbonate solution (4.0 eq.) and stirred overnight at while in the Table that follows the products are defined by means of the group R1 and the associated educts are commercially available or known from the literature.

| Example | R1 | Empirical formula | Mass spectrum | $R_f$ value | Yield (%) |
|---|---|---|---|---|---|
| 110 | ![4-Cl-phenyl] | $C_{27}H_{30}Cl_2N_2O_3$ | 501/503/505[M + H]$^+$ | 0.30 (A) | 4 |
| 111 | ![3-Cl-phenyl] | $C_{27}H_{30}Cl_2N_2O_3$ | 501/503/505[M + H]$^+$ | 0.30 (A) | 4 |
| 112 | ![2-Cl-phenyl] | $C_{27}H_{30}Cl_2N_2O_3$ | 501/503/505[M + H]$^+$ | 0.30 (A) | 6 |
| 113 | ![4-OMe-phenyl] | $C_{28}H_{33}ClN_2O_4$ | 497/499/501[M + H]$^+$ | 0.27 (A) | 8 |
| 114 | ![4-Me-phenyl] | $C_{28}H_{33}ClN_2O_4$ | 481/483[M + H]$^+$ | 0.6 (B) | 21 |

Eluant:
(A) dichloromethane/MeOH/conc. aqueous ammonia = 90:10:1
(B) EtOAc/MeOH/conc. aqueous ammonia = 90:10:1

EXAMPLE 115

115) N-[3-chloro-4-(2-piperazin-1-yl-ethoxy)-phenyl]-2-(2-chloro-4-trifluoromethyl-phenoxy)-acetamide

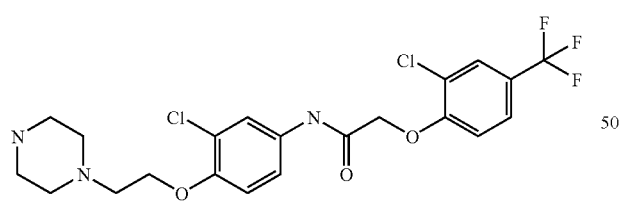

0.200 g (0.338 mmol) of tert.butyl 4-(2-{2-chloro-4-[2-(2-chloro-4-trifluoromethyl-phenoxy)-acetylamino]-phenoxy}-ethyl)-piperazin-1-carboxylate (from Example 103) were dissolved in 5.0 mL dichloromethane. After the addition of 0.5 mL (6.760 mmol) of trifluoroacetic acid the mixture was stirred for 2 hours at RT. The reaction solution was evaporated down i. vac. and the residue combined with sat. aqueous sodium hydrogen carbonate solution. The aqueous phase was extracted with EtOAc. The org. phase was dried over magnesium sulphate, filtered and evaporated down i. vac. Further purification was carried out by column chromatography.

Yield: 0.032 g (16% of theory)
$C_{21}H_{22}C_{12}F_3N_3O_3*2$ $CH_2O_2$ (M=584.381)
Calc.: Molpeak(M+H)$^+$: 492/494/496 (Cl$_2$)
Found: Molpeak (M+H)$^+$: 492/494/496 (Cl$_2$)
$R_f$ value: 0.22 (silica gel, dichloromethane/MeOH/conc. aqueous ammonia 90:10:1).

EXAMPLE 116

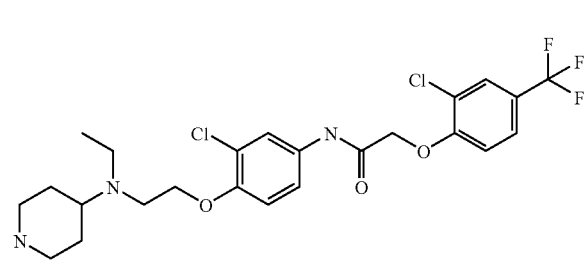

116) N-{3-chloro-4-[2-(ethyl-piperidin-4-yl-amino)-ethoxy]-phenyl}-2-(2-chloro-4-trifluoromethyl-phenoxy)-acetamide 0.180 g (0.284 mmol) of tert.butyl 4-[(2-{2-chloro-4-[2-(2-chloro-4-trifluoromethyl-phenoxy)-acetylamino]-phe noxy}-ethyl)-ethyl-amino]-piperidine-1-carboxylate (from Example 97) were dissolved in 5.0 mL dichloromethane. After the addition of 0.44 mL (5.680 mmol) of trifluoroacetic acid the mixture was stirred for 2 hours at RT. The reaction solution was evaporated down i. vac. and the residue combined with sat. aqueous sodium hydrogen carbonate solution. The aqueous phase was extracted with EtOAc. The org. phase was dried over magnesium sulphate, filtered and evaporated down i. vac. Further purification was carried out by column chromatography.

Yield: 0.011 g (6% of theory)

$C_{24}H_{28}Cl_2F_3N_3O_3 * 2\ CH_2O_2$ (M=626.462)

Calc.: Molpeak(M+H)$^+$: 534/536/538 (Cl$_2$)

Found: Molpeak (M+H)$^+$: 534/536/538 (Cl$_2$)

$R_f$ value: 0.25 (silica gel, dichloromethane/MeOH/conc. aqueous ammonia 90:10:1).

EXAMPLE 117

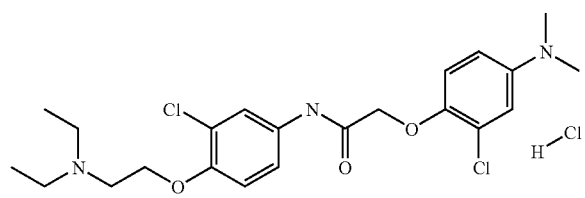

117) N-[3-chloro-4-(2-diethylamino-ethoxy)-phenyl]-2-(2-chloro-4-dimethylamino -phenoxy)-acetamide 94.7 mg (0.200 mmol) of 2-(4-amino-2-chloro-phenoxy)-N-[3-chloro-4-(2-diethylamino-ethoxy)-phenyl]-acetamide (from Example 118), 0.149 mL (37%, 2.000 mmol) of formaldehyde solution and 62.8 mg (1.000 mmol) of sodium cyanoborohydride was placed in 5.0 mL acetonitrile at RT. The pH was adjusted to 4-5 with glacial acetic acid with stirring. After 1 hour the reaction mixture was acidified with 12% HCl and stirred for 10 minutes. Then it was made slightly alkaline with 20% potassium carbonate solution. The aqueous phase was extracted with EtOAc. The org. phase was dried over magnesium sulphate, filtered and evaporated down i. vac. The residue was purified by column chromatography (silica gel; EtOAc/10% conc. aqueous ammonia in MeOH 100:0→5:95). The oily residue was combined with ethereal HCl, evaporated down i. vac. and dissolved in 10 mL isopropanol. The precipitate formed was filtered off and dried i. vac.

Yield: 0.035 g (36% of theory)

$C_{22}H_{29}Cl_2N_3O_3 * HCl$ (M=490.862)

Calc.: Molpeak(M+H)$^+$: 454/456/458 (Cl$_2$)

Found: Molpeak (M+H)$^+$: 454/456/458 (Cl$_2$)

$R_f$ value: 0.40 (silica gel, dichloromethane/MeOH/conc. aqueous ammonia 90:10:1)

EXAMPLE 118

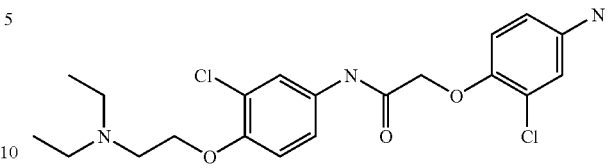

118) 2-(4-amino-2-chloro-phenoxy)-N-[3-chloro-4-(2-diethylamino-ethoxy)-phenyl]-acetamide 0.310 g (0.679 mmol) of N-[3-chloro-4-(2-diethylamino-ethoxy)-phenyl]-2-(2-chloro-4-nitro-phenoxy)-acetamide (from Example 66) was dissolved in 10.0 mL of EtOAc. After the addition of 0.030 g Pt/C (5%) the mixture was hydrogenated at RT under 15 psi H$_2$ atmosphere for 5 hours. The reaction mixture was filtered and the filtrate was evaporated down i. vac. The residue was dissolved with a little EtOH. The precipitate formed was filtered off and dried i. vac.

Yield: 0.050 g (17% of theory)

$C_{20}H_{25}Cl_2N_3O_3$ (M=426.347)

Calc.: Molpeak(M+H)$^+$: 426/428/430 (Cl$_2$)

Found: Molpeak (M+H)$^+$: 426/428/430 (Cl$_2$)

$R_f$ value: 0.24 (silica gel, dichloromethane/MeOH/conc. aqueous ammonia 90:10:1).

EXAMPLE 119

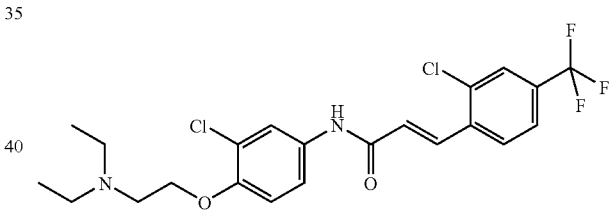

119) (E)-N-[3-chloro-4-(2-diethylamino-ethoxy)-phenyl]-3-(2-chloro-4-trifluoromethyl-phenyl)-acrylamide 0.29 mL (2.10 mmol) of triethylamine was added to a solution of 0.28 g (1.00 mmol) of 3-chloro-4-(2-diethylamino-ethoxy)-phenylamine-hydrochloride (intermediate product Z1b), 0.25 g (1.00 mmol) of (E)-3-(2-chloro-4-trifluoromethyl-phenyl)-acrylic acid (Z37b) and 0.34 g (1.05 mmol) of TBTU in 10 mL abs. THF and the mixture was stirred for 1 hour at RT. The reaction mixture was evaporated down i. vac. and the residue was combined with dichloromethane and water. The org. phase was separated off, washed with sat. aqueous sodium bicarbonate solution and water and evaporated down i. vac. The residue was purified by column chromatography (silica gel, gradient dichloromethane/10% conc. aqueous ammonia in MeOH 100: 0→5:95).

Yield: 150 mg (32% of theory)

$C_{22}H_{23}Cl_2F_3N_2O_2$ (M=475.342)

Calc.: Molpeak(M+H)$^+$: 475/477/479

Found: Molpeak (M+H)$^+$: 475/477/479 (Cl$_2$)

$R_f$ value: 0.2 (silica gel, dichloromethane/MeOH/conc. aqueous ammonia 95:5:1)

EXAMPLE 120

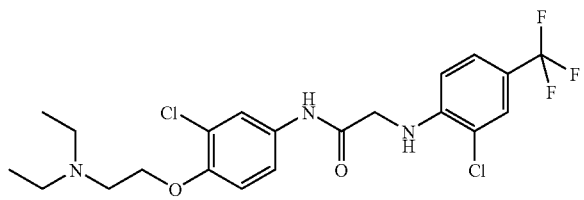

120) N-[3-chloro-4-(2-diethylamino-ethoxy)-phenyl]-2-(2-chloro-4-trifluoromethyl-phenylamino)-acetamide A solution of 0.228 g (0.511 mmol) of 2-bromo-N-[3-chloro-4-(2-diethylamino-ethoxy)-phenyl]-acetamide-hydrobromide (intermediate product Z1c) and 0.200 g (1.023 mmol) of 2-chloro-4-trifluoromethyl-phenylamine in 5 mL DMF was stirred for 16 hours at 90° C. and then for 24 hours at 120° C. The reaction mixture was cooled to RT, diluted with water and exhaustively extracted with EtOAc. The combined org. extracts were dried over magnesium sulphate and evaporated down i. vac. The residue was dissolved in DMF and purified by HPLC-MS (Stable Bond C18; 3.5 μm; water:acetonitrile:formic acid 9:1:0.01→1:9:0.01 over 9 min).

Yield: 11 mg (5% of theory)
$C_{21}H_{24}Cl_2F_3N_3O_2$ (M=478.346)
Calc.: Molpeak(M+H)$^+$: 478/480/482
Found: Molpeak (M+H)$^+$: 478/480/482 (Cl$_2$)
$R_f$ value: 0.24 (silica gel, dichloromethane/MeOH/conc. aqueous ammonia 90:10:1).

EXAMPLE 121

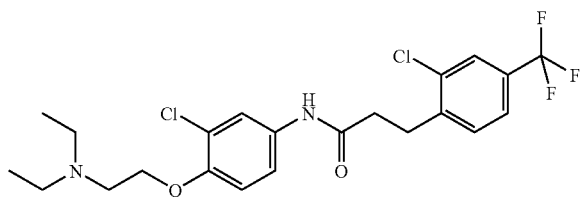

121 a) 3-(2-chloro-4-trifluoromethyl-phenyl)-propionic acid 2.00 g (7.981 mmol) of (E)-3-(2-chloro-4-trifluoromethyl-phenyl)-acrylic acid (Z37b) was added at RT to a suspension of 0.500 g Raney nickel in abs. MeOH and the mixture was hydrogenated for 4 hours at 50 psi H$_2$ atmosphere. The catalyst was filtered off and the filtrate evaporated down i. vac.

Yield: 1.90 g (94% of theory)
$C_{10}H_8ClF_3O_2$ (M=252.622)
Calc.: Molpeak(M−H)$^-$: 251/253
Found: Molpeak (M+H)$^+$: 251/253 (Cl)

121 b) N-[3-chloro-4-(2-diethylamino-ethoxy)-phenyl]-3-(2-chloro-4-trifluoromethyl phenyl)-propionamide The product was obtained analogously to Example 119 starting from 0.400 g (1.433 mmol) of 3-chloro-4-(2-diethylamino-ethoxy)-phenylamine-hydrochloride (intermediate product Z1b) and 0.362 g (1.433 mmol) of 3-(2-chloro-4-trifluoromethyl-phenyl)-propionic acid.

Yield: 340 mg (50% of theory)
$C_{22}H_{25}Cl_2F_3N_2O_2$ (M=477.358)
Calc.: Molpeak(M−H)$^-$: 477/479/481
Found: Molpeak (M+H)$^+$: 477/479/481 (Cl$_2$)
$R_f$ value: 0.30 (silica gel, dichloromethane/MeOH/conc. aqueous ammonia 90:10:1)

EXAMPLE 122

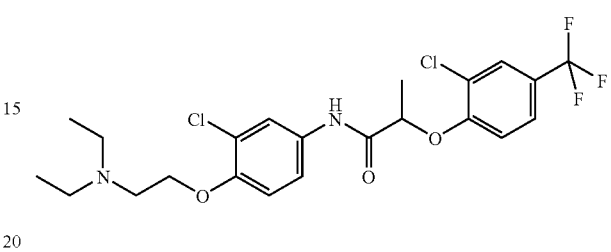

122a) ethyl 2-(2-chloro-4-trifluoromethyl-phenoxy)-propionate 10.00 g (50.87 mmol) of 2-chloro-4-trifluoromethyl-phenol, 7.11 mL (55.00 mmol) of ethyl 2-bromopropionate and 7.60 g (55 mmol) of potassium carbonate in 100 mL DMF was stirred for 16 hours at 50° C. and then filtered. The filtrate was evaporated down i. vac., combined with water and exhaustively extracted with EtOAc. The combined org. extracts were washed with 10% aqueous sodium carbonate solution and water, dried over sodium sulphate and evaporated down i. vac.

Yield: 14.10 g (93% of theory)
$C_{12}H_{12}ClF_3O_3$ (M=296.676)
Calc.: Molpeak(M+Na)$^+$: 319/321
Found: Molpeak (M+Na)$^+$: 319/321 (Cl)
$R_f$ value: 0.6 (silica gel, EtOAc/petroleum ether 4:1)

122b) 2-(2-chloro-4-trifluoromethyl-phenoxy)-propionic acid 50 mL (0.100 mol) of 2 M aqueous NaOH solution was added to a solution of 14.00 g (0.047 mol) of ethyl 2-(2-chloro-4-trifluoromethyl-phenoxy)-propionate in 100 mL EtOH and the mixture was refluxed for 1 hour. EtOH was evaporated off i. vac., the residue was diluted with ice water and acidified with 2 M aqueous HCl. The precipitate formed was filtered off, washed with water and dried at 70° C. i. vac.

Yield: 12.10 g (96% of theory)
$C_{10}H_8ClF_3O_3$ (M=268.622)
Calc.: Molpeak(M−H)$^-$: 267/269
Found: Molpeak (M−H)$^-$: 267/269 (Cl)

122c) N-[3-chloro-4-(2-diethylamino-ethoxy)-phenyl]-2-(2-chloro-4-trifluoromethyl -phenoxy)-propionamide-hydrochloride 0.342 mL (2.000 mmol) of ethyl-diisopropylamine was added to a solution of 0.364 g (1.500 mmol) of 3-chloro-4-(2-diethylamino-ethoxy)-phenylamine (intermediate product Z1b), 0.403 g (1.500 mmol) of 2-(2-chloro-4-trifluoromethyl-phenoxy)-propionic acid and 0.562 g (1.750 mmol) of TBTU in 10 mL abs. THF and the mixture was stirred for 1 hour at RT. The reaction mixture was evaporated down i. vac. and the residue combined with dichloromethane and water. The org. phase was separated off, washed with sat. aqueous sodium bicarbonate solution and water and evaporated down i. vac. The residue was purified by column chromatography (silica gel, gradient dichloromethane/10% conc. aqueous ammonia in MeOH 100:0→5:95).

Yield: 450 mg (57% of theory)
$C_{22}H_{25}Cl_2F_3N_2O_3$*HCl (M=529.818)
Calc.: Molpeak(M+H)$^+$: 493/495/497
Found: Molpeak (M+H)$^+$: 493/495/497 (Cl$_2$)
R$_f$ value: 0.30 (silica gel, dichloromethane/MeOH/conc. aqueous ammonia 95:5:0.5).

EXAMPLE 123

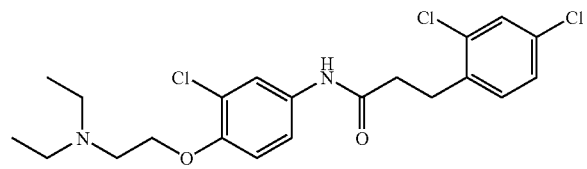

123) N-[3-chloro-4-(2-diethylamino-ethoxy)-phenyl]-3-(2,4-dichloro-phenyl)-propionamide A solution of 0.271 g (1.236 mmol) of (3-(2,4-dichloro-phenyl)-propionic acid in 3.00 mL thionyl chloride was stirred for 2 hours at RT, evaporated down i. vac. and dissolved in 10 mL dichloromethane. This solution of the acid chloride was slowly added dropwise, while cooling with ice, to a solution of 0.300 (1.236 mmol) of 3-chloro-4-(2-diethylamino-ethoxy)-phenylamine (intermediate product Z1b) and 0.32 mL (1.854 mmol) of ethyl-diisopropylamine in 10 mL dichloromethane and the mixture was stirred for 16 hours at RT. The reaction mixture was washed with sat. aqueous sodium bicarbonate solution, dried over magnesium sulphate and evaporated down i. vac. The residue was dissolved in EtOAc and purified by column chromatography (silica gel, EtOAc/MeOH/conc. aqueous ammonia 90:10:1).

Yield: 60 mg (11% of theory)
$C_{21}H_{25}Cl_3N_2O_2$ (M=443.)
Calc.: Molpeak(M−Na)$^-$: 441/443/445
Found: Molpeak (M−Na)$^-$: 441/443/445 (Cl$_2$)
R$_f$ value: 0.27 (silica gel, dichloromethane/MeOH/conc. aqueous ammonia 90:10:1)

EXAMPLE 124

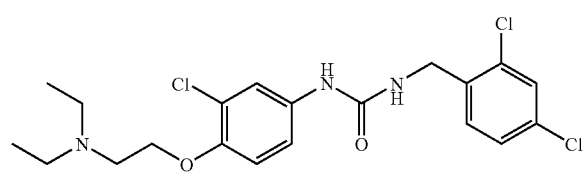

124) 1-[3-chloro-4-(2-diethylamino-ethoxy)-phenyl]-3-(2,4-dichloro-benzyl)-urea 203 mg (1.236 mmol) of CDT in 4 mL DMF was added to a solution of 345 mg (1.236 mmol) of 3-chloro-4-(2-diethylamino-ethoxy)-phenylamine-hydrochloride (intermediate product Z1b) and 0.56 mL (4.000 mmol) of triethylamine in 40 mL THF and the mixture was stirred for 2 hours at RT. 176 mg (1.236 mmol) of 2,4-dichloro-benzylamine was added, the reaction mixture was refluxed for 4 hours and then evaporated down i. vac. The residue was purified by column chromatography (silica gel, dichloromethane/MeOH/conc. aqueous ammonia 80:20:1) and the product was triturated with diisopropylether.

Yield: 300 mg (55% of theory)
$C_{20}H_{24}Cl_3N_3O_2$ (M=444.792)
Calc.: Molpeak(M+H)$^+$: 444/446/448
Found: Molpeak (M+H)$^+$: 444/446/448 (Cl$_3$)
R$_f$ value: 0.73 (silica gel, dichloromethane/MeOH/conc. aqueous ammonia 80:20:1)

EXAMPLE 125

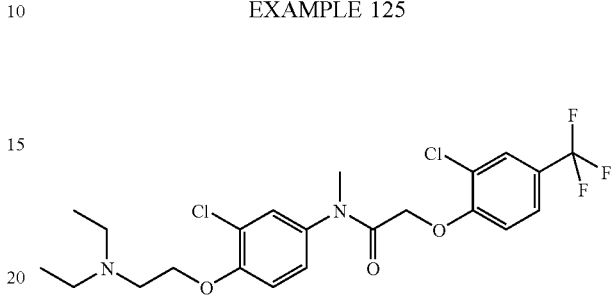

125a) tert.butyl [3-chloro-4-(2-diethylamino-ethoxy)-phenyl]-carbaminate 0.31 mL (2.266 mmol) of triethylamine was added to a solution of 0.500 g (2.06 mmol) of 3-chloro-4-(2-diethylamino-ethoxy)-phenylamine and 0.495 g (2.266 mmol) of Boc-anhydride in 10 mL dichloromethane at RT and the mixture was stirred for 48 hours. The reaction mixture was diluted with dichloromethane and the org. phase was washed with sat. aqueous sodium bicarbonate solution. The combined org. extracts were dried over magnesium sulphate and evaporated down i. vac. Column chromatography (silica gel, dichloromethane/MeOH/conc. aqueous ammonia 90:10:1) yielded the product.

Yield: 500 mg (71% of theory)
$C_{17}H_{27}ClN_2O_3$ (M=342.869)
Calc.: Molpeak(M+H$^+$: 343/345
Found: Molpeak (M+H)$^+$: 343/345 (Cl)

125b) [3-chloro-4-(2-diethylamino-ethoxy)-phenyl]-methyl-amine

Under a nitrogen atmosphere a solution of 500 mg (1.458 mmol) of tert.butyl [3-chloro-4-(2-diethylamino-ethoxy)-phenyl]-carbaminate in 10 mL THF was slowly added dropwise to a suspension of 165 mg (4.374 mmol) of lithium aluminium hydride in 20 mL abs. THF and the mixture was stirred for 16 hours at RT. 165 µL of water, 165 µL of 15% aqueous NaOH solution and a further 495 µL water was added and the precipitate formed was filtered off. The filtrate was dried over magnesium sulphate, evaporated down i. vac. and the residue was purified by column chromatography (silica gel, EtOAc/MeOH/conc. aqueous ammonia 90:10:1).

Yield: 180 mg (48% of theory)
$C_{13}H_{21}ClN_2O$ (M=256.778)
Calc.: Molpeak(M+H)$^+$: 257/259
Found: Molpeak (M+H)$^+$: 257/259 (Cl)
R$_f$ value: 0.61 (silica gel, EtOAc/MeOH/conc. aqueous ammonia 90:10:1)

125c) N-[3-chloro-4-(2-diethylamino-ethoxy)-phenyl]-2-(2-chloro-4-trifluoromethyl-phenoxy)-N-methyl-acetamide 293 mg (0.911 mmol) of TBTU and 123 mg (0.911 mmol) of HOBT were added to a suspension of 231 mg (0.911 mmol) of (2-chloro-4-trifluoromethyl-phenoxy)-acetic acid (intermediate product Z2b) in 5 mL abs. THF and the mixture was stirred for 10 minutes at RT. 180 mg (0.701 mmol) of [3-chloro-4-(2-diethylamino-ethoxy)-phenyl]-methyl-amine and 0.18 mL (1.051 mmol) of ethyl-diisopropylamine were added, the mixture was stirred for 16 hours at RT and evaporated down i. vac. The residue was purified by column chromatography (silica gel, silica gel, dichloromethane/MeOH/conc. aqueous ammonia 85:15:1).

Yield: 150 mg (43% of theory)
$C_{22}H_{25}Cl_2F_3N_2O_3$ (M=493.357)
Calc.: Molpeak(M+H)$^+$: 493/495/497
Found: Molpeak (M+H)$^+$: 493/495/497 (Cl$_2$)
$R_f$ value: 0.416 (silica gel, dichloromethane/MeOH/conc. aqueous ammonia 90:10:1).

EXAMPLE 126

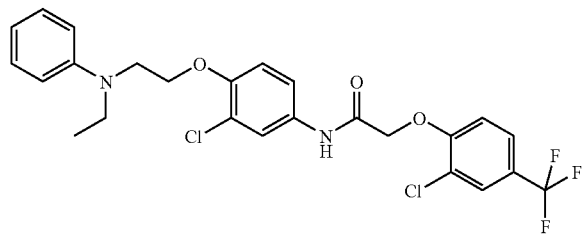

126) N-{3-chloro-4-[2-(ethyl-phenyl-amino)-ethoxy]-phenyl}-2-(2-chloro-4-trifluoromethyl-phenoxy)-acetamide The product was obtained according to general working method V starting from 0.422 g (0.616 mmol) N-[3-chloro-4-(2-oxo-ethoxy)-phenyl]-2-(2-chloro-4-trifluoromethyl-phenoxy)-acetamide (Z3d) and 0.094 mL (0.739 mmol) N-ethylaniline.

Yield: 20 mg (6.2% of theory)
$C_{25}H_{23}Cl_2F_3N_2O_3$ (M=527.375)
Calc.: molpeak (M−H)$^-$: 525/527/529
Found: molpeak (M−H)$^-$: 525/527/529 (Cl$_2$)
$R_f$ value: 0.94 (silica gel, EtOAc)

EXAMPLE 127

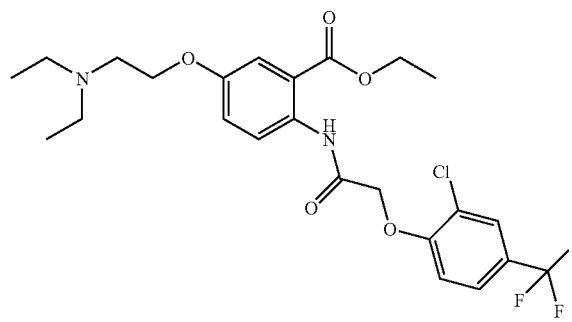

ethyl 2-[2-(2-chloro-4-trifluoromethyl-phenoxy)-acetylamino]-5-(2-diethylamino-ethoxy)-benzoate The product was obtained according to general working method I starting from 1.00 g (3.567 mmol) (2-chloro-4-trifluoromethyl-phenoxy)-acetic acid (Z2b) and 0.908 g (3.567 mmol) ethyl 2-amino-5-(2-diethylamino-ethoxy)-benzoate (Z25c).

Yield: 1.700 g (92% of theory)
$C_{24}H_{28}ClF_3N_2O_5$ (M=516.949)
Calc.: molpeak (M−H)$^-$: 515/517
Found: molpeak (M−H)$^-$: 515/517 (Cl)
$R_f$ value: 0.35 (silica gel, EtOAc/MeOH/conc. aqueous ammonia 90:10:1).

EXAMPLE 128

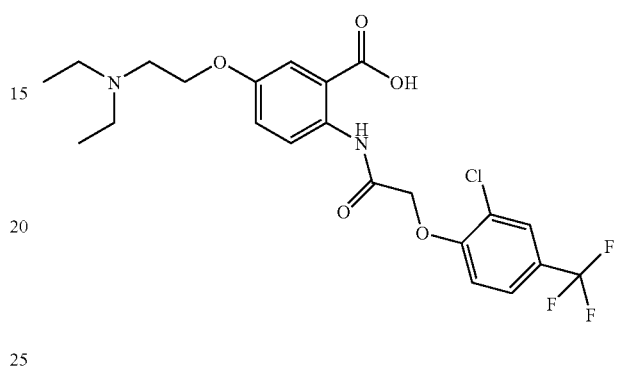

128) 2-[2-(2-chloro-4-trifluoromethyl-phenoxy)-acetylamino]-5-(2-diethylamino-ethoxy)-benzoic acid 10 mL aqueous NaOH (1N) was added to a solution of 0.900 g (1.741 mmol) ethyl 2-[2-(2-chloro-4-trifluoromethyl-phenoxy)-acetylamino]-5-(2-diethylamino-ethoxy)-benzoate (Example 127) in 30 mL EtOH and the mixture was stirred for 2 h at RT.

The reaction mixture was acidified with 10 mL aqueous HCl (1M) and treated with ultrasound for 30 min. The precipitate was filtered off, washed with water and dried at 50° C. i. vac.

Yield: 0.640 g (75% of theory)
$C_{22}H_{24}ClF_3N_2O_5$ (M=488.895)
Calc.: molpeak (M−H)$^-$: 487/489
Found: molpeak (M−H)$^-$: 487/489 (Cl)

EXAMPLE 129

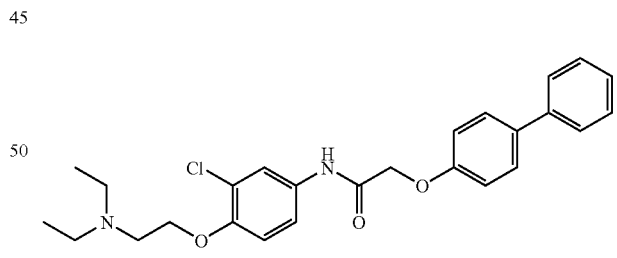

129) 2-(biphenyl-4-yloxy)-N-[3-chloro-4-(2-diethylamino-ethoxy)-phenyl]-acetamide The product was prepared according to general working method I from (biphenyl-4-yloxy)-acetic acid and 3-chloro-4-(2-diethylamino-ethoxy)-phenylamine.

Yield: 0.560 g (58% of theory)
$C_{26}H_{29}ClN_2O_3$ (M=452.986)
Calc.: molpeak (M+H)$^+$: 453/455
Found: molpeak (M+H)$^+$: 453/455 (Cl)
$R_f$ value: 0.76 (silica gel, dichloromethane/MeOH/cyclohexane conc. aqueous ammonia 75:15:15:1).

EXAMPLE 130

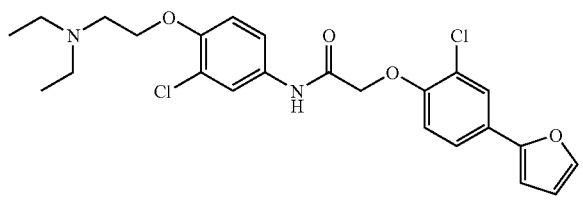

130a) ethyl (2-chloro-4-furan-2-yl-phenoxy)-acetate 3.5 mL aqueous sodium carbonate solution (1 M) was added to a solution of 1.00 g (3.407 mmol) ethyl (4-bromo-2-chloro-phenoxy)-acetate (Z26), 0.784 g (6.800 mmol) 2-furanboric acid and 0.196 g (0.170 mmol) tetrakis-triphenylphosphine-palladium in 65 mL dioxane and the mixture was refluxed for 4 h. The reaction mixture was cooled to RT, evaporated down i. vac. , diluted with water and exhaustively extracted with EtOAc. The combined org. phases were washed with saturated aqueous sodium bicarbonate, water and saturated aqueous NaCl, dried over sodium sulphate and evaporated down i. vac. Column chromatography (silica gel, petroleum ether/EtOAc 3:1) yielded the product.

Yield: 0.800 g (84% of theory)
$C_{14}H_{13}ClO_4$ (M=280.710)
Calc.: molpeak $(M+H)^+$: 281/283
Found: molpeak $(M+H)^+$: 281/283 (Cl)
$R_f$ value: 0.56 (silica gel, petroleum ether/EtOAc 3:1).

130b) (2-chloro-4-furan-2-yl-phenoxy)-acetic acid 0.40 g (10.00 mmol) NaOH in 5 mL water was added to a solution of 0.280 g (2.672 mmol) ethyl (2-chloro-4-furan-2-yl-phenoxy)-acetate (130a) in 20 mL abs. EtOH and the mixture was stirred for 16 h at RT. The reaction mixture was diluted with water and acidified to pH 1 with semiconc. aqueous HCl. The precipitate was filtered off, washed with water and dried in a HV.

Yield: 0.630 g (93% of theory)
$C_{12}H_9ClO_4$ (M=252.656)
Calc.: molpeak $(M-H)^-$: 251/253
Found: molpeak $(M-H)^-$: 251/253 (Cl)

130c) N-[3-chloro-4-(2-diethylamino-ethoxy)-phenyl]-2-(2-chloro-4-furan-2-yl -phenoxy)-acetamide The product was prepared according to general working method I from 2-chloro-4-furan-2-yl-phenoxy)-acetic acid (1 30b) and 3-chloro-4-(2-diethylamino-ethoxy)-phenylamine (Z1b).

Yield: 0.380 g (79% of theory)
$C_{24}H_{26}Cl_2N_2O_4$ (M=477.392)
Calc.: molpeak $(M+H)^+$: 477/479/481
Found: molpeak $(M+H)^+$: 477/479/481 $(Cl_2)$
$R_f$ value: 0.70 (Alox, dichloromethane/MeOH 30:1).

EXAMPLE 131

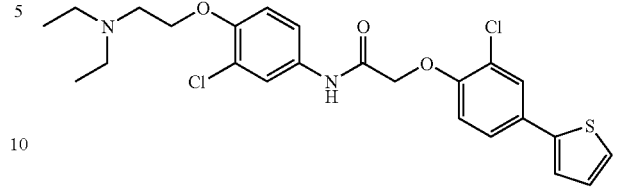

131a) ethyl (2-chloro-4-thiophen-2-yl-phenoxy)-acetate
Prepared analogously to Example 130a from ethyl (4-bromo-2-chloro-phenoxy)-acetate (Z26) and thiophene-2-boric acid.
Yield: 0.730 g (72% of theory)
$C_{14}H_{13}ClO_3S$ (M=296.775)
Calc.: molpeak $(M+H)^+$: 297/299
Found: molpeak $(M+H)^+$: 297/299 (Cl)
$R_f$ value: 0.60 (silica gel, petroleum ether/EtOAc 3:1).

131b) (2-chloro-4-thiophen-2-yl-phenoxy)-acetic acid
Prepared analogously to Example 130b from ethyl (2-chloro-4-thiophen-2-yl-phenoxy)-acetate (131a).
Yield: 0.600 g (95% of theory)
$C_{12}H_9ClO_3S$ (M=268.721)
Calc.: molpeak $(M+H)^+$: 267/269
Found: molpeak $(M+H)^+$: 267/269 (Cl)

131 c) N-[3-chloro-4-(2-diethylamino-ethoxy)-phenyl]-2-(2-chloro-4-thiophen-2-yl -phenoxy)-acetamide
The product was prepared according to general working method I from 2-chloro-4-thiophen-2-yl-phenoxy)-acetic acid (131b) and 3-chloro-4-(2-diethylamino-ethoxy)-phenylamine (Z1b).
Yield: 0.410 g (83% of theory)
$C_{24}H_{26}Cl_2N_2O_3S$ (M=493.456)
Calc.: molpeak $(M+H)^+$: 491/493/495
Found: molpeak $(M+H)^+$: 491/493/495 $(Cl_2)$
$R_f$ value: 0.64 (Alox, dichloromethane/MeOH 30:1).

EXAMPLE 132

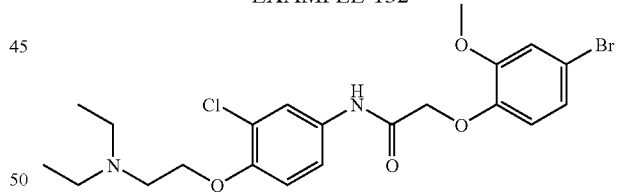

132a) ethyl 2-(4-bromo-2-methoxy-phenoxy)-acetate
Prepared analogously to Intermediate product Z2a from ethyl bromo-acetate and 2-methoxy-4-bromophenol.
Yield: 3.600 g (83% of theory)
$C_{11}H_{13}BrO_4$ (M=289.128)
Calc.: molpeak $(M+H)^+$: 289/291
Found: molpeak $(M+H)^+$: 289/291 (Br).

132b) 2-(4-bromo-2-methoxy-phenoxy)-acetic acid
Prepared analogously to Example 130b from ethyl 2-(4-bromo-2-methoxy-phenoxy)-acetate (132a).
Yield: 3.250 g (quant. yield)
$C_9H_9BrO_4$ (M=289.128)
Calc.: molpeak $(M+H)^+$: 261/263
Found: molpeak $(M+H)^+$: 261/263 (Br).

132c) 2-(4-bromo-2-methoxy-phenoxy)-N-[3-chloro-4-(2-diethylamino-ethoxy)-phenyl]-acetamide The product was prepared according to general working method I from 2-(4-bromo-2-methoxy-phenoxy)-acetic acid (132b) and 3-chloro-4-(2-diethylamino-ethoxy)-phenylamine (Z1b).

Yield: 0.050 g (20% of theory)
$C_{21}H_{26}BrClN_2O_4$ (M=485.809)
Calc.: molpeak (M+H)$^+$: 485/487/489
Found: molpeak (M+H)$^+$: 485/487/489 (BrCl)
$R_f$ value: 0.55 (silica gel, dichloromethane/MeOH 9:1).

EXAMPLE 133

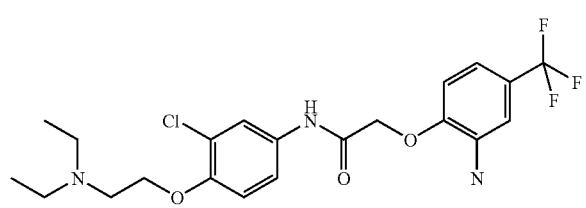

133) 2-(2-amino-4-trifluoromethyl-phenoxy)-N-[3-chloro-4-(2-diethylamino-ethoxy)-phenyl]-acetamide A suspension of 0.280 g (0.570 mmol) 2-(2-amino-4-trifluoromethyl-phenoxy)-N-[3-chloro-4-(2-diethylamino-ethoxy)-phenyl]-acetamide (Example 65) and 50 mg Raney nickel in 10 mL MeOH was hydrogenated for 5 h at 50 psi. The catalyst was filtered off and the filtrate evaporated down i. vac. Column chromatography (Alox, N, act. II-III, gradient dichloromethane/MeOH 49:1 19:1) yielded the product.

Yield: 0.180 g (69% of theory)
$C_{21}H_{25}ClF_3N_3O_3$ (M=459.900)
Calc.: molpeak (M+H)$^+$: 460/462
Found: molpeak (M+H)$^+$: 460/462 (Cl)
$R_f$ value: 0.42 (Alox, dichloromethane/MeOH 19:1).

EXAMPLE 134

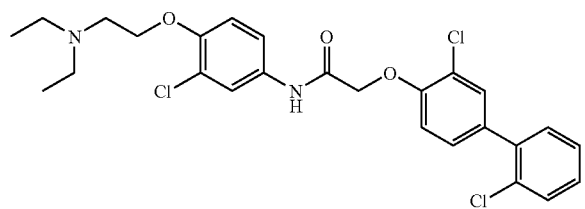

134a) ethyl (3,2'-dichloro-biphenyl-4-yloxy)-acetate
Prepared analogously to Example 130a from ethyl (4-bromo-2-chloro-phenoxy)-acetate (Z26) and 2-chlorophenylboric acid.

Yield: 1.070 g (97% of theory)
$C_{16}H_{14}Cl_2O_3$ (M=325.194)
$R_f$ value: 0.58 (silica gel, petroleum ether/EtOAc 3:1).

134b) (3,2'-dichloro-biphenyl-4-yloxy)-acetic acid
Prepared analogously to Example 130b from ethyl (3,2'-dichloro-biphenyl-4-yloxy)-acetate (134a).

Yield: 0.900 g (92% of theory)
$C_{14}H_{10}Cl_2O_3$ (M=297.140)
Calc.: molpeak (M-H)$^-$: 295/297/299
Found: molpeak (M-H)$^-$: 295/297/299 (Cl$_2$)

134c) N-[3-chloro-4-(2-diethylamino-ethoxy)-phenyl]-2-(3,2'-dichloro-biphenyl-4-yloxy)-acetamide The product was prepared according to general working method I from (3,2'-dichloro-biphenyl-4-yloxy)-acetic acid (134b) and 3-chloro-4-(2-diethylamino-ethoxy)-phenylamine (Z1b).

Yield: 0.250 g (48% of theory)
$C_{26}H_{27}Cl_3N_2O_3$ (M=521.876)
Calc.: molpeak (M+H)$^+$: 521/523/525/527
Found: molpeak (M+H)$^+$: 521/523/525/527 (Cl$_3$)
$R_f$ value: 0.65 (Alox, dichloromethane/MeOH 30:1).

EXAMPLE 135

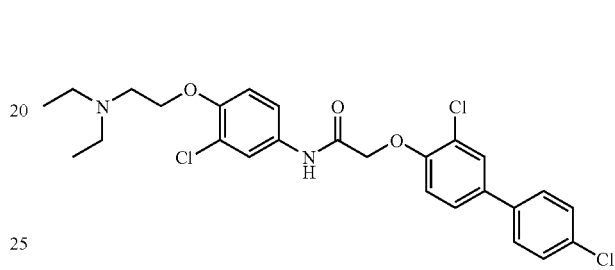

135a) ethyl (3,4'-dichloro-biphenyl-4-yloxy)-acetate
Prepared analogously to Example 130a from ethyl (4-bromo-2-chloro-phenoxy)-acetate (Z26) and 4-chlorophenylboric acid.

Yield: 0.430 g (68% of theory)
$C_{16}H_{14}Cl_2O_3$ (M=325.194)
$R_f$ value: 0.62 (silica gel, petroleum ether/EtOAc 3:1).

135b) (3,4'-dichloro-biphenyl-4-yloxy)-acetic acid
Prepared analogously to Example 130b from ethyl (3,4'-dichloro-biphenyl-4-yloxy)-acetate (135a).

Yield: 0.299 g (76% of theory)
$C_{14}H_{10}Cl_2O_3$ (M=297.140)
Calc.: molpeak (M-H)$^-$: 295/297/299
Found: molpeak (M-H)$^-$: 295/297/299 (Cl$_2$)

135c) N-[3-chloro-4-(2-diethylamino-ethoxy)-phenyl]-2-(3,4'-dichloro-biphenyl-4-yloxy)-acetamide The product was prepared according to general working method I from (3,4'-dichloro-biphenyl-4-yloxy)-acetic acid (135b) and 3-chloro-4-(2-diethylamino-ethoxy)-phenylamine (Z1b).

Yield: 0.280 g (60% of theory)
$C_{26}H_{27}Cl_3N_2O_3$ (M=521.876)
Calc.: molpeak (M+H)$^+$: 521/523/525/527
Found: molpeak (M+H)$^+$: 521/523/525/527 (Cl$_3$)
$R_f$ value: 0.48 (Alox, dichloromethane/MeOH 50:1).

EXAMPLE 136

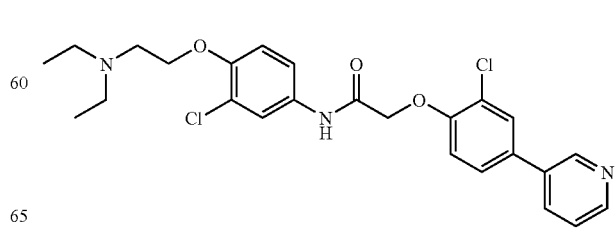

136a) ethyl (2-chloro-4-pyridin-3-yl-phenoxy)-acetate
Prepared analogously to Example 130a from ethyl (4-bromo-2-chloro-phenoxy)-acetate (Z26) and pyridine-3-boric acid.
Yield: 0.420 g (58% of theory)
$C_{16}H_{14}ClNO_3$ (M=291.737)
$R_f$ value: 0.45 (silica gel, petroleum ether/EtOAc 1:3).

136b) (2-chloro-4-pyridin-3-yl-phenoxy)-acetic acid
250 mg (6.250 mmol) NaOH in 10 mL water was added to a solution of 0.400 g (1.371 mmol) ethyl (2-chloro-4-pyridin-3-yl-phenoxy)-acetate in 40 mL abs. EtOH and the mixture was stirred for 1 h at RT. The reaction mixture was acidified with aqueous HCl (1 M) to pH 7.5, the precipitate was filtered off and washed with water.
Yield: 0.269 g (74% of theory)
$C_{13}H_{10}ClNO_3$ (M=263.683)
Calc.: molpeak $(M+Na)^+$: 264/266
Found: molpeak $(M+Na)^+$: 264/266 $(Cl_3)$ 136c) N-[3-chloro-4-(2-diethylamino-ethoxy)-phenyl]-2-(2-chloro-4-pyridin-3-yl-phenoxy)-acetamide
The product was prepared according to general working method I from (2-chloro-4-pyridin-3-yl-phenoxy)-acetic acid (136b) and 3-chloro-4-(2-diethylamino-ethoxy)-phenylamine (Z1b).
Yield: 0.328 g (75% of theory)
$C_{25}H_{27}Cl_2N_3O_3$ (M=488.418)
Calc.: molpeak $(M+H)^+$: 488/490/492
Found: molpeak $(M+H)^+$: 488/490/492 $(Cl_2)$
$R_f$ value: 0.47 (Alox, dichloromethane/MeOH 30:1).

EXAMPLE 137

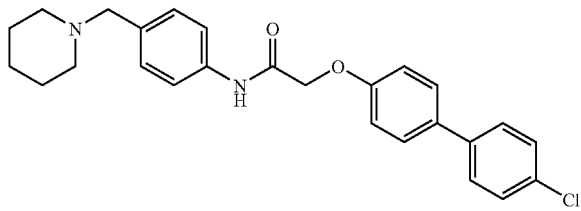

137a) (4'-chloro-biphenyl-4-yloxy)-acetic acid
1.5 mL TFA was added to a solution of 0.750 g (2.000 mmol) tert-butyl (4'-chloro-biphenyl-4-yloxy)-acetate in 20 mL dichloromethane and the mixture was stirred for 16 h at RT. The reaction mixture was evaporated down i. vac. and diluted with 1 M aqueous NaOH and EtOAc. The precipitate was filtered off and dried at 80° C. i. vac.
Yield: 0.522 g (quant. yield)
$C_{14}H_{11}ClO_3$ (M=262.695)
Calc.: molpeak $(M-H)^-$: 261/263
Found: molpeak $(M-H)^-$: 261/263 (Cl)

137b) 2-(4'-chloro-biphenyl-4-yloxy)-N-(4-piperidin-1-yl-methyl-phenyl)-acetamide
The product was prepared according to general working method I from (4'-chloro-biphenyl4-yloxy)-acetic acid (137a) and 4-piperidin-ylmethyl-phenylamine.
Yield: 0.140 g (40% of theory)
$C_{26}H_{27}ClN_2O_2$ (M=434.970)
Calc.: molpeak $(M+H)^+$: 435/437
Found: molpeak $(M+H)^+$: 435/437 (Cl)
$R_f$ value: 0.40 (silica gel, dichloromethane/MeOH 9:1).

EXAMPLE 138

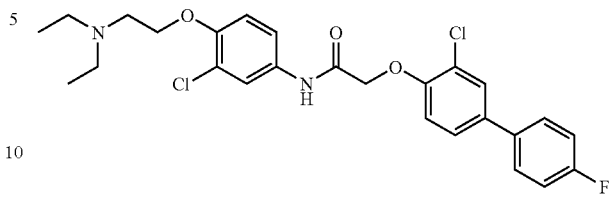

138a) ethyl (3-chloro-4'-fluoro-biphenyl-4-yloxy)-acetate
Prepared analogously to Example 130a from ethyl (4-bromo-2-chloro-phenoxy)-acetate (Z26) and 4-fluoro-phenylboric acid.
Yield: 0.850 g (81% of theory)
$C_{16}H_{14}ClFO_3$ (M=308.740)
Calc.: molpeak $(M+H)^+$: 309/311
Found: molpeak $(M+H)^+$: 309/311 (Cl)
$R_f$ value: 0.45 (silica gel, petroleum ether/EtOAc 3:1).

138b) (3-chloro-4'-fluoro-biphenyl-4-yloxy)-acetic acid
Prepared analogously to Example 130b from ethyl (3-chloro-4'-fluoro-biphenyl-4-yloxy)-acetate (138a).
Yield: 0.520 g (67% of theory)
$C_{14}H_{10}ClFO_3$ (M=280.685)
Calc.: molpeak $(M-H)^-$: 279/281
Found: molpeak $(M-H)^-$: 279/281 (Cl)

138c) N-[3-chloro-4-(2-diethylamino-ethoxy)-phenyl]-2-(3-chloro-4'-fluoro-biphenyl-4-yloxy)-acetamide
The product was prepared according to general working method I from (3-chloro-4'-fluoro-biphenyl-4-yloxy)-acetic acid (138b) and 3-chloro-4-(2-diethylamino-ethoxy)-phenylamine (Z1b).
Yield: 0.440 g (87% of theory)
$C_{26}H_{27}C_{12}FN_2O_3$ (M=505.421)
Calc.: molpeak $(M+H)^+$: 505/507/509
Found: molpeak $(M+H)^+$: 505/507/509 $(Cl_2)$
$R_f$ value: 0.46 (Alox, dichloromethane/MeOH 50:1).

EXAMPLE 139

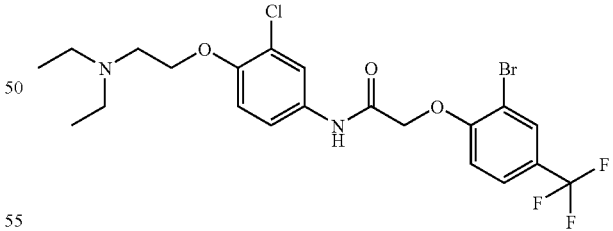

139a) ethyl (2-bromo4-trifluoromethyl-phenoxy)-acetate
A solution of 2.650 g (11.000 mmol) 2-bromo-4-trifluoromethyl-phenol and 1.47 mL 13.20 mmol) ethyl bromoacetate in 20 mL Hünig base was stirred for 5 h at 120° C. The reaction mixture was diluted with EtOAc and the org. phase was washed with water, saturated aqueous sodium bicarbonate and saturated aqueous NaCl, dried over magnesium sulphate and evaporated down i. vac. Column chromatography (silica gel, gradient dichloromethane/MeOH 100:0→19:1) yielded the product.

Yield: 2.80 g (78% of theory)
$C_{11}H_{10}BrF_3O_3$ (M=327.100)
Calc.: molpeak (M+H)$^+$: 327/329
Found: molpeak (M+H)$^+$: 327/329 (Br)
$R_f$ value: 0.85 (silica gel, dichloromethane).

139b) (2-bromo-4-trifluoromethyl-phenoxy)-acetic acid

Prepared analogously to Example 130b from ethyl (2-bromo-4-trifluoromethyl-phenoxy)-acetate (139a).
Yield: 2.150 g (84% of theory)
$C_9H_6BrF_3O_3$ (M=299.046)
Calc.: molpeak (M−H)$^-$: 297/299
Found: molpeak (M−H)$^-$: 297/299 (Br)
$R_f$ value: 0.35 (silica gel, dichloromethane/MeOH 49:1).

139c) 2-(2-bromo-4-trifluoromethyl-phenoxy)-N-[3-chloro-4-(2-diethylamino-ethoxy)-phenyl]-acetamide The product was prepared according to general working method I from (2-bromo-4-trifluoromethyl-phenoxy)-acetic acid (139b) and 3-chloro-4-(2-diethylamino-ethoxy)-phenylamine (Z1b).
Yield: 0.450 g (86% of theory)
$C_{21}H_{23}BrClF_3N_2O_3$ (M=523.781)
Calc.: molpeak (M+H)$^+$: 523/525/527
Found: molpeak (M+H)$^+$: 523/525/527 (BrCl)
$R_f$ value: 0.45 (silica gel, dichloromethane/MeOH 9:1).

EXAMPLE 140

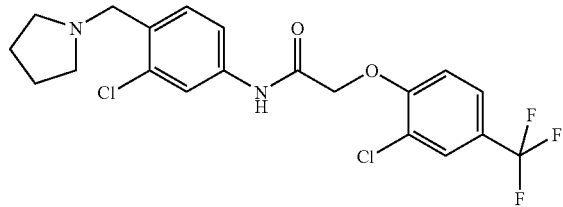

140a) 1-(2-chloro-4-nitro-benzyl)-pyrrolidine 10.50 g (74.452 mmol) potassium carbonate was added to a solution of 7.400 g (29.543 mmol) of 1-bromomethyl-2-chloro-4-nitro-benzene and 5.00 mL (59.300 mmol) pyrrolidine in 150 mL acetonitrile and the mixture was stirred for 16 h at RT. The reaction mixture was diluted with 200 mL dichloromethane, filtered and the filtrate evaporated down i. vac. The residue was taken up in EtOAc, the org. phase was washed with water, dried over magnesium sulphate and evaporated down i. vac. The crude product was used in the next reaction step without any further purification.
Yield: 6.100 g (86% of theory)
$C_{11}H_{13}ClN_2O_2$ (M=240.691)
Calc.: molpeak (M+H)$^+$: 241/243
Found: molpeak (M+H)$^+$: 241/243 (Cl)
$R_f$ value: 0.38 (silica gel, petroleum ether/EtOAc 2:1).

140b) 3-chloro-4-pyrrolidin-1-ylmethyl-phenylamine

A suspension of 1.00 g (4.155 mmol) 1-(2-chloro-4-nitro-benzyl)-pyrrolidine (140a) and 100 mg Raney nickel in 30 mL MeOH were hydrogenated at RT and 10 psi. The catalyst was filtered off and the filtrate evaporated down i. vac.
Yield: 0.840 g (96% of theory)
$C_{11}H_{15}ClN_2$ (M=210.709)
Calc.: molpeak (M+H)$^+$: 211/213
Found: molpeak (M+H)$^+$: 211/213 (Cl)

$R_f$ value: 0.78 (silica gel, dichloromethane/MeOH/cyclohexane/conc. aqueous ammonia 75:15:15:1).

140c) N-(3-chloro-4-pyrrolidin-1-ylmethyl-phenyl)-2-(2-chloro-4-trifluoromethyl phenoxy)-acetamide The product was prepared according to general working method I from (2-chloro-4-trifluoromethyl-phenoxy)-acetic acid (Z2b) and 3-chloro-4-pyrrolidin-1-ylmethyl-phenylamine (140b).
Yield: 0.360 g (51% of theory)
$C_{20}H_{19}Cl_2F_3N_2O_2$ (M=447.288)
Calc.: molpeak (M+H)$^+$: 447/449/451
Found: molpeak (M+H)$^+$: 447/449/451 (Cl$_2$)
$R_f$ value: 0.58 (silica gel, dichloromethane/EtOAc/MeOH/conc. aqueous ammonia 350:75:75:10).

EXAMPLE 141

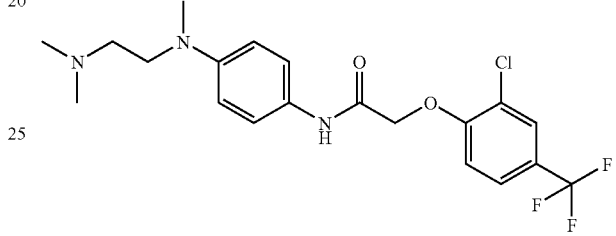

141a) N,N,N'-trimethyl-N'-(4-nitro-phenyl)-ethane-1,2-diamine 3.600 g (25.514 mmol) 1-fluoro-4-nitrobenzene and 8.00 mL (62.948 mmol) N,N,N'-trimethyl-ethylene-1,2-diamine were stirred for 1 h at 100° C. and then cooled to RT. The reaction mixture was diluted with water and exhaustively extracted with ether. The combined org. phases were dried over sodium sulphate and evaporated down i. vac.
Yield: 5.771 g (quant. yield)
$C_{11}H_{17}N_3O_2$ (M=223.277)
Calc.: molpeak (M+H)$^+$: 224
Found: molpeak (M+H)$^+$: 224
$R_f$ value: 0.32 (silica gel, EtOAc/EtOH/conc. aqueous ammonia 50:10:1).

141b) N-(2-dimethylamino-ethyl)-N-methylbenzene-1,4-diamine

A suspension of 5.770 g (25.842 mmol), N,N'-trimethyl-N'-(4-nitro-phenyl)-ethane-1,2-diamine (141a) and 0.60 g Pd/C (10%) in EtOH was hydrogenated for 4.5 h at 50 psi. The catalyst was filtered off and the filtrate evaporated down i. vac. The crude product was further reacted immediately.
Yield: 3.162 g (63% of theory)
$C_{11}H_{19}N_3$ (M=1943.294)

141c) 2-(2-chloro-4-trifluoromethyl-phenoxy)-N-{4-[(2-dimethylamino-ethyl)-methyl-amino]-phenyl}-acetamide The product was prepared according to general working method I from (2-chloro-4-trifluoromethyl-phenoxy)-acetic acid (Z2b) and N-(2-dimethylamino-ethyl)-N-methylbenzene-1,4-diamine (141b).
Yield: 0.110 g (37% of theory)
$C_{20}H_{23}ClF_3N_3O_2$ (M=429.873)
Calc.: molpeak (M+H)$^+$: 430/432
Found: molpeak (M+H)$^+$: 430/432 (Cl)
$R_f$ value: 0.37 (silica gel, dichloromethane/MeOH/conc. aqueous ammonia 90:10:1).

EXAMPLE 142

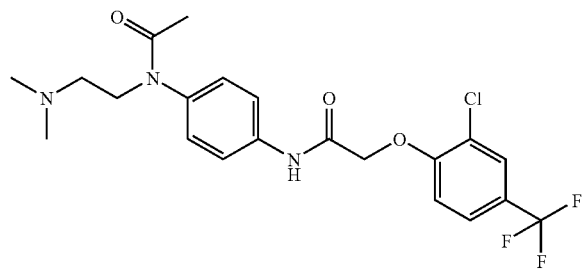

142a) N-(2-dimethylamino-ethyl)-N-(4-nitro-phenyl)-acetamide

A solution of 50 g (0.239 mol) N,N-dimethyl-N'-(4-nitrophenyl)-ethane-1,2-diamine in 500 mL acetic anhydride was stirred for 3.5 h at 130° C., then evaporated down i. vac. and neutralised with saturated aqueous sodium bicarbonate. The residue was exhaustively extracted with EtOAc, the combined org. phases were dried over sodium sulphate and evaporated down i. vac.

Yield: 58.36 g (97% of theory)
$C_{12}H_{17}N_3O_3$ (M=251.288)
Calc.: molpeak $(M+H)^+$: 252
Found: molpeak $(M+H)^+$: 252
$R_f$ value: 0.55 (silica gel, dichloromethane/MeOH/conc. aqueous ammonia 90:10:1).

142b) N-(4-amino-phenyl)-N-(2-dimethylamino-ethyl)-acetamide

Prepared analogously to Example 141b starting from -(2-dimethylamino-ethyl)-N-(4-nitro-phenyl)-acetamide) (142a).

Yield: 50.66 g (99% of theory)
$C_{12}H_{19}N_3O$ (M=221.305)
Calc.: molpeak $(M+H)^+$: 222
Found: molpeak $(M+H)^+$: 222
$R_f$ value: 0.50 (silica gel, dichloromethane/MeOH/conc. aqueous ammonia 90:10:1).

142c) N-{4-[acetyl-(2-dimethylamino-ethyl)-amino]-phenyl}-2-(2-chloro-4-trifluoromethyl-phenoxy)-acetamide The product was prepared according to general working method I from (2-chloro-4-trifluoromethyl-phenoxy)-acetic acid (Z2b) and N-(4-amino-phenyl)-N-(2-dimethylamino-ethyl)-acetamide (142b).

Yield: 0.200 g (64% of theory)
$C_{21}H_{23}ClF_3N_3O_3$ (M=457.884)
Calc.: molpeak $(M+H)^+$: 458/460
Found: molpeak $(M+H)^+$: 458/460 (Cl)
$R_f$ value: 0.64 (Alox, dichloromethane/MeOH 19:1).

EXAMPLE 143

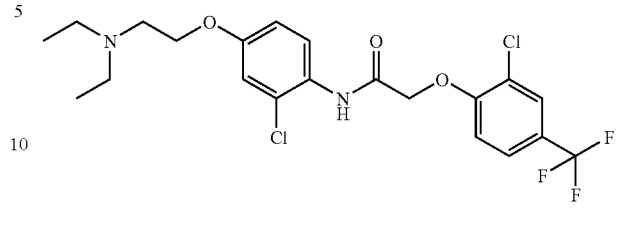

143) N-[2-chloro-4-(2-diethylamino-ethoxy)-phenyl]-2-(2-chloro-4-trifluoromethyl-phenoxy)-acetamide 0.141 mL (1.080 mmol) chloroformic acid-isopropylester was added dropwise at −10° C. to a solution of 0.254 g (0.982 mmol) (2-chloro-4-trifluoromethyl-phenoxy)-acetic acid (Z2b) and 0.119 mL (1.080 mmol) N-methylmorpholine in 20 mL abs. THF and the mixture was stirred for a further 10 min. 0.250 g (1.031 mmol) 2-chloro-4-(2-diethylamino-ethoxy)-phenylamine (Z27b) was added, the mixture was stirred for 1 h at RT and then evaporated down i. vac. Water was added and the aqueous phase was exhaustively extracted with dichloromethane. The combined org. phases were dried over sodium sulphate, evaporated down i. vac. and the residue stirred with ether. The precipitate was filtered off, washed with ether and dried in a HV.

Yield: 0.210 g (45% of theory)
$C_{21}H_{23}Cl_2F_3N_2O_3$ (M=479.330)
Calc.: molpeak $(M+H)^+$: 479/481/483
Found: molpeak $(M+H)^+$: 479/481/483 ($Cl_2$)
$R_f$ value: 0.67 (Alox, dichloromethane/MeOH 39:1).

EXAMPLE 144

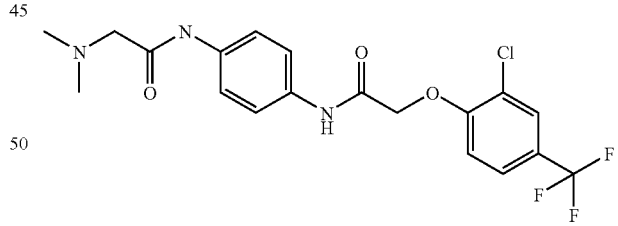

144) 2-(2-chloro-4-trifluoromethyl-phenoxy)-N-[4-(2-dimethylamino-acetylamino)-phenyl]-acetamide Prepared analogously to Example 143 starting from (2-chloro-4-trifluoromethyl-phenoxy)-acetic acid (Z2b) and N-(4-amino-phenyl)-2-dimethylamino-acetamide.

Yield: 0.270 g (64% of theory)
$C_{19}H_{19}ClF_3N_3O_3$ (M=429.830)
Calc.: molpeak $(M+H)^+$: 430/432
Found: molpeak $(M+H)^+$: 430/432 (Cl)
$R_f$ value: 0.82 (Alox, dichloromethane/MeOH 39:1).

EXAMPLE 145

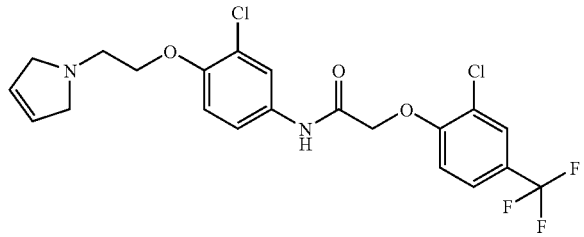

145) N-{3-chloro-4-[2-(2,5-dihydro-pyrrol-1-yl)-ethoxy]-phenyl}-2-(2-chloro-4-trifluoromethyl-phenoxy)-acetamide A solution of 0.145 g (0.300 mmol) of N-[4-(2-bromo-ethoxy)-3-chloro-phenyl]-2-(2-chloro-4-trifluoromethyl-phenoxy)-acetamide (Z28b) and 30.6 µL (0.400 mmol) 2,5-dihydro-1H-pyrrole in 2 mL Hünig base was stirred for 3h at 80° C. and then evaporated down i. vac. Column chromatography (Alox, neutral, act. II-III, gradient dichloromethane/MeOH 20:0→19:1) yielded the product.

Yield: 85 mg (60% of theory)
$C_{21}H_{19}Cl_2F_3N_2O_3$ (M=475.298)
Calc.: molpeak (M+H)$^+$: 475/477/479
Found: molpeak (M+H)$^+$: 475/477/479 (Cl$_2$)
R$_f$ value: 0.35 (Alox, dichloromethane/MeOH 19:1).

EXAMPLE 146

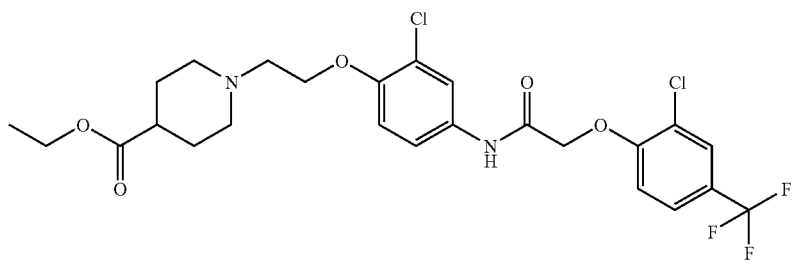

146) ethyl 1-(2-{2-chloro-4-[2-(2-chloro-4-trifluoromethyl-phenoxy)-acetylamino]-phenoxy}-ethyl)-piperidine4-carboxylate Prepared analogously to Example 145 starting from N-[4-(2-bromo-ethoxy)-3-chloro-phenyl]-2-(2-chloro-4-trifluoromethyl-phenoxy)-acetamide (Z28b) and ethyl piperidine-4-carboxylate.

Yield: 190 mg (82% of theory)
$C_{25}H_{27}Cl_2F_3N_2O_5$ (M=563.406)
Calc.: molpeak (M+H)$^+$: 563/565/567
Found: molpeak (M+H)$^+$: 563/565/567 (Cl$_2$)
R$_f$ value: 0.52 (silica gel, dichloromethane/MeOH 9:1).

EXAMPLE 147

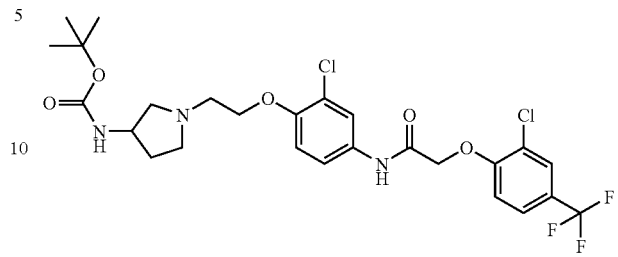

147) tert-butyl [1-(2-{2-chloro-4-[2-(2-chloro-4-trifluoromethyl-phenoxy) -acetylamino]-phenoxy}-ethyl)-pyrrolidin-3-yl]-carbaminate Prepared analogously to Example 145 starting from N-[4-(2-bromo-ethoxy)-3-chloro-phenyl]-2-(2-chloro-4-trifluoromethyl-phenoxy)-acetamide (Z28b) and tert-butyl pyrrolidin-3-yl-carbaminate.

Yield: 230 mg (95% of theory)
$C_{26}H_{30}Cl_2F_3N_3O_5$ (M=592.447)
Calc.: molpeak (M+H)$^+$: 592/594/596
Found: molpeak (M+H)$^+$: 592/594/596 (Cl$_2$)
R$_f$ value: 0.55 (silica gel, dichloromethane/MeOH 19:1).

EXAMPLE 148

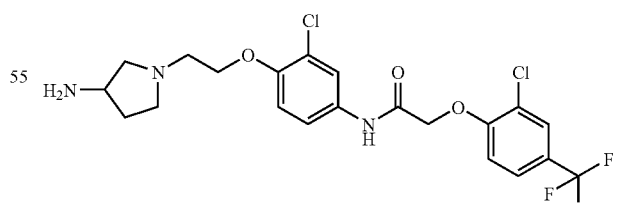

148) N-{4-[2-(3-amino-pyrrolidin-1-yl)-ethoxy]-3-chlorophenyl}-2-(2-chloro-4-trifluoromethyl-phenoxy)-acetamide 0.80 mL (10.380 mmol) TFA was added at RT to a solution of 0.230 g (0.340 mmol) tert-butyl [1-(2-{2-chloro-4-[2-(2-chloro-4-trifluoromethyl-phenoxy)-acetylamino]-phenoxy}-ethyl)-pyrrolidin-3-yl]-carbaminate (Example 147) in 2 mL dichloromethane and the mixture was stirred for 16 h. The reaction mixture was evaporated down i. vac. and the residue triturated with ether. The precipitate was filtered off, washed with ether and dried in a HV. The product was obtained as the bis-trifluoroacetate salt.

Yield: 230 mg (94% of theory)
$C_{21}H_{22}Cl_2F_3N_3O_3 \cdot 2\ C_2HF_3O_2$ (M=720.378)
Calc.: molpeak (M+H)$^+$: 492/494/496
Found: molpeak (M+H)$^+$: 492/494/496 (Cl$_2$)
$R_f$ value: .0.45 (Alox, dichloromethane/MeOH 19:1).

EXAMPLE 149

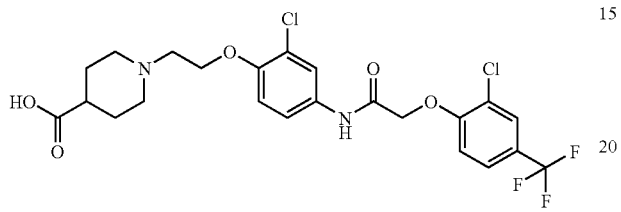

149) 1-(2-{2-chloro-4-[2-(2-chloro-4-trifluoromethyl-phenoxy)-acetylamino]-phenoxy}-ethyl)-piperidin-4-carboxylic acid 2 mL aqueous NaOH (1 M) was added at RT to a solution of 150 mg (0.270 mmol) ethyl 1-(2-{2-chloro-4-[2-(2-chloro-4-trifluoromethyl-phenoxy)-acetylamino]-phenoxy}-ethyl)-piperidine-4-carboxylate (Example 146) in 4 mL EtOH and the mixture was stirred for 16 h. The reaction mixture was neutralised with 2 mL aqueous HCl (1 M), evaporated down i. vac. and the crude product was purified by column chromatography (silica gel, dichloromethane/MeOH 4:1).

Yield: 100 mg (69% of theory)
$C_{23}H_{23}Cl_2F_3N_2O_5$ (M=535.351)
Calc.: molpeak (M+H)$^+$: 535/537/539
Found: molpeak (M+H)$^+$: 535/537/539 (Cl$_2$)
$R_f$ value: 0.35 (silica gel, dichloromethane/MeOH 4:1).

EXAMPLE 150

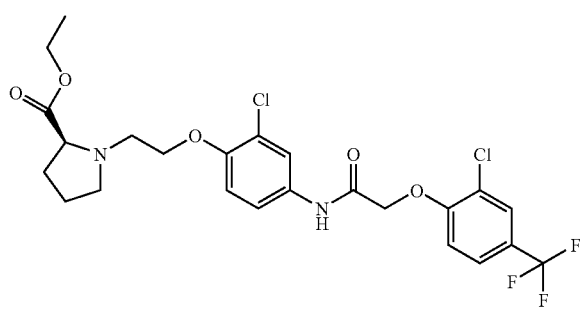

150) ethyl (S)-1-(2-{2-chloro-4-[2-(2-chloro-4-trifluoromethyl-phenoxy)-acetylamino]-phenoxy}-ethyl)-pyrrolidine-2-carboxylate Prepared analogously to Example 145 starting from N-[4-(2-bromo-ethoxy)-3-chloro-phenyl]-2-(2-chloro-4-trifluoromethyl-phenoxy)-acetamide (Z28b) and ethyl (S )-pyrrolidine-2-carboxylate Yield: 200 mg (89% of theory)
$C_{24}H_{25}Cl_2F_3N_2O_5$ (M=549.378)
Calc.: molpeak (M+H)$^+$: 549/551/553
Found: molpeak (M+H$^+$: 549/551/553 (Cl$_2$)
$R_f$ value: 0.53 (Alox, dichloromethane/MeOH 49:1).

EXAMPLE 151

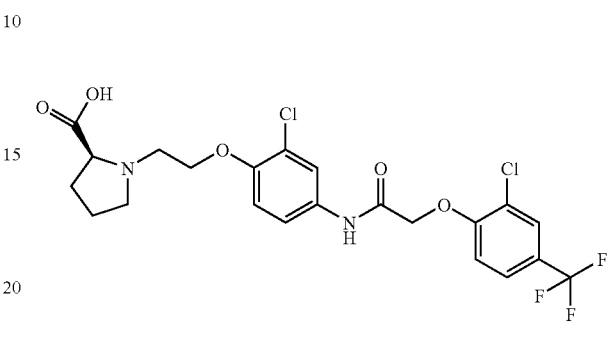

151) (S)-1-(2-{2-chloro-4-[2-(2-chloro-4-trifluoromethyl-phenoxy)-acetylamino]-phenoxy}-ethyl)-pyrrolidine-2-carboxylic acid Prepared analogously to Example 149 starting from ethyl (S)-1-(2-{2-chloro-4-[2-(2-chloro-4-trifluoromethyl-phenoxy)-acetylamino]-phenoxy}-ethyl)-pyrrolidine-2-carboxylate (Example 150).

Yield: 114 mg (30% of theory)
$C_{22}H_{21}Cl_2F_3N_2O_5$ (M=521.324)
Calc.: molpeak (M+H)$^+$: 521/523/525
Found: molpeak (M+H)$^+$: 521/523/525 (Cl$_2$).

EXAMPLE 152

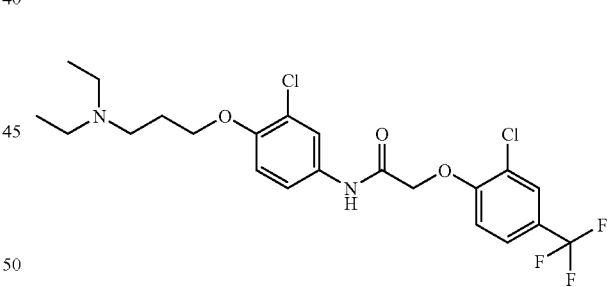

152) N-[3-chloro-4-(3-diethylamino-propoxy)-phenyl]-2-(2-chloro-4-trifluoromethyl -phenoxy)-acetamide Prepared analogously to Example 145 starting from N-[4-(2-bromo-ethoxy)-3-chloro-phenyl]-2-(2-chloro-4-trifluoromethyl-phenoxy)-acetamide (Z28b) and 3-chloro-4-(3-diethylamino-propoxy)-phenylamine (Z29b).

Yield: 330 mg (68% of theory)
$C_{22}H_{25}Cl_2F_3N_2O_3$ (M=493.357)
Calc.: molpeak (M+H)$^+$: 493/495/497
Found: molpeak (M+H)$^+$: 493/495/497 (Cl$_2$).
$R_f$ value: 0.30 (silica gel, dichloromethane/MeOH/conc. aqueous ammonia 90:10:0.1).

EXAMPLE 153

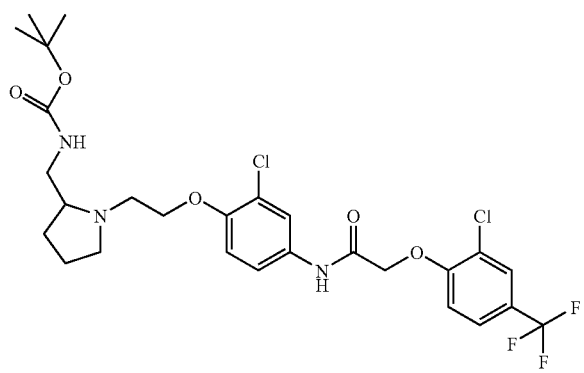

153) tert. butyl [1-(2-{2-chloro-4-[2-(2-chloro-4-trifluoromethyl-phenoxy) -acetylamino]-phenoxy}-ethyl)-pyrrolidin-2-ylmethyl]-carbaminate Prepared analogously to Example 143 starting from N-[4-(2-bromo-ethoxy)-3-chloro-phenyl]-2-(2-chloro-4-trifluoromethyl-phenoxy)-acetamide (Z28b) and tert-butyl pyrrolidin-2-ylmethyl-carbaminate.

Yield: 280 mg (quant. yield)
$C_{27}H_{32}Cl_2F_3N_3O_5$ (M=606.474)
Calc.: molpeak (M–H)⁻: 604/606/608
Found: molpeak (M–H)⁻: 604/606/608 ($Cl_2$).
$R_f$ value: 0.85 (Alox, dichloromethane/MeOH 19:1).

EXAMPLE 154

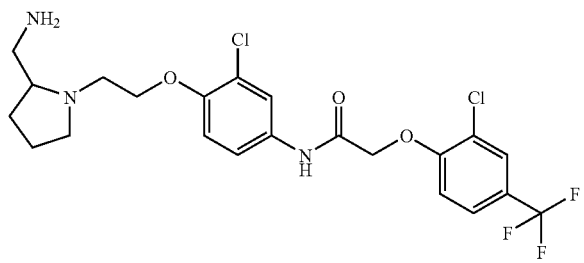

154) N-{4-[2-(2-aminomethyl-pyrrolidin-1-yl)-ethoxy]-3-chloro-phenyl}-2-(2-chloro-4-trifluoromethyl-phenoxy)-acetamide Prepared analogously to Example 148 starting from tert. butyl [1-(2-{2-chloro-4-[2-(2-chloro-4-trifluoromethyl-phenoxy)-acetylamino]-phenoxy}-ethyl)-pyrrolidin-2-ylmethyl]-carbaminate (Example 153).

Yield: 280 mg (quant. yield)
$C_{22}H_{24}Cl_2F_3N_3O_3 \cdot C_2HF_3O_2$ (M=734.405)
Calc.: molpeak (M–H)⁻: 504/506/508
Found: molpeak (M–H)⁻: 504/506/508 ($Cl_2$).
$R_f$ value: 0.14 (Alox, dichloromethane/MeOH 19:1).

EXAMPLE 155

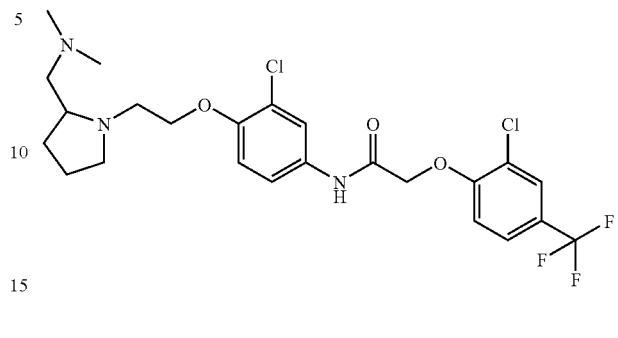

155) N-{3-chloro-4-[2-(2-dimethylaminomethyl-pyrrolidin-1-yl)-ethoxy]-phenyl}-2-(2-chloro-4-trifluoromethyl-phenoxy)-acetamide 0.46 mL (6.080 mmol) formaldehyde (37% in water) was added to a solution of 250 mg (0.340 mmol) N-{4-[2-(2-aminomethyl-pyrrolidin-1-yl)-ethoxy]-3-chloro-phenyl}-2-(2-chloro-4-trifluoromethyl-phenoxy)-acetamide (Example 154) in 7 mL MeOH and the mixture was stirred for 1 h at RT. 103 mg (2.720 mmol) sodium borohydride was added batchwise and the mixture was stirred for a further 16 h at RT. The reaction mixture was evaporated down i. vac. and the residue was taken up in dichloromethane. The org. phase was washed with saturated aqueous sodium bicarbonate, dried over sodium sulphate and evaporated down i. vac. Column chromatography (silica gel, dichloromethane/MeOH 49:1) yielded the product.

Yield: 170 mg (94% of theory)
$C_{24}H_{28}Cl_2F_3N_3O_3$ (M=534.410)
Calc.: molpeak (M+H)⁺: 534/536/538
Found: molpeak (M+H)⁺: 534/536/538 ($Cl_2$).
$R_f$ value: 0.58 (Alox, dichloromethane/MeOH 19:1).

EXAMPLE 156

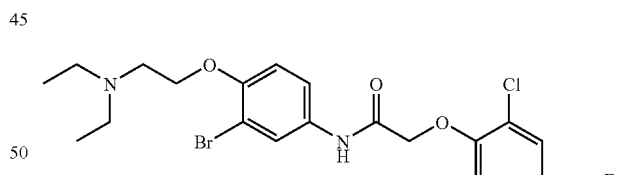

156) N-[3-bromo-4-(2-diethylamino-ethoxy)-phenyl]-2-(2-chloro-4-trifluoromethyl -phenoxy)-acetamide Prepared analogously to Example 143 starting from (2-chloro-4-trifluoromethyl-phenoxy)-acetic acid (Z2b) and 3-bromo-4-(2-diethylamino-ethoxy)-phenylamine (Z30b).

Yield: 0.310 g (60% of theory)
$C_{21}H_{23}BrClF_3N_2O_3$ (M=523.781)
Calc.: molpeak (M+H)⁺: 523/525/527
Found: molpeak (M+H)⁺: 523/525/527 (BrCl).
$R_f$ value: 0.64 (Alox, dichloromethane/MeOH 39:1).

EXAMPLE 157

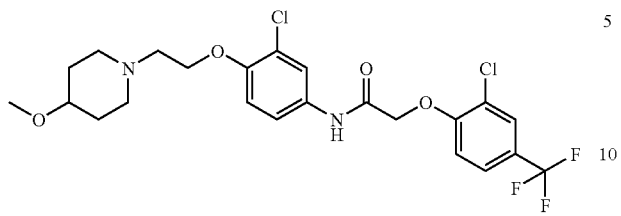

157) N-{3-chloro-4-[2-(4-methoxy-piperidin-1-yl)-ethoxy]-phenyl}-2-(2-chloro-4-trifluoromethyl-phenoxy)-acetamide Prepared analogously to Example 145 starting from N-[4-(2-bromo-ethoxy)-3-chloro-phenyl]-2-(2-chloro-4-trifluoromethyl-phenoxy)-acetamide (Z28b) and 4-methoxy-piperidine.

Yield: 0.200 g (94% of theory)
$C_{23}H_{25}Cl_2F_3N_2O_4$ (M=521.368)
Calc.: molpeak (M+H)$^+$: 521/523/525
Found: molpeak (M+H)$^+$: 521/523/525 (Cl$_2$).
$R_f$ value: 0.75 (Alox, dichloromethane/MeOH 49:1).

EXAMPLE 158

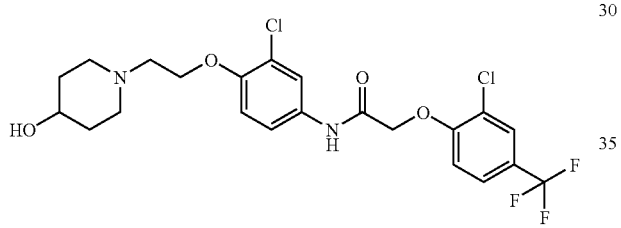

158) N-{3-chloro-4-[2-(4-hydroxy-piperidin-1-yl)-ethoxy]-phenyl}-2-(2-chloro-4-trifluoromethyl-phenoxy)-acetamide Prepared analogously to Example 145 starting from N-[4-(2-bromo-ethoxy)-3-chloro-phenyl]-2-(2-chloro-4-trifluoromethyl-phenoxy)-acetamide (Z28b) and 4-hydroxy-piperidine.

Yield: 0.190 g (91% of theory)
$C_{22}H_{23}Cl_2F_3N_2O_4$ (M=507.341)
Calc.: molpeak (M+H)$^+$: 507/509/511
Found: molpeak (M+H)$^+$: 507/509/511 (Cl$_2$).
$R_f$ value: 0.55 (Alox, dichloromethane/MeOH 19:1).

EXAMPLE 159

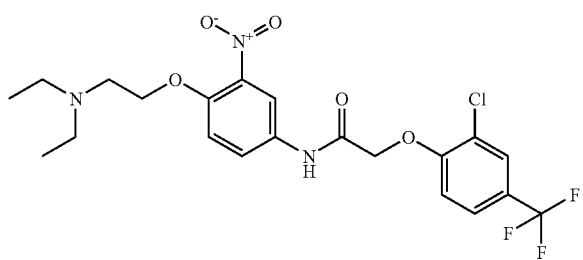

159) 2-(2-chloro-4-trifluoromethyl-phenoxy)-N-[4-(2-diethylamino-ethoxy)-3-nitro-phenyl]-acetamide Prepared analogously to Example 143 starting from (2-chloro-4-trifluoromethyl-phenoxy)-acetic acid (Z2b) and 4-(2-diethylamino-ethoxy)-3-nitro-phenylamine (Z31a).

Yield: 0.410 g (45% of theory)
$C_{21}H_{23}ClF_3N_3O_5$ (M=489.883)
Calc.: molpeak (M+H)$^+$: 490/492
Found: molpeak (M+H)$^+$: 490/492 (Cl).
$R_f$ value: 0.46 (silica gel, dichloromethane/MeOH 9:1).

EXAMPLE 160

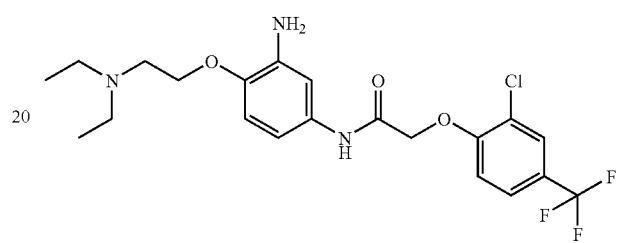

160) N-[3-amino-4-(2-diethylamino-ethoxy)-phenyl]-2-(2-chloro-4-trifluoromethyl -phenoxy)-acetamide A suspension of 330 mg (0.674 mmol) 2-(2-chloro-4-trifluoromethyl-phenoxy)-N-[4-(2-diethylamino-ethoxy)-3-nitro-phenyl]-acetamide (Example 160) and 200 mg Raney nickel was hydrogenated at RT and 3 bar. The catalyst was filtered off and the filtrate evaporated down i. vac.

Yield: 0.310 g (quant. yield)
$C_{21}H_{25}ClF_3N_3O_3$ (M=459.900)
Calc.: molpeak (M+H)$^+$: 460/462
Found: molpeak (M+H)$^+$: 460/462 (Cl).
$R_f$ value: 0.45 (silica gel, dichloromethane/MeOH 9:1).

EXAMPLE 161

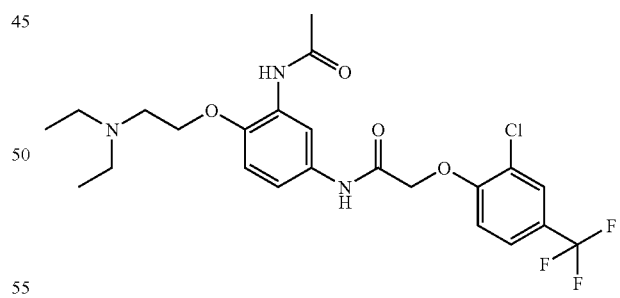

161) N-[3-acetylamino-4-(2-diethylamino-ethoxy)-phenyl]-2-(2-chloro-4-trifluoromethyl-phenoxy)-acetamide A solution of 100 mg (0.217 mmol) N-[3-amino-4-(2-diethylamino-ethoxy)-phenyl]-2-(2-chloro-4-trifluoromethyl-phenoxy)-acetamide (Example 160) in 10 mL acetic anhydride was stirred for 3 h at 100° C. and then evaporated down i. vac. The residue was combined with saturated aqueous sodium bicarbonate and exhaustively extracted with EtOAc. The combined org. phases were dried over sodium sulphate, evaporated down i. vac. and the residue was stirred with ether. The precipitate was filtered off, washed with ether and dried in a HV.

Yield: 0.108 g (quant. yield)
$C_{23}H_{27}ClF_3N_3O_4$ (M=501.938)
Calc.: molpeak (M+H)$^+$: 502/504
Found: molpeak (M+H)$^+$: 502/504 (Cl).
$R_f$ value: 0.42 (silica gel, dichloromethane/MeOH 9:1).

EXAMPLE 162

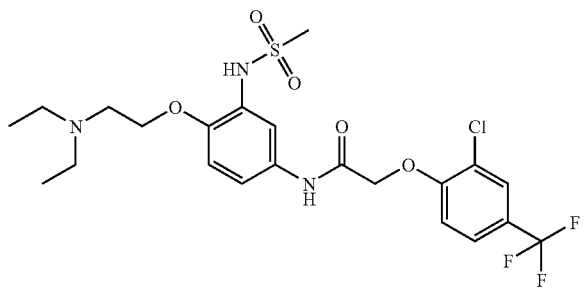

162) 2-(2-chloro-4-trifluoromethyl-phenoxy)-N-[4-(2-diethylamino-ethoxy)-3-methanesulphonylamino-phenyl]-acetamide A solution of 100 mg (0.217 mmol) N-[3-amino-4-(2-diethylamino-ethoxy)-phenyl]-2-(2-chloro-4-trifluoromethyl-phenoxy)-acetamide (Example 160) in 5 mL pyridine was added at 0° C. to 18 μL (0.239 mmol) of methanesulphonylchloride, the mixture was slowly heated to RT and stirred for 3 h at RT. The reaction mixture was poured onto ice water and the aqueous phase was exhaustively extracted with EtOAc. The combined org. phases were dried over sodium sulphate and evaporated down i. vac. The residue was lyophilised.

Yield: 0.080 g (87% of theory)
$C_{22}H_{27}ClF_3N_3O_5S$ (M=537.990)
Calc.: molpeak (M+H)$^+$: 538/540
Found: molpeak (M+H)$^+$: 538/540 (Cl).
$R_f$ value: 0.40 (silica gel, dichloromethane/MeOH 9:1).

EXAMPLE 163

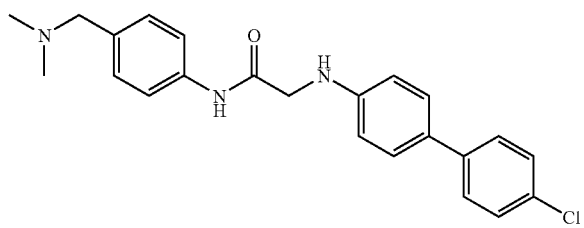

163a) 2-(4-bromo-phenylamino)-N-(4-dimethylaminomethyl-phenyl)-acetamide

The product was prepared according to general working method I from (4-bromo-phenylamino)-acetic acid and 4-dimethylaminomethyl-phenylamine.

Yield: 1.340 g (28% of theory)
$C_{17}H_{20}BrN_3O$ (M=362.272)
Calc.: molpeak (M+H)$^+$: 362/364
Found: molpeak (M+H)$^+$: 362/364 (Cl).
$R_f$ value: 0.68 (Alox, dichloromethane/MeOH 19:1).

163b) 2-(4'-chloro-biphenyl-4-ylamino)-N-(4-dimethylaminomethyl-phenyl)-acetamide Prepared analogously to Example 130a starting from 2-(4-bromo-phenylamino)-N-(4-dimethylaminomethyl-phenyl)-acetamide (Example 163a) and 4-chloro-phenyl-boric acid.

Yield: 0.160 g (41% of theory)
$C_{23}H_{24}ClN_3O$ (M=393.920)
Calc.: molpeak (M+H)$^+$: 394/396
Found: molpeak (M+H)$^+$: 394/396 (Cl).
$R_f$ value: 0.48 (silica gel, dichloromethane/MeOH/conc. aqueous ammonia 90:10:1).

EXAMPLE 164

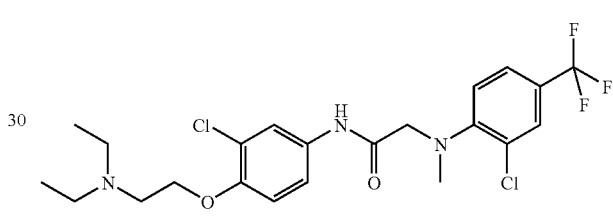

164a) (2-chloro-4-trifluoromethyl-phenyl)-methyl-amine 7.04 mL (59.059 mmol) N,N-dimethyl-formamide-dimethylacetal was added to a solution of 2.100 g (10.738 mmol) 2-chloro-4-trifluoromethoxy-phenylamine in 10 mL DMF under a nitrogen atmosphere and the mixture was stirred for 5 h at 60° C. and for 16 h at RT. 1.421 g (37.583 mmol) sodium borohydride was added and the mixture was stirred for another 3 h at 60° C. Saturated aqueous sodium bicarbonate was added and the mixture was extracted with EtOAc. The org. phase was dried over sodium sulphate and evaporated down i. vac. at 30° C. Column chromatography (silica gel, petroleum ether) yielded the product.

Yield: 1.100 g (49% of theory)
$C_8H_7ClF_3N$ (M=209.600)
Calc.: molpeak (M+H)$^+$: 210/212
Found: molpeak (M+H)$^+$: 210/212 (Cl).
$R_f$ value: 0.75 (silica gel, petroleum ether/EtOAc 9:1).

164b) N-[3-chloro-4-(2-diethylamino-ethoxy)-phenyl]-2-[(2-chloro-4-trifluoromethyl-phenyl)-methyl-amino]-acetamide A solution of 0.200 g (0.450 mmol) 2-bromo-N-[3-chloro-4-(2-diethylamino-ethoxy)-phenyl]-acetamide-hydrobromide and 0.141 g (0.675 mmol) (2-chloro-4-trifluoromethyl-phenyl)-methyl-amine (Example 164a) in 2 mL DMF was heated to 100° C. for 2 h in the microwave. The reaction mixture was evaporated down i. vac., diluted with 3 mL DMF and purified by HPLC-MS (Stable Bond C18; 3.5 μm; water:acetonitrile:formic acid 9:1:0.01→1:9:0.01 over 9 min). The product was obtained as the formate salt.

Yield: 36 mg (15% of theory)

$C_{22}H_{26}Cl_2F_3N_3O_2 * CH_2O_2$ (M=538.399)

Calc.: molpeak (M+H)+: 492/494/496

Found: molpeak (M+H)+: 492/494/496 (Cl$_2$).

R$_f$ value: 0.69 (silica gel, EtOAc/MeOH/conc. aqueous ammonia 90:10:1).

EXAMPLE 165

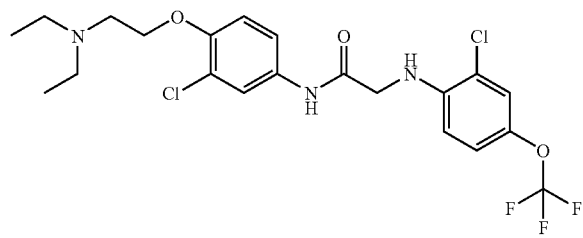

165a) ethyl (2-chloro-4-trifluoromethoxy-phenyl-amino)-acetate 0.566 mL (5.000 mmol) ethyl bromoacetate was added at RT to a solution of 0.95 g (4.266 mmol) (2-chloro-4-trifluoromethyl-phenyl)-methyl-amine in 10 mL Hünig base and the mixture was refluxed for 4 h. Water was added and the aqueous phase was exhaustively extracted with EtOAc. The combined org. phases were washed with water, saturated aqueous sodium bicarbonate and saturated aqueous NaCl, dried over sodium sulphate and evaporated down i. vac. The crude product was used in the next reaction step without any further purification.

Yield: 1.200 g (57% of theory)

$C_{11}H_{11}ClF_3NO_3$ (M=297.663)

R$_f$ value: 0.68 (silica gel, petroleum ether/EtOAc 3:1).

165b) (2-chloro-4-trifluoromethoxy-phenyl-amino)-acetic acid

Prepared analogously to Intermediate product Z2b starting from ethyl [(2-chloro-4-trifluoromethyl-phenyl)-methyl-amino]-acetate (Example 165a).

Yield: 0.630 g (97% of theory)

$C_9H_7ClF_3NO_3$ (M=209.600)

Calc.: molpeak (M+H)+: 210/212

Found: molpeak (M+H)+: 210/212 (Cl).

R$_f$ value: 0.75 (silica gel, petroleum ether/EtOAc 9:1).

165c) N-[3-chloro-4-(2-diethylamino-ethoxy)-phenyl]-2-(2-chloro-4-trifluoromethoxy-phenylamino)-acetamide The product was prepared according to general working method I from (2-chloro-4-trifluoromethoxy-phenyl-amino)-acetic acid (Example 165b) and 3-chloro-4-(2-diethylamino-ethoxy)-phenylamine (Z1b).

Yield: 0.220 g (44% of theory)

$C_{21}H_{24}Cl_2F_3N_3O_3$ (M=494.345)

Calc.: molpeak (M−H)−: 492/494/496

Found: molpeak (M−H)−: 492/494/496 (Cl).

R$_f$ value: 0.48 (Alox, dichloromethane/MeOH 30:1).

EXAMPLE 166

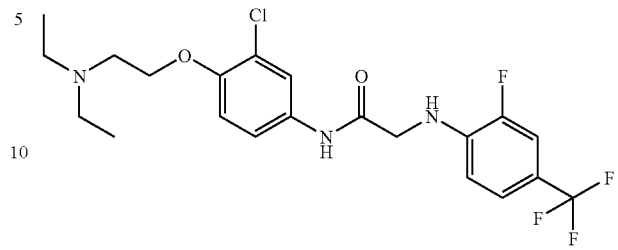

166a) ethyl (2-fluoro-4-trifluoromethyl-phenylamino)-acetate

Prepared analogously to Example 165a starting from 2-fluoro-4-trifluoromethyl-phenylamine and ethyl bromoacetate. The crude product was purified by column chromatography (silica gel, gradient dichloromethane/MeOH 20:0→19:1).

Yield: 0.980 g (82% of theory)

$C_{11}H_{11}F_4NO_2$ (M=265.209)

Calc.: molpeak (M+H)+: 266

Found: molpeak (M+H)+: 266

R$_f$ value: 0.72 (silica gel, petroleum ether/EtOAc 3:1).

166b) (2-fluoro-4-trifluoromethyl-phenylamino)-acetic acid

Prepared analogously to Intermediate product Z2b starting from ethyl (2-fluoro-4-trifluoromethyl-phenylamino)-acetate (Example 166a). The crude product was purified by column chromatography (silica gel, gradient dichloromethane/MeOH 20:0→19:1).

Yield: 0.670 g (79% of theory)

$C_9H_7F_4NO_2$ (M=237.155)

Calc.: molpeak (M−H)−: 236

Found: molpeak (M−H)−: 236.

166c) N-[3-chloro-4-(2-diethylamino-ethoxy)-phenyl]-2-(2-fluoro-4-trifluoromethyl-phenylamino -acetamide The product was obtained according to general working method I starting from (2-fluoro-4-trifluoromethyl-phenylamino)-acetic acid (Example 166b) and 3-chloro-4-(2-diethylamino-ethoxy)-phenylamine (Z1b).

Yield: 0.150 g (32% of theory)

$C_{21}H_{24}ClF_4N_3O_2$ (M=461.891)

Calc.: molpeak (M+H)+: 462/464

Found: molpeak (M+H)+: 462/464 (Cl)

EXAMPLE 167

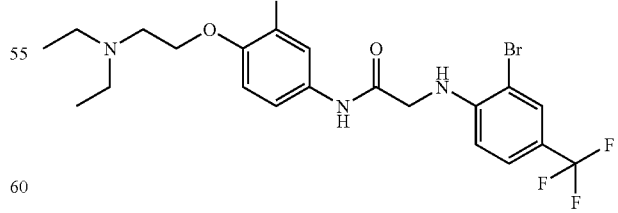

167a) ethyl (2-bromo-4-trifluoromethyl-phenylamino)-acetate

Prepared analogously to Example 166a starting from 2-bromo-4-trifluoromethyl-phenylamine and ethyl bromoacetate.

Yield: 1.200 g (36% of theory)
$C_{11}H_{11}BrF_3NO_2$ (M=326.115)
$R_f$ value: 0.72 (silica gel, petroleum ether/EtOAc 3:1).

167b) (2-bromo-4-trifluoromethyl-phenylamino)-acetic acid

Prepared analogously to Intermediate product Z2b starting from ethyl (2-bromo-4-trifluoromethyl-phenylamino)-acetate (Example 167a).

Yield: 0.438 g (quant. yield)
$C_9H_7BrF_3NO_2$ (M=298.061)
Calc.: molpeak (M−H)⁻: 296/298
Found: molpeak (M−H)⁻: 296/298.

167c) 2-(2-bromo-4-trifluoromethyl-phenylamino)-N-[3-chloro-4-(2-diethylamino-ethoxy)-phenyl]-acetamide The product was obtained according to general working method I starting from (2-bromo-4-trifluoromethyl-phenylamino)-acetic acid (Example 167b) and 3-chloro-4-(2-diethylamino-ethoxy)-phenylamine (Z1b).

Yield: 0.300 g (84% of theory)
$C_{21}H_{24}BrClF_3N_3O_2$ (M=522.797)
Calc.: molpeak (M+H)⁺: 522/524/526
Found: molpeak (M+H)⁺: 522/524/526 (BrCl)
$R_f$ value: 0.45 (silica gel, dichloromethane/MeOH 9:1).

EXAMPLE 168

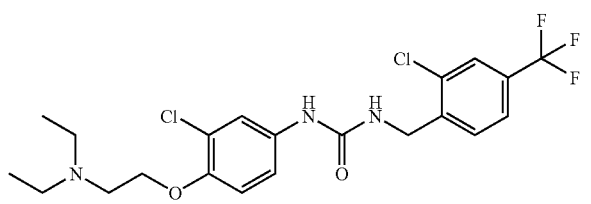

168a) 2-chloro-4-trifluoromethyl-benzylamine

A suspension of 1.000 g (4.865 mmol) 2-chloro-4-trifluoromethyl-benzonitrile and 100 mg Raney nickel in conc. methanolic ammonia was hydrogenated for 20 h at RT and 3 bar. The catalyst was filtered off and the filtrate was evaporated down i. vac.

Yield: 0.870 g (85% of theory)
$C_8H_7ClF_3N$ (M=209.600)
Calc.: molpeak (M+H)⁺: 210/212
Found: molpeak (M+H)⁺: 210/212 (Cl)
$R_f$ value: 0.48 (silica gel, petroleum ether/EtOAc 2:1).

168b) 1-[3-chloro-4-(2-diethylamino-ethoxy)-phenyl]-3-(2-chloro-4-trifluoromethyl-benzyl)-urea 0.770 g (4.457 mmol) CDT was added at 0° C. to a solution of 0.870 g (4.151 mmol) 2-chloro-4-trifluoromethyl-benzylamine (Example 168a) in 50 mL abs. THF and the mixture was stirred for 1 h at RT. 1.080 g (4.449 mmol) 3-chloro-4-(2-diethylamino-ethoxy)-phenylamine (Z1b) was added and the mixture was refluxed for 5 h. The reaction mixture was evaporated down i. vac. and the residue was taken up in dichloromethane. The org. phase was washed with 15% aqueous potassium carbonate, dried over sodium sulphate and evaporated down i. vac.

The crude product was triturated with diisopropylether, the precipitate was filtered off, washed with diisopropylether and dried in a HV.

Yield: 0.570 g (29% of theory)
$C_{21}H_{24}Cl_2F_3N_3O_2$ (M=478.346)
Calc.: molpeak (M+H)⁺: 478/480/482
Found: molpeak (M+H)⁺: 478/480/482 (Cl₂)
$R_f$ value: 0.36 (silica gel, dichloromethane/MeOH/cyclohexane/conc. aqueous ammonia 70:15:15:2).

EXAMPLE 169

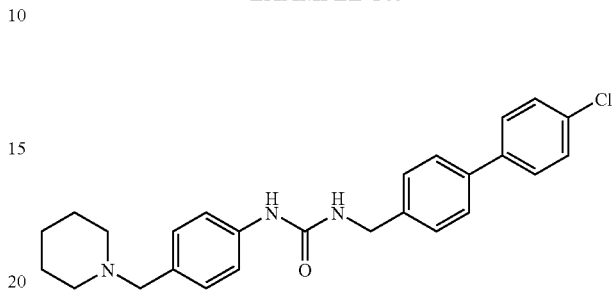

169) 1-(4'-chloro-biphenyl-4-ylmethyl)-3-(4-piperidin-1-ylmethyl-phenyl)-urea

Prepared analogously to Example 168b starting from C-(4'-chloro-biphenyl-4-yl)-methylamine and 4-piperidin-1-ylmethyl-phenylamine. The crude product was purified by column chromatography (Alox, neutral, act. II-III, dichloromethane/MeOH 98:2).

Yield: 0.390 g (90% of theory)
$C_{26}H_{28}ClN_3O$ (M=433.986)
Calc.: molpeak (M+H)⁺: 434/436
Found: molpeak (M+H)⁺: 434/436 (Cl)
$R_f$ value: 0.42 (Alox, dichloromethane/MeOH 39:1).

EXAMPLE 170

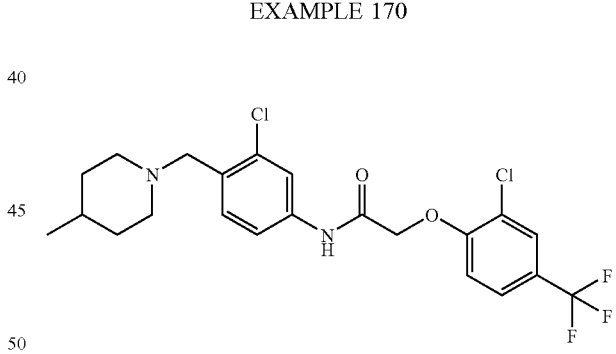

170) N-[3-chloro-4-(4-methyl-piperidin-1-ylmethyl)-phenyl]-2-(2-chloro-4-trifluoromethyl-phenoxy)-acetamide 0.24 mL (2.000 mmol) 4-methylpiperidine was added to a solution of 0.206 g (0.500 mmol) N-(3-chloro-4-chloromethyl-phenyl)-2-(2-chloro-4-trifluoromethyl-phenoxy)-acetamide (Z32b) in 5 mL abs. THF and the mixture was refluxed for 2 h. The reaction mixture was poured onto ice water, the precipitate was filtered off, washed with water and dried in a HV.

Yield: 0.214 g (90% of theory)
$C_{22}H_{23}Cl_2F_3N_2O_2$ (M=475.342)
Calc.: molpeak (M+H)⁺: 475/477/479
Found: molpeak (M+H)⁺: 475/477/479 (Cl₂)
$R_f$ value: 0.66 (Alox, petroleum ether/EtOAc 3:1).

EXAMPLE 171

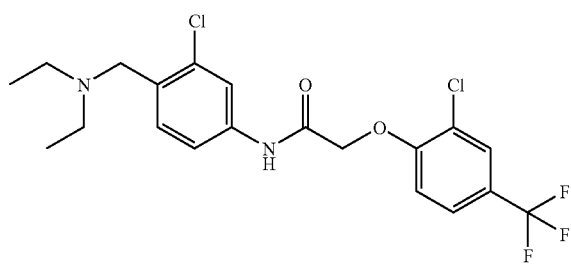

171) N-(3-chloro-4-diethylaminomethyl-phenyl)-2-(2-chloro-4-trifluoromethyl-phenoxy)-acetamide Prepared analogously to Example 170 starting from N-(3-chloro-4-chloromethyl-phenyl)-2-(2-chloro-4-trifluoromethyl-phenoxy)-acetamide (Z32b) and diethylamine. The crude product was recrystallised from petroleum ether.

Yield: 0.154 g (69% of theory)

$C_{20}H_{21}Cl_2F_3N_2O_2$ (M=449.304)

Calc.: molpeak $(M+H)^+$: 449/451/453

Found: molpeak $(M+H)^+$: 449/451/453 ($Cl_2$)

$R_f$ value: 0.53 (Alox, petroleum ether/EtOAc 3:1).

EXAMPLE 172

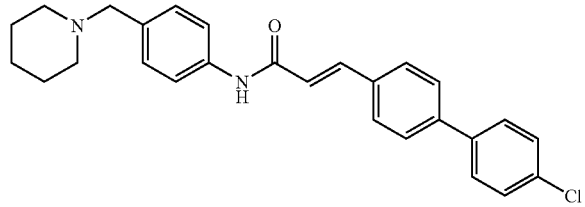

172) (E)-3-(4'-chloro-biphenyl-4-yl)-N-(4-piperidin-1-ylmethyl-phenyl)-acrylamide A solution of 0.544 g (2.103 mmol) (E)-3-(4'-chloro-biphenyl-4-yl)-acrylic acid, 0.440 g (2.313 mmol) 4-piperidin-1-ylmethyl-phenylamine, 0.736 g (2.313 mmol) TBTU, 0.313 g (2.313 mmol) HOBt and 1.025 mL (7.361 mmol) triethylamine in 10 mL DMF was stirred for 3 h at RT and then poured onto ice water and a little EtOAc. The precipitate was filtered off, washed with water and dried at 80° C. i. vac.

Yield: 0.154 g (69% of theory)

$C_{27}H_{27}ClN_2O$ (M=430.982)

Calc.: molpeak $(M+H)^+$: 431/433

Found: molpeak $(M+H)^+$: 431/433 (Cl)

$R_f$ value: 0.31 (silica gel, dichloromethane/MeOH 9:1).

EXAMPLE 173

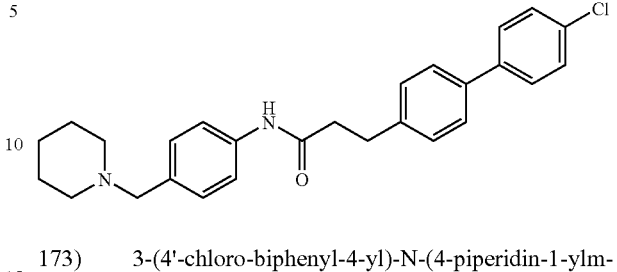

173) 3-(4'-chloro-biphenyl-4-yl)-N-(4-piperidin-1-ylmethyl-phenyl)-propionamide

A suspension of 0.200 g (0.464 mmol) (E)-3-(4'-chloro-biphenyl-4-yl)-N-(4-piperidin-1-ylmethyl-phenyl)-acrylamide (Example 172) and 100 mg Raney nickel in 50 mL EtOAc was hydrogenated at RT and 50 psi. The catalyst was filtered off, the filtrate was evaporated down i. vac. and the residue was triturated with ether. The precipitate was filtered off, washed with ether and dried at 50° C. i. vac.

Yield: 55 mg (27% of theory)

$C_{27}H_{29}ClN_2O$ (M=432.998)

Calc.: molpeak $(M+H)^+$: 433/435

Found: molpeak $(M+H)^+$: 433/435 (Cl)

$R_f$ value: 0.23 (silica gel, dichloromethane/MeOH 9:1).

EXAMPLE 174

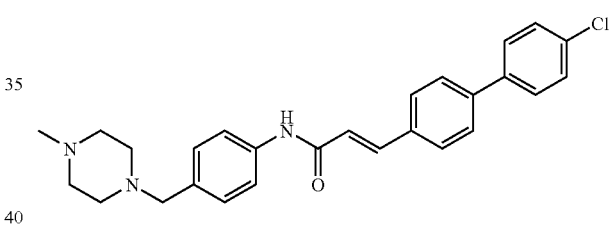

174) (E)-3-(4'-chloro-biphenyl-4-yl)-N-[4-(4-methyl-piperazin-1-ylmethyl)-phenyl]-acrylamide Prepared analogously to Example 172 starting from (E)-3-(4'-chloro-biphenyl-4-yl)-acrylic acid and 4-(4-methyl-piperazin-1-ylmethyl)-phenylamine. The crude product was purified by column chromatography (silica gel, dichloromethane/MeOH/conc. aqueous ammonia 90:10:0.1).

Yield: 0.410 g (61% of theory)

$C_{27}H_{28}ClN_3O$ (M=445.997)

Calc.: molpeak $(M+H)^+$: 446/448

Found: molpeak $(M+H)^+$: 446/448 (Cl)

$R_f$ value: 0.40 (silica gel, dichloromethane/MeOH 9:1).

EXAMPLE 175

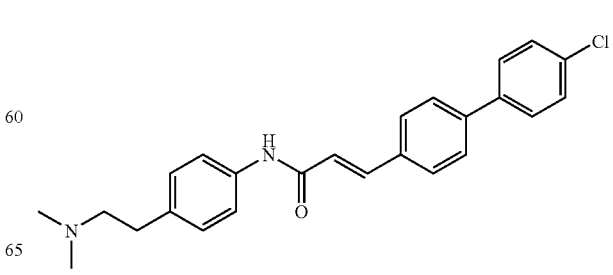

175) (E)-3-(4'-chloro-biphenyl-4-yl)-N-[4-(2-dimethylamino-ethyl)-phenyl]-acrylamide Prepared analogously to Example 172 starting from (E)-3-(4'-chloro-biphenyl-4-yl)-acrylic acid and 4-(2-dimethylamino-ethyl)-phenylamine.

Yield: 0.350 g (58% of theory)
$C_{25}H_{25}ClN_2O$ (M=404.944)
Calc.: molpeak (M+H)$^+$: 405/407
Found: molpeak (M+H)$^+$: 405/407 (Cl)
$R_f$ value: 0.40 (silica gel, dichloromethane/MeOH/conc. aqueous ammonia 90:10:0.1).

EXAMPLE 176

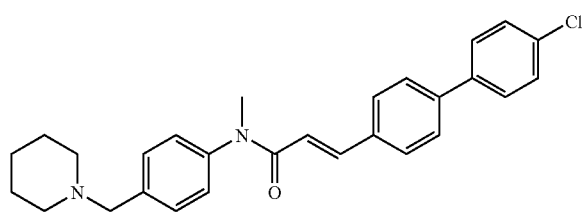

176) (E)-3-(4'-chloro-biphenyl-4-yl)-N-methyl-N-(4-piperidin-1-ylmethyl-phenyl)-acrylamide Prepared analogously to Example 172 starting from (E)-3-(4'-chloro-biphenyl-4-yl)-acrylic acid and methyl-(4-piperidin-1-ylmethyl-phenyl)-amine.

Yield: 0.200 g (45% of theory)
$C_{28}H_{29}ClN_2O$ (M=445.009)
Calc.: molpeak (M+H)$^+$: 445/447
Found: molpeak (M+H)$^+$: 445/447 (Cl)
$R_f$ value: 0.60 (silica gel, dichloromethane/MeOH/conc. aqueous ammonia 90:10:0.1).

EXAMPLE 177

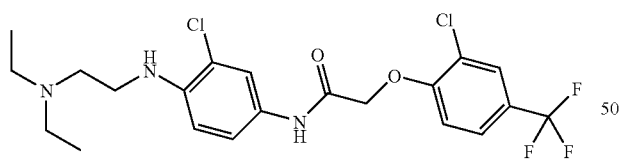

177) N-[3-chloro-4-(2-diethylamino-ethylamino)-phenyl]-2-(2-chloro-4-trifluoromethyl-phenoxy)-acetamide The product was prepared according to general working method I starting from 0.270 g (1.060 mmol) (2-chloro-4-trifluoromethyl-phenoxy)-acetic acid (Z2b) and 0.260 g (1.080 mmol) 2-chloro-N'-(2-diethylamino-ethyl)-benzene-1,4-diamine (Z42b).

Yield: 0.340 g (67% of theory)
$C_{21}H_{24}Cl_2N_3O_2$ (M=478.346)
Calc.: molpeak (M+H)$^+$: 478/480/482
Found: molpeak (M+H)$^+$: 478/480/482 (Cl$_2$)
$R_f$ value: 0.45 (Alox, dichloromethane/MeOH 45:1).

EXAMPLE 178

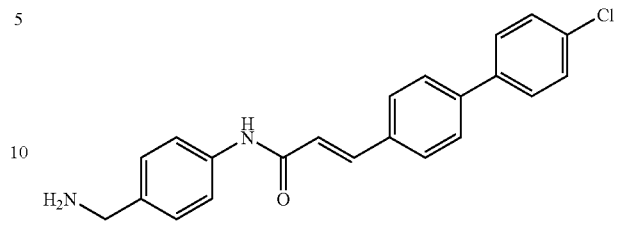

178a) tert-butyl {4-[(E)-3-(4'-chloro-biphenyl-4-yl)-acryloylamino]-benzyl}-carbaminate Prepared analogously to Example 172 starting from (E)-3-(4'-chloro-biphenyl-4-yl)-acrylic acid and tert-butyl (4-amino-benzyl)-carbaminate. The crude product was stirred with MeOH, the precipitate was filtered off and dried in a HV.

Yield: 1.000 g (72% of theory)
$C_{27}H_{27}CN_2O_3$ (M=462.981)
Calc.: molpeak (M+H)$^+$: 463/465
Found: molpeak (M+H)$^+$: 463/465 (Cl)
$R_f$ value: 0.70 (silica gel, dichloromethane/MeOH 9:1).

178b) (E)-N-(4-aminomethyl-phenyl)-3-(4'-chloro-biphenyl-4-yl)-acrylamide 5 mL TFA was added at RT to a suspension of 0.950 g (2.050 mmol) tert-butyl {4-[(E)-3-(4'-chloro-biphenyl-4-yl)-acryloylamino]-benzyl}-carbaminate in 50 mL abs. dichloromethane and the mixture was stirred for 2 h at RT. The reaction mixture was evaporated down i. vac., combined with toluene and again evaporated down i. vac. The residue was triturated with ether, the precipitate was filtered off and dried i. vac. at 80° C. The product was obtained as the trifluoroacetate salt.

Yield: 0.930 g (95% of theory)
$C_{22}H_{19}ClN_2O * C_2HF_3O_2$ (M=476.887)
Calc.: molpeak (M+H)$^+$: 363/365
Found: molpeak (M+H)$^+$: 363/365 (Cl)
$R_f$ value: 0.40 (silica gel, dichloromethane/MeOH/conc. aqueous ammonia 90:10:0.1).

EXAMPLE 179

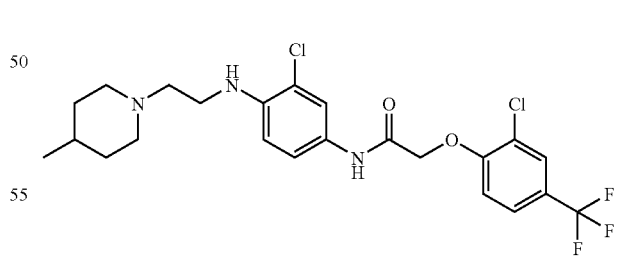

179) N-{3-chloro-4-[2-(4-methyl-piperidin-1-yl)-ethylamino]-phenyl}-2-(2-chloro-4-trifluoro-methyl-phenoxy)-acetamide The product was prepared according to general working method I starting from 0.270 g (1.060 mmol) (2-chloro-4-trifluoromethyl-phenoxy)-acetic acid (Z2b) and 0.290 g (1.080 mmol) 2-chloro-N'-[2-(4-methyl-piperidin-1-yl)-ethyl]-benzene-1,4-diamine (Z43d).

Yield: 0.360 g (67% of theory)
$C_{23}H_{26}Cl_2F_3N_3O_2$ (M=503.384)
Calc.: molpeak (M+H)$^+$: 504/506/508
Found: molpeak (M+H)$^+$: 504/506/508 (Cl$_2$)
R$_f$ value: 0.44 (Alox, dichloromethane/MeOH 49:1).

EXAMPLE 180

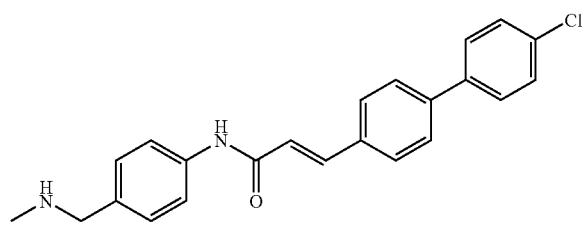

180a) tert-butyl {4-[(E)-3-(4'-chloro-biphenyl-4-yl)-acryloylamino]-benzyl}-methyl-carbaminate Prepared analogously to Example 172 starting from (E)-3-(4'-chloro-biphenyl4-yl)-acrylic acid and tert-butyl (4-amino-benzyl)-methyl-carbaminate (Z33b). The crude product was stirred with MeOH, the precipitate was filtered off and dried in a HV.
Yield: 0.620 g (43% of theory)
$C_{28}H_{29}ClN_2O_3$ (M=477.008)
Calc.: molpeak (M+H)$^+$: 477/479
Found: molpeak (M+H)$^+$: 477/479 (Cl)
R$_f$ value: 0.80 (silica gel, dichloromethane/MeOH 9:1).

180b) (E)-3-(4'-chloro-biphenyl-4-yl)-N-(4-methylaminomethyl-phenyl)-acrylamide

Prepared analogously to Example 178 starting from tert-butyl {4-[(E)-3-(4'-chloro-biphenyl-4-yl)-acryloylamino]-benzyl}-methyl-carbaminate (Example 179). The product was obtained as the trifluoroacetate salt.
Yield: 0.540 g (87% of theory)
$C_{23}H_{21}ClN_2O * C_2HF_3O_2$ (M=490.914)
Calc.: molpeak (M+H)$^+$: 377/379
Found: molpeak (M+H)$^+$: 377/379 (Cl)
R$_f$ value: 0.40 (silica gel, dichloromethane/MeOH/conc. aqueous ammonia 90:10:0.1).

EXAMPLE 181

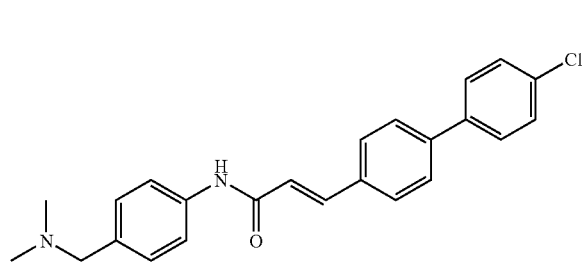

181) (E)-3-(4'-chloro-biphenyl-4-yl)-N-(4-dimethylaminomethyl-phenyl)-acrylamide 1.00 mL formaldehyde (37% in water) was added at 0° C. to a solution of 0.100 g (0.280 mmol) (E)-3-(4'-chloro-biphenyl-4-yl)-N-(4-methylaminomethyl-phenyl)-acrylamide (Example 180) in 1 mL formic acid and the mixture was stirred for 1 h at RT and 2 h at 90° C. The reaction mixture was poured onto ice water and the aqueous phase was exhaustively extracted with EtOAc. The combined org. phases were dried over sodium sulphate, evaporated down i. vac. and the residue stirred with ether. The precipitate was filtered off, washed with ether and dried i. vac. at 100° C.
Yield: 81 mg (74% of theory)
$C_{24}H_{23}ClN_2O$ (M=390.917)
Calc.: molpeak (M+H)$^+$: 391/393
Found: molpeak (M+H)$^+$: 391/393 (Cl)
R$_f$ value: 0.50 (silica gel, dichloromethane/MeOH/conc. aqueous ammonia 90:10:0.1).

EXAMPLE 182

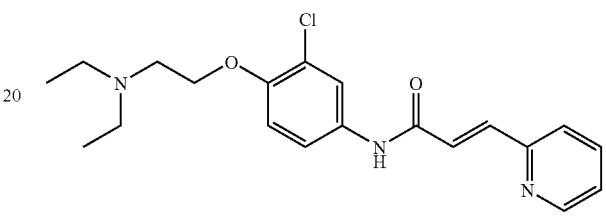

182) (E)-N-[3-chloro-4-(2-diethylamino-ethoxy)-phenyl]-3-pyridin-2-yl-acrylamide Prepared analogously to Example 172 starting from (E)-3-pyridin-2-yl-acrylic acid and 3-chloro-4-(2-diethylamino-ethoxy)-phenylamine (Z2b) at RT (72 h). The crude product was purified by column chromatography (silica gel, dichloromethane/MeOH/conc. aqueous ammonia 90:10:0.1) and recrystallisation from petroleum ether.
Yield: 0.930 g (50% of theory)
$C_{20}H_{24}ClN_3O_2$ (M=373.886)
Calc.: molpeak (M+H)$^+$: 374/376
Found: molpeak (M+H)$^+$: 374/376 (Cl)
R$_f$ value: 0.40 (silica gel, dichloromethane/MeOH/conc. aqueous ammonia 90:10:0.1).

EXAMPLE 183

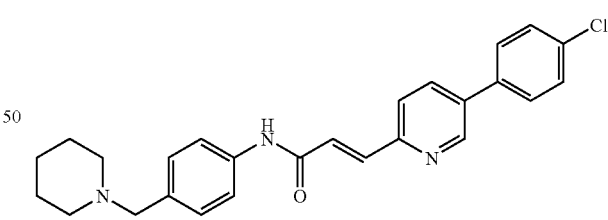

183) (E)-3-[5-(4-chloro-phenyl)-pyridin-2-yl]-N-(4-piperidin-1-ylmethyl-phenyl)-acrylamide Prepared analogously to Example 143 starting from (E)-3-[5-(4-chloro-phenyl)-pyridin-2-yl]-acrylic acid (Z34b) and 4-piperidin-1-ylmethyl-phenylamine. The crude product was purified by column chromatography (silica gel, dichloromethane/EtOH/conc. aqueous ammonia 50:10:0.1).
Yield: 0.450 g (52% of theory)
$C_{26}H_{26}ClN_3O$ (M=431.970)
Calc.: molpeak (M+H)$^+$: 432/434
Found: molpeak (M+H)$^+$: 432/434 (Cl)

$R_f$ value: 0.50 (silica gel, dichloromethane/MeOH/conc. aqueous ammonia 90:10:0.1).

EXAMPLE 184

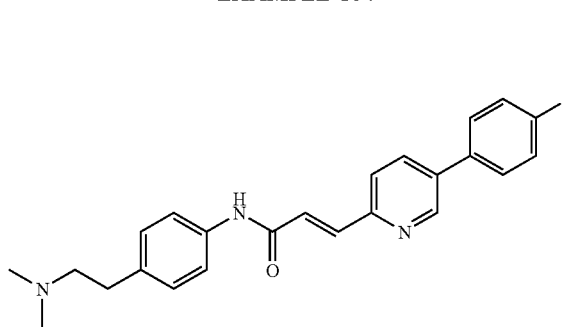

184) (E)-3-[5-(4-chloro-phenyl)-pyridin-2-yl]-N-[4-(2-dimethylamino-ethyl)-phenyl]-acrylamide Prepared analogously to Example 143 starting from (E)-3-[5-(4-chloro-phenyl)-pyridin-2-yl]-acrylic acid (Z34b) and 4-(2-dimethylamino-ethyl)-phenylamine. The crude product was purified by column chromatography (silica gel, dichloromethane/EtOH/conc. aqueous ammonia 50:10:0.1).

Yield: 0.140 g (45% of theory)
$C_{24}H_{24}ClN_3O$ (M=405.931)
Calc.: molpeak $(M+H)^+$: 406/408
Found: molpeak $(M+H)^+$: 406/408 (Cl)
$R_f$ value: 0.60 (silica gel, dichloromethane/MeOH/conc. aqueous ammonia 90:10:0.1).

EXAMPLE 185

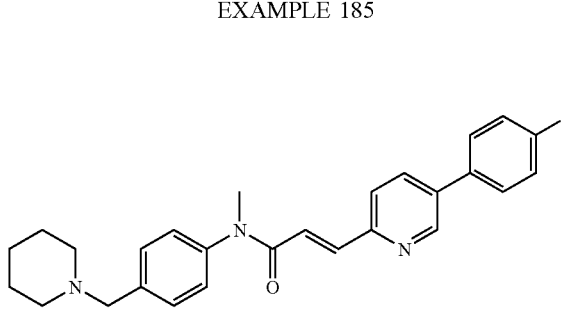

185) (E)-3-[5-(4-chloro-phenyl)-pyridin-2-yl]-N-methyl-N-(4-piperidin-1-ylmethyl-phenyl)-acrylamide Prepared analogously to Example 143 starting from (E)-3-[5-(4-chloro-phenyl)-pyridin-2-yl]-acrylic acid (Z34b) and methyl-(4-piperidin-1-ylmethyl-phenyl)-amine. The crude product was purified by column chromatography (silica gel, dichloromethane/EtOH/conc. aqueous ammonia 50:10:0.1).

Yield: 0.300 g (67% of theory)
$C_{27}H_{28}ClN_3O$ (M=445.997)
Calc.: molpeak $(M+H)^+$: 446/448
Found: molpeak $(M+H)^+$: 446/448 (Cl)
$R_f$ value: 0.70 (silica gel, dichloromethane/MeOH/conc. aqueous ammonia 90:10:0.1).

EXAMPLE 186

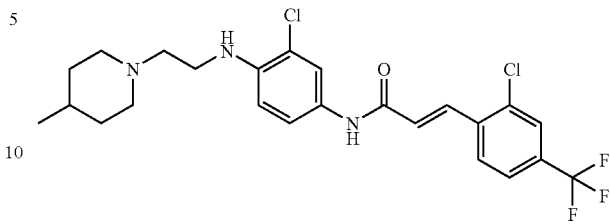

186) (E)-N-{3-chloro-4-[2-(4-methyl-piperidin-1-yl)-ethylamino]-phenyl}-3-(2-chloro-4-trifluoromethyl-phenyl)-acrylamide The product was prepared according to general working method I starting from 0.250 g (1.000 mmol) (E)-3-(2-chloro-4-trifluoromethyl-phenyl)-acrylic acid (Z37b) and 0.270 g (1.000 mmol) 2-chloro-N'[2-(4-methyl-piperidin-1-yl)-ethyl]-benzene-1,4-diamine (Z43d) and purified by column chromatography (Alox, neutral, act. II-III gradient dichloromethane/MeOH 100:0→49:1).

Yield: 0.220 g (44% of theory)
$C_{24}H_{26}Cl_2F_3N_3O$ (M=500.396)
Calc.: molpeak $(M+H)^+$: 500/502/504
Found: molpeak $(M+H)^+$: 500/502/504 ($Cl_2$)
$R_f$ value: 0.70 (Alox, dichloromethane/MeOH 49:1).

EXAMPLE 187

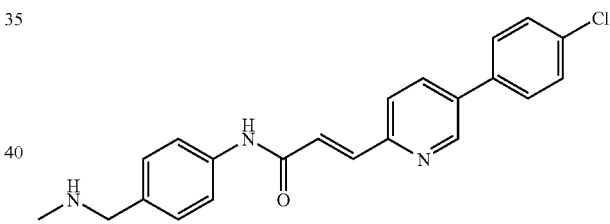

187a) tert-butyl (4-{(E)-3-[5-(4-chloro-phenyl)-pyridin-2-yl]-acryloylamino}-benzyl)-methyl-carbaminate Prepared analogously to Example 182 starting from (E)-3-[5-(4-chloro-phenyl)-pyridin-2-yl]-acrylic acid (Z34b) and tert-butyl (4-amino-benzyl)-carbaminate. The crude product was stirred with MeOH, the precipitate was filtered off and dried in a HV.

Yield: 0.620 g (86% of theory)
$C_{27}H_{28}ClN_3O_3$ (M=477.996)
Calc.: molpeak $(M+H)^+$: 478/480
Found: molpeak $(M+H)^+$: 478/480 (Cl)
$R_f$ value: 0.60 (silica gel, dichloromethane/MeOH 9:1).

187b) (E)-3-[5-(4-chloro-phenyl)-pyridin-2-yl]-N-(4-methylaminomethyl-phenyl)-acrylamide Prepared analogously to Example 178b starting from tert-butyl (4-{(E)-3-[5-(4-chloro-phenyl)-pyridin-2-yl]-acryloylamino}-benzyl)-methyl-carbaminate. The product was obtained as the trifluoroacetate salt.

Yield: 0.500 g (81% of theory)
$C_{22}H_{20}ClN_3O * C_2HF_3O_2$ (M=491.901)
Calc.: molpeak $(M+H)^+$: 378/380
Found: molpeak $(M+H)^+$: 278/380 (Cl)

R$_f$ value: 0.30 (silica gel, dichloromethane/MeOH/conc. aqueous ammonia 90:10:0.1).

EXAMPLE 188

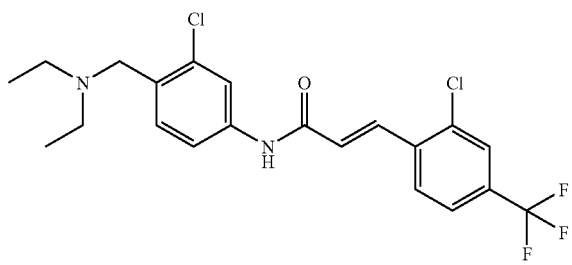

188) (E)-N-(3-chloro-4-diethylaminomethyl-phenyl)-3-(2-chloro-4-trifluoromethyl-phenyl)-acrylamide Prepared analogously to Example 143 starting from (E)-3-(2-chloro-4-trifluoromethyl-phenyl)-acrylic acid (Z37b) and 3-chloro-4-diethylaminomethyl-phenylamine (Z35b). The crude product was purified by column chromatography (Alox, neutral, act. II-III, petroleum ether/EtOAc 3:1).

Yield: 0.192 g (43% of theory)

C$_{21}$H$_{21}$Cl$_2$F$_3$N$_2$O (M=445.316)

Calc.: molpeak (M+H)$^+$: 445/447/449

Found: molpeak (M+H)$^+$: 445/447/449 (Cl$_2$)

R$_f$ value: 0.53 (Alox, petroleum ether/EtOAc 3:1).

EXAMPLE 189

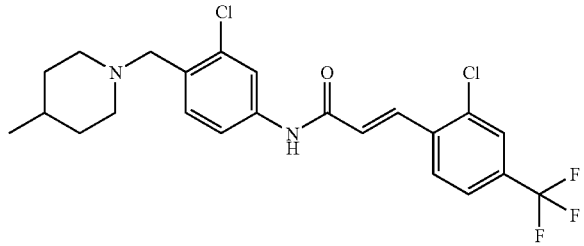

189) (E)-N-[3-chloro-4-(4-methyl-piperidin-1-ylmethyl)-phenyl]-3-(2-chloro-4-trifluoromethyl-phenyl)-acrylamide Prepared analogously to Example 143 starting from (E)-3-(2-chloro-4-trifluoromethyl-phenyl)-acrylic acid (Z37b) and 3-chloro-4-(4-methyl-piperidin-1-ylmethyl)-phenylamine (Z36b). The crude product was purified by column chromatography (Alox, neutral, act. II-III, petroleum ether/EtOAc 3:1).

Yield: 0.176 g (37% of theory)

C$_{23}$H$_{23}$Cl$_2$F$_3$N$_2$O (M=471.354)

Calc.: molpeak (M+H)$^+$: 471/473/475

Found: molpeak (M+H)$^+$: 471/473/475 (Cl$_2$)

R$_f$ value: 0.47 (Alox, dichloromethane/MeOH 50:1).

EXAMPLE 190

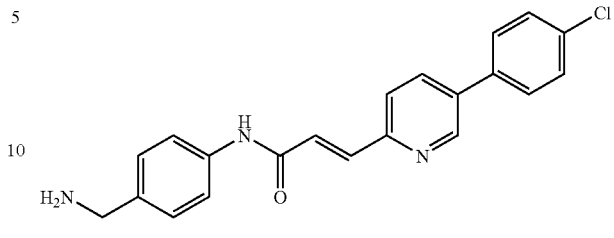

190a) tert-butyl (4-{(E)-3-[5-(4-chloro-phenyl)-pyridin-2-yl]-acryloylamino}-benzyl)-carbaminate Prepared analogously to Example 182 starting from tert-butyl (E)-3-[5-(4-chloro-phenyl)-pyridin-2-yl]-acrylic acid (Z34b) and (4-amino-benzyl)-methyl-carbaminate (Z33b). The crude product was stirred with MeOH, the precipitate was filtered off and dried in a HV.

Yield: 0.610 g (88% of theory)

C$_{26}$H$_{26}$ClN$_3$O$_3$ (M=463.968)

Calc.: molpeak (M+H)$^+$: 464/466

Found: molpeak (M+H)$^+$: 464/466 (Cl)

R$_f$ value: 0.60 (silica gel, dichloromethane/MeOH 9:1).

190b) (E)-N-(4-aminomethyl-phenyl)-3-[5-(4-chloro-phenyl)-pyridin-2-yl]-acrylamide Prepared analogously to Example 178 starting from tert-butyl (4-{(E)-3-[5-(4-chloro-phenyl)-pyridin-2-yl]-acryloylamino}-benzyl)-carbaminate (Example 186). The product was obtained as the trifluoroacetate salt.

Yield: 0.600 g (99% of theory)

C$_{21}$H$_{18}$ClN$_3$O * C$_2$HF$_3$O$_3$ (M=477.874)

Calc.: molpeak (M–H)$^-$: 362/364

Found: molpeak (M–H)$^-$: 362/364 (Cl)

R$_f$ value: 0.40 (silica gel, dichloromethane/MeOH/conc. aqueous ammonia 90:10:0.1).

EXAMPLE 191

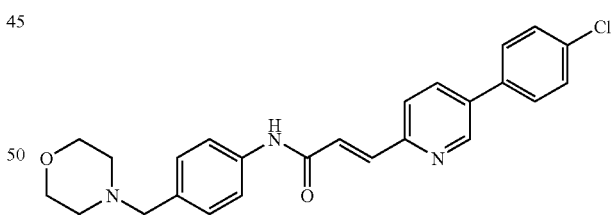

191) (E)-3-[5-(4-chloro-phenyl)-pyridin-2-yl]-N-(4-morpholin-4-ylmethyl-phenyl)-acrylamide 80 μL (0.930 mmol) morpholine was added to a solution of 0.130 g (0.310 mmol) (E)-N-(4-chloromethyl-phenyl)-3-[5-(4-chloro-phenyl)-pyridin-2-yl]-acrylamide (Z38b) in 20 mL THF and the mixture was stirred for 5 h at 50° C. and 5 h at 75° C. A further 200 μL of morpholine were added and the mixture was stirred for 5 h at 70° C. The reaction mixture was evaporated down i. vac. and the residue was purified by column chromatography (silica gel, dichloromethane/MeOH/conc. aqueous ammonia 90:10:0.1). The product was stirred with ether, the precipitate was filtered off and dried i. vac. at 70° C.

Yield: 80 mg (60% of theory)

C$_{25l}$H$_{24}$ClN$_3$O$_2$ (M=433.942)

Calc.: molpeak (M+H)$^+$: 434/436

Found: molpeak (M+H)$^{+-}$: 434/436 (Cl)

R$_f$ value: 0.50 (silica gel, dichloromethane/MeOH 9:1).

EXAMPLE 192

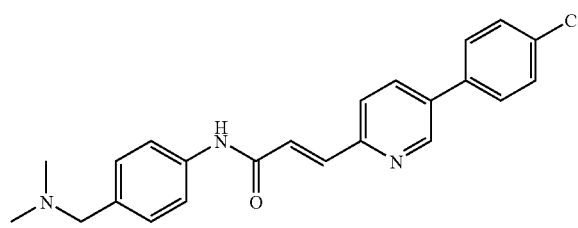

192) (E)-3-[5-(4-chloro-phenyl)-pyridin-2-yl]-N-(4-dimethylaminomethyl-phenyl)-acrylamide Prepared analogously to Example 181 starting from (E)-N-(4-aminomethyl-phenyl)-3-[5-(4-chloro-phenyl)-pyridin-2-yl]-acrylamide (Example 190).

Yield: 0.120 g (56% of theory)

C$_{23}$H$_{22}$ClN$_3$O (M=391.904)

Calc.: molpeak (M+H)$^+$: 392/394

Found: molpeak (M+H)$^+$: 392/394 (Cl)

R$_f$ value: 0.30 (silica gel, dichloromethane/MeOH/conc. aqueous ammonia 90:10:0.1).

EXAMPLE 193

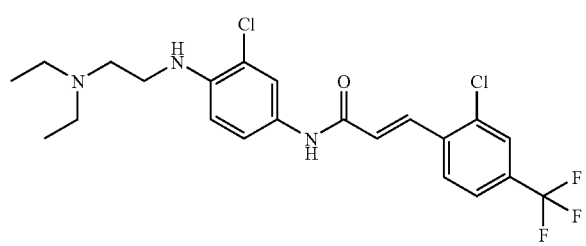

193) (E)-N-[3-chloro-4-(2-diethylamino-ethylamino)-phenyl]-3-(2-chloro-4-trifluoromethyl-phenyl)-acrylamide Prepared in DMF analogously to Example 143 starting from (E)-3-(2-chloro-4-trifluoromethyl-phenyl)-acrylic acid (Z37b) and 2-chloro-N'-(2-diethylamino-ethyl)-benzene-1,4-diamine (Z42b). The crude product was purified by column chromatography (Alox, neutral, act. II-III, dichloromethane/MeOH 49:1) and by trituration in ether/petroleum ether.

Yield: 0.215 g (45% of theory)

C$_{22}$H$_{24}$Cl$_2$F$_3$N$_3$O (M=474.357)

Calc.: molpeak (M+H)$^+$: 474/476/478

Found: molpeak (M+H)$^+$: 474/476/478 (Cl$_2$)

R$_f$ value: 0.58 (Alox, dichloromethane/MeOH 49:1).

EXAMPLE 194

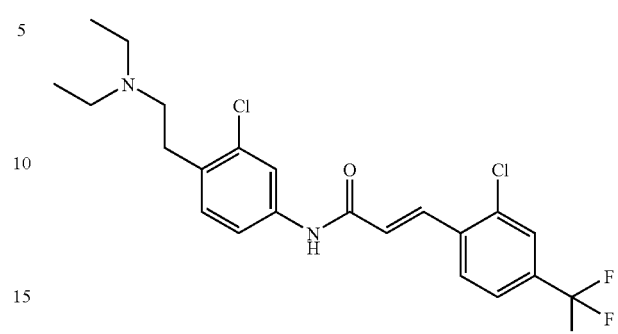

194) (E)-N-[3-chloro-4-(2-diethylamino-ethyl)-phenyl]-3-(2-chloro-4-trifluoromethyl -phenyl)-acrylamide Prepared in DMF analogously to Example 143 starting from (E)-3-(2-chloro-4-trifluoromethyl-phenyl)-acrylic acid (Z37b) and 3-chloro-4-(2-diethylamino-ethyl)-phenylamine (Z44d). The reaction mixture was poured onto ice water, the precipitate was filtered off, washed with water and dried in a HV. The residue was triturated with ether, the precipitate was filtered off, washed with ether and dried in a HV.

Yield: 0.278 g (60% of theory)

C$_{22}$H$_{23}$Cl$_2$F$_3$N$_2$O (M=459.343)

Calc.: molpeak (M+H)$^+$: 459/461/463

Found: molpeak (M+H)$^+$: 459/461/463 (Cl$_2$)

R$_f$ value: 0.32 (Alox, petroleum ether/EtOAc 1:1).

EXAMPLE 195

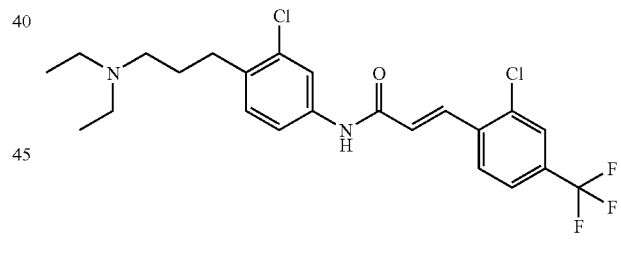

195) (E)-N-[3-chloro-4-(3-diethylamino-propyl)-phenyl]-3-(2-chloro-4-trifluoromethyl-phenyl)-acrylamide A solution of 0.290 g (0.603 mmol) (E)-N-[4-(3-bromo-propyl)-3-chloro-phenyl]-3-(2-chloro-4-trifluoromethyl-phenyl)-acrylamide (Z45d) in 2 mL diethylamine was heated to 100° C. in a sealed reaction vessel in the microwave for 5 min. The reaction mixture was diluted with EtOAc, the org. phase was washed with water, dried over sodium sulphate and evaporated down i. vac. The residue was triturated with ether, the precipitate was filtered off, washed with ether and dried in a HV.

Yield: 0.180 g (63% of theory)

C$_{23}$H$_{25}$Cl$_2$F$_3$N$_2$O (M=473.370)

Calc.: molpeak (M+H)$^+$: 473/475/477

Found: molpeak (M+H)$^+$: 473/475/477 (Cl$_2$)

R$_f$ value: 0.33 (Alox, dichloromethane/MeOH 30:1).

EXAMPLE 196

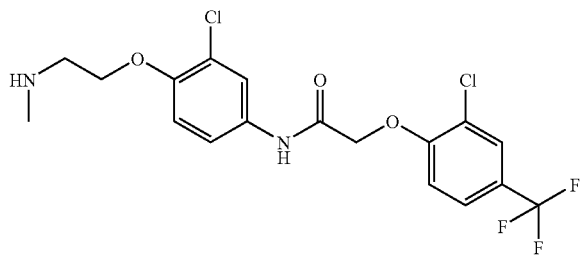

196a) N-[4-(N-tert.butoxycarbonyl-2-methylamino-ethoxy)-3-chloro-phenylamine]-2-(2-chloro-4-trifluoromethyl-phenoxy)-acetamide The product was prepared analogously to Example 143 from 260 mg (1.00 mmol) (2-chloro-4-trifluoromethyl-phenoxy)-acetic acid (Z2b), 0.120 mL (1.10 mmol) N-methylmorpholine, 0.140 mL (1.10 mmol) isobutyl chloroformate and 330 mg (1.10 mmol) 4-(N-tert.butoxycarbonyl-2-methylamino-ethoxy)-3-chloro-phenylamine (Z40b).

Yield: 0.54 g (100% of theory)
$C_{23}H_{25}Cl_2F_3N_2O_5$ (M=537.36)
Calc.: molpeak (M−H)⁻: 535/537/539
Found: molpeak (M−H)⁻: 535/537/539 (Cl₂)
$R_f$ value: 0.75 (silica gel, dichloromethane/methanol 19:1)

196b) N-[4-(2-methylamino-ethoxy)-3-chloro-phenylamine]-2-(2-chloro-4-trifluoromethyl-phenoxy)-acetamide The product was obtained analogously to Example 115 from 560 mg (1.04 mmol) N-[4-(N-tert.butoxycarbonyl-2-methylamino-ethoxy)-3-chloro-phenylamine]-2-(2-chloro-4-trifluoromethyl-phenoxy)-acetamide.

Yield: 0.43 g (94% of theory)
$C_{18}H_{17}Cl_2F_3N_2O_3$ (M=437.24)
Calc.: molpeak (M+H)⁺: 437/439/441
Found: molpeak (M+H)⁺: 437/439/441
$R_f$ value: 0.35 (silica gel, dichloromethane/MeOH 9:1)

EXAMPLE 197

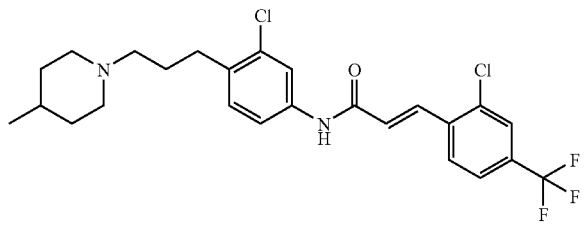

197) 2-(2-chloro-4-trifluoromethyl-phenoxy)-N-[4-(2-diethylamino-ethoxy)-3-methyl-phenyl]-acetamide 0.290 g (0.603 mmol) (E)-N-[4-(3-bromo-propyl)-3-chloro-phenyl]-3-(2-chloro-4-trifluoromethyl-phenyl)-acrylamide (Z45d) and 0.270 g (2.614 mmol) 4-methylpiperidine was heated to 100° C. in a sealed reaction vessel in the microwave for 5 min.

The reaction mixture was diluted with EtOAc, the precipitate formed was filtered off, stirred with 1 N aqueous NaOH solution, washed with water and dried in a HV.

Yield: 0.280 g (93% of theory)
$C_{25}H_{27}Cl_2F_3N_2O$ (M=499.408)
Calc.: molpeak (M+H)⁺: 499/501/503
Found: molpeak (M+H)⁺: 499/501/503 (Cl₂)
$R_f$ value: 0.33 (Alox, dichloromethane/MeOH 30:1).

EXAMPLE 198

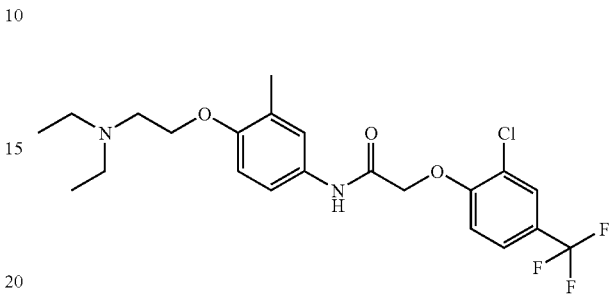

198) N-[4-(2-diethylamino-ethoxy)-3-methyl-phenyl]-2-(2-chloro-4-trifluoromethyl-phenoxy)-acetamide The product was prepared according to general working method I from 100 mg (0.40 mmol) (2-chloro-4-trifluoromethyl-phenoxy)-acetic acid (Z2b) and 100 mg (0.44 mmol) 4-(2-diethylamino-ethoxy)-3-methyl-phenylamine (Z39b). The product was obtained as the formate salt.

Yield: 51 mg (25% of theory)
$C_{22}H_{26}ClF_3N_2O_3$ (M=458.91)
Calc.: molpeak (M+H)⁺: 459/461
Found: molpeak (M+H)⁺: 459/461
$R_f$ value: 0.4 (silica gel, dichloromethane/MeOH 9:1)

EXAMPLE 199

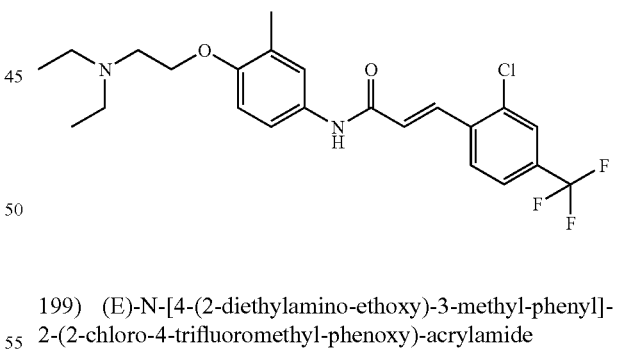

199) (E)-N-[4-(2-diethylamino-ethoxy)-3-methyl-phenyl]-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 100 mg (0.44 mmol) 4-(2-diethylamino-ethoxy)-3-methyl-phenylamine (Z39b). The product was obtained as the formate salt.

Yield: 44 mg (22% of theory)
$C_{23}H_{26}ClF_3N_2O_2$ (M=454.92)
Calc.: molpeak (M+H)⁺: 454/456
Found: molpeak (M+H)⁺: 455/456
$R_f$ value: 0.2 (silica gel, dichloromethane/MeOH 9:1)

EXAMPLE 200

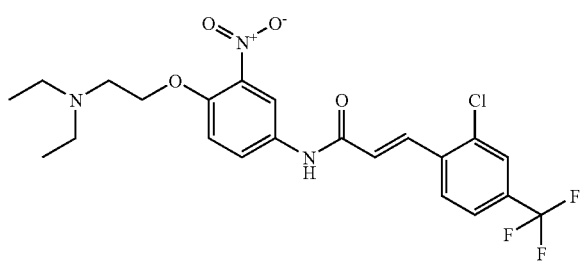

200) (E)-3-(2-chloro-4-trifluoromethyl-phenyl)-N-[4-(2-diethylamino-ethoxy)-3-nitro-phenyl]-acrylamide The product was prepared analogously to Example 119 from 100 mg (0.40 mmol) (E)-3-(2-chloro-4-trifluoromethyl-phenyl)-acrylic acid (Z37b) and 110 mg (0.44 mmol) 4-(2-diethylamino-ethoxy)-3-nitro-phenylamine (Z31 a). The product was obtained as the formate salt.

Yield: 27 mg (13% of theory)

$C_{22}H_{23}ClF_3N_3O_4$ (M=485.89)

Calc.: molpeak (M+H)$^+$: 485/487

Found: molpeak (M+H)$^+$: 486/488

$R_f$ value: 0.3 (silica gel, dichloromethane/MeOH 9:1)

EXAMPLE 201

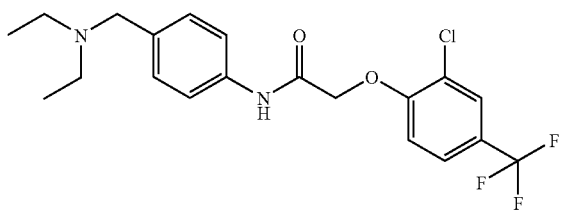

201) N-(4-diethylaminomethyl-phenyl)-2-(2-chloro-4-trifluoromethyl-phenoxy)-acetamide The product was prepared according to general working method I from 100 mg (0.40 mmol) (2-chloro-4-trifluoromethyl-phenoxy)-acetic acid (Z2b) and 80 mg (0.44 mmol) 4-diethylaminomethyl-phenylamine (for preparation see WO 01/27081). The product was obtained as the formate salt.

Yield: 92 mg (50% of theory)

$C_{20}H_{22}ClF_3N_2O_2$ (M=414.85)

Calc.: molpeak (M+H)$^+$: 414/416

Found: molpeak (M+H)$^+$: 415/417

$R_f$ value: 0.25 (silica gel, dichloromethane/MeOH 9:1)

EXAMPLE 202

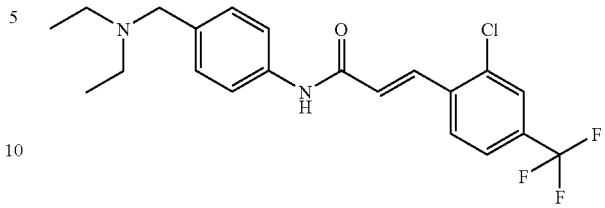

202) (E)-N-(4-diethylaminomethyl-phenyl)-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 80 mg (0.44 mmol) 4-diethylaminomethyl-phenylamine (for preparation see WO 01/27081). The product was obtained as the formate salt.

Yield: 27 mg (15% of theory)

$C_{21}H_{22}ClF_3N_2O$ (M=410.87)

Calc.: molpeak (M+H)$^+$: 410/412

Found: molpeak (M+H)$^+$: 411/413

$R_f$ value: 0.15 (silica gel, dichloromethane/MeOH 9:1)

EXAMPLE 203

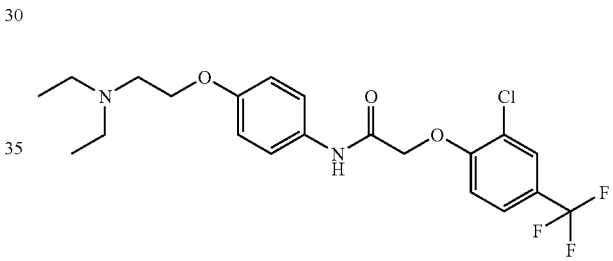

203) N-[4-(2-diethylamino-ethoxy)-phenyl]-2-(2-chloro-4-trifluoromethyl-phenoxy)-acetamide The product was prepared according to general working method I from 100 mg (0.40 mmol) (2-chloro-4-trifluoromethyl-phenoxy)-acetic acid (Z2b) and 90 mg (0.44 mmol) 4-(2-diethylamino-ethoxy)-phenylamine (Z5b). The product was obtained as the formate salt.

Yield: 45 mg (23% of theory)

$C_{21}H_{24}ClF_3N_2O_3$ (M=444.88)

Calc.: molpeak (M+H)$^+$: 444/446

Found: molpeak (M+H)$^+$: 445/447

$R_f$ value: 0.3 (silica gel, dichloromethane/MeOH 9:1)

EXAMPLE 204

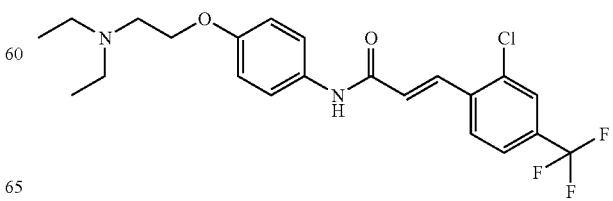

204) (E)-N-[4-(2-diethylamino-ethoxy)-phenyl]-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 90 mg (0.44 mmol) 4-(2-diethylamino-ethoxy)-phenylamine (Z5b). The product was obtained as the formate salt.

Yield: 35 mg (18% of theory)
$C_{22}H_{24}ClF_3N_2O_2$ (M=440.89)
Calc.: molpeak $(M+H)^+$: 440/442
Found: molpeak $(M+H)^+$: 441/443
$R_f$ value: 0.2 (silica gel, dichloromethane/MeOH 9:1)

EXAMPLE 205

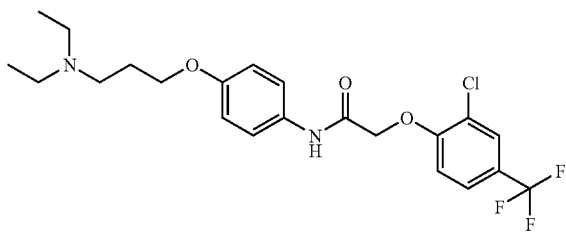

205) N-[4-(3-diethylamino-propyloxy)-phenyl]-2-(2-chloro-4-trifluoromethyl-phenoxy)-acetamide The product was prepared according to general working method I from 100 mg (0.40 mmol) (2-chloro-4-trifluoromethyl-phenoxy)-acetic acid (Z2b) and 100 mg (0.44 mmol) 4-(3-diethylamino-propyloxy)-phenylamine (for preparation see WO 99/52869). The product was obtained as the formate salt.

Yield: 48 mg (23.8% of theory)
$C_{22}H_{26}ClF_3N_2O_3$ (M=458.91)
Calc.: molpeak $(M+H)^+$: 458/460
Found: molpeak $(M+H)^+$: 459/61
$R_f$ value: 0.40 (silica gel, dichloromethane/MeOH 9:1)

EXAMPLE 206

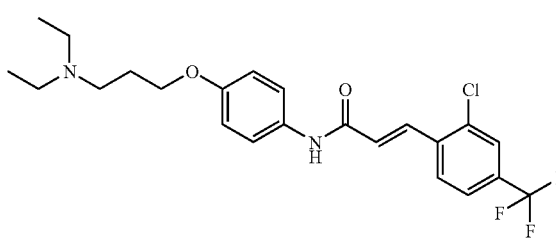

206) (E)-N-[4-(3-diethylamino-propyloxy)-phenyl]-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 100 mg (0.44 mmol) 4-(3-diethylamino-propyloxy)-phenylamine (for preparation see WO 99/52869). The product was obtained as the formate salt.

Yield: 33 mg (16% of theory)
$C_{23}H_{26}ClF_3N_2O_2$ (M=454.92)
Calc.: molpeak $(M+H)^+$: 454/456
Found: molpeak $(M+H)^+$: 455/7
$R_f$ value: 0.39 (silica gel, dichloromethane/MeOH 9:1)

EXAMPLE 207

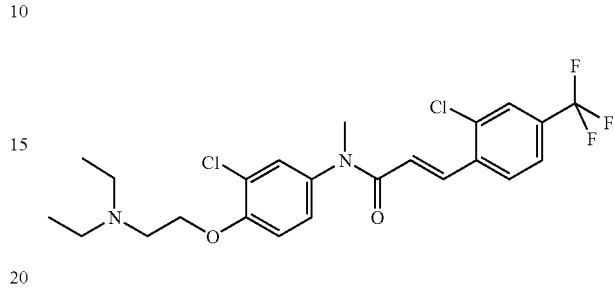

207) (E)-N-[3-chloro-4-(2-diethylamino-ethoxy)-phenyl]-N-methyl-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 110 mg (0.44 mmol) N-[3-chloro-4-(2-diethylamino-ethoxy)-phenyl]-methylamine (Z125b). The product was obtained as the formate salt.

Yield: 38 mg (18% of theory)
$C_{23}H_{25}Cl_2F_3N_2O_2$ (M=489.36)
Calc.: molpeak $(M+H)^+$: 487/489/491
Found: molpeak $(M+H)^+$: 489/91/93
$R_f$ value: 0.48 (silica gel, dichloromethane/MeOH 9:1)

EXAMPLE 208

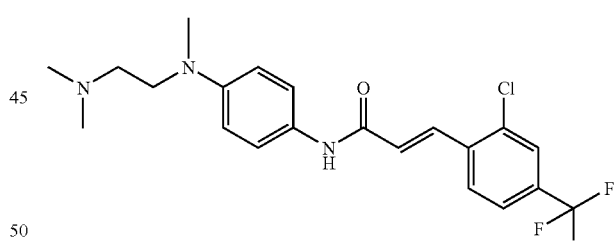

208) (E)-N-{4-[N-(2-dimethylamino-ethyl)-N-methyl-amino]-phenyl}-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 90 mg (0.44 mmol) N-(2-dimethylamino-ethyl)-N-methyl-benzene-1,4-diamine (Z141b). The product was obtained as the formate salt.

Yield: 34 mg (18% of theory)
$C_{21}H_{23}ClF_3N_3O$ (M=425.88)
Calc.: molpeak $(M+H)^+$: 425/427
Found: molpeak $(M+H)^+$: 426/8
$R_f$ value: 0.29 (silica gel, dichloromethane/MeOH 9:1)

EXAMPLE 209

209) (E)-N-[4-(2-diethylamino-ethyl)-phenyl]-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 90 mg (0.44 mmol) 4-(2-diethylamino-ethyl)-phenylamine (for preparation see WO 01/27081). The product was obtained as the formate salt.

Yield: 27 mg (14% of theory)
$C_{22}H_{24}ClF_3N_2O$ (M=424.89)
Calc.: molpeak (M+H)$^+$: 424/426
Found: molpeak (M+H)$^+$: 425/27
$R_f$ value: 0.30 (silica gel, dichloromethane/MeOH 9:1)

EXAMPLE 210

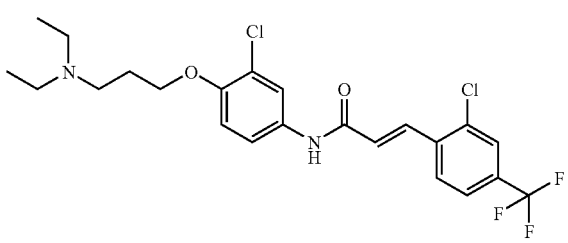

210) (E)-N-[3-chloro-4-(3-diethylamino-propyloxy)-phenyl]-2-(2-chloro-4-trifluoromethyl-phenoxy)-acrylamide The product was prepared analogously to Example 119 from 100 mg (0.40 mmol) (E)-3-(2-chloro-4-trifluoromethyl-phenyl)-acrylic acid (Z37b) and 110 mg (0.44 mmol) 3-chloro-4-(3-diethylamino-propyloxy)-phenylamine (Z29b). The product was obtained as the formate salt.

Yield: 38 mg (18% of theory)
$C_{23}H_{25}Cl_2F_3N_2O_2$ (M=489.36)
Calc.: molpeak (M+H)$^+$: 489/491
Found: molpeak (M+H)$^+$: 489/91/93
$R_f$ value: 0.36 (silica gel, dichloromethane/MeOH 9:1)

EXAMPLE 211

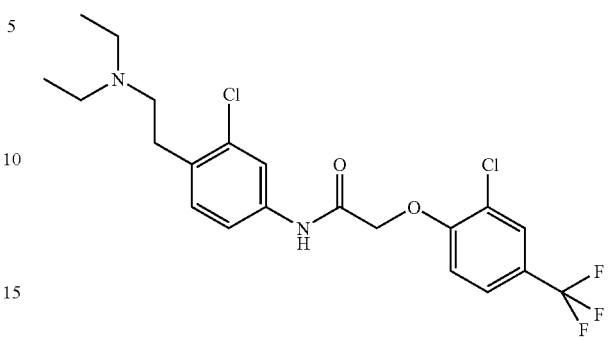

211) N-[3-chloro-4-(2-diethylamino-ethyl)-phenyl]-2-(2-chloro-4-trifluoromethyl-phenoxy)-acetamide Prepared analogously to Example 143 starting from (2-chloro-4-trifluoromethyl-phenoxy)-acetic acid (Z2b) and 3-chloro-4-(2-diethylamino-ethyl)-phenylamine (Z44d). The reaction mixture was poured onto ice water and the aqueous phase was extracted with EtOAc. The org. phase was dried over sodium sulphate and evaporated down i. vac. The residue was purified by column chromatography (Alox, neutral, act. II-III, gradient petroleum ether/EtOAc 5:2→1:1).

Yield: 0.258 g (65% of theory)
$C_{21}H_{23}Cl_2F_3N_2O_2$ (M=463.331)
Calc.: molpeak (M+H)$^+$: 463/465/467
Found: molpeak (M+H)$^+$: 463/465/467 (Cl$_2$)
$R_f$ value: 0.46 (Alox, petroleum ether/EtOAc 1:1)

EXAMPLE 212

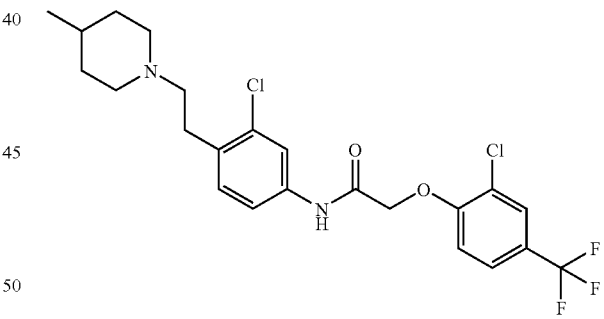

212) N-{3-chloro-4-[2-(4-methyl-piperidin-1-yl)-ethyl]-phenyl}-2-(2-chloro-4-trifluoromethyl-phenoxy)-acetamide Prepared analogously to Example 143 starting from (2-chloro-4-trifluoromethyl-phenoxy)-acetic acid (Z2b) and 3-chloro-4-[2-(4-methyl-piperidin-1-yl)-ethyl]-phenylamine (Z46c). The reaction mixture was poured onto ice water and the aqueous phase was extracted with EtOAc. The org. phase was dried over sodium sulphate and evaporated down i. vac. The residue was purified by column chromatography (Alox, neutral, act. II-III, gradient petroleum ether/EtOAc 3:1→1:1).

Yield: 0.218 g (52% of theory)
$C_{23}H_{25}Cl_2F_3N_2O_2$ (M=489.369)
Calc.: molpeak (M+H)$^+$: 489/491/493

Found: molpeak (M+H)$^+$: 489/491/493 (Cl$_2$)
R$_f$ value: 0.46 (Alox, petroleum ether/EtOAc 1:1)

EXAMPLE 213

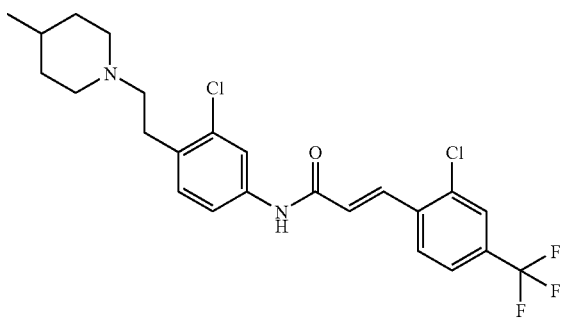

213) (E)-N-{3-chloro-4-[2-(4-methyl-piperidin-1-yl)-ethyl]-phenyl}-3-(2-chloro-4-trifluoromethyl-phenyl)-acrylamide Prepared in DMF analogously to Example 143 starting from (E)-3-(2-chloro-4-trifluoromethyl-phenyl)-acrylic acid (Z37b) and 3-chloro-4-[2-(4-methyl-piperidin-1-yl)-ethyl]-phenylamine (Z46c). The crude product was purified by column chromatography (Alox, neutral, act. II-III, gradient petroleum ether/EtOAc 3:1→2:1) and then triturated with petroleum ether.

Yield: 0.240 g (51% of theory)
C$_{24}$H$_{25}$Cl$_2$F$_3$N$_2$O (M=485.381)
Calc.: molpeak (M+H)$^+$: 485/487/489
Found: molpeak (M+H)$^+$: 485/487/489 (Cl$_2$)
R$_f$ value: 0.38 (Alox, petroleum ether/EtOAc 1:1)

EXAMPLE 214

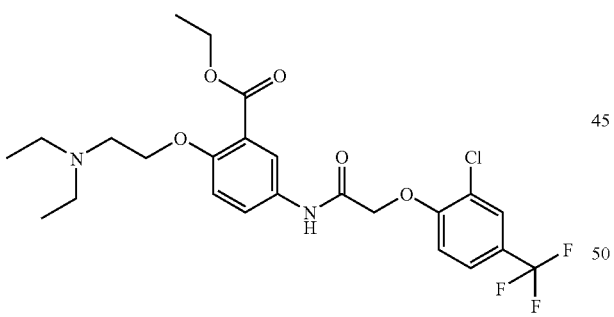

214) ethyl 5-[2-(2-chloro-4-trifluoromethyl-phenoxy)-acetylamino]-2-(2-diethylamino-ethoxy)-benzoate Prepared analogously to Example 143 starting from (2-chloro-4-trifluoromethyl-phenoxy)-acetic acid (Z2b) and ethyl 5-amino-2-(2-diethylamino-ethoxy)-benzoate. The reaction mixture was evaporated down i. vac. and the residue was dissolved in dichloromethane. The org. phase was washed with water, dried over sodium sulphate and evaporated down i. vac. Purification by column chromatography (Alox, neutral, act. II-III, gradient petroleum ether/EtOAc 70:30→50:50) yielded the product.

Yield: 1.220 g (59% of theory)
C$_{24}$H$_{28}$ClF$_3$N$_2$O$_5$ (M=516.949)

Calc.: molpeak (M+H)$^+$: 517/519
Found: molpeak (M+H)$^+$: 517/519 (Cl) R$_f$ value: 0.62 (Alox, petroleum ether/EtOAc 2:1)

EXAMPLE 215

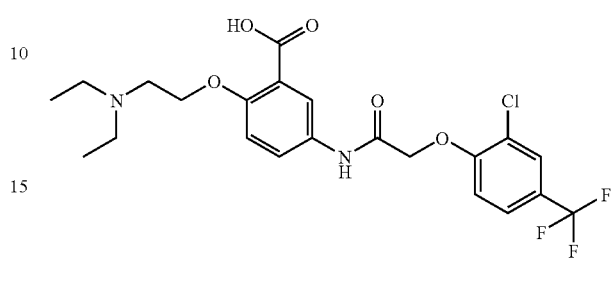

215) 5-[2-(2-chloro-4-trifluoromethyl-phenoxy)-acetylamino]-2-(2-diethylamino-ethoxy) -benzoic acid 4.00 mL 1 M aqueous NaOH solution was added to a solution of 1.00 g (1.934 mmol) ethyl 5-[2-(2-chloro-4-trifluoromethyl-phenoxy)-acetylamino]-2-(2-diethylamino-ethoxy)-benzoate in 30 mL EtOH and the mixture was stirred for 3 h at RT. 4.00 mL 1 M aqueous HCl was added and again the mixture was stirred for 1 h. The reaction mixture was evaporated down i. vac., combined with water and the precipitate was filtered off.

Yield: 0.220 g (23% of theory)
C$_{22}$H$_{24}$ClF$_3$N$_2$O$_5$ (M=488.895)
Calc.: molpeak (M+H)$^+$: 487/489
Found: molpeak (M+H)$^+$: 487/489 (Cl)
R$_f$ value: 0.36 (silica gel, dichloromethane/MeOH 9:1)

EXAMPLE 216

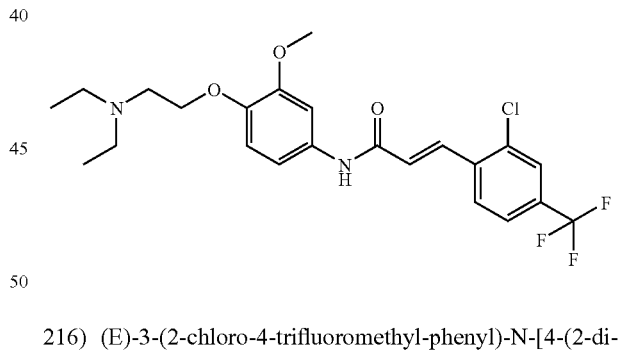

216) (E)-3-(2-chloro-4-trifluoromethyl-phenyl)-N-[4-(2-diethylamino-ethoxy)-3-methoxy-phenyl]-acrylamide The product was prepared according to general working method I starting from 0.100 g (0.400 mmol) (E)-3-(2-chloro-4-trifluoromethyl-phenyl)-acrylic acid (Z37b) and 0.121 g (0.440 mmol) 4-(2-diethylamino-ethoxy)-3-methoxy-phenylamine. The crude product was purified by HPLC (Stable Bond C18; 3.5 µm; water/acetonitrile/formic acid 9:1:0.01→1:9:0.01 over 9 min) and the product was obtained as the formate salt.

Yield: 41 mg (20% of theory)
C$_{23}$H$_{26}$ClF$_3$N$_2$O$_3$ * CH$_2$O$_2$ (M=516.949)
Calc.: molpeak (M+H)$^+$: 471/473
Found: molpeak (M+H)$^+$: 471/473 (Cl)
R$_f$ value: 0.35 (silica gel, dichloromethane/MeOH 9:1)

The following compounds may be prepared analogously to the foregoing Examples:
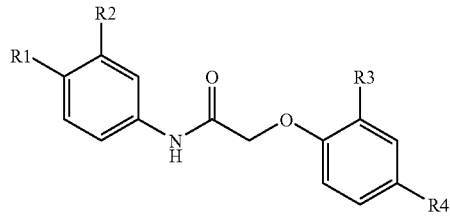
| Example | R1 | R2 | R3 | R4 |
|---|---|---|---|---|
| 217 | H3C-CH2-N(CH2CH3)-CH2CH2CH2-O- | —OMe | —Cl | —CF3 |
| 218 | H3C-CH2-N(CH2CH3)-CH2CH2CH2-O- | —Br | —Cl | —CF3 |
| 219 | H3C-CH2-N(CH2CH3)-CH2CH2CH2-O- | —CN | —Cl | —CF3 |
| 220 | H3C-CH2-N(CH2CH3)-CH2CH2CH2-O- | —F | —Cl | —CF3 |
| 221 | H3C-CH2-N(CH2CH3)-CH2CH2CH2-O- | —CH3 | —Cl | —CF3 |
| 222 | H3C-CH2-N(CH2CH3)-CH2CH2-O- | —F | —Cl | —CF3 |
| 223 | H3C-CH2-N(CH2CH3)-CH2CH2-O- | —F | —Cl | —CF3 |
| 224 | H3C-CH2-N(CH2CH3)-CH2CH2-O- | —COOEt | —Cl | —CF3 |

-continued
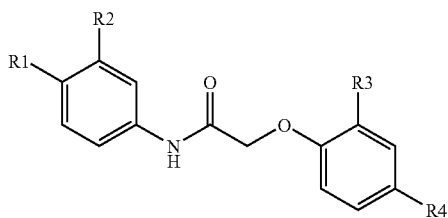
| Example | R1 | R2 | R3 | R4 |
| --- | --- | --- | --- | --- |
| 225 | 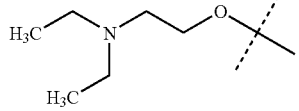 | —COOH | —Cl | —CF$_3$ |
| 226 | 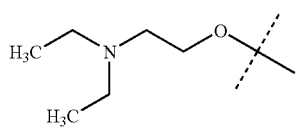 | —CONH$_2$ | —Cl | —CF$_3$ |
| 227 | 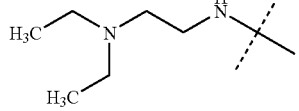 | —Cl | —Cl | —CF$_3$ |
| 228 | 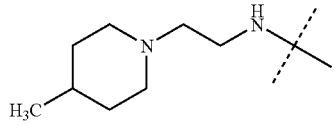 | —Cl | —Cl | —CF$_3$ |
| 229 | 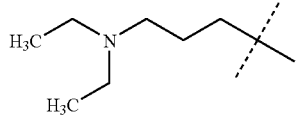 | —Cl | —Cl | —CF$_3$ |
| 230 | 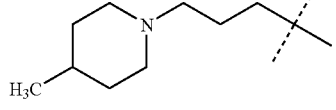 | —Cl | —Cl | —CF$_3$ |
| 231 | 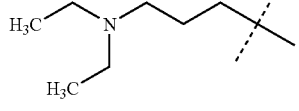 | —H | —Cl | —CF$_3$ |
| 232 | 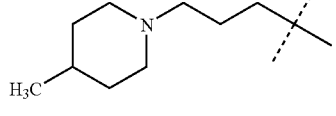 | —H | —Cl | —CF$_3$ |
| 233 | 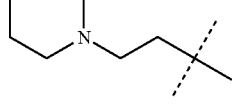 | —Cl | —Cl | —CF$_3$ |

-continued

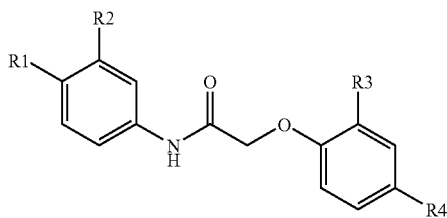

| Example | R1 | R2 | R3 | R4 |
|---|---|---|---|---|
| 234 | HO-piperidine-N-CH₂CH₂C(CH₃)₂- | —Cl | —Cl | —CF₃ |
| 235 | 2-(hydroxymethyl)piperidine-N-CH₂CH₂C(CH₃)₂- | —Cl | —Cl | —CF₃ |
| 236 | 2-((dimethylamino)methyl)piperidine-N-CH₂CH₂C(CH₃)₂- | —Cl | —Cl | —CF₃ |
| 237 | pyrrolidine-N-CH₂CH₂C(CH₃)₂- | —Cl | —Cl | —CF₃ |
| 238 | 3-pyrroline-N-CH₂CH₂C(CH₃)₂- | —Cl | —Cl | —CF₃ |
| 240 | 2-((dimethylamino)methyl)pyrrolidine-N-CH₂CH₂C(CH₃)₂- | —Cl | —Cl | —CF₃ |
| 241 | 2-(hydroxymethyl)pyrrolidine-N-CH₂CH₂C(CH₃)₂- | —Cl | —Cl | —CF₃ |
| 242 | 2-(methoxymethyl)pyrrolidine-N-CH₂CH₂C(CH₃)₂- | —Cl | —Cl | —CF₃ |

-continued
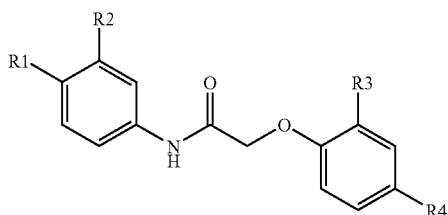
| Example | R1 | R2 | R3 | R4 |
|---|---|---|---|---|
| 243 | piperidine-N-CH2CH2C(CH3)2- | —Br | —Cl | —CF3 |
| 244 | 4-hydroxypiperidine-N-CH2CH2C(CH3)2- | —Br | —Cl | —CF3 |
| 245 | pyrrolidine-N-CH2CH2C(CH3)2- | —Br | —Cl | —CF3 |
| 246 | 2,5-dihydropyrrole-N-CH2CH2C(CH3)2- | —Br | —Cl | —CF3 |
| 247 | 2-((dimethylamino)methyl)pyrrolidine-N-CH2CH2C(CH3)2- | —Br | —Cl | —CF3 |
| 248 | 2-(hydroxymethyl)pyrrolidine-N-CH2CH2C(CH3)2- | —Br | —Cl | —CF3 |
| 249 | piperidine-N-CH2CH2C(CH3)2- | —OMe | —Cl | —CF3 |
| 250 | 4-hydroxypiperidine-N-CH2CH2C(CH3)2- | —OMe | —Cl | —CF3 |
| 251 | pyrrolidine-N-CH2CH2C(CH3)2- | —OMe | —Cl | —CF3 |

-continued
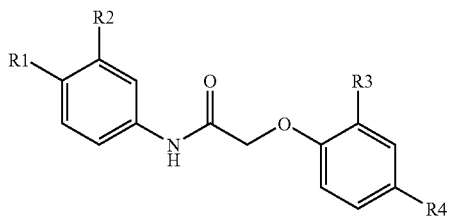
| Example | R1 | R2 | R3 | R4 |
| --- | --- | --- | --- | --- |
| 252 | 3-pyrrolin-1-yl-neopentyl | —OMe | —Cl | —CF₃ |
| 253 | 2-((dimethylamino)methyl)pyrrolidin-1-yl-neopentyl | —OMe | —Cl | —CF₃ |
| 254 | 2-(hydroxymethyl)pyrrolidin-1-yl-neopentyl | —OMe | —Cl | —CF₃ |
| 255 | piperidin-1-yl-neopentyl | —Cl | —Cl | —Br |
| 256 | 4-hydroxypiperidin-1-yl-neopentyl | —Cl | —Cl | —Br |
| 257 | pyrrolidin-1-yl-neopentyl | —Cl | —Cl | —Br |
| 258 | 3-pyrrolin-1-yl-neopentyl | —Cl | —Cl | —Br |
| 259 | 2-((dimethylamino)methyl)pyrrolidin-1-yl-neopentyl | —Cl | —Cl | —Br |

-continued
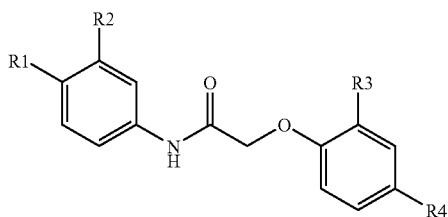
| Example | R1 | R2 | R3 | R4 |
|---|---|---|---|---|
| 260 | 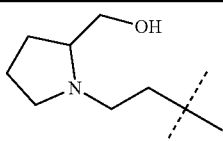 | —Cl | —Cl | —Br |
| 261 | 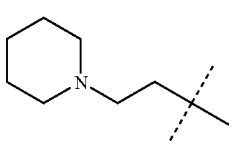 | —Cl | —Cl | —Ph |
| 262 | 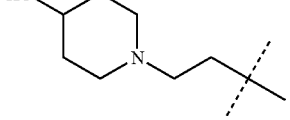 | —Cl | —Cl | —Ph |
| 263 | 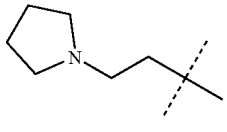 | —Cl | —Cl | —Ph |
| 364 | 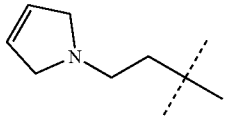 | —Cl | —Cl | —Ph |
| 265 | 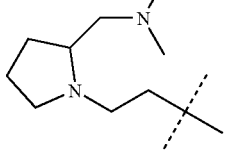 | —Cl | —Cl | —Ph |
| 266 | 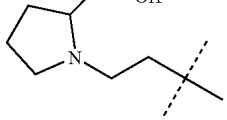 | —Cl | —Cl | —Ph |
| 267 | 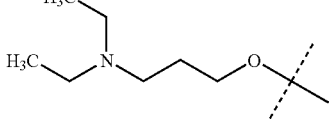 | —Cl | —Cl | —Ph |
| 268 | 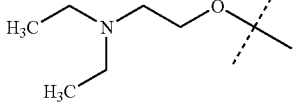 | —Br | —Cl | —Ph |

-continued
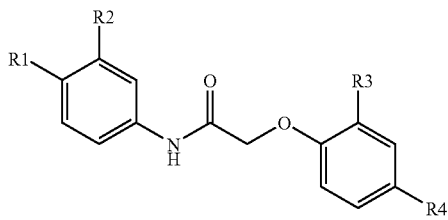
| Example | R1 | R2 | R3 | R4 |
|---|---|---|---|---|
| 269 | 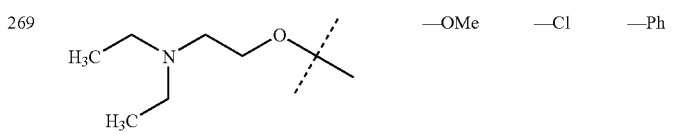 | —OMe | —Cl | —Ph |
| 270 | 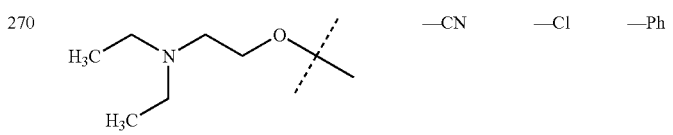 | —CN | —Cl | —Ph |
The following compounds may be prepared analogously to the foregoing Examples:
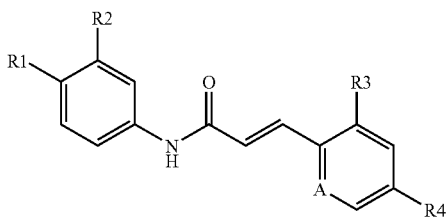
| Number | R1 | R2 | R3 | R4 | A |
|---|---|---|---|---|---|
| 271 |  | —OMe | —Cl | —CF$_3$ | CH |
| 272 | 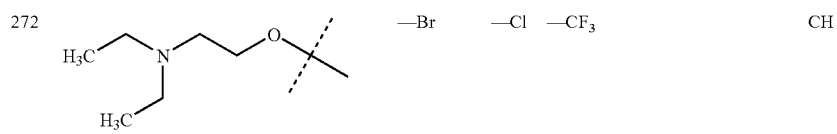 | —Br | —Cl | —CF$_3$ | CH |
| 273 | 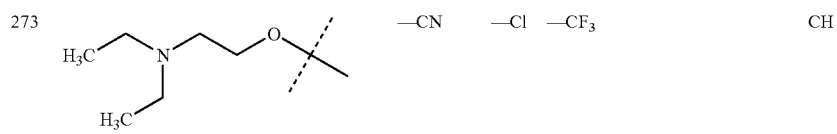 | —CN | —Cl | —CF$_3$ | CH |
| 274 |  | —F | —Cl | —CF$_3$ | CH |

-continued
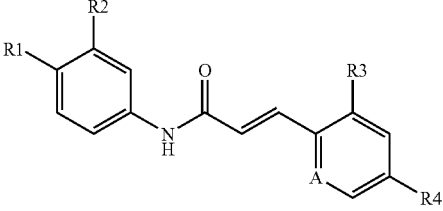
| Number | R1 | R2 | R3 | R4 | A |
|---|---|---|---|---|---|
| 275 | 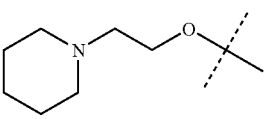 | —Cl | —Cl | —CF$_3$ | CH |
| 276 | 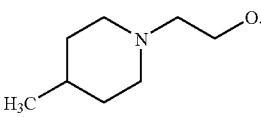 | —Cl | —Cl | —CF$_3$ | CH |
| 277 | 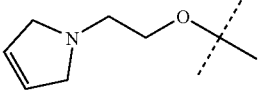 | —Cl | —Cl | —CF$_3$ | CH |
| 278 | 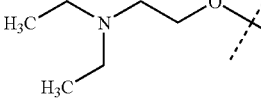 | —NO$_2$ | —Cl | —CF$_3$ | CH |
| 279 | 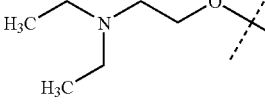 | —COOEt | —Cl | —CF$_3$ | CH |
| 280 | 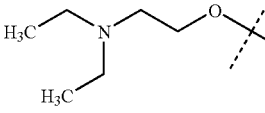 | —COOH | —Cl | —CF$_3$ | CH |
| 281 | 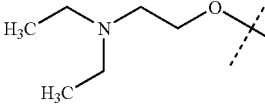 | —CONH$_2$ | —Cl | —CF$_3$ | CH |
| 282 | 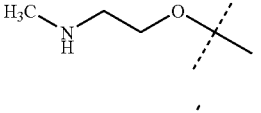 | —Cl | —Cl | —CF$_3$ | CH |
| 283 | 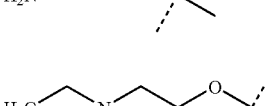 | —Cl | —Cl | —CF$_3$ | CH |
| 284 | 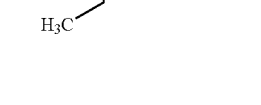 | —Cl | —Cl | —Ph | CH |

-continued

| Number | R1 | R2 | R3 | R4 | A |
|---|---|---|---|---|---|
| 285 | (H3C-CH2)2N-CH2- | —H | —H | 4-Cl-C6H4- | CH |
| 286 | pyrrolidin-1-yl-CH2- | —H | —H | 4-Cl-C6H4- | CH |
| 287 | 2,5-dihydro-1H-pyrrol-1-yl-CH2- | —H | —H | 4-Cl-C6H4- | CH |
| 288 | 4-methylpiperidin-1-yl-CH2- | —H | —H | 4-Cl-C6H4- | CH |
| 289 | 3,5-dimethylpiperidin-1-yl-CH2- | —H | —H | 4-Cl-C6H4- | CH |
| 290 | morpholin-4-yl-CH2- | —H | —H | 4-Cl-C6H4- | CH |
| 291 | thiomorpholin-4-yl-CH2- | —H | —H | 4-Cl-C6H4- | CH |
| 292 | azetidin-1-yl-CH2- | —H | —H | 4-Cl-C6H4- | CH |

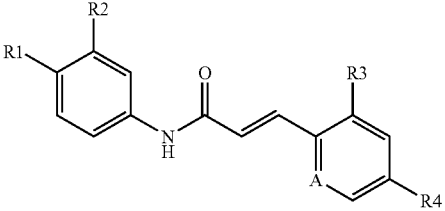

-continued
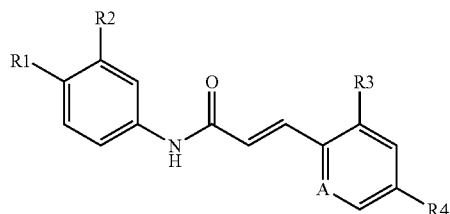
| Number | R1 | R2 | R3 | R4 | A |
|---|---|---|---|---|---|
| 301 | azetidinyl-CH2-C(CH3)2- | —H | —H | 4-Cl-phenyl | N |
| 302 | cyclopropyl-CH2-NH-C(CH3)2- | —H | —H | 4-Cl-phenyl | N |
| 303 | (H3C-CH2)2N-C(CH3)2- | —Cl | —H | 4-Cl-phenyl | CH |
| 304 | pyrrolidinyl-C(CH3)2- | —Cl | —H | 4-Cl-phenyl | CH |
| 305 | 2,5-dihydropyrrolyl-C(CH3)2- | —Cl | —H | 4-Cl-phenyl | CH |
| 306 | 4-methylpiperidinyl-C(CH3)2- | —Cl | —H | 4-Cl-phenyl | CH |
| 307 | 3,5-dimethylpiperidinyl-C(CH3)2- | —Cl | —H | 4-Cl-phenyl | CH |
| 308 | morpholinyl-C(CH3)2- | —Cl | —H | 4-Cl-phenyl | CH |

-continued

| Number | R1 | R2 | R3 | R4 | A |
|---|---|---|---|---|---|
| 309 | thiomorpholin-N-ylmethyl | —Cl | —H | 4-chlorophenyl | CH |
| 310 | azetidin-N-ylmethyl | —Cl | —H | 4-chlorophenyl | CH |
| 311 | cyclopropylmethyl-NH-methyl | —Cl | —H | 4-chlorophenyl | CH |
| 312 | piperidin-N-ylmethyl | —Cl | —H | 4-chlorophenyl | CH |
| 313 | 4-methylpiperazin-N-ylmethyl | —Cl | —H | 4-chlorophenyl | CH |
| 314 | (CH₃)₂N-methyl | —Cl | —H | 4-chlorophenyl | CH |
| 315 | (CH₃CH₂)₂N-methyl | —Cl | —H | 4-chlorophenyl | N |
| 316 | pyrrolidin-N-ylmethyl | —Cl | —H | 4-chlorophenyl | N |

-continued
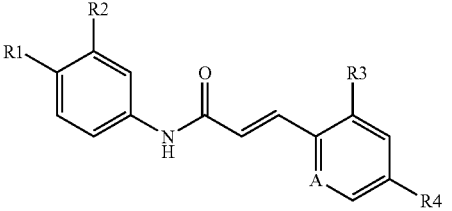
| Number | R1 | R2 | R3 | R4 | A |
|---|---|---|---|---|---|
| 317 | 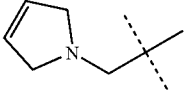 | —Cl | —H | 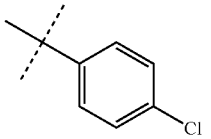 | N |
| 318 | 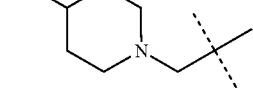 | —Cl | —H | 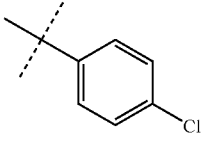 | N |
| 319 | 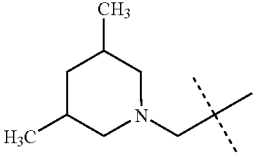 | —Cl | —H | 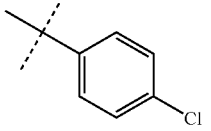 | N |
| 320 | 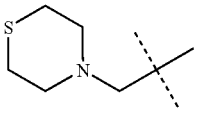 | —Cl | —H | 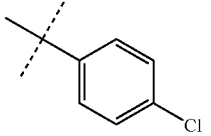 | N |
| 321 | 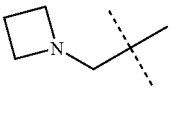 | —Cl | —H | 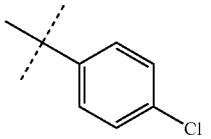 | N |
| 322 | 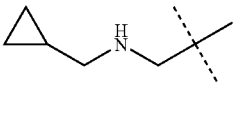 | —Cl | —H | 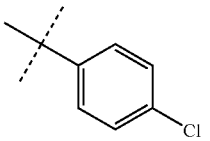 | N |
| 323 | 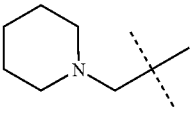 | —Cl | —H | 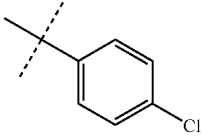 | N |
| 324 | 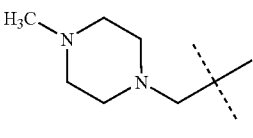 | —Cl | —H | 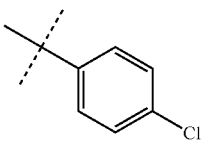 | N |

-continued

| Number | R1 | R2 | R3 | R4 | A |
|---|---|---|---|---|---|
| 325 | (CH3)2N-CH2-C(CH3)2- | —Cl | —H | 4-Cl-C6H4- | N |
| 326 | (C2H5)2N-CH2-C(CH3)2- | —H | —H | 4-OCH3-C6H4- | CH |
| 327 | pyrrolidin-1-yl-CH2-C(CH3)2- | —H | —H | 4-OCH3-C6H4- | CH |
| 328 | 2,5-dihydro-pyrrol-1-yl-CH2-C(CH3)2- | —H | —H | 4-OCH3-C6H4- | CH |
| 329 | 4-methyl-piperidin-1-yl-CH2-C(CH3)2- | —H | —H | 4-OCH3-C6H4- | CH |
| 330 | 3,5-dimethyl-piperidin-1-yl-CH2-C(CH3)2- | —H | —H | 4-OCH3-C6H4- | CH |
| 331 | morpholin-4-yl-CH2-C(CH3)2- | —H | —H | 4-OCH3-C6H4- | CH |
| 332 | thiomorpholin-4-yl-CH2-C(CH3)2- | —H | —H | 4-OCH3-C6H4- | CH |

-continued
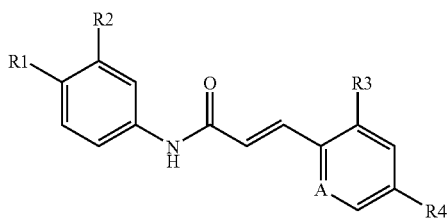
| Number | R1 | R2 | R3 | R4 | A |
|---|---|---|---|---|---|
| 333 | azetidinyl-CH2-C(CH3)2- | —H | —H | 4-methoxyphenyl | CH |
| 334 | cyclopropyl-CH2-NH-C(CH3)2- | —H | —H | 4-methoxyphenyl | CH |
| 335 | piperidinyl-CH2-C(CH3)2- | —H | —H | 4-methoxyphenyl | CH |
| 336 | 4-methylpiperazinyl-CH2-C(CH3)2- | —H | —H | 4-methoxyphenyl | CH |
| 337 | (CH3)2N-CH2-C(CH3)2- | —H | —H | 4-methoxyphenyl | CH |
| 338 | (CH3CH2)2N-CH2-C(CH3)2- | —H | —H | 4-methoxyphenyl | N |
| 339 | pyrrolidinyl-CH2-C(CH3)2- | —H | —H | 4-methoxyphenyl | N |
| 340 | 2,5-dihydropyrrolyl-CH2-C(CH3)2- | —H | —H | 4-methoxyphenyl | N |

-continued

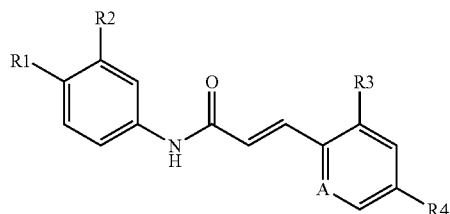

| Number | R1 | R2 | R3 | R4 | A |
|---|---|---|---|---|---|
| 341 | 4-methylpiperidin-1-ylmethyl | —H | —H | 4-methoxyphenyl | N |
| 342 | 3,5-dimethylpiperidin-1-ylmethyl | —H | —H | 4-methoxyphenyl | N |
| 343 | morpholin-4-ylmethyl | —H | —H | 4-methoxyphenyl | N |
| 344 | thiomorpholin-4-ylmethyl | —H | —H | 4-methoxyphenyl | N |
| 345 | azetidin-1-ylmethyl | —H | —H | 4-methoxyphenyl | N |
| 346 | (cyclopropylmethylamino)methyl | —H | —H | 4-methoxyphenyl | N |
| 347 | piperidin-1-ylmethyl | —H | —H | 4-methoxyphenyl | N |
| 348 | (4-methylpiperazin-1-yl)methyl | —H | —H | 4-methoxyphenyl | N |

-continued

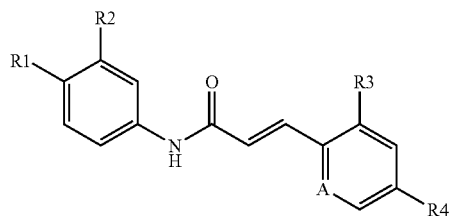

| Number | R1 | R2 | R3 | R4 | A |
|---|---|---|---|---|---|
| 349 | (CH₃)(H₃C)N-CH₂-C(CH₃)₂- | —H | —H | 4-methoxyphenyl | N |
| 350 | (H₃C-CH₂)₂N-CH₂-C(CH₃)₂- | —H | —F | 4-chlorophenyl | CH |
| 351 | pyrrolidin-1-yl-CH₂-C(CH₃)₂- | —H | —F | 4-chlorophenyl | CH |
| 352 | 2,5-dihydropyrrol-1-yl-CH₂-C(CH₃)₂- | —H | —F | 4-chlorophenyl | CH |
| 353 | 4-methylpiperidin-1-yl-CH₂-C(CH₃)₂- | —H | —F | 4-chlorophenyl | CH |
| 354 | 3,5-dimethylpiperidin-1-yl-CH₂-C(CH₃)₂- | —H | —F | 4-chlorophenyl | CH |
| 355 | morpholin-4-yl-CH₂-C(CH₃)₂- | —H | —F | 4-chlorophenyl | CH |
| 356 | thiomorpholin-4-yl-CH₂-C(CH₃)₂- | —H | —F | 4-chlorophenyl | CH |

-continued
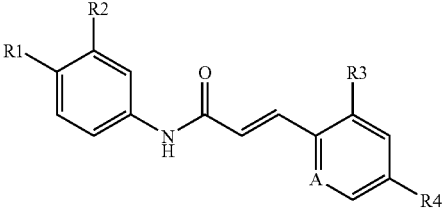
| Number | R1 | R2 | R3 | R4 | A |
|---|---|---|---|---|---|
| 357 | 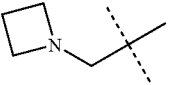 | —H | —F | 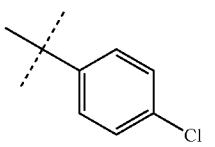 | CH |
| 358 | 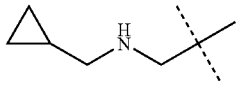 | —H | —F | 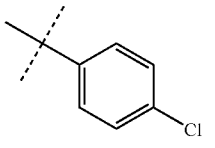 | CH |
| 359 | 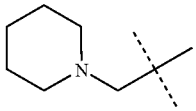 | —H | —F | 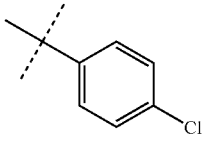 | CH |
| 360 | 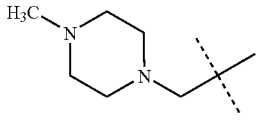 | —H | —F | 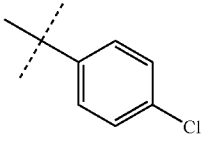 | CH |
| 361 | 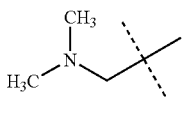 | —H | —F | 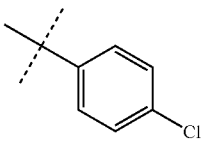 | CH |
| 362 | 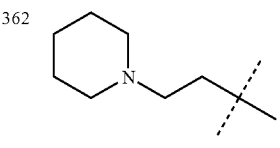 | —Cl | —Cl | —CF$_3$ | CH |
| 363 | 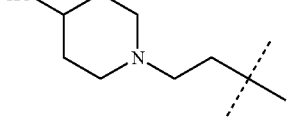 | —Cl | —Cl | —CF$_3$ | CH |
| 364 | 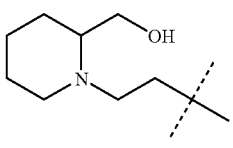 | —Cl | —Cl | —CF$_3$ | CH |

-continued

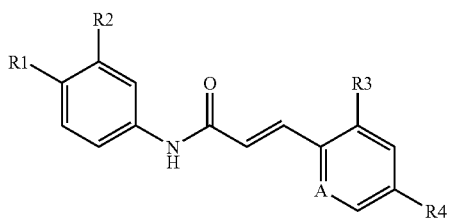

| Number | R1 | R2 | R3 | R4 | A |
|---|---|---|---|---|---|
| 365 | (2-((dimethylamino)methyl)piperidin-1-yl), N-neopentyl | —Cl | —Cl | —CF₃ | CH |
| 366 | pyrrolidin-1-yl, N-neopentyl | —Cl | —Cl | —CF₃ | CH |
| 367 | 2,5-dihydro-1H-pyrrol-1-yl, N-neopentyl | —Cl | —Cl | —CF₃ | CH |
| 368 | 2-((dimethylamino)methyl)pyrrolidin-1-yl, N-neopentyl | —Cl | —Cl | —CF₃ | CH |
| 369 | 2-(hydroxymethyl)pyrrolidin-1-yl, N-neopentyl | —Cl | —Cl | —CF₃ | CH |
| 370 | 2-(methoxymethyl)pyrrolidin-1-yl, N-neopentyl | —Cl | —Cl | —CF₃ | CH |
| 371 | piperidin-1-yl, N-neopentyl | —Br | —Cl | —CF₃ | CH |
| 372 | 4-hydroxypiperidin-1-yl, N-neopentyl | —Br | —Cl | —CF₃ | CH |

-continued
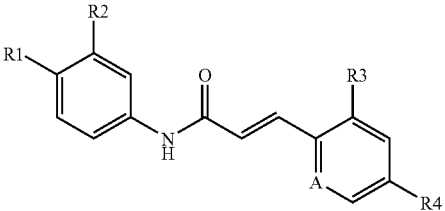
| Number | R1 | R2 | R3 | R4 | A |
|---|---|---|---|---|---|
| 373 | 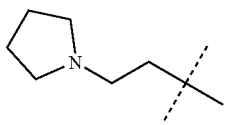 | —Br | —Cl | —CF$_3$ | CH |
| 374 | 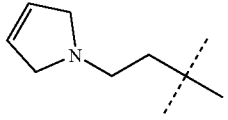 | —Br | —Cl | —CF$_3$ | CH |
| 375 | 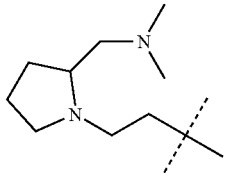 | —Br | —Cl | —CF$_3$ | CH |
| 376 | 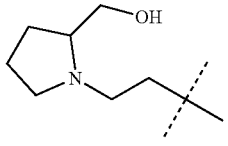 | —Br | —Cl | —CF$_3$ | CH |
| 377 | 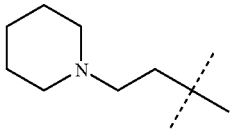 | —OMe | —Cl | —CF$_3$ | CH |
| 378 | 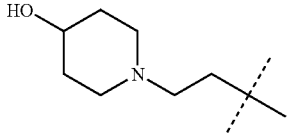 | —OMe | —Cl | —CF$_3$ | CH |
| 379 | 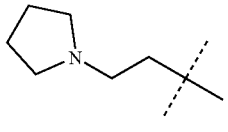 | —OMe | —Cl | —CF$_3$ | CH |
| 380 | 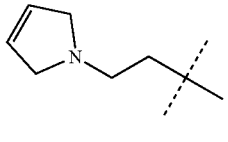 | —OMe | —Cl | —CF$_3$ | CH |

-continued
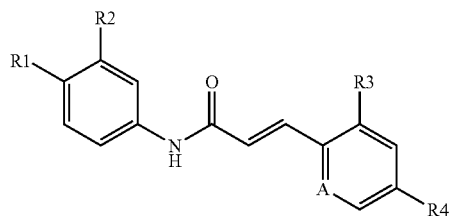
| Number | R1 | R2 | R3 | R4 | A |
|---|---|---|---|---|---|
| 381 | 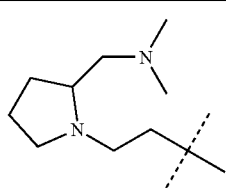 | —OMe | —Cl | —CF₃ | CH |
| 382 | 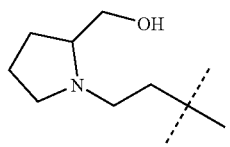 | —OMe | —Cl | —CF₃ | CH |
| 383 | 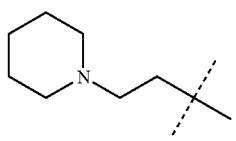 | —Cl | —Cl | —Ph | CH |
| 384 | 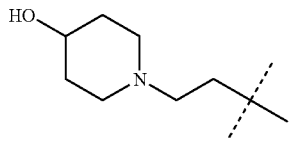 | —Cl | —Cl | —Ph | CH |
| 385 | 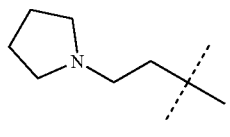 | —Cl | —Cl | —Ph | CH |
| 386 | 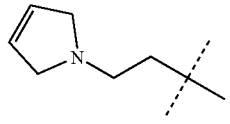 | —Cl | —Cl | —Ph | CH |
| 387 | 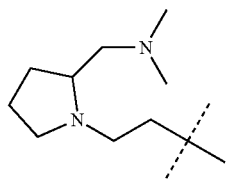 | —Cl | —Cl | —Ph | CH |
| 388 | 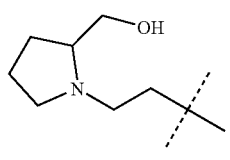 | —Cl | —Cl | —Ph | CH |

-continued

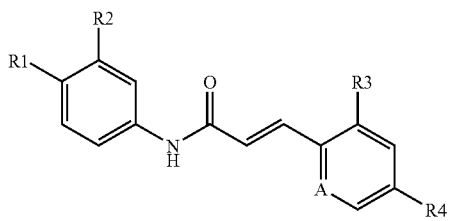

| Number | R1 | R2 | R3 | R4 | A |
|---|---|---|---|---|---|
| 389 | piperidin-N-CH2CH2C(CH3)2- | —Cl | —H | —Ph | N |
| 390 | HO-piperidin-N-CH2CH2C(CH3)2- | —Cl | —H | —Ph | N |
| 391 | pyrrolidin-N-CH2CH2C(CH3)2- | —Cl | —H | —Ph | N |
| 392 | 2,5-dihydropyrrol-N-CH2CH2C(CH3)2- | —Cl | —H | —Ph | N |
| 393 | 2-((dimethylamino)methyl)pyrrolidin-N-CH2CH2C(CH3)2- | —Cl | —H | —Ph | N |
| 394 | 2-(hydroxymethyl)pyrrolidin-N-CH2CH2C(CH3)2- | —Cl | —H | —Ph | N |

Some test methods for determining an MCH-receptor antagonistic activity will now be described. In addition, other test methods known to the skilled man are used, e.g. by inhibiting the MCH-receptor-mediated inhibition of cAMP production, as described by Hoogduijn M et al. in "Melanin-concentrating hormone and its or are expressed and functional in human skin", Biochem. Biophys. Res Commun. 296 (2002) 698-701 and by biosensory measurement of the binding of MCH to the MCH receptor in the presence of antagonistic substances by plasmon resonance, as described by Karlsson OP and Lofas S. in "Flow-Mediated On-Surface Reconstitution of G-Protein Coupled Receptors for Applications in Surface Plasmon Resonance Biosensors", Anal. Biochem. 300 (2002), 132-138. Other methods of testing antagonistic activity to MCH receptors are contained in the references and patent documents mentioned hereinbefore, and the description of the test methods used is hereby incorporated in this application.

| MCH-1 receptor binding test | |
|---|---|
| Method: | MCH binding to hMCH-1R transfected cells |
| Species: | Human |
| Test cell: | hMCH-1R stably transfected into CHO/Galpha16 cells |
| Results: | IC50 values |

Membranes from CHO/Galpha 16 cells stably transfected with human hMCH-1R are resuspended using a syringe (needle 0.6×25 mm) and diluted in test buffer (50 mM HEPES, 10 mM MgCl$_2$, 2 mM EGTA, pH 7.00; 0.1% bovine serum albumin (protease-free), 0.021% bacitracin, 1 μg/mL aprotinin, 1 μg/mL leupeptin and 1 μM phosphoramidone) to a concentration of 5 to 15 μg/mL. 200 microlitres of this membrane fraction (contains 1 to 3 μg of protein) are incubated for 60 minutes at ambient temperature with 100 pM of $^{125}$I-tyrosyl melanin concentrating hormone ($^{125}$I-MCH commercially obtainable from NEN) and increasing concentrations of the test compound in a final volume of 250 microlitres. After the incubation the reaction is filtered using a cell harvester through 0.5% PEI treated glass fibre filters (GF/B, Unifilter Packard). The membrane-bound radioactivity retained on the filter is then determined after the addition of scintillator substance (Packard Microscint 20) in a measuring device (TopCount of Packard).

The non-specific binding is defined as bound radioactivity in the presence of 1 micromolar MCH during the incubation period.

The analysis of the concentration binding curve is carried out on the assumption of one receptor binding site.

Standard:

Non-labelled MCH competes with labelled $^{125}$I-MCH for the receptor binding with an IC50 value of between 0.06 and 0.15 nM.

The KD value of the radioligand is 0.156 nM.

| MCH-1 receptor-coupled $Ca^{2+}$ mobilisation test | |
|---|---|
| Method: | Calcium mobilisation test with human MCH (FLIPR$^{384}$) |
| Species: | Human |
| Test cells: | CHO/Galpha 16 cells stably transfected with hMCH-R1 |
| Results: | 1st measurement: % stimulation of the reference (MCH $10^{-6}$M) |
| | 2nd measurement: pKB value |
| Reagents: | HBSS (10 ×) (GIBCO) |
| | HEPES buffer (1 M) (GIBCO) |
| | Pluronic F-127 (Molecular Probes) |
| | Fluo-4 (Molecular Probes) |
| | Probenecid (Sigma) |
| | MCH (Bachem) |
| | bovine serum albumin (Serva) |
| | (protease-free) |
| | DMSO (Serva) |
| | Ham's F12 (BioWhittaker) |
| | FCS (BioWhittaker) |
| | L-Glutamine (GIBCO) |
| | Hygromycin B (GIBCO) |
| | PENStrep (BioWhittaker) |
| | Zeocin (Invitrogen) |

Clonal CHO/Galpha16 hMCH-R1 cells are cultivated in Ham's F12 cell culture medium (with L-glutamine; BioWhittaker; Cat.No.: BE12-615F). This contains per 500 ml 10% FCS, 1% PENStrep, 5 ml L-glutamine (200 mM stock solution), 3 ml hygromycin B (50 mg/mL in PBS) and 1.25 ml zeocin (100 μg/mL stock solution). One day before the experiment the cells are plated on a 384-well microtitre plate (black-walled with a transparent base, made by Costar) in a density of 2500 cells per cavity and cultivated in the above medium overnight at 37° C., 5% $CO_2$ and 95% relative humidity. On the day of the experiment the cells are incubated with cell culture medium to which 2 mM Fluo-4 and 4.6 mM Probenicid have been added, at 37° C. for 45 minutes. After charging with fluorescent dye the cells are washed four times with Hanks buffer solution (1×HBSS, 20 mM HEPES), which is combined with 0.07% Probenicid. The test substances are diluted in Hanks buffer solution, combined with 2.5% DMSO. The background fluorescence of non-stimulated cells is measured in the presence of substance in the 384-well microtitre plate five minutes after the last washing step in the FLIPR$^{384}$ apparatus (Molecular Devices; excitation wavelength: 488 nm; emission wavelength: bandpass 510 to 570 nm). To stimulate the cells MCH is diluted in Hanks buffer with 0.1% BSA, pipetted into the 384-well cell culture plate 35 minutes after the last washing step and the MCH-stimulated fluorescence is then measured in the FLIPR$^{384}$ apparatus.

Data Analysis:

1st measurement: The cellular $Ca^{2+}$ mobilisation is measured as the peak of the relative fluorescence minus the background and is expressed as the percentage of the maximum signal of the reference (MCH $10^{-6}$M). This measurement serves to identify any possible agonistic effect of a test substance.

2nd measurement: The cellular $Ca^{2+}$ mobilisation is measured as the peak of the relative fluorescence minus the background and is expressed as the percentage of the maximum signal of the reference (MCH $10^{-6}$M, signal is standardised to 100%). The EC50 values of the MCH dosage activity curve with and without test substance (defined concentration) are determined graphically by the GraphPad Prism 2.01 curve program. MCH antagonists cause the MCH stimulation curve to shift to the right in the graph plotted.

The inhibition is expressed as a pKB value:

$$pKB = \log(EC_{50(testsubstance+MCH)}/EC_{50(MCH)}-1) - \log c_{(testsubstance)}$$

The compounds according to the invention, including the salts thereof, exhibit an MCH-receptor antagonistic activity in the tests mentioned above. Using the MCH-1 receptor binding test described above an antagonistic activity is obtained in a dosage range from about $10^{-10}$ to $10^{-5}$ M, particularly from $10^{-9}$ to $10^{-6}$ M.

The following IC50 values were determined using the MCH-1 receptor binding test described above:

| Compound according to Example no. | Structure | IC50 value |
|---|---|---|
| 12 | 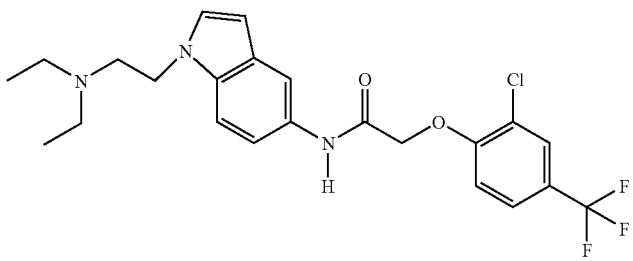 | 41 nM |
| 34 | 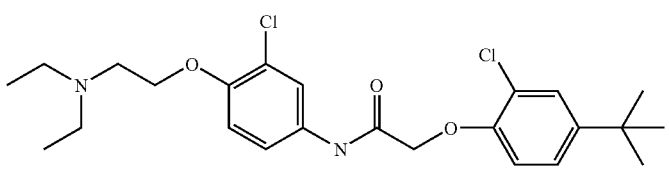 | 17 nM |

Some examples of formulations will be described hereinafter, wherein the term "active substance" denotes one or more compounds according to the invention, including the salts thereof. In the case of one of the combinations with one or more active substances described, the term "active substance" also includes the additional active substances.

EXAMPLE A

Capsules for Powder Inhalation Containing 1 mg Active Substance

| Composition: 1 capsule for powder inhalation contains: | |
|---|---|
| active substance | 1.0 mg |
| lactose | 20.0 mg |
| hard gelatine capsules | 50.0 mg |
| | 71.0 mg |

Method of Preparation:

The active substance is ground to the particle size required for inhalation. The ground active substance is homogeneously mixed with the lactose. The mixture is packed into hard gelatine capsules.

EXAMPLE B

Inhalable Solution for Respimat® Containing 1 mg Active Substance

| Composition: 1 spray contains: | |
|---|---|
| active substance | 1.0 mg |
| benzalkonium chloride | 0.002 mg |
| disodium edetate | 0.0075 mg |
| purified water ad | 15.0 µl |

Method of Preparation:

The active substance and benzalkonium chloride are dissolved in water and packed into Respimat®) cartridges.

EXAMPLE C

Inhalable solution for Nebulisers Containing 1 mg Active Substance

| Composition: 1 vial contains: | |
|---|---|
| active substance | 0.1 g |
| sodium chloride | 0.18 g |
| benzalkonium chloride | 0.002 g |
| purified water ad | 20.0 ml |

Method of Preparation:

The active substance, sodium chloride and benzalkonium chloride are dissolved in water.

EXAMPLE D

Propellant Type Metered Dose Aerosol Containing 1 mg Active Substance

| Composition: 1 spray contains: | |
|---|---|
| active substance | 1.0 mg |
| lecithin | 0.1% |
| propellant gas ad | 50.0 µl |

Method of Preparation:

The micronised active substance is homogeneously suspended in the mixture of lecithin and propellant gas. The suspension is transferred into a pressurised contained with a metering valve.

EXAMPLE E

Nasal Spray Containing 1 mg Active Substance

| Composition: | |
|---|---|
| active substance | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active substance and the excipients are dissolved in water and transferred into a corresponding container.

EXAMPLE F

Injectable Solution Containing 5 mg of Active Substance per 5 ml

| Composition: | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

EXAMPLE G

Injectable Solution Containing 100 mg of Active Substance per 20 ml

| Composition: | |
|---|---|
| active substance | 100 mg |
| monopotassium dihydrogen phosphate = $KH_2PO_4$ | 12 mg |
| disodium hydrogen phosphate = $Na_2HPO_4.2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

EXAMPLE H

Lyophilisate Containing 10 mg of Active Substance

| Composition: | |
|---|---|
| Active substance | 10 mg |
| Mannitol | 300 mg |
| human serum albumin | 20 mg |

Preparation:

Mannitol is dissolved in water for injections (Wfl); human serum albumin is added; active ingredient is dissolved with heating; made up to specified volume with Wfl; transferred into vials; freeze-dried.

| Solvent for lyophilisate: | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

EXAMPLE I

Tablets Containing 20 mg of Active Substance

| Composition: | |
|---|---|
| active substance | 20 mg |
| lactose | 120 mg |

-continued

| Composition: | |
|---|---|
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

EXAMPLE J

Capsules Containing 20 mg Active Substance

| Composition: | |
|---|---|
| active substance | 20 mg |
| maize starch | 80 mg |
| highly dispersed silica | 5 mg |
| magnesium stearate | 2.5 mg |

Preparation:

Active substance, maize starch and silica are homogeneously mixed; mixed with magnesium stearate; the mixture is packed into size 3 hard gelatine capsules in a capsule filling machine.

EXAMPLE K

Suppositories Aontaining 50 mg of Active Substance

| Composition: | |
|---|---|
| active substance | 50 mg |
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

EXAMPLE L

Injectable Solution Containing 10 mg of Active Substance per 1 ml

| Composition: | |
|---|---|
| active substance | 10 mg |
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

What is claimed is:
1. An amide compound of formula I

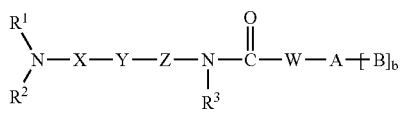

wherein
R$^1$, R$^2$ independently of one another denote H, a C$_{1-8}$-alkyl or C$_{3-7}$-cycloalkyl group optionally substituted by the group R$^{11}$, while a —CH$_2$— group in position 3 or 4 of a 5-, 6- or 7-membered cycloalkyl group may be replaced by —O—, —S— or —NR$^{13}$—, or a phenyl or pyridinyl group optionally mono- or polysubstituted by the group R$^{12}$ and/or monosubstituted by nitro, with the proviso that at least one of the groups R$^1$, R$^2$ has a meaning other than H, or R$^1$ and R$^2$ form a C$_{2-8}$-alkylene bridge wherein
one or two —CH$_2$— groups may be replaced independently of one another by —CH═N— or —CH═CH— and/or
one or two —CH$_2$— groups may be replaced independently of one another by —O—, —S—, —SO—, —(SO$_2$)—, —C═N—O—R$^{18}$—, —CO—, —C(═CH$_2$)— or —NR$^{13}$— in such a way that heteroatoms are not directly connected to one another, while in the above-defined alkylene bridge one or more H atoms may be replaced by R$^{14}$, and
while the above-defined alkylene bridge may be substituted by one or two identical or different carbo- or heterocyclic groups Cy in such a way that the bond between the alkylene bridge and the group Cy is formed
via a single or double bond,
via a common C atom forming a spirocyclic ring system,
via two common, adjacent C and/or N atoms forming a fused bicyclic ring system or
via three or more C and/or N atoms forming a bridged ring system, R$^3$ denotes H, C$_{1-6}$-alkyl, C$_{3-7}$-cycloalkyl or C$_{3-7}$-cycloalkyl-C$_{1-4}$-alkyl, X denotes a C$_{1-4}$-alkylene bridge and if the group Y is linked to X via a C atom, it may also denote —CH$_2$—CH═CH—, —CH$_2$—C≡C—, C$_{2-4}$-alkylenoxy or C$_{2-4}$-alkylene-NR$^4$,
while the bridge X may be attached to R$^1$ including the N atom attached to R$^1$ and X forming a heterocyclic group, and
two C atoms or one C and one N atom of the alkylene bridge may be joined together by an additional C$_{1-4}$-alkylene bridge, and
a C atom may be substituted by R$^{10}$ and/or one or two C atoms in each case may be substituted with one or two identical or different substituents selected from C$_{1-6}$-alkyl, C$_{3-7}$-cycloalkyl, and C$_{3-7}$-cycloalkyl-C$_{1-3}$- alkyl, while two alkyl substituents may be joined together, forming a carbocyclic ring system, and with the proviso that the group X with the meaning $C_{2-4}$-alkyleneoxy has no hydroxy substituents;

W is selected from among —$CR^{6a}R^{6b}$—O—, —$CR^{7a}$=$CR^{7c}$—, —$CR^{6a}R^{6b}$—$NR^8$—, and —$NR^8$—$CR^{6a}R^{6b}$—, Z denotes a single bond, $C_{1-4}$-alkylene, wherein two adjacent C atoms may be joined together with an additional $C_{1-4}$-alkylene bridge,
while a C atom of the alkylene bridge may be substituted with $R^{10}$ and/or one or two C atoms independently of one another may be substituted with one or two identical or different $C_{1-6}$-alkyl groups, while two alkyl groups may be joined together, forming a carbocyclic ring, and Y is selected from among the following bivalent cyclic groups

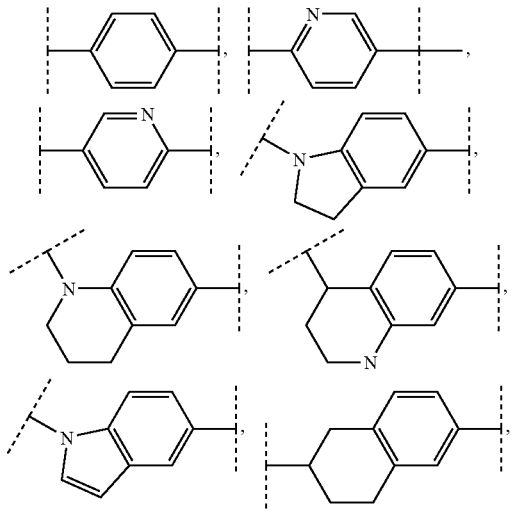

while the above-mentioned cyclic groups may be mono- or polysubstituted by $R^{20}$ at one or more C atoms, and in the case of a phenyl group may also additionally be monosubstituted by nitro, and/or one or more NH group may be substituted by $R^{21}$, A denotes one of the meanings given for Cy,
B denotes one of the meanings given for Cy,
b denotes the value 0 or 1,
Cy denotes a carbo- or heterocyclic group selected from one of the following:
   a saturated 3- to 7-membered carbocyclic group,
   an unsaturated 4- to 7-membered carbocyclic group,
   a phenyl group,
   a saturated 4- to 7-membered or unsaturated 5- to 7-membered heterocyclic group with an N, O or S atom as heteroatom,
   a saturated or unsaturated 5- to 7-membered heterocyclic group with two or more N atoms or with one or two N atoms and an O or S atom as heteroatoms,
   an aromatic heterocyclic 5- or 6-membered group with one or more identical or different heteroatoms selected from N, O and/or S,
while the above-mentioned 4-, 5-, 6- or 7-membered groups may be attached via two common, adjacent C atoms fused to a phenyl or pyridine ring, and
in the above-mentioned 5-, 6- or 7-membered groups one or two non-adjacent —$CH_2$— groups may be replaced independently of one another by a —CO—, —C(=$CH_2$)—, —(SO)— or —($SO_2$)— group, and
the above-mentioned saturated 6- or 7-membered groups may also be present as bridged ring systems with an imino, N-($C_{1-4}$-alkyl)-imino, methylene, $C_{1-4}$-alkyl-methylene or di-($C_{1-4}$-alkyl)-methylene bridge, and the above-mentioned cyclic groups may be mono- or polysubstituted at one or more C atoms with $R^{20}$, in the case of a phenyl group they may also additionally be monosubstituted with nitro, and/or one or more NH groups may be substituted with $R^{21}$, $R^4$ denotes H or $C_{1-6}$-alkyl,
$R^{6a}$, $R^{6b}$ denotes H, $C_{1-4}$-alkyl or $CF_3$,
$R^{7a}$, $R^{7c}$, denotes H, F, $C_{1-4}$-alkyl or $CF_3$,
$R^8$ denotes H, $C_{1-4}$-alkyl, $C_{3-7}$-cycloalkyl or $C_{3-7}$-cycloalkyl-$C_{1-3}$-alkyl,
$R^{10}$ denotes hydroxy, ω-hydroxy-$C_{1-3}$-alkyl, $C_{1-4}$-alkoxy, ω-($C_{1-4}$-alkoxy)-$C_{1-3}$-alkyl, $C_{1-4}$-alkoxycarbonyl, amino, $C_{1-4}$-alkyl-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, amino-$C_{1-3}$-alkoxy, $C_{1-4}$-alkyl-amino-$C_{1-3}$-alkoxy, di-($C_{1-4}$-alkyl)-amino-$C_{1-3}$-alkoxy or cyclo-$C_{3-6}$-alkyleneimino-$C_{1-3}$-alkoxy, aminocarbonyl, $C_{1-4}$-alkyl-aminocarbonyl, di-($C_{1-4}$-alkyl)-aminocarbonyl or cyclo-$C_{3-6}$-alkyleneimino-carbonyl,
$R^{11}$ denotes $C_{2-6}$-alkenyl, $C_{2-6}$-alkynyl, $R^{15}$—O, $R^{15}$—O—CO, $R^{15}$—CO—O, $R^{16}R^{17}N$, $R^{18}R^{19}N$—CO or Cy,
$R^{12}$ has one of the meanings given for $R^{20}$,
$R^{13}$ has one of the meanings given for $R^{17}$, with the exception of carboxy,
$R^{14}$ denotes halogen, $C_{1-6}$-alkyl, $C_{2-6}$-alkenyl, $C_{2-6}$-alkynyl, $R^{15}$—O, $R^{15}$—O—CO, $R^{15}$—CO, $R^{15}$—CO—O, $R^{16}R^{17}N$, $R^{18}R^{19}N$—CO, $R^{15}$—O—$C_{1-3}$-alkyl, $R^{15}$—O—CO—$C_{1-3}$-alkyl, $R^{15}$—O—CO—NH, $R^{15}$—$SO_2$—NH, $R^{15}$—O—CO—NH—$C_{1-3}$-alkyl-, $R^{15}$—$SO_2$—NH—$C_{1-3}$-alkyl-, $R^{15}$—CO—$C_{1-3}$-alkyl, $R^{15}$—CO—O—$C_{1-3}$-alkyl, $R^{16}R^{17}N$—$C_{1-3}$-alkyl, $R^{18}R^{19}N$—CO—$C_{1-3}$-alkyl or Cy—$C_{1-3}$-alkyl,
$R^{15}$ denotes H, $C_{1-4}$-alkyl, $C_{3-7}$-cycloalkyl, $C_{3-7}$-cycloalkyl-$C_{1-3}$-alkyl, phenyl, phenyl-$C_{1-3}$-alkyl, pyridinyl or pyridinyl-$C_{1-3}$-alkyl,
$R^{16}$ denotes H, $C_{1-6}$-alkyl, $C_{3-7}$-cycloalkyl, $C_{3-7}$-cycloalkyl-$C_{1-3}$-alkyl, $C_{4-7}$-cycloalkenyl, $C_{4-7}$-cycloalkenyl-$C_{1-3}$-alkyl, ω-hydroxy-$C_{2-3}$-alkyl, ω-($C_{1-4}$-alkoxy)-$C_{2-3}$-alkyl, amino-$C_{2-6}$-alkyl, $C_{1-4}$-alkyl-amino-$C_{2-6}$-alkyl, di-($C_{1-4}$-alkyl)-amino-$C_{2-6}$-alkyl or cyclo-$C_{3-6}$-alkyleneimino-$C_{2-6}$-alkyl,
$R^{17}$ has one of the meanings given for $R^{16}$ or denotes phenyl, phenyl-$C_{1-3}$-alkyl, pyridinyl, dioxolan-2-yl, —CHO, $C_{1-4}$-alkylcarbonyl, carboxy, hydroxycarbonyl-$C_{1-3}$-alkyl, $C_{1-4}$-alkoxycarbonyl, $C_{1-4}$-alkoxycarbonyl-$C_{1-3}$-alkyl, $C_{1-4}$-alkylcarbonylamino-$C_{2-3}$-alkyl, N-($C_{1-4}$-alkylcarbonyl)-N-($C_{1-4}$-alkyl)-amino-$C_{2-3}$-alkyl, $C_{1-4}$-alkylsulphonyl, $C_{1-4}$-alkylsulphonylamino-$C_{2-3}$-alkyl or N-($C_{1-4}$-alkylsulphonyl)-N($C_{1-4}$-alkyl)-amino-$C_{2-3}$-alkyl,
$R^{18}$, $R^{19}$ independently of one another denote H or $C_{1-6}$-alkyl,
$R^{20}$ denotes halogen, hydroxy, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy-$C_{1-4}$-alkyl, $R^{22}$—$C_{1-3}$-alkyl or one of the meanings given for $R^{22}$,
$R^{21}$ denotes $C_{1-4}$-alkyl, ω-hydroxy-$C_{2-3}$-alkyl, ω-$C_{1-4}$-alkoxy-$C_{2-6}$-alkyl, ω-$C_{1-4}$-alkyl-amino-$C_{2-6}$-alkyl, ω-di-($C_{1-4}$-alkyl)-amino-$C_{2-6}$-alkyl, ω-cyclo-$C_{3-6}$- alkyleneimino-$C_{2-6}$-alkyl, phenyl-$C_{1-3}$-alkyl, $C_{1-4}$-alkyl-carbonyl, $C_{1-4}$-alkoxy-carbonyl or $C_{1-4}$-alkylsulphonyl, $R^{22}$ denotes phenyl-$C_{1-3}$-alkoxy, OHC, HO—N=HC, $C_{1-4}$-alkoxy-N=HC, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylamino-carbonyl, di-($C_{1-4}$-alkyl)-aminocarbonyl, cyclo-$C_{3-6}$-alkyl-amino-carbonyl, cyclo-$C_{3-6}$-alkyleneimino-carbonyl, cyclo-$C_{3-6}$-alkyleneimino-$C_{2-4}$-alkyl-aminocarbonyl, phenyl-amino-carbonyl, $C_{1-4}$-alkyl-sulphonyl, $C_{1-4}$-alkyl-sulphinyl, $C_{1-4}$-alkyl-sulphonylamino, amino, $C_{1-4}$-alkylamino, di-($C_{1-4}$-alkyl)-amino, $C_{1-4}$-alkyl-carbonyl-amino, cyclo-$C_{3-6}$-alkyleneimino, phenyl-$C_{1-3}$-alkylamino or N-($C_{1-4}$-alkyl)-phenyl-$C_{1-3}$-alkylamino, acetylamino, propionylamino, phenylcarbonylamino, phenylcarbonylmethylamino, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, or aminocarbonyl-amino, while in the above-mentioned groups and residues, in each case one or more C atoms may additionally be mono- or polysubstituted by F and/or in each case one or two C atoms may additionally be monosubstituted by Cl or Br independently of one another and/or in each case one or more phenyl rings may additionally, independently of one another, have one, two or three substituents selected from among F, Cl, Br, I, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, cyano, difluoromethoxy, trifluoromethoxy, amino-$C_{1-3}$-alkyl, $C_{1-3}$-alkylamino-$C_{1-3}$-alkyl- and di-($C_{1-3}$-alkyl)-amino-$C_{1-3}$-alkyl and/or may be monosubstituted by nitro, and the H atom of any carboxy group present or an H atom bonded to an N atom may each be replaced by a group which can be cleaved in vivo, or a tautomer, the diastereomer, or enantiomers, thereof or mixtures thereof, or a salt thereof, with the following provisos (M1), and (M2)

(M1) in the event that W denotes —CH=CH— and Y denotes a phenylene group and Z is a single bond, then the bridges X and Z at the phenylene ring of the group Y are in the para position to one another and at least one of the following conditions is met:

(a) the group Y meaning phenylene is at least monosubstituted,
(b) b has the value 0 and the group A is at least disubstituted,
(c) b has the value 1;

(M2) the following individual compounds are not included:
3-(4-chloro-phenyl)-N-{2-[4-(2-diethylamino-ethoxy)-phenyl]-ethyl}-acrylamide, N-{2-[3-(4-{2-[2-(4-chloro-phenoxy)-acetylamino]-ethyl}-phenoxy)-2-hydroxy-propylamino]-ethyl}-isobutyramide,
cyclopentanecarboxylic acid {2-[3-(4-{2-[2-(4-chloro-phenoxy)-acetylamino]-ethyl}-phenoxy)-2-hydroxy-propylamino]-ethyl}-amide, and
2-(4-chloro-phenoxy)-N-(2-{4-[2-hydroxy-3-(2-phenylacetylamino-ethylamino)-propoxy]-phenyl}-ethyl)-acetamide.

2. An amide compounds according to claim 1, wherein:

$R^1$, $R^2$ independently of one another denote H, a $C_{1-8}$-alkyl or $C_{3-7}$-cycloalkyl group optionally substituted by the group $R^{11}$, or a phenyl group optionally mono- or polysubstituted by the group $R^{12}$ and/or monosubstituted by nitro, with the proviso that at least one of the groups $R^1$, $R^2$ has a meaning other than H, or $R^1$ and $R^2$ form a $C_{2-8}$-alkylene bridge wherein
one or two —CH$_2$— groups independently of one another may be replaced by —CH=N— or —CH=CH— and/or
one or two —CH$_2$— groups independently of one another may be replaced by —O—, —S—, —CO—, —C(=CH$_2$)— or —NR$^{13}$— so that heteroatoms are not directly connected to one another,
while in the alkylene bridge defined above one or more H atoms may be replaced by $R^{14}$, and
while the alkylene bridge defined hereinbefore may be substituted with one or two identical or different carbo- or heterocyclic groups Cy so that the bond between the alkylene bridge and the group Cy is made
via a single or double bond,
via a common C atom forming a spirocyclic ring system,
via two common adjacent C and/or N atoms forming a fused bicyclic ring system or
via three or more C and/or N atoms forming a bridged ring system, X denotes an unbranched $C_{1-4}$-alkylene bridge and if the group Y is linked to X via a C atom, it may also denote —CH$_2$—CH=CH—, —CH$_2$—C≡C—, $C_{2-4}$-alkyleneoxy or $C_{2-4}$-alkylene-NR$^4$,
while the bridge X may be connected to $R^1$ including the N atom attached to $R^1$ and X forming a heterocyclic group, and
two C atoms or a C and an N atom of the alkylene bridge may be joined together by an additional $C_{1-4}$-alkylene bridge, and
a C atom may be substituted by $R^{10}$ and/or one or two C atoms in each case may be substituted by one or two identical or different $C_{1-6}$-alkyl groups, and
with the proviso that the group X with the meaning $C_{2-4}$-alkyleneoxy has no hydroxy substituents; and Z denotes a single bond, or $C_{1-4}$-alkylene, wherein two adjacent C atoms may be joined together by an additional $C_{1-4}$-alkylene bridge,
while a C atom of the alkylene bridge may be substituted by $R^{10}$ and/or one or two C atoms independently of one another may be substituted by one or two identical or different $C_{1-6}$-alkyl groups,
b has the value 0,
$R^{10}$ denotes hydroxy, ω-hydroxy-$C_{1-3}$-alkyl, $C_{1-4}$-alkoxy, ω-($C_{1-4}$-alkoxy)-$C_{1-3}$-alkyl, amino, $C_{1-4}$-alkyl-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, di-($C_{1-4}$-alkyl)-amino-$C_{1-3}$-alkyl, cyclo-$C_{3-6}$-alkylene-imino-$C_{1-3}$-alkyl, amino-$C_{1-3}$-alkoxy, $C_{1-4}$-alkyl-amino-$C_{1-3}$-alkoxy, di-($C_{1-4}$-alkyl)-amino-$C_{1-3}$-alkoxy or cyclo-$C_{3-6}$-alkyleneimino-$C_{1-3}$-alkoxy, $R^{14}$ denotes halogen, $C_{1-6}$-alkyl, $R^{15}$—O, $R^{15}$—O—CO, $R^{15}$—CO, $R^{15}$—CO—O, $R^{16}R^{17}$N, $R^{18}R^{19}$N—CO, $R^{15}$—O—$C_{1-3}$-alkyl-, $R^{15}$—O—CO—$C_{1-3}$-alkyl, $R^{15}$—CO—$C_{1-3}$-alkyl, $R^{15}$—CO—O—$C_{1-3}$-alkyl, $R^{16}R^{17}$N—$C_{1-3}$-alkyl, $R^{18}R^{19}$N—CO—$C_{1-3}$-alkyl or Cy—$C_{1-3}$-alkyl, $R^{15}$ denotes H, $C_{1-4}$-alkyl, $C_{3-7}$-cycloalkyl, $C_{3-7}$-cycloalkyl-$C_{1-3}$-alkyl, phenyl or phenyl-$C_{1-3}$-alkyl, $R^{17}$ has one of the meanings given for $R^{16}$ or denotes phenyl, phenyl-$C_{1-3}$-alkyl, $C_{1-4}$-alkylcarbonyl, hydroxycarbonyl-$C_{1-3}$-alkyl, $C_{1-4}$-alkylcarbonylamino-$C_{2-3}$-alkyl, N-($C_{1-4}$-alkylcarbonyl)-N-($C_{1-4}$-alkyl)-amino-$C_{2-3}$-alkyl, $C_{1-4}$-alkylsulphonyl, $C_{1-4}$- alkylsulphonylamino-$C_{2-3}$-alkyl or N-($C_{1-4}$-alkylsulphonyl)-N($C_{1-4}$-alkyl)-amino-$C_{2-3}$-alkyl, $R^{20}$ denotes halogen, hydroxy, cyano, $C_{1-6}$-alkyl, $C_{3-7}$-cycloalkyl, $C_{3-7}$-cycloalkyl-$C_{1-3}$-alkyl, hydroxy-$C_{1-4}$-alkyl, $R^{22}$—$C_{1-3}$-alkyl or one of the meanings given for $R^{22}$, $R^{21}$ denotes $C_{1-4}$-alkyl, ω-hydroxy-$C_{2-3}$-alkyl, ω-$C_{1-4}$-alkoxy-$C_{2-6}$-alkyl, ω-$C_{1-4}$-alkyl-amino-$C_{2-6}$-alkyl, ω-di-($C_{1-4}$-alkyl)-amino-$C_{2-6}$-alkyl, ω-cyclo-$C_{3-6}$-alkyleneimino-$C_{2-6}$-alkyl, phenyl, phenyl-$C_{1-3}$-alkyl, $C_{1-4}$-alkyl-carbonyl, carboxy, $C_{1-4}$-alkoxy-carbonyl or $C_{1-4}$-alkylsulphonyl, $R^{22}$ denotes phenyl, phenyl-$C_{1-3}$-alkoxy, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, cyclo-$C_{3-6}$-alkyleneimino-carbonyl, $C_{1-4}$-alkyl-sulphonyl, $C_{1-4}$-alkyl-sulphinyl, $C_{1-4}$-alkyl-sulphonylamino, amino, $C_{1-4}$-alkylamino, di-($C_{1-4}$-alkyl)-amino, cyclo-$C_{3-6}$-alkyleneimino, phenyl-$C_{1-3}$-alkylamino, N-($C_{1-4}$-alkyl)-phenyl-$C_{1-3}$-alkyl-amino, acetylamino, propionylamino, phenylcarbonylamino, phenylcarbonylmethylamino, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, or aminocarbonylamino-amine.

3. An amide compounds according to claim 1, wherein:

$R^1$, $R^2$ independently of one another denote H, $C_{1-6}$-alkyl, $C_{3-7}$-cycloalkyl, $C_{3-7}$-cycloalkyl-$C_{1-3}$-alkyl, ω-hydroxy-$C_{2-3}$-alkyl, ω-($C_{1-4}$-alkoxy)-$C_{2-3}$-alkyl, $C_{1-4}$-alkyl, carboxyl-$C_{1-4}$-alkyl, amino-$C_{2-4}$-alkyl, $C_{1-4}$-alkyl-amino-$C_{2-4}$-alkyl, di-($C_{1-4}$-alkyl)-amino-$C_{2-4}$-alkyl, cyclo-$C_{3-6}$-alkyleneimino-$C_{2-4}$-alkyl, pyrrolidinyl, N-($C_{1-4}$-alkyl)-pyrrolidinyl, pyrrolidinyl-$C_{1-3}$-alkyl, N-($C_{1-4}$-alkyl)-pyrrolidinyl-$C_{1-3}$-alkyl, piperidinyl, N-($C_{1-4}$-alkyl)-piperidinyl, piperidinyl-$C_{1-3}$-alkyl, N-($C_{1-4}$-alkyl)-piperidinyl-$C_{1-3}$-alkyl, phenyl, phenyl-$C_{1-3}$-alkyl, pyridyl or pyridyl-$C_{1-3}$-alkyl, with the proviso that at least one of the group $R^1$, $R^2$ has a meaning other than H, while in the above-mentioned groups and residues one or more C atoms may be mono- or polysubstituted by F and/or one or two C atoms may independently of one another be monosubstituted by Cl or Br, and the phenyl or pyridyl group may be mono- or polysubstituted by the group $R^{12}$ and/or may be monosubstituted by nitro.

4. An amide compounds according to claim 1, wherein:

$R^1$ and $R^2$ form an alkylene bridge according to claim 1 in such a way that $R^1R^2N$— denotes a group selected from azetidine, pyrrolidine, piperidine, azepan, 2,5-dihydro-1H-pyrrole, 1,2,3,6-tetrahydro-pyridine, 2,3,4,7-tetrahydro-1H-azepine, 2,3,6,7-tetrahydro-1H-azepine, piperazine, wherein the free imine function is substituted by $R^{13}$, piperidin-4-one, piperidin-4-one-oxime, piperidin-4-one-O—$C_{1-4}$-alkyl-oxime, morpholine and thiomorpholine, while one or more H atoms may be replaced by $R^{14}$, and/or the abovementioned groups may be substituted by one or two identical or different carbo- or heterocyclic groups Cy.

5. An amide compounds according to claim 1, wherein: the group

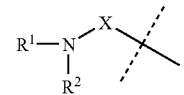

is defined according to one of the following partial formulae

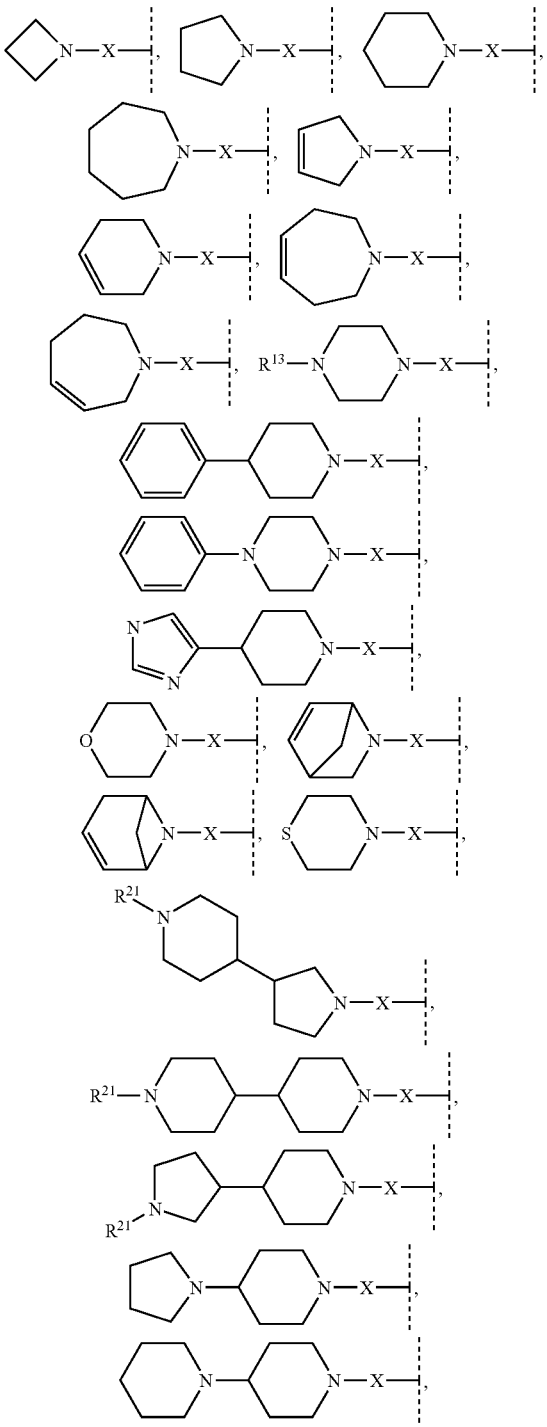

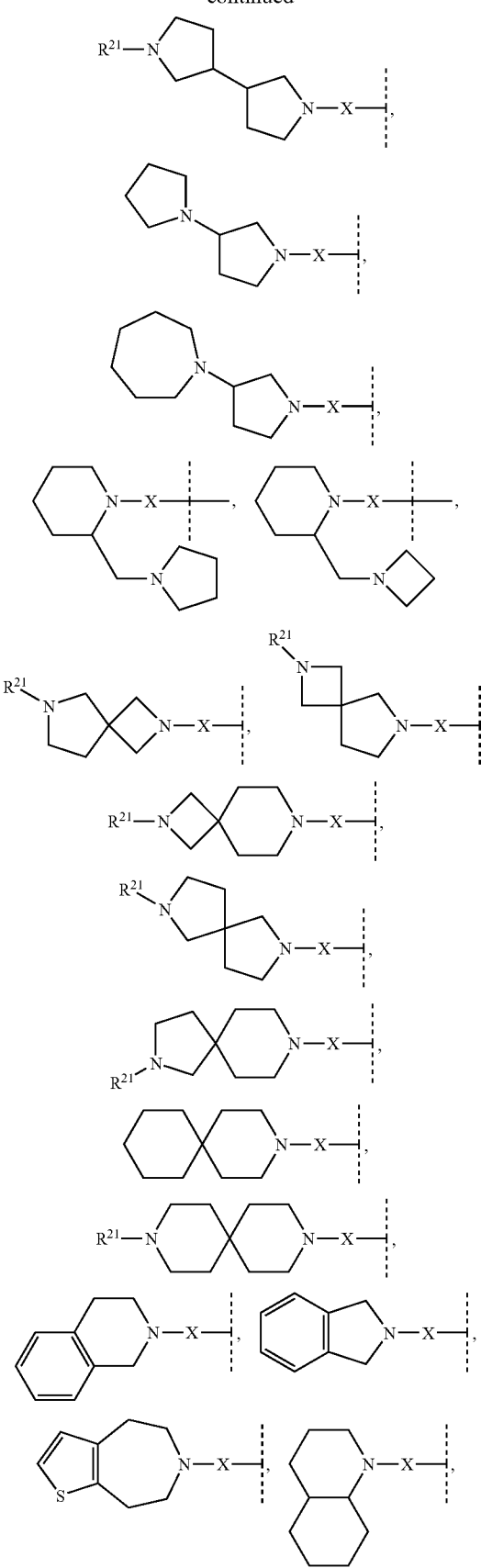

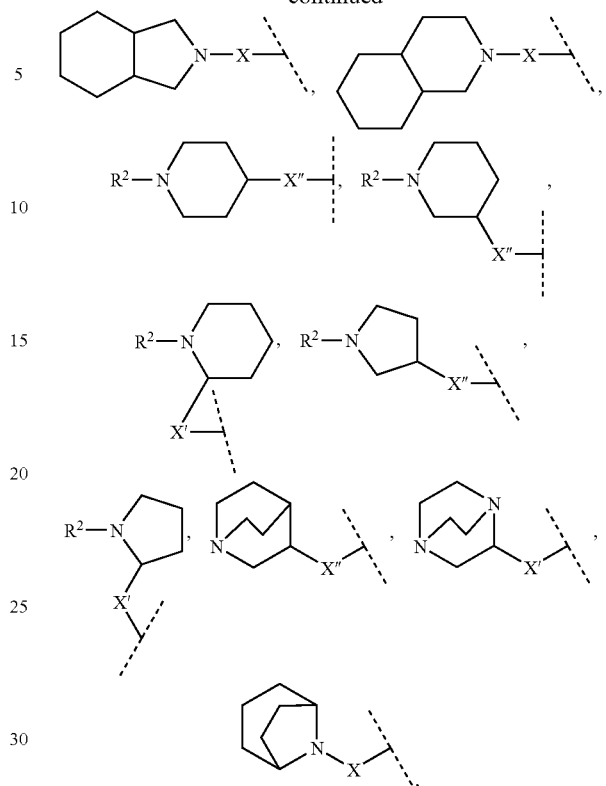

wherein one or more H atoms of the heterocycle formed by the group $R^1R^2N$— may be replaced by $R^{14}$ and the ring attached to the heterocycle formed by the group $R^1R^2N$— may be mono- or polysubstituted by $R^{20}$ at one or more C atoms, and in the case of a phenyl ring it may also additionally be monosubstituted by nitro and X', X" independently of one another denote a single bond or $C_{1-3}$-alkylene and if the group Y is linked to X' or X" via a C atom, may also denote —$C_{1-3}$-alkylene-O—, —$C_{1-3}$-alkylene-NH— or —$C_{1-3}$-alkylene-N($C_{1-3}$-alkyl)—, and while in the definitions given hereinbefore for X', X" in each case a C atom may be substituted by $R^{10}$, and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together forming a carbocyclic ring system, and in X', X" independently of one another in each case one or more C atoms may be mono- or polysubstituted by F and/or in each case one or two C atoms independently of one another may be monosubstituted by Cl or Br.

6. An amide compounds according to claim 1, wherein:
X denotes —$CH_2$—, —$CH_2$—$CH_2$—, or —$CH_2$—$CH_2$—$CH_2$—, and if the group Y is linked to X via a C atom, it also denotes —$CH_2$—CH=CH—, —$CH_2$—C≡C—, —$CH_2$—$CH_2$—O—, —$CH_2$—$CH_2$—$CH_2$—O— or —$CH_2$—$CH_2$—$NR^4$— or —$CH_2$—$CH_2$—$CH_2$—$NR^4$—, while the bridge X may be connected to $R^1$ including the N atom attached to $R^1$ and X, forming a heterocyclic group, and while, in X, a C atom may be substituted by a hydroxy, ω-hydroxy-$C_{1-3}$-alkyl, ω-($C_{1-4}$-alkoxy)-$C_{1-3}$-alkyl and/or $C_{1-4}$-alkoxy group, and/or one or two C atoms independently of one another may each be substituted by one or two identical or different $C_{1-4}$-alkyl groups selected from $C_{1-6}$-alkyl, $C_{3-7}$-cycloalkyl, or $C_{3-7}$-cycloalkyl-$C_{1-3}$-alkyl, while two alkyl substituents may be joined together, forming a carbocyclic ring system, and in each case one or more C atoms may be mono- or polysubstituted by F and/or in each case one or two C atoms may independently of one another be monosubstituted by Cl or Br.

7. An amide compounds according to claim 1, wherein:
Z is a single bond, —$CH_2$— or —$CH_2$—$CH_2$—, while one or two C atoms independently of one another may be mono- or disubstituted by F, $Ch_3$ or $CF_3$ and/or monosubstituted by Cl.

8. An amide compounds according to claim 1, wherein:
W denotes —$CH_2$—O—, —$CH_2$—$NR^8$—, or —CH=CH—,
wherein in each case one or two C atoms may be substituted independently of one another by F, $CH_3$ or $CF_3$.

9. An amide compounds according to one claim 1, wherein:
the group A denotes phenyl, pyridyl or naphthyl,
while the above-mentioned cyclic groups may be mono- or polysubstituted by $R^{20}$ at one or more C atoms, and in the case of a phenyl group may also additionally be monosubstituted by nitro, and/or one or more NH groups may be substituted by $R^{21}$.

10. An amide compound according to claim 1, wherein:
b has the value 0.

11. An amide compound according to claim 1, wherein:
b has the value 1 and B has a meaning selected from among phenyl, furanyl, thienyl and pyridyl,
while the above-mentioned cyclic groups may be mono- or polysubstituted by $R^{20}$ at one or more C atoms, and in the case of a phenyl group may also additionally be monosubstituted by nitro.

12. An amide compound according to claim 1, wherein:
$R^{20}$ denotes F, Cl, Br, I, OH, cyano, $C_{1-4}$-alkyl, $C_{1-4}$-alkoxy, difluoromethyl, trifluoromethyl, difluoromethoxy, trifluoromethoxy, amino, $C_{1-3}$-alkyl-amino, di-$C_{1-3}$-alkyl-amino, carboxy or $C_{1-4}$-alkoxy-carbonyl, while substituents $R^{20}$ occurring repeatedly may have the same or different meanings and in the case of a phenyl ring this may additionally also be monosubstituted by nitro.

13. An amide compound according to claim 1 selected from the following compounds:
(1) N-[3-chloro-4-(2-piperidin-1-yl-ethoxy)-phenyl]-2-(2-chloro-4-trifluoromethyl-phenoxy)-acetamide
(2) 2-(2-chloro-4-trifluoromethyl-phenoxy)-N-[3-cyano-4-(2-diethylamino-ethoxy)-phenyl]-acetamide
(3) 2-(2-chloro-4-trifluoromethyl-phenoxy)-N-[1-(2-diethylamino-ethyl)-2,3-dihydro-1H-indol-5-yl]-acetamide
(4) N-[3-chloro-4-(3-diethylamino-prop-1-ynyl)-phenyl]-2-(2-chloro-4-trifluoromethyl-phenoxy)-acetamide
(5) 2-(2-chloro-4-trifluoromethyl-phenoxy)-N-[1-(2-diethylamino-ethyl)-2,3-dimethyl-1H-indol-5-yl]-acetamide
(6) 2-(2-chloro-4-trifluoromethyl-phenoxy)-N-[1-(2-diethylamino-ethyl)-1H-indol-5-yl]-acetamide
(7) 2-(2-chloro-4-trifluoromethyl-phenoxy)-N-[4-(2-diethylamino-ethoxy)-3-methoxy-phenyl]-acetamide
(8) 2-(3-chloro-biphenyl-4-yloxy)-N-[3-chloro-4-(2-diethylamino-ethoxy)-phenyl]-acetamide
(9) N-[3-chloro-4-(2-diethylamino-ethoxy)-phenyl]-2-(2-chloro-4-trifluoromethyl-phenoxy)-acetamide
(10) 2-(4-tert.-butyl-2-chloro-phenoxy)-N-[3-chloro-4-(2-diethylamino-ethoxy)-phenyl]-acetamide
(11) 3-chloro-4-{[3-chloro-4-(2-diethylamino-ethoxy)-phenylcarbamoyl]-methoxyl }-benzoic acid-methyl-ester
(12) N-[3-chloro-4-(2-diethylamino-ethoxy)-phenyl]-2-(2,4-dibromo-phenoxy)-acetamide
(13) 2-(4-bromo-2-chloro-phenoxy)-N-[3-chloro-4-(2-diethylamino-ethoxy)-phenyl]-acetamide
(14) N-[3-chloro-4-(2-diethylamino-ethoxy)-phenyl]-2-(4-iodo-2-methyl-phenoxy)-acetamide
(15) methyl (2-{2-chloro-4-[2-(2,4-dichloro-phenoxy)-acetylamino]-phenoxyl}-ethylamino)-acetate
(16) N-[3-chloro-4-(2-pyrrolidine-1-yl-ethoxy)-phenyl]-2-(2-chloro-4-trifluoromethyl-phenoxy)-acetamide
(17) N-{3-chloro-4-[2-(ethyl-propyl-amino)-ethoxy]-phenyl}-2-(2-chloro-4-trifluoromethyl-phenoxy)-acetamide
(18) N-{3-chloro-4-[2-(ethyl-methyl-amino)-ethoxy]-phenyl}-2-(2-chloro-4-trifluoromethyl-phenoxy)-acetamide
(19) N-[3-chloro-4-(2-diethylamino-ethoxy)-phenyl]-2-(2-chloro-4-dimethylamino-phenoxy)-acetamide
(20) (E)-N-[3-chloro-4-(2-diethylamino-ethoxy)-phenyl]-3-(2-chloro-4-trifluoromethyl-phenyl)-acrylamide
(21) N-[3-chloro-4-(2-diethylamino-ethoxy)-phenyl]-2-(2-chloro-4-trifluoromethyl-phenylamino)-acetamide
(22) N-[3-chloro-4-(2-diethylamino-ethoxy)-phenyl]-2-(2-chloro-4-furan-2-yl-phenoxy)-acetamide
(23) N-[3-chloro-4-(2-diethylamino-ethoxy)-phenyl]-2-(2-chloro-4-thiophene-2-yl-phenoxy)-acetamide
(24) N-[3-chloro-4-(2-diethylamino-ethoxy)-phenyl]-2-(2-chloro-4-pyridin-3-yl-phenoxy)-acetamide
(25) 2-(2-bromo-4-trifluoromethyl-phenoxy)-N-[3-chloro-4-(2-diethylamino-ethoxy)-phenyl]-acetamide
(26) N-{3-chloro-4-[2-(2,5-dihydro-pyrrole-1-yl)-ethoxy]-phenyl}-2-(2-chloro-4-trifluoromethyl-phenoxy)-acetamide
(27) ethyl 1-(2-{2-chloro-4-[2-(2-chloro-4-trifluoromethyl-phenoxy)-acetylamino]-phenoxy}-ethyl)-piperidine-4-carboxylate
(28) N-[3-chloro-4-(3-diethylamino-propoxy)-phenyl]-2-(2-chloro-4-trifluoromethyl-phenoxy)-acetamide
(29) N-{4-[2-(2-aminomethyl-pyrrolidin-1-yl )-ethoxy]-3-chloro-phenyl}-2-(2-chloro-4-trifluoromethyl-phenoxy)-acetamide
(30) N-{3-chloro-4-[2-(2-dimethylaminomethyl-pyrrolidin-1-yl )-ethoxy]-phenyl}-2-(2-chloro-4-trifluoromethyl-phenoxy)-acetamide
(31) N-[3-bromo-4-(2-diethylamino-ethoxy)-phenyl]-2-(2-chloro-4-trifluoromethyl-phenoxy)-acetamide
(32) N-{3-chloro-4-[2-(4-methoxy-piperidin-1-yl)-ethoxy]-phenyl}-2-(2-chloro-4-trifluoromethyl-phenoxy)-acetamide
(33) N-{3-chloro-4-[2-(4-hydroxy-piperidin-1-yl)-ethoxy]-phenyl}-2-(2-chloro-4-trifluoromethyl-phenoxy)-acetamide
(34) 2-(2-chloro-4-trifluoromethyl-phenoxy)-N-[4-(2-diethylamino-ethoxy)-3-nitro-phenyl]-acetamide
(35) N-[3-chloro-4-(2-diethylamino-ethoxy)-phenyl]-2-(2-chloro-4-trifluoromethoxy-phenylamino)-acetamide

(36) N-[3-chloro-4-(2-diethylamino-ethoxy)-phenyl]-2-(2-fluoro-4-trifluoromethyl-phenylamino)-acetamide
(37) 2-(2-bromo-4-trifluoromethyl-phenylamino)-N-[3-chloro-4-(2-diethylamino-ethoxy)-phenyl]-acetamide
(38) (E)-3-(4'-chloro-biphenyl-4-yl)-N-(4-piperidin-1-yl-methyl-phenyl)-acrylamide
(39) N-[3-chloro-4-(2-diethylamino-ethylamino)-phenyl]-2-(2-chloro-4-trifluoromethyl-phenoxy)-acetamide
(40) N-{3-chloro-4-[2-(4-methyl-piperidin-1-yl)-ethylamino]-phenyl}-2-(2-chloro-4-trifluoromethyl-phenoxy)-acetamide
(41) (E)-3-(4'-chloro-biphenyl-4-yl)-N-(4-dimethylaminomethyl-phenyl)-acrylamide
(42) (E)-3-[5-(4-chloro-phenyl)-pyridin-2-yl]-N-(4-piperidin-1-ylmethyl-phenyl)-acrylamide
(43) (E)-N-{3-chloro-4-[2-(4-methyl-piperidin-1-yl)-ethylamino]-phenyl}3-(2-chloro-4-trifluoromethyl-phenyl)-acrylamide
(44) (E)-N-[3-chloro-4-(4-methyl-piperidin-1-ylmethyl)-phenyl]-3-(2-chloro-4-trifluoromethyl-phenyl)-acrylamide
(45) 2-(2-chloro-4-trifluoromethyl-phenoxy)-N-[4-(2-diethylamino-ethoxy)-3-methyl-phenyl]-acetamide
(46) (E)-3-(2-chloro-4-trifluoromethyl-phenyl)-N-[4-(2-diethylamino-ethoxy)-3-methyl-phenyl]-acrylamide
(47) (E)-3-(2-chloro-4-trifluoromethyl-phenyl)-N-[4-(2-diethylamino-ethoxy)-3-methoxy-phenyl]-acrylamide
(48) (E)-N-[3-chloro-4-(2-diethylamino-ethyl)-phenyl]-3-(2-chloro-4-trifluoromethyl-phenyl)-acrylamide
(49) N-[3-chloro-4-(2-diethylamino-ethyl)-phenyl]-2-(2-chloro-4-trifluoromethyl-phenoxy)-acetamide and
(50) N-{3-chloro-4-[2-(4-methyl-piperidin-1-yl)-ethyl]-phenyl}-2-(2-chloro-4-trifluoromethyl-phenoxy)-acetamide including the salts thereof.

14. A physiologically acceptable salt of an amide compound of formula I according to claim 1.

15. A composition comprising at least one amide compound according to claim 1 together with one or more inert carriers and/or diluents.

16. A method for influencing the eating behaviour of a mammal to reduce body weight or prevent increase in body weight comprising administering thereto at least one amide compound according to claim 1.

17. A method for treating a urinary problem, selected from the group consisting of urinary incontinence, overactive bladder, urgency, nycturia and enuresis, in a mammal comprising administering thereto at least one amide compound according to claim 1.

* * * * *